(12) United States Patent
Cheng et al.

(10) Patent No.: US 9,586,891 B2
(45) Date of Patent: Mar. 7, 2017

(54) ESTROGEN RECEPTOR LIGANDS

(75) Inventors: Aiping Cheng, Huddinge (SE); Neeraj Garg, Huddinge (SE); Lars Krüger, Huddinge (SE); Joakim Löfstedt, Huddinge (SE); Eva Koch, Huddinge (SE); Konrad Koehler, Huddinge (SE); Lars Hagberg, Huddinge (SE); Daniel Nöteberg, Huddinge (SE)

(73) Assignee: Karo Pharma AB, Stockholm (SE)

( * ) Notice: Subject to any disclaimer, the term of this patent is extended or adjusted under 35 U.S.C. 154(b) by 113 days.

(21) Appl. No.: 14/234,916

(22) PCT Filed: Aug. 2, 2012

(86) PCT No.: PCT/EP2012/065134
§ 371 (c)(1),
(2), (4) Date: Apr. 7, 2014

(87) PCT Pub. No.: WO2013/017654
PCT Pub. Date: Feb. 7, 2013

(65) Prior Publication Data
US 2014/0323518 A1 Oct. 30, 2014

(30) Foreign Application Priority Data
Aug. 4, 2011 (GB) .................................. 1113538.1

(51) Int. Cl.
*C07C 251/48* (2006.01)
*A61K 31/381* (2006.01)
*C07D 261/08* (2006.01)
*C07D 207/327* (2006.01)
*C07D 213/58* (2006.01)
*C07D 215/12* (2006.01)
*C07D 217/14* (2006.01)
*C07D 231/12* (2006.01)
*C07D 233/64* (2006.01)
*C07D 235/16* (2006.01)
*C07D 277/30* (2006.01)
*C07D 277/34* (2006.01)
*C07D 295/155* (2006.01)
*C07D 307/54* (2006.01)
(Continued)

(52) U.S. Cl.
CPC .......... *C07C 251/48* (2013.01); *A61K 31/155* (2013.01); *A61K 31/341* (2013.01); *A61K 31/381* (2013.01); *A61K 31/416* (2013.01); *A61K 31/42* (2013.01); *A61K 31/4418* (2013.01); *A61K 31/47* (2013.01); *A61K 31/472* (2013.01); *C07C 209/68* (2013.01); *C07D 207/327* (2013.01); *C07D 213/58* (2013.01); *C07D 215/12* (2013.01); *C07D 215/14* (2013.01); *C07D 217/14* (2013.01); *C07D 217/16* (2013.01); *C07D 231/12* (2013.01); *C07D 233/64* (2013.01); *C07D*

*235/16* (2013.01); *C07D 261/08* (2013.01); *C07D 277/30* (2013.01); *C07D 277/34* (2013.01); *C07D 295/155* (2013.01); *C07D 307/54* (2013.01); *C07D 307/68* (2013.01); *C07D 307/87* (2013.01); *C07D 317/60* (2013.01); *C07D 333/20* (2013.01); *C07D 333/24* (2013.01); *C07D 409/10* (2013.01); *C07D 413/10* (2013.01)

(58) Field of Classification Search
None
See application file for complete search history.

(56) References Cited

U.S. PATENT DOCUMENTS 3,519,675 A 7/1970 Lednicer
3,658,833 A 4/1972 Kabas et al.
(Continued)

FOREIGN PATENT DOCUMENTS

DE 2909754 A1 9/1980
EP 2258694 12/2010
(Continued)

OTHER PUBLICATIONS

Danziger, Automated Site-Directed Drug Design: A General Algorithm for Knowledge Acquisition about Hydrogen-Bonding Regions at Protein Surfaces, Proceedings of the Royal Society of London. Series B, Biological Sciences, 1989, 236(1283), pp. 101-113.*

(Continued)

*Primary Examiner* — San-Ming Hui
*Assistant Examiner* — Andrew Lee
(74) *Attorney, Agent, or Firm* — Cantor Colburn LLP

(57) ABSTRACT

Compounds of formula (I) or a pharmaceutically acceptable ester, amide, carbamate or salt thereof, including a salt of such an ester, amide or carbamate in which $R^1$ to $R^9$ have meanings as defined in the Specification, are useful as estrogen receptor ligands.

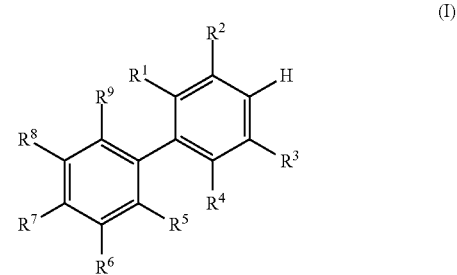

19 Claims, No Drawings

(51) Int. Cl.

| | | |
|---|---|---|
| *C07D 307/68* | (2006.01) | |
| *C07D 307/87* | (2006.01) | |
| *C07D 317/60* | (2006.01) | |
| *C07D 333/20* | (2006.01) | |
| *C07D 409/10* | (2006.01) | |
| *C07D 413/10* | (2006.01) | |
| *C07C 209/68* | (2006.01) | |
| *A61K 31/155* | (2006.01) | |
| *A61K 31/341* | (2006.01) | |
| *A61K 31/416* | (2006.01) | |
| *A61K 31/42* | (2006.01) | |
| *A61K 31/4418* | (2006.01) | |
| *A61K 31/47* | (2006.01) | |
| *A61K 31/472* | (2006.01) | |
| *C07D 215/14* | (2006.01) | |
| *C07D 217/16* | (2006.01) | |
| *C07D 333/24* | (2006.01) | |

(56) References Cited

U.S. PATENT DOCUMENTS

| | | |
|---|---|---|
| 3,799,943 A | 3/1974 | Bell et al. |
| 3,845,037 A | 10/1974 | Rosen et al. |
| 3,878,225 A | 4/1975 | Allen et al. |
| 4,056,624 A | 11/1977 | Lassman et al. |
| 4,182,764 A | 1/1980 | Cragoe, Jr. et al. |
| 4,559,354 A | 12/1985 | Fuhrer et al. |
| 5,096,919 A | 3/1992 | Wasley et al. |
| 5,470,854 A | 11/1995 | von Angerer et al. |
| 5,688,810 A | 11/1997 | Jones et al. |
| 5,691,376 A | 11/1997 | Caggiano et al. |
| 5,777,089 A | 7/1998 | Beckmann et al. |
| 6,174,840 B1 | 1/2001 | Pauson et al. |
| 6,281,214 B1 | 8/2001 | Akasaka et al. |
| 6,339,046 B1 | 1/2002 | Nebel et al. |
| 6,342,503 B1 | 1/2002 | Aldrich et al. |
| 6,358,972 B1 | 3/2002 | Filla et al. |
| 6,380,185 B1 | 4/2002 | Koko et al. |
| 6,503,938 B1 | 1/2003 | Von Angerer et al. |
| 6,689,770 B2 | 2/2004 | Wexler et al. |
| 6,794,415 B2 | 9/2004 | Lesuisse et al. |
| 6,821,783 B1 | 11/2004 | Comely et al. |
| 6,835,745 B2 | 12/2004 | Coghlan et al. |
| 6,903,238 B2 | 6/2005 | McDevitt et al. |
| 6,911,468 B2 | 6/2005 | Matsumoto et al. |
| 7,157,491 B2 | 1/2007 | Mewshaw et al. |
| 7,247,734 B2 | 7/2007 | Drysdale et al. |
| 7,250,440 B2 | 7/2007 | Mewshaw et al. |
| 7,427,630 B2 | 9/2008 | Di Fabio et al. |
| 7,612,201 B2 | 11/2009 | Beswick et al. |
| 7,674,818 B2 | 3/2010 | Jennings et al. |
| 7,674,938 B2 | 3/2010 | Kobayashi et al. |
| 7,807,672 B2 | 10/2010 | Deng et al. |
| 7,932,284 B2 | 4/2011 | Lopez |
| 8,067,434 B2 | 11/2011 | Ibrahim et al. |
| 8,093,302 B2 | 1/2012 | Thomas et al. |
| 8,110,588 B2 | 2/2012 | Nardi et al. |
| 8,129,424 B2 | 3/2012 | Bennani et al. |
| 8,148,384 B2 | 4/2012 | Penning et al. |
| 8,227,500 B2 | 7/2012 | Shimizu et al. |
| 8,338,642 B2 | 12/2012 | Kohen et al. |
| 8,653,072 B2 | 2/2014 | Rhonnstad et al. |
| 8,653,112 B2 | 2/2014 | Lofstedt et al. |
| 2003/0220377 A1 | 11/2003 | Chesworth |
| 2004/0077701 A1 | 4/2004 | Huebner et al. |
| 2006/0074128 A1 | 4/2006 | Miller et al. |
| 2006/0239909 A1 | 10/2006 | Anderson et al. |
| 2007/0021495 A1 | 1/2007 | Katzenellenbogen et al. |
| 2007/0088067 A1 | 4/2007 | Tidwell et al. |
| 2007/0248672 A1 | 10/2007 | Farina et al. |
| 2007/0249706 A1 | 10/2007 | Merrill et al. |
| 2008/0021217 A1 | 1/2008 | Borchardt et al. |
| 2008/0033049 A1 | 2/2008 | Mewshaw et al. |
| 2008/0226718 A1 | 9/2008 | Farina et al. |
| 2009/0176764 A1 | 7/2009 | Miller et al. |
| 2009/0312349 A1 | 12/2009 | Flynn et al. |
| 2010/0210524 A1 | 8/2010 | Apelqvist et al. |
| 2011/0030364 A1 | 2/2011 | Persson et al. |
| 2011/0112142 A1 | 5/2011 | Noteberg et al. |
| 2011/0201555 A1 | 8/2011 | Rhonnstad et al. |
| 2011/0243865 A1 | 10/2011 | Yokoyama et al. |
| 2011/0293520 A1 | 12/2011 | Giese et al. |
| 2012/0009142 A1 | 1/2012 | Karp et al. |
| 2012/0189545 A1 | 7/2012 | Klunk et al. |
| 2012/0189623 A1 | 7/2012 | Boyce et al. |
| 2012/0202861 A1 | 8/2012 | Wennerstal et al. |

FOREIGN PATENT DOCUMENTS

| | | |
|---|---|---|
| GB | 2459133 A | 10/2009 |
| JP | 2011122855 | 5/2001 |
| JP | 2008195642 | 8/2008 |
| WO | 9527692 A1 | 10/1995 |
| WO | 9959581 A1 | 11/1999 |
| WO | 0019994 A1 | 4/2000 |
| WO | 0066555 | 11/2000 |
| WO | 03016267 A1 | 2/2003 |
| WO | 03066579 A2 | 8/2003 |
| WO | 2004089939 A1 | 10/2004 |
| WO | 2004099122 A2 | 11/2004 |
| WO | 2008006626 A1 | 1/2008 |
| WO | 2008064830 A1 | 6/2008 |
| WO | 2009121910 A1 | 10/2009 |
| WO | 2011042474 A1 | 4/2011 |
| WO | 2012022776 A | 2/2012 |
| WO | 2012136772 A1 | 10/2012 |

OTHER PUBLICATIONS

Simone, Oncology: Introduction, Cecil Textbook of Medicine, 20th Edition, 1996 vol. 1, pp. 1004-1010.*

Albrecht et al., "In Vitro Metabolism of 2-[6-(4-Chlorophenyl)-2,2-dimethyl-7-phenyl-2,3-dihydro-1H-pyrrolizin-5-yl] Acetic Acid (Licofelone, ML3000), an Inhibitor of Cyclooxygenase-1 and -2 and 5-Lipoxygenase" Drug Metabolism and Disposition, vol. 36, No. 5 (2008), pp. 894-903.

Alesso et al., "Synthesis and Nuclear Magnetic Resonance Spectroscopy of Indane Structures: Indanes Mono- and Disubstituted in the Pentagonal Ring" Canadian Journal of Chemistry, vol. 69, (1991), pp. 1166-1170.

Alesso et al., "Synthesis and NMR Spectroscopy of Indane Structures: Substituted Indan-1-OLS" Anales De Quimica, vol. 89, (1993), pp. 242-245.

Altomare et al., "Human and Mouse Mesotheliomas Exhibit Elevated AKT/PKB Activity, Which can be Targeted Pharmacologically to Inhibit Tumor Cell Growth" Oncogene, 24, (2005), pp. 6080-6089.

Anstead et al., "Optimizing of 2,3-Diarylindenes as Fluorescent Estrogens: Variation of the Acceptor Group, Ortho Substitution of the 2-Ring, and C-1 Methylation" J. Med. Chem. 31, (1988), pp. 1754-1761.

Anstead et al., "Hydroxylated 2,3-Diarylindenes: Synthesis, Estrogen Receptor Binding Affinity, and Binding Orientation Considerations" J. Steroid Biochem., vol. 33, No. 5, (1989), pp. 877-887.

Anstead et al., "2,3-Diarylindenes and 2,3-Diarylindenones: Synthesis, Molecular Structure, Photochemistry, Estrogen Receptor Binding Affinity, and Comparisons with Related Triarylethylenes" J. Med. Chem., 31, (1988), pp. 1316-1326.

Arafa et al., "Tangeretin Sensitizes Cisplatin-Resistant Human Ovarian Cancer Cells through Downregulation of Phosphoinositide 3-Kinase/Akt Signaling Pathway" Cancer Research, 69, (2009), pp. 8910-8917.

Assony et al., "Derivatives of Sulfenic Acids. XXXII. The Synthesis of Azulenes via the Interactions of Arylacetylenes with Sulfenyl Halides. Part 1. 1,2,3-Triphenylazulene" Chemistry and Industry, vol. 80, (1958), pp. 5978-5982.

(56) References Cited

OTHER PUBLICATIONS

Banwell et al., "Synthesis, X-Ray Crystal Structure and Tubulin-Binding Properties of a Benzofuran Analogue of the Potent Cytotic Agent Combretastatin A4", Aust. J. Chem, 52, (1999), pp. 767-774.
Banwell et al., "Synthesis, X-Ray Crystal Structure and Tubulin-Binding Properties of a Benzofuran Analogue of the Potent Cytotic Agent Combretastatin A4", Aust. J. Chem, 52, (1999), pp. 767-774. Chemical Abstract No. 1999:716753, Abstract Only.
Bell et al., "Basic Ethers of 1-(p-Hydroxyphenyl)-2-phenyl-1,2,3,4-tetrahydroquinoline and 1-(p-Hydroxyphenyl)-2-phenylindole. Antifertility Agents" Journal of Medicinal Chemistry, vol. 13, No. 4 (1970), pp. 664-668. CAPLUS Accession No. 1970:445293.
Bell et al., Basic Ethers of 1-(p-hydroxyphenyl)-2-phenyl-1,2,3,4-tetrahydroquinoline and 1-(p-hydroxyphenyl)-2-phenylindole. Antifertility agents Journal of Medicinal Chemistry (1970), 13(4), 664-8. Chemical Abstract, CAS No: 27382-61-2.
Benders et al., "ESR Spectra of Semidiones Derived from Indandione-1,3" Journal of Molecular Structure, 19, (1973), pp. 431-440.
Benders et al., "ESR Spectra of Semidiones Derived from Indandione-1,3" Journal of Molecular Structure, 19, (1973), pp. 431-440. Chemical Abstract Registration No. 1974:144916, Abstract Only.
Bossard et al., "Potential Role of Estrogen Receptor Beta as a Tumor Suppressor of Epithelial Ovarian Cancer" ERβ Controls Ovarian Carcinogenesis, vol. 7, Issue 9, Sep. 2012, 10 Pages.
Caruana et al., "Palladium(II)- and Mercury(II)-Catalyzed Rearrangements of Propargyl Acetates" Tetrahedron, 63, (2007), pp. 10646-10656.
CAS Registry No. 723295-01-0 entered on Aug. 7, 2004.
Cattaneo et al., "Synthesis of New Estrogens" Farmaco, Edizione Scientifica., vol. 15, 10, (1960) pp. 632-641, CAS No. 95956-56-2, Abstract Only.
Catteneo et al., "Sintesi Di Nuovi Composti Ad Attivita Estrogena" Il Farmaco Ed. Sc. vol. XV, 10, (1960), pp. 632-641.
Cedres et al., "Exploratory Analysis of Activation of PTEN-PI3K Pathway and Downstream Proteins in Malignant Pleural Mesothelioma (MPM)" Lung Cancer, 77, (2012), pp. 192-198.
Chai et al., "A Cell-Based Assay that Targets Methionine Aminopeptidase in a Physiologically Relevant Enviroment" Bioorganic and Medicinal Chemistry Letters, 20, (2010), pp. 2129-2132.
Churruca et al., "A New, Expeditious Entry to the Benzophenanthrofuran Framework by a Pd-catalyzed C- and O-arylation/PIFA-mediated oxidative coupling Sequence" European Journal of Organic Chemistry, 12, (2005), pp. 2481-2490.
Churruca et al., "A New, Expeditious Entry to the Benzophenanthrofuran Framework by a Pd-catalyzed C- and O-arylation/PIFA-mediated oxidative coupling Sequence" European Journal of Organic Chemistry, 12, (2005), pp. 2481-2490. Chemical Abstract No. 2005:571939, Abstract Only.
Clegg et al., "Differential Response of Estrogen Receptor Subtypes to 1,3-Diarylindene and 2,3-Diarylindene Ligands" J. Med. Chem., 48, (2005), pp. 5989-6003.
Collini et al., "7-Substituted 2-phenyl-benzofurans as ERβ Selective Ligands" Bioorganic and Medicinal Chemistry Letters, 14, (2004), pp. 4925-4929.
Cui et al., "Estrogen Synthesis and Signaling Pathways During Ageing: From Periphery to Brain" Trends Mol Med., 19 (3): Mar. 2013, pp. 197-209.
Davies et al., "Derivatives of Indene and of Butyric Acid" The Chemical Society, (1947). pp. 1697-1698.
German Patent No. 2707268, Date of Issue: Aug. 31, 1978; Chemical Abstract No. 1978:579858, Abstract Only.
German Patent No: 19907063, Date of Issue: Feb. 24, 2000, Chemical Abstract Registration No. 2000:592993, English Abstract Only.
Dresner-Pollak et al., "Estrogen Receptor Beta Gene Variant is Associated with Vascular Dementia in Elderly Women" Genet Test Mol Biomarkers, 13(3), Jun. 2009, pp. 339-342.

Erber et al., "2-Phenylbenzo[b]furans: Relationship Between Structure, Estrogen Receptor Affinity and Cytostatic Activity Against Mammary Tumor Cells" Anti-Cancer Drug Design, 6, (1991), pp. 417-426. Chemical Abstract No. 1992: 120397, Abstract Only.
Erber et al., "2-Phenylbenzo[b]furans: Relationship Between Structure, Estrogen Receptor Affinity and Cytostatic Activity Against Mammary Tumor Cells" Anti-Cancer Drug Design, 6, (1991), pp. 417-426.
Fernandez-Mateos et al., "Synthesis of Active Antifeedant CDE Fragments of 11-Ketoepoxyazadiradione Based on an Electrocyclization Reaction Catalyzed by Perchloric Acid" J. Org. Chem, 63, (1998), pp. 9440-9447.
Fernandez-Mateos et al., "The Nazarov Cyclization of β-cargonyl-β'-furyl-divinyl Ketones and Related Compounds as Induced by Perchloric Acid" Tetrahedron, 57, (2001), pp. 1049-1057.
Fernandez-Mateos et al., "Synthesis of the Insect Antifeedant CDE Molecular Fragment of 12-ketoepoxyazadiradione and Related Compounds" Tetrahedron, 61, (2005), pp. 12264-12274.
Fink et al., "Novel Structural Templates for Estrogen-receptor Ligands and Prospects for Combinatorial Synthesis of Estrogens" Chemistry and Biology, vol. 6, No. 4, (1999), pp. 205-219.
Goettmann et al., "Highly Regioselective Terminal Alkynes Hydroformylation and Pauson-Khand reaction Catalysed by Mesoporous Organised Zirconium Oxide Based Powers" Chem. Commun. (2006), pp. 180-182.
Hahne et al., "Downregulation of AKT Reverses Platinum Resistance of Human Overian Cancers in vitro" Oncology Reports, 28, (2012), pp. 2023-2028.
Halon et al., "Loss of Estrogen Receptor Beta Expression Correlates with Shorter Overall Survival and Lack of Clinical Response to Chemotherapy in Ovarian Cancer Patients" Anticancer Research, 31, (2011), pp. 711-718.
Harris, "Estrogen Receptor-β: Recent Lessons from in Vivo Studies" Molecular Endocrinology, 21(1), (2007)), pp. 1-13).
Hartman et al., "Combined Treatment with Cisplatin and Sirolimus to Enhance Cell Death in Human Mesothelioma" The Journal of Thoracic and Cardiovascular Surgery, vol. 138, No. 5, (2009), pp. 1233-1240.
Hoda et al., "Temsirolimus Inhibits Malignant Pleural Mesothelioma Growth in Vitro and in Vivo" Journal of Thoracic Oncology, vol. 6, No. 5, (2011), pp. 852-863.
Islam et al., "Structural Isomets in the Perkin Reaction: Part IV*—4,5-Diiodo- & 6,7-Diiodo-3-benzalphthalides & their Reactions" Indian Journal of Chemistry, vol. 16B, (1978), pp. 301-304.
Islam et al., "4,5,6,7,-Tetraiodo-3-Benzalphthalides and Related Compounds" Egypt J. Chem. 22, No. 2, (1979), pp. 135-141.
Ito et al., "A Medium-term Rat Liver Bioassay for Rapid in vivo Detection of Carcinogenic Potential of Chemicals" Cancer Sci. vol. 94, No. 1, (2003), pp. 3-8.
Iwasawa et al., "Rearrangement of 1-(1-Alkynyl)cyclopropanols to 2-Cyclopentenones via there Hexacarbonyldicobalt Compleses. A new Use of Alkyne-Co2(CO)6 Complexes in Organic Synthesis" J. Am. Chem., 120, (1998), pp. 3903-3914.
Japanese Patent No. 04178488, Published Nov. 10, 1990, Chemical Abstract Registration No. 1993:179715, Abstract Only.
Japanese Patent No. 2006306755, Published Apr. 27, 2005, Chemical Abstract Registration No. 2006:1174156, Abstract Only.
Japanese Patent No. 2004155731, Date of Issue: Jun. 3, 2004, Chemical Abstract Registration No. 2004:17612, Abstract Only.
Karthikeyan et al., "Synthesis and Antinociceptive Activity of Pyrazolyl Isoxazolines and Pyrazolyl Isoxazoles" Bioorganic & Medicinal Chemistry Letters, 19, (2009), pp. 3370-3373.
Kaufmann et al., "Antimitotic Activities of 2-phenylindole-3-carbaldehydes in Human Breast Cancer Cells" Bioorganic & Medicinal Chemistry, 15, (2007), pp. 5122-5136.
Khan et al., "Indole Derivatives as Antibacterial Agents. Structure-Activity Relationship" Park J. Sci. Ind. Res. 43(4), (2000), pp. 238-240.
Khand et al., "Organocobalt Complexes. Part XI. A General Synthetic Route to Cyclopentenones using Acetylenehexacarbonyldicobalt Complexes" J. Chem. Research, 9, (1977), pp. 168-187.

(56) References Cited

OTHER PUBLICATIONS

Koehler et al., "Reflections on the Discovery and Significance of Estrogen Receptor β" Endocrine Reviews, 26(3), (2005), pp. 465-478.

Landry et al., "Purification and Reconstitution of Chloride Channels from Kidney and Trachea" Science, vol. 244, (1988), pp. 1469-1472.

Landry et al., "Purification and Reconstitution of Chloride Channels from Kidney and Trachea" Science, vol. 244, (1988), pp. 1469-1472. Chemical Abstract Resistration No. 1989:511189, Abstract Only.

Lapouyade et al., "Photophysics of Donor-Acceptor Substituted Stilbenes. A Time-Resolved Fluoresence Study Using Selectively Bridged Dimethylamino Cyano Model Compounds" The Journal of Physical Chemistry, vol. 96, No. 24, (1992), pp. 9643-9650.

Lapouyade et al., "Photophysics of Donor-Acceptor Substituted Stilbenes. A Time-Resolved Fluoresence Study Using Selectively Bridged Dimethylamino Cyano Model Compounds" The Journal of Physical Chemistry, vol. 96, No. 24, (1992), pp. 9643-9650. Chemical Abstract Registry No. 1992:661356, Abstract Only.

Lesuisse et al., "Biphenyls as Surrogates of the Steroidal Backbone. Part 1: Synthesis and Estrogen Receptor Affinity of an Original Series of Polysubstituted Biphenyls" Bioorganic and Medicinal Chemistry Letters, 11, (2001), pp. 1709-1712.

Manente et al., "Estrogen Receptor β Activation Impairs Mitochondrial Oxidative Metabolism and Affects Malignant Mesothelioma Cell Growth in vitro and in vivo" Oncogenesis (2013), pp. 1-10.

Matsumoto et al., "Palladium-Catalyzed Dehydrative Aromatization of Cyclohexenone Oximers to Anilines" Synthetic Communications, vol. 24, No. 10, (1994), pp. 1441-1446. Abstract Only, XP-002686882.

Matsumoto et al., "Palladium-Catalyzed Dehydrative Aromatization of Cyclohexenone Oximes to Anilines" Synthetic Communications, 24(10), (1994), pp. 1441-1446.

McDevitt et al., "Estrogen Receptor Ligands: Design and Synthesis of New 2-Arylindene-1-Ones" Bioorganic and Medicinal Chemistry Letters, 15, (2005), pp. 3137-3142.

Mehta et al., "Decahydro-1,3,5-Methenocyclopenta[cd]pentalene (Trishomocubane) Framework: Novel Photochemical Synthesis, Acid-Catalysed Cyclo-reversion, and Possible Role as a Solar Energy Storage System" J. Chem. Soc., Chem. Commun. (1982), pp. 218-219.

Mewshaw et al., "ERβ Ligands. Part 5: Synthesis and Structure-Activity Relationships of a Series of 4'-Hydroxyphenyl-arylcarbaldehyde Oxime Derivatives" Bioorganic and Medicinal Chemistry Letters, 17, (2007), pp. 902-906.

Miller et al., "Selective Estrogen Receptor Modulator Treatment and Prevention of Osteoporosis" Drugs of the Future, 27(2), (2002), pp. 117-121.

Minutolo et al., "Synthesis, Binding Affinity, and Transcriptional Activity of Hydroxy-and Methoxy-Substituted 3,4-Diarylsalicylaldoximes on Estrogen Receptors a and β" Bioorganic and Medicinal Chemistry, 11, (2003), pp. 1247-1257.

Minutolo et al., "Synthesis, Binding Affinity, and Transcriptional Activity of Hydroxy-and Methoxy-Substituted 3,4-Diarylsalicylaldoximes on Estrogen Receptors a and β" Bioorganic and Medicinal Chemistry, 11, (2003), pp. 1247-1257. Chemical Abstract Registration No. 2003:195823, Abstract Only.

Mukherjee et al., "Pharmacophore Mapping of Arylbenzothiophene Derivatives for MCF Cell Inhibition Using Classical and 3D Space Modeling Approaches" Journal of Molecular Graphics and Modelling, 26, (2008), pp. 884-892.

Mukherjee et al., "Pharmacophore Mapping of Arylbenzothiophene Derivatives for MCF Cell Inhibition Using Classical and 3D Space Modeling Approaches" Journal of Molecular Graphics and Modelling, 26, (2008), pp. 884-892. Chemical Abstract No. 2007:1409941, Abstract Only.

Nagarajan et al., "Antiiplantation Agents: Part III—1,2-Diaryl-4,5-polymethylenepyrroles and 1,2-Diaryl-4-oxo- and 1,2-Diaryl-4-hydroxy-4,5,6,7-tetrahydroindoles" Indian Journal of Chemistry, vol. 24B, (1985), pp. 98-111.

Naoum et al., "Synthesis of Novel Nitro-substituted Triaryl Pyrazole Derivatives as Potential Estrogen Receptor Ligands" Molecules, 12, (2007), pp. 1259-1273.

Narasimhan et al., "A New Reaction of o-Benzoquinone with N-Acetyl-DL-Tryptophan (a 3-Substituted Indole) and Characterisation of the Product" Indian Journal of Biochemistry & Biophysics, vol. 23, (1986), pp. 215-219.

Narasimhan et al., "A New Reaction of o-Benzoquinone with N-Acetyl-DL-Tryptophan (a 3-Substituted Indole) and Characterisation of the Product" Indian Journal of Biochemistry & Biophysics, vol. 23, (1986), pp. 215-219. Chemical Abstract Only.

Nilsson et al., "Oestrogen Receptors and Selective Oestrogen Receptor Modulators: Molecular and Cellular Pharmacology" Pharmacology and Toxicology, 96, (2005), pp. 15-25.

Nilsson et al., "Development of Subtype-Selective Oestrogen Receptor-Based Therapeutics" Nature Reviews, vol. 10, (2011), pp. 778-792.

Perrot et al., Preparation of Substituted 2,3-diarylbenzofurans Sciences Chimiques, 265(5), (1967), pp. 320-323. Chemical Abstract No. 1968:39388, Abstract Only.

Perrot et al., "Synthesis of Substituted 2,3-diarylbenzo [b] furans" Bulletin de la Societe Chimique de France, 9-10, Pt. 2, (1974), pp. 2225-2232. Chemical Abstract No. 1975:97904, Abstract Only.

Pfeiffer et al., "Autoxidation Phenomena in the Anils of the Indandione Series. II" Journal Fuer Praktische Chime, 159, (1941), pp. 13-35.

Pfeiffer et al., "Autoxidation Phenomena in the Anils of the Indandione Series. II" Journal Fuer Praktische Chime, 159, (1941), pp. 13-35, Chemical Abstract Registration No. 1942:39206, Abstract Only.

Pisarenko et al., Kinetics of Reversible Recombination of 2[p-(dimethylamino)phenyl]-1,3-dioxo-2-indanyl Radicals Izvestiya Akademii Nauk SSR, 8, (1988), pp. 1734-1738.

Pisarenko et al., Kinetics of Reversible Recombination of 2[p-(dimethylamino)phenyl]-1,3-dioxo-2-indanyl Radicals Izvestiya Akademii Nauk SSR, 8, (1988), pp. 1734-1738. Chemical Abstract Registration No. 1989:134637, Abstract Only.

Rango et al., "Antimycobacterial Pyrroles: Synthesis, Anti-*Mycobacterium tuberculosis* Activity and QSAR Studies" Bioorganic and Medicinal Chemistry, 8, (2000), pp. 1423-1432.

Chemical Abstract Registration No. 1025991-22-3; Entered on Jun. 6, 2008, 1 Page.

Shen et al., "Radester, a Novel Inhibitor of the Hsp90 Protein Folding Machinery" Organic Letters, vol. 7, No. 11, (2005), pp. 2157-2160.

Shen et al., "Radester, a Novel Inhibitor of the Hsp90 Protein folding Machinery" Organic Letters, vol. 7, No. 11, (2005), pp. 2157-2160. Abstract Only.

Silverman et al., "The Synthesis of Some Indene and Dihydronaphthalene Derivatives Related to Stilbestrol" Journal of Organic Chem. 11, (1946), pp. 34-49.

Sivanesan et al., "In-silico Screening Using Flexible Ligand Binding Pockets: A Molecular Dynamics-based Approach" Journal of Computer-Aided Molecular Design, 19, (2005), pp. 213-228.

Strohmeir et al., "Hydroxy-3-(hydroxyphenyl)indoles. Relationship Between Structure and Estrogen Receptor Affinity" Arch. Pharm, 318, (1985), pp. 421-431.

Takaya et al., "Chemical Determination of the Absolute structures of Resveratrol Dimers, Ampelopsins A, B, D and F" Tetrahedron 58, (2002), pp. 7259-7265.

Vicente et al. "Palladium-Assisted Formation of Carbon-Carbon Bonds. 6.1 Study of the Reactivity of (o-Formylaryl)- or (o-Acetylaryl)palladium Complex with Alkynes. Synthesis of Indenoses and Indenols" Organometallics, 15, (1996), pp. 3509-3519.

Wang et al., "Discovery of Inhibitors of *Escherichia coli* Methionine Aminopeptidase with the Fe (II)-Form Selectivity and Anti-

(56) References Cited

OTHER PUBLICATIONS bacterial Activity" Journal of Medicinal Chemistry, 51(19), (2008), pp. 6110-6120. Chemical Abstract No. 2008:1129691, Abstract Only.

Wang et al., "Anti-Inflammatory Properties and Regulatory Mechanism of a Novel Derivative of Artemisinin in Experimental Autoimmune Encephalomyelitis" The Journal of Immunology, 179, (2007), pp. 5958-5965.

Wiglenda et al., "Structure-Activity Relationship Study to Understand the Estrogen Receptor-Dependent Gene Activation of Aryl- and Alkyl-Substituted 1H-Imidazoles" Journal of Med. Chem., 50, (2007), pp. 1475-1484.

US2011/243865; "Melanin Production Inhibitor"; Published: Oct. 6, 2011; 1 Page; Pola Chemical Industries Inc.; Chemical Abstract Only.

Yahyazadeh et al., "Synthesis and Spectral Characteristics of 5-Amino-4-Cyanoimidazoles from Amidines" Asian Journal of Chemistry, vol. 17, No. 1, (2005), pp. 609-611.

Yang et al., ERβ Ligands. Part 2: Synthesis and Structure-Activity Relationships of a Series of 4-Hydroxy-Biphenyl-Carbaldehyde Oxime Derivatives Bioorganic and Medicinal Chemistry, 12, (2004), pp. 2553-2570.

Zimmermann et al., "Estrogenic and Antiestrogenic Activities of 2,4-diphenylfuran-based Ligands of Estrogen Receptors a and β" Journal of Steroid Biochemistry and Molecular Biology, 104, (2007), 259-268.

Allen et al.; "Carboxyarylindoles as Nonsteroidal Antiinflammatory Agents"; J. Med. Chem., vol. 19, No. 9; 1976; pp. 318-325.

Bowe et al.; "The hop phytoestrogen, 8-prenylnaringenin, reverses the ovariectomyinduced rise in skin temperature in an animal model of menopausal hot flushes"; J. Endocrinol., vol. 191; 2006; pp. 399-405.

Leitman et al.; MF101: a multi-component botanical selective estrogen receptor beta modulator for the treatment of menopausal vasomotor symptoms; Expert Opin. Investig. Drugs, vol. 21, No. 7; 2012; pp. 1031-1042.

Opas et al.; "Control of rat tail skin temperature regulation by estrogen receptorbeta selective ligand"; Maturitas (2009), doi:10.1016/j.maturitas.2009.07.007.

Opas et al.; "Estrogenic control of thermoregulation in KRαKO and ERβKO mice"; Maturitas, vol. 53; 2006; pp. 210-216.

Wang et al., "Molecular Imaging Reveals a Role for AKT in Resistance to Cisplatin for Ovarian Endometrioid Adenocarcinoma" Clin Cancer Res. 19, (2013), pp. 158-169.

* cited by examiner

ESTROGEN RECEPTOR LIGANDS

CROSS-REFERENCE TO RELATED APPLICATIONS

This is a U.S. National Stage Application of PCT/EP2012/065134 filed Aug. 2, 2012, which claims priority from GB Patent Application 1113538.1, filed Aug. 4, 2011, both of which are herein incorporated by reference in their entireties.

FIELD OF INVENTION

This invention relates to compounds which are estrogen receptor ligands and are preferably selective for the estrogen receptor β isoform, to methods of preparing such compounds and to methods for using such compounds in treatment of diseases related to the estrogen receptor such as depressive disorders, anxiety disorders, Alzheimer's disease, cognitive disorders, osteoporosis, elevated blood triglyceride levels, atherosclerosis, endometriosis, urinary incontinence, autoimmune disease, and cancer of the lung, colon, breast, uterus and prostate.

BACKGROUND OF INVENTION

The estrogen receptor (ER) is a ligand activated mammalian transcription factor involved in the up and down regulation of gene expression. The natural hormone for the estrogen receptor is β-17-estradiol (E2) and closely related metabolites. Binding of estradiol to the estrogen receptor causes a dimerization of the receptor and the dimer in turn binds to estrogen response elements (ERE's) on DNA. The ER/DNA complex recruits other transcription factors responsible for the transcription of DNA downstream from the ERE into mRNA which is eventually translated into protein. Alternatively the interaction of ER with DNA may be indirect through the intermediacy of other transcription factors, most notably fos and jun. Since the expression of a large number of genes is regulated by the estrogen receptor and since the estrogen receptor is expressed in many cell types, modulation of the estrogen receptor through binding of either natural hormones or synthetic ER ligands can have profound effects on the physiology and pathophysiology of the organism.

Historically it has been believed there was only one estrogen receptor. However a second subtype (ER-β) has been discovered. While both the "classical" ER-α and the more recently discovered ER-β are widely distributed in different tissues, they nevertheless display markedly different cell type and tissue distributions. Therefore synthetic ligands which are either ER-α or ER-β selective may preserve the beneficial effects of estrogen while reducing the risk of undesirable side effects.

Estrogens are critical for sexual development in females. In addition, estrogens play an important role in maintaining bone density, regulation of blood lipid levels, and appear to have neuroprotective effects. Consequently decreased estrogen production in post-menopausal women is associated with a number of diseases such as osteoporosis, atherosclerosis, depression and cognitive disorders. Conversely certain types of proliferative diseases such as breast and uterine cancer and endometriosis are stimulated by estrogens and therefore antiestrogens (i.e., estrogen antagonists) have utility in the prevention and treatment of these types of disorders.

The efficacy of the natural estrogen, 17β-estradiol, for the treatment of various forms of depressive illness has also been demonstrated and it has been suggested that the antidepressant activity of estrogen may be mediated via regulation of tryptophan hydroxylase activity and subsequent serotonin synthesis (See, e.g., Lu N Z, Shlaes T A, Cundlah C, Dziennis S E, Lyle R E, Bethea C L, "Ovarian steroid action on tryptophan hydroxylase protein and serotonin compared to localization of ovarian steroid receptors in midbrain of guinea pigs." Endocrine 11:257-267, 1999). The pleiotropic nature of natural estrogen precludes its widespread, more chronic use due to the increased risk of proliferative effects on breast, uterine and ovarian tissues. The identification of the estrogen receptor, ERβ, has provided a means by which to identify more selective estrogen agents which have the desired anti-depressant activity in the absence of the proliferative effects which are mediated by ERα. Thus, it has been shown that therapeutic agents having ERβ-selectivity are potentially effective in the treatment of depression.

What is needed in the art are compounds that can produce the same positive responses as estrogen replacement therapy without the negative side effects. Also needed are estrogen-like compounds that exert selective effects on different tissues of the body.

The synthesis of a series of polysubstituted biphenyl compounds and their binding affinity towards the human recombinant estrogen receptor alpha is disclosed in D. Lesuisse et al, *Bioorg. Med. Chem. Lett.*, 2001, 11, 1709-1712. A series of 4-hydroxy-biphenyl-carbaldehyde oxime derivatives and their binding affinity towards the estrogen receptor (ER) subtypes ERα and ERβ is disclosed in C. Yang et al, *Bioorg. Med. Chem. Lett.*, 2004, 12, 2553-2570 and also in WO 2004/099122. Further aryl-carbaldehyde oxime derivatives and their use as estrogenic agents are described in WO 2004/103941. Certain other biphenyl compounds and their use in the treatment of multiple sclerosis are disclosed in WO 2006/105442.

The compounds of the present invention are ligands for estrogen receptors and as such may be useful for treatment or prevention of a variety of conditions related to estrogen functioning.

SUMMARY OF THE INVENTION

This invention provides a compound of formula (I) or a pharmaceutically acceptable ester, amide, carbamate or salt thereof, including a salt of such an ester, amide or carbamate

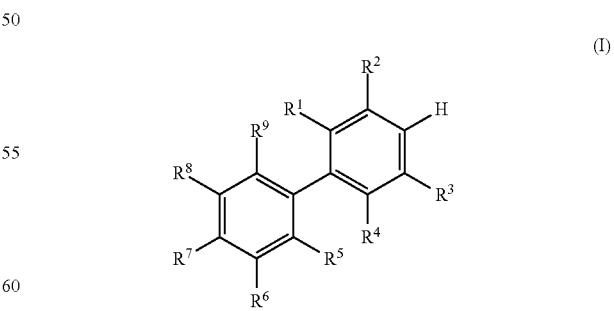

in which
$R^1$ is selected from the group consisting of optionally substituted 5-10 membered heterocyclyl, optionally substituted phenyl, optionally substituted naphthyl, optionally substituted $C_{3-8}$cycloalkyl, optionally substituted $C_{5-6}$cycloalkenyl, optionally substituted phenylC$_{2-4}$alkenyl, C$_{2-8}$alkenyl, haloC$_{2-8}$alkenyl, dihaloC$_{2-8}$alkenyl, trihaloC$_{2-8}$alkenyl, and C$_{3-8}$cycloalkylC$_{2-4}$alkenyl, wherein when said heterocyclyl, phenyl or naphthyl group or part of group is substituted, it is substituted with from 1 to 5 substituents, each substituent being independently selected from the group consisting of OR$^A$, N(R$^B$)$_2$, halogen, cyano, nitro, —C(O)C$_{1-4}$alkyl, C$_{1-6}$alkyl, C$_{2-6}$alkenyl, C$_{2-6}$alkynyl, haloC$_{1-6}$ alkyl, dihaloC$_{1-6}$alkyl and trihaloC$_{1-6}$alkyl, and when said C$_{3-8}$cycloalkyl or C$_{5-6}$cycloalkenyl group is substituted, it is substituted with 1, 2 or 3 substituents selected from C$_{1-5}$alkyl, C$_{1-5}$alkenyl C$_{1-5}$alkynyl, C$_{1-5}$alkyl substituted with up to 3 halogen atoms, —CO—C$_{1-5}$alkyl, and halogen;

R$^2$ is selected from the group consisting of —C(NH$_2$)=N—OH, —C(O)N(R$^C$)$_2$, cyano, —CHO, —CH=N—OH, —C(O)NH—OH, —C(CO$_2$H)=N—OH, —C(O—C$_{1-4}$alkyl)=NH, —C(NH$_2$)=N—NH$_2$, —C(O)—C(O)—NH$_2$, —C(O)CO$_2$H, —CO$_2$H, —CH$_2$—CO$_2$H, —CH(OH) CO$_2$H, —CH$_2$NH—CONH$_2$, —CH$_2$SO$_3$H, —NH—C(NH$_2$)=NH, —NH—C(O)NH$_2$, —N=C(—NH—CH$_2$CH$_2$—NH—), N(R$^B$)$_2$, N(OH)$_2$, NHSO$_2$R$^D$, —S—CN, —S—C(NH$_2$)=NH, —S—C(NH$_2$)=N—OH, SO$_2$N(R$^E$)$_2$, SO$_3$H, cyanoC$_{1-6}$alkyl, and optionally substituted 5-10 membered heterocyclyl containing from one to three nitrogen atoms, wherein when said heterocyclyl group is substituted, it is substituted with from 1 to 3 substituents, each substituent being independently selected from the group consisting of OR$^A$, N(R$^B$)$_2$, halogen, cyano, nitro, —C(O)C$_{1-4}$alkyl, C$_{1-6}$alkyl, C$_{2-6}$alkenyl, C$_{2-6}$alkynyl, haloC$_{1-6}$alkyl, dihaloC$_{1-6}$alkyl and trihaloC$_{1-6}$alkyl;

R$^3$ is selected from the group consisting of hydrogen, halogen, cyano, C$_{1-6}$alkyl, C$_{2-6}$alkenyl, C$_{2-6}$alkynyl, C$_{3-8}$cycloalkyl, C$_{3-8}$cycloalkylC$_{1-6}$alkyl, haloC$_{1-6}$alkyl, dihalo-C$_{1-6}$alkyl, trihaloC$_{1-6}$alkyl, optionally substituted phenyl, optionally substituted phenylC$_{1-4}$alkyl, optionally substituted 5-10 membered heterocyclyl, and optionally substituted 5-10 membered heterocyclylC$_{1-4}$alkyl, wherein when said phenyl or heterocyclyl group or part of group is substituted, it is substituted with from 1 to 5 substituents, each substituent being independently selected from the group consisting of OR$^A$, N(R$^B$)$_2$, halogen cyano, nitro, C$_{1-6}$alkyl, C$_{2-4}$alkenyl, C$_{2-6}$alkynyl, haloC$_{1-6}$alkyl, dihaloC$_{1-6}$alkyl and trihaloC$_{1-6}$alkyl;

R$^4$ is selected from the group consisting of hydrogen, halogen, cyano, C$_{1-6}$alkyl, C$_{2-6}$alkenyl, C$_{2-6}$alkynyl, and haloC$_{1-6}$alkyl, dihaloC$_{1-6}$alkyl, and trihaloC$_{1-6}$alkyl;

each of R$^5$, R$^6$, R$^8$ and R$^9$ is independently selected from the group consisting of hydrogen, OR$^A$, N(R$^B$)$_2$, halogen, cyano, nitro, —C(O)C$_{1-4}$alkyl, C$_{1-6}$alkyl, C$_{2-6}$alkenyl, C$_{2-6}$alkynyl, haloC$_{1-6}$ alkyl, dihaloC$_{1-6}$alkyl and trihaloC$_{1-6}$alkyl;

R$^7$ is OR$^A$;

or R$^6$ and R$^7$ may, together with the atoms they are attached to, form a 5-, 6- or 7-membered cyclic group optionally containing one to three heteroatoms selected from O, N and S, said 5-, 6- or 7-membered cyclic group being optionally substituted with one of more groups selected from OR$^A$, cyano, nitro, C$_{1-6}$ alkyl, C$_{2-6}$alkenyl, C$_{2-6}$alkynyl, halo C$_{1-6}$ alkyl, dihalo C$_{1-6}$ alkyl and trihalo C$_{1-6}$alkyl; and each R$^A$, each R$^B$, each R$^C$, each R$^D$ and each R$^E$ is independently selected from the group consisting of hydrogen, C$_{1-6}$alkyl, C$_{2-6}$alkenyl, C$_{2-6}$alkynyl, C$_{3-8}$cycloalkyl and C$_{3-8}$cycloalkylC$_{1-6}$alkyl; each optionally substituted by from 1 to 3 halogen atoms.

Compounds of the invention have surprisingly been found to be ligands of the estrogen receptor. The compounds accordingly have use in the treatment or prophylaxis of conditions associated with estrogen receptor activity.

DETAILED DESCRIPTION OF INVENTION

The compounds of the invention may contain chiral (asymmetric) centers or the molecule as a whole may be chiral. The individual stereoisomers (enantiomers and diastereoisomers) and mixtures of these are within the scope of the present invention.

Certain compounds of the invention contain an oxime group which may be present as the (E) or (Z) oxime isomer. The individual (E) and (Z) oxime isomers and mixtures of these are within the scope of the present invention. Throughout the specification, where the oxime structure is shown with a wavy line bond, this indicates either that a single isomer is present but the stereochemistry is unknown, or that a mixture of both isomers is present.

The present invention provides compounds that are estrogen receptor ligands. The term "estrogen receptor ligand" as used herein is intended to cover any moiety which binds to an estrogen receptor. The ligand may act as an agonist, a partial agonist, an antagonist or a partial antagonist. The ligand may be ERβ selective or display mixed ERα and ERβ activity. For example, the ligand may act both as an agonist or a partial agonist of ERβ and as an antagonist or a partial antagonist of ERα. Compounds of the present invention are preferably estrogen receptor ligands that display ERβ selective agonism.

In one embodiment, hereinafter referred to as embodiment R$^1$(A), R$^1$ represents an optionally substituted 5-10 membered heterocyclyl, wherein when said heterocyclyl group is substituted, it is substituted with from 1 to 5 substituents, each substituent being independently selected from the group consisting of OR$^A$, N(R$^B$)$_2$, halogen, cyano, nitro, —C(O)C$_{1-4}$alkyl, C$_{1-6}$alkyl, C$_{2-6}$alkenyl, C$_{2-6}$alkynyl, haloC$_{1-6}$alkyl, dihaloC$_{1-6}$alkyl and trihaloC$_{1-6}$alkyl.

In another embodiment, hereinafter referred to as embodiment R$^1$(B), R$^1$ represents an optionally substituted phenyl or naphthyl group, wherein when said phenyl or naphthyl group is substituted, it is substituted with from 1 to 5 substituents, each substituent being independently selected from the group consisting of OR$^A$, N(R$^B$)$_2$, halogen, cyano, nitro, —C(O)C$_{1-4}$alkyl, C$_{1-6}$alkyl, C$_{2-6}$alkenyl, C$_{2-6}$alkynyl, haloC$_{1-6}$ alkyl, dihaloC$_{1-6}$alkyl and trihaloC$_{1-6}$alkyl. Within embodiment R$^1$(B), preferably R$^1$ represents an optionally substituted phenyl group.

In another embodiment, hereinafter referred to as embodiment R$^1$(C), R$^1$ represents an optionally substituted C$_{3-8}$cycloalkyl or optionally substituted C$_{5-6}$cycloalkenyl group, wherein when said C$_{3-8}$cycloalkyl or C$_{5-6}$cycloalkenyl group is substituted, it is substituted with 1, 2 or 3 substituents selected from C$_{1-5}$alkyl, C$_{1-5}$alkenyl, C$_{1-5}$alkynyl, C$_{1-5}$alkyl substituted with up to 3 halogen atoms, —CO—C$_{1-5}$alkyl, and halogen.

In another embodiment, hereinafter referred to as embodiment R$^1$(D), R$^1$ represents an optionally substituted phenylC$_{2-4}$alkenyl, C$_{2-8}$alkenyl, haloC$_{2-8}$alkenyl, dihaloC$_{2-8}$alkenyl, trihaloC$_{2-8}$alkenyl, or C$_{3-8}$cycloalkylC$_{2-4}$alkenyl, wherein when said phenyl part of group is substituted, it is substituted with from 1 to 5 substituents, each substituent being independently selected from the group consisting of OR$^A$ N(R$^B$)$_2$, halogen, cyano, nitro, —C(O)C$_{1-4}$alkyl, C$_{1-6}$alkyl, C$_{2-6}$alkenyl, C$_{2-6}$alkynyl, haloC$_{1-6}$alkyl, dihaloC$_{1-6}$alkyl and trihaloC$_{1-6}$alkyl.

When R$^1$ represents a C$_{2-8}$alkenyl, haloC$_{2-8}$alkenyl, dihaloC$_{2-8}$alkenyl, or trihaloC$_{2-8}$alkenyl, group, this may for example be a $C_{2-6}$alkenyl, halo$C_{2-6}$alkenyl, dihalo$C_{2-6}$alkenyl, or trihalo$C_{2-6}$alkenyl group. When $R^1$ represents a $C_{3-8}$cycloalkyl group, this may for example be a $C_{3-6}$cycloalkyl group. When $R^1$ represents a $C_{3-8}$cycloalkyl$C_{1-4}$alkenyl group, this may for example be a $C_{3-6}$cycloalkyl$C_{1-4}$alkenyl group. When $R^1$ represents a $C_{5-6}$cycloalkenyl group, this may for example be a cyclopentenyl group.

When $R^1$ represents a heterocyclyl group, the heterocyclyl group may be saturated or unsaturated and may contain one or more O, N and/or S atoms. Suitable heterocyclyl groups include furyl, thienyl, pyrrolyl, pyrrolinyl, pyrrolidinyl, oxazolyl, isoxazolyl, thiazolyl, isothiazolyl, imidazolyl, imidazolinyl, imidazolidine, pyrazolyl, pyrazolinyl, pyrazolidinyl, pyridyl, morpholinyl, benzofuryl, quinolinyl, dioxazolyl, benzimidazolyl, and piperidyl. In one preferred embodiment, the heterocyclyl group is 6-membered or, especially, 5-membered; it may be unsaturated, especially aromatic, or saturated. Furyl, pyrrolyl, thienyl, isoxazolyl, isothiazolyl, pyrazolyl and pyridyl are preferred heterocyclyl groups, with isoxazolyl, isothiazolyl, pyridyl, and pyrrolidinyl being particularly preferred groups. In another embodiment, the heterocyclyl group may be 9- or 10-membered, for example it may be a benzofuryl, dioxazolyl or benzimidazolyl group. A heterocyclyl group $R^1$ may include 1 to 5, for example 1 to 3, particularly 1 or 2, substituents. Preferred substituents are selected from $OR^A$, $N(R^B)_2$, halogen, cyano, nitro, —$C(O)C_{1-4}$alkyl, $C_{1-6}$alkyl, $C_{2-6}$alkenyl, $C_{2-6}$alkynyl, halo$C_{1-6}$alkyl, dihalo$C_{1-6}$alkyl and trihalo$C_{1-6}$alkyl. More preferred substituents are selected from halogen, cyano, $C_{1-4}$alkyl (especially methyl or ethyl), trihalo$C_{1-4}$alkyl (especially trifluoromethyl), —$C(O)C_{1-4}$alkyl, and $OR^A$ in which $R^A$ preferably represents a hydrogen atom or a $C_{1-4}$alkyl group. Still more preferred substituents are selected from halogen, cyano, $C_{1-4}$alkyl (especially methyl or ethyl), and trihalo$C_{1-4}$alkyl (especially trifluoromethyl). Especially preferred substituents are selected from halogen, cyano and $C_{1-4}$alkyl (especially methyl or ethyl), especially halogen and $C_{1-4}$alkyl (especially methyl or ethyl). In one preferred embodiment $R^1$ is isoxazolyl, isothiazolyl, pyridyl, or pyrrolidinyl optionally substituted by up to 3, for example 1 or 2, substituents independently selected from halogen atoms and methyl and ethyl groups. In another embodiment, $R^1$ is a 5-membered, aromatic heterocyclyl group substituted by two methyl groups. When said group contains only one ring heteroatom, an additional substituent, for example a halogen atom, may also be present.

A phenyl, naphthyl or phenyl$C_{2-4}$alkenyl group $R^1$ may include 1 to 5, for example 1 to 3, particularly 1 or 2, substituents. Preferred substituents for a phenyl, naphthyl or phenyl$C_{2-4}$alkenyl group $R^L$ include those mentioned above for a heterocyclyl group $R^1$.

Further preferred substituents for a phenyl, naphthyl or phenyl$C_{2-4}$alkenyl group $R^1$ are selected from $OR^A$, halogen, $C_{1-6}$alkyl, $C_{2-6}$alkenyl, $C_{2-6}$alkynyl, halo$C_{1-6}$alkyl, dihalo$C_{1-6}$alkyl and trihalo$C_{1-46}$alkyl. More preferred substituents are selected from halogen (especially fluorine or chlorine), $C_{1-4}$alkyl (especially methyl or ethyl), $C_{2-4}$alkenyl (especially ethenyl), $C_{2-4}$alkynyl (especially ethynyl), trihalo$C_{1-4}$alkyl (especially trifluoromethyl), and $OR^A$ in which $R^A$ preferably represents a hydrogen atom, a $C_{1-4}$alkyl group or a trihalo$C_{1-4}$alkyl group. Still more preferred substituents are selected from halogen (especially fluorine or chlorine), $C_{1-4}$alkyl (especially methyl or ethyl), $C_{2-4}$alkenyl (especially ethenyl), $C_{2-4}$alkynyl (especially ethynyl), trifluoromethyl, and $OR^A$ in which $R^A$ represents hydrogen, methyl, ethyl or trifluoromethyl. Especially preferred substituents are selected from halogen (especially fluorine or chlorine), methyl, methoxy and trifluoromethyl.

Preferably, $R^1$ is selected from the group consisting of optionally substituted 5-10 membered heterocyclyl, optionally substituted phenyl, optionally substituted naphthyl, optionally substituted $C_{5-6}$cycloalkenyl, optionally substituted phenyl$C_{2-4}$alkenyl, $C_{2-8}$alkenyl, $C_2$halo$C_{2-8}$alkenyl, dihalo$C_{2-8}$alkenyl, trihalo$C_{2-8}$alkenyl, and $C_{3-8}$cycloalkyl$C_{2-4}$alkenyl, wherein when said heterocyclyl or phenyl or naphthyl group or part of group is substituted, it is substituted with from 1 to 5 substituents, each substituent being independently selected from the group consisting of $OR^A$, $N(R^B)_2$, halogen, cyano, nitro, $C_{1-6}$alkyl, halo$C_{1-6}$alkyl, dihalo$C_{1-6}$alkyl and trihalo$C_{1-6}$alkyl, and wherein when said $C_{5-6}$cycloalkenyl group is substituted, it is substituted with 1 or 2 substituents selected from halogen atoms and methyl groups (hereinafter referred to as embodiment $R^1$(E). More preferably, $R^1$ is selected from the group consisting of optionally substituted 5-10 membered heterocyclyl, optionally substituted phenyl, optionally substituted phenyl$C_{2-4}$alkenyl, cyclopentenyl, $C_{2-8}$alkenyl, and $C_{3-8}$cycloalkyl$C_{2-4}$alkenyl, wherein when said heterocyclyl or phenyl group or part of group is substituted, it is substituted with from 1 to 5 substituents, each substituent being independently selected from the group consisting of $OR^A$, halogen, $C_{1-6}$alkyl, halo$C_{1-6}$ alkyl, dihalo$C_{1-6}$alkyl and trihalo$C_{1-6}$alkyl. Still more preferably, $R^1$ is selected from the group consisting of optionally substituted 5-10 membered heterocyclyl, optionally substituted phenyl, optionally substituted phenyl$C_{2-4}$alkenyl, cyclopentenyl, and $C_{2-6}$alkenyl, wherein when said heterocyclyl or phenyl group or part of group is substituted, it is substituted with from 1 to 5 substituents, each substituent being independently selected from the group consisting of $OR^A$, halogen, $C_{1-4}$alkyl, and trihalo$C_{1-4}$alkyl (hereinafter referred to as embodiment $R^1$(F)).

In one preferred embodiment, hereinafter referred to as embodiment $R^1$(G), $R^1$ represents an optionally substituted 5-10 membered heterocyclyl (for example an optionally substituted 5- or 6-membered heterocyclyl, for example a pyridyl, pyrrolidinyl, isoxazolyl, isothiazolyl, pyrrolyl, thienyl or furyl group, especially an isoxazolyl, isothiazolyl, pyridyl, or pyrrolidinyl group, or an optionally substituted 9- or 10-membered heterocyclyl such as a benzolfuryl, dioxazolyl or benzimidazolyl group), and wherein when said heterocyclyl group is substituted, it is substituted with from 1 to 3 substituents, each substituent being independently selected from the group consisting of $OR^A$, halogen, $C_{1-4}$alkyl, $C_{2-4}$alkenyl, $C_{2-4}$alkynyl, and trihalo$C_{1-4}$alkyl, and each $R^A$ represents hydrogen or $C_{1-4}$alkyl. In this embodiment, $R^1$ may for example represent a 5-membered aromatic heterocyclyl group (for example an isoxazolyl, isothiazolyl, pyrrolyl, thienyl or furyl group) which is substituted by two methyl groups. In a particularly preferred embodiment, $R^1$ represents isoxazolyl, isothiazolyl, pyrrolyl, pyrazolyl, pyridyl, or pyrrolidinyl optionally substituted by up to 3, for example 1 or 2, substituents independently selected from halogen atoms and methyl and ethyl groups (hereinafter referred to as embodiment $R^1$(H)). In an alternative embodiment, $R^1$ may include 3,5-dimethylisoxazol-4-yl, 3,5-dimethylisothiazol-4-yl, 2-fluoro-3,5-dimethyl-fur-4-yl, 3,5-dimethyl-fur-4-yl, or 3,5-dimethyl-thiophen-4-yl.

In an alternative preferred embodiment, $R^1$ represents an optionally substituted phenyl group, wherein when said phenyl group is substituted, it is substituted with from 1 to 5 substituents, more preferably from 1 to 3 substituents, each substituent being independently selected from the group consisting of $OR^A$, halogen, $C_{1-6}$alkyl, $C_{2-6}$alkenyl, $C_{2-6}$alkynyl, halo$C_{1-6}$ alkyl, dihalo$C_{1-6}$alkyl and trihalo-$C_{1-6}$alkyl. In this embodiment, more preferably $R^1$ represents an optionally substituted phenyl, group wherein when said phenyl group is substituted, it is substituted with from 1 to 5 substituents, more preferably from 1 to 3 substituents, each substituent being independently selected from the group consisting of halogen (especially fluorine or chlorine), $C_{1-4}$alkyl (especially methyl or ethyl), $C_{2-4}$alkenyl (especially ethenyl), $C_{2-4}$alkynyl (especially ethynyl), trihalo-$C_{1-4}$alkyl (especially trifluoromethyl), and $OR^A$ in which $R^A$ preferably represents a hydrogen atom, a $C_{1-4}$alkyl group or a trihalo$C_{1-4}$alkyl group. Most preferably, $R^1$ represents an optionally substituted phenyl group, wherein when said phenyl group is substituted, it is substituted with from 1 to 3 substituents, each substituent being independently selected from the group consisting of halogen (especially fluorine or chlorine), $C_{1-4}$alkyl (especially methyl or ethyl), $C_{2-4}$alkenyl (especially ethenyl), $C_{2-4}$alkynyl (especially ethynyl), trihalo$C_{1-4}$alkyl (especially trifluoromethyl), and $OR^A$ in which $R^A$ preferably represents a hydrogen atom, a $C_{1-4}$alkyl group or a trihalo$C_{1-4}$alkyl group (hereinafter referred to as embodiment $R^1(I)$).

In a particularly preferred embodiment, hereinafter referred to as embodiment $R^1(J)$, $R^1$ represents a phenyl group, optionally substituted with 1 or 2 substituents, each substituent being independently selected from the group consisting of halogen (especially fluorine or chlorine), $C_{1-4}$alkyl (especially methyl or ethyl), $C_{2-4}$alkenyl (especially ethenyl), $C_{2-4}$alkynyl (especially ethynyl), trifluoromethyl, and $OR^A$ in which $R^A$ represents hydrogen, methyl, ethyl or trifluoromethyl.

In one embodiment, $R^1$ represents an optionally substituted naphthyl group, wherein the optional substituents and preferred substitutents are as given above for an optionally substituted phenyl group (hereinafter referred to as embodiment $R^1(K)$).

In one embodiment, $R^1$ represents an optionally substituted phenyl$C_{2-4}$alkenyl group, wherein the optional substituents and preferred substituents on the phenyl portion are as given above for an optionally substituted phenyl group (hereinafter referred to as embodiment $R^1(L)$).

In one embodiment, $R^1$ represents a $C_{2-8}$alkenyl, halo$C_{2-8}$alkenyl, dihalo$C_{2-8}$alkenyl, trihalo$C_{2-8}$alkenyl, or $C_{3-8}$cycloalkyl$C_{2-4}$alkenyl group (hereinafter referred to as embodiment $R^1(M)$).

In one embodiment, $R^1$ represents a cyclopentenyl group (hereinafter referred to as embodiment $R^1(N)$).

In one embodiment, hereinafter referred to as embodiment $R^2(A)$, $R^2$ is selected from the group consisting of —C(NH$_2$)=N—OH, —C(O)N(R$^C$)$_2$, cyano, —CHO, —CH=N—OH, —C(O)NH—OH, —C(CO$_2$H)=N—OH, —C(O—C$_{1-4}$alkyl)=NH, —C(NH$_2$)=N—NH$_2$, —C(O)—C(O)—NH$_2$, —CH$_2$NH—CONH$_2$, C$_{1-6}$alkyl-NH$_2$, —NH—C(NH$_2$)=NH, —NH—C(O)NH$_2$, —N=C(—NH—CH$_2$CH$_2$—NH—), N(OH)$_2$, —S—CN, —S—C(NH$_2$)=NH, —S—C(NH$_2$)=N—OH, cyanoC$_{1-6}$alkyl, and an optionally substituted 5-6 membered heterocyclyl containing from one to three nitrogen atoms; wherein when said heterocyclyl group is substituted, it is substituted with from 1 to 3 substituents, each substituent being independently selected from the group consisting of OH, halogen, cyano, nitro, C$_{1-14}$alkyl, haloC$_{1-4}$alkyl, dihaloC$_{1-4}$alkyl and trihaloC$_{1-4}$alkyl. Preferably, $R^2$ represents —C(NH$_2$)=N—OH, —C(O)NH$_2$, cyano, —CHO, —CH=N—OH, C$_{1-6}$alkyl-NH$_2$, or an optionally substituted 5-6 membered heterocyclyl containing from one to three nitrogen atoms (hereinafter referred to as embodiment $R^2(B)$. More preferably $R^2$ represents C(NH$_2$)=N—OH, —C(O)NH$_2$, cyano, —CH=N—OH, or an optionally substituted 5-membered heterocyclyl containing from one to two nitrogen atoms, such as an optionally substituted pyrrolyl or pyrazolyl group, especially unsubstituted pyrazolyl (hereinafter referred to as embodiment $R^2(C)$). Most preferably $R^2$ represents —C(NH$_2$)=N—OH, —C(O)NH$_2$, —CH=N—OH, or cyano (hereinafter referred to as embodiment $R^2(D)$).

The above preferred embodiments for $R^2$, particularly embodiments $R^2A$, $R^2B$, $R^2C$ and $R^2D$, may be present together with any of the specific embodiments, for example any one of embodiments $R^1A$ to $R^1N$, and especially any one of embodiments $R^1A$, $R^1B$, $R^1C$ and $R^1D$, mentioned for $R^1$ above.

In one embodiment, hereinafter referred to as embodiment $R^3(A)$, $R^3$ is preferably selected from the group consisting of hydrogen, halogen, cyano, $C_{1-6}$alkyl, $C_{2-6}$alkenyl, $C_{2-6}$alkynyl, $C_{3-8}$cycloalkyl, $C_{3-8}$cycloalkyl$C_{1-6}$alkyl, halo$C_{1-6}$alkyl, dihalo$C_{1-6}$alkyl, trihalo$C_{1-6}$alkyl, optionally substituted phenyl, and optionally substituted phenyl-$C_{1-4}$alkyl, wherein when said phenyl group or part of group is substituted, it is substituted with from 1 to 3 substituents, each substituent being independently selected from the group consisting of $OR^A$, $N(R^B)_2$, halogen cyano, nitro, $C_{1-4}$alkyl, and trihalo$C_{1-4}$alkyl. In this embodiment, more preferably, $R^3$ is selected from the group consisting of hydrogen, halogen, $C_{1-6}$alkyl, $C_{2-6}$alkenyl, $C_{2-6}$alkynyl, $C_{3-8}$cycloalkyl, $C_{3-8}$cycloalkyl$C_{1-6}$alkyl, halo$C_{1-6}$alkyl, dihalo$C_{1-6}$alkyl, trihalo$C_{1-6}$alkyl, phenyl, and phenyl-$C_{1-4}$alkyl (hereinafter referred to as embodiment $R^3(B)$. In this embodiment, $R^3$ most preferably represents hydrogen, halogen (especially chlorine or bromine), $C_{1-6}$alkyl, $C_{2-6}$alkenyl, trihalo$C_{1-4}$alkyl (especially trifluoromethyl), phenyl, or phenyl$C_{1-2}$alkyl (hereinafter referred to as embodiment $R^3(C)$. For example, $R^3$ may represent hydrogen, chlorine, bromine, $C_{1-4}$alkyl, $C_{2-4}$alkenyl, trifluoromethyl, phenyl, or phenyl$C_{1-2}$alkyl; especially hydrogen, chlorine, bromine, $C_{1-4}$alkyl, $C_{2-4}$alkenyl, or trifluoromethyl (hereinafter referred to as embodiment $R^3(D)$).

In an alternative embodiment, $R^3$ is selected from the group consisting of halogen, cyano, $C_{1-6}$alkyl, $C_{2-6}$alkenyl, $C_{2-6}$alkynyl, $C_{3-8}$cycloalkyl, $C_{3-8}$cycloalkyl$C_{1-6}$alkyl, halo$C_{1-6}$alkyl, dihalo$C_{1-6}$alkyl, trihalo$C_{1-6}$alkyl, optionally substituted phenyl, optionally substituted phenyl$C_{1-4}$alkyl, optionally substituted 5-10 membered heterocyclyl, and optionally substituted 5-10 membered heterocyclyl-$C_{1-4}$alkyl, wherein when said phenyl or heterocyclyl group or part of group is substituted, it is substituted with from 1 to 3 substituents, each substituent being independently selected from the group consisting of $OR^A$, $N(R)_2$, halogen cyano, nitro, $C_{1-6}$alkyl, $C_{2-6}$alklenyl, $C_{2-6}$alkynyl, halo-$C_{1-6}$alkyl, dihalo$C_{1-6}$alkyl and trihalo$C_{1-6}$alkyl. In this embodiment, $R^3$ is preferably selected from the group consisting of halogen, cyano, $C_{1-6}$alkyl, $C_{2-6}$alkenyl, $C_{2-6}$alkynyl, $C_{3-8}$cycloalkyl, $C_{3-8}$cycloalkyl$C_{1-6}$alkyl, halo$C_{1-4}$alkyl, dihalo$C_{1-6}$ alkyl, trihalo$C_{1-6}$alkyl, optionally substituted phenyl, and optionally substituted phenyl$C_{1-4}$alkyl, wherein when said phenyl group or part of group is substituted, it is substituted with from 1 to 3 substituents, each substituent being independently selected from the group consisting of $OR^A$, $N(R^B)_2$, halogen cyano, nitro, $C_{1-4}$alkyl, and trihalo-$C_{1-4}$alkyl. In this embodiment, $R^3$ is more preferably selected from the group consisting of halogen, cyano, $C_{1-6}$alkyl, $C_{2-6}$alkenyl, $C_{2-6}$alkynyl, $C_{3-8}$cycloalkyl, $C_{3-8}$cycloalkyl$C_{1-6}$alkyl, halo$C_{1-6}$alkyl, dihalo$C_{1-6}$alkyl, trihalo-$C_{1-6}$alkyl, phenyl, and phenyl$C_{1-4}$alkyl. Most preferably, $R^3$ represents halogen (especially chlorine or bromine), cyano, $C_{1-6}$alkyl, $C_{2-6}$alkenyl, trihalo$C_{1-4}$alkyl (especially trifluoromethyl), phenyl, or phenyl$C_{1-2}$alkyl. For example, $R^3$ may represent chlorine, bromine, cyano, $C_{1-4}$alkyl, $C_{2-4}$alkenyl, trifluoromethyl, phenyl, or phenyl$C_{1-2}$alkyl; especially chlorine, bromine, $C_{1-4}$alkyl, $C_{2-4}$alkenyl, or trifluoromethyl.

The above preferred embodiments for $R^3$, particularly embodiments $R^3A$, $R^3B$, $R^3C$ and $R^3D$, may be present together with any of the specific embodiments mentioned for $R^1$ and/or $R^2$ above.

Preferably, $R^4$ is selected from the group consisting of hydrogen, halogen, cyano, $C_{1-6}$alkyl, and trihalo$C_{1-6}$alkyl (hereinafter referred to as embodiment $R^4(A)$. More preferably, $R^4$ is selected from the group consisting of hydrogen, halogen, cyano, $C_{1-4}$alkyl, and trihalo$C_{1-4}$alkyl (especially trifluoromethyl) (hereinafter referred to as embodiment $R^4(B)$). Most preferably, $R^4$ is selected from the group consisting of hydrogen, halogen, and $C_{1-4}$alkyl (hereinafter referred to as embodiment $R^4(C)$.

The above preferred embodiments for $R^4$, particularly embodiments $R^4A$, $R^4B$, and $R^4C$, may be present together with any of the specific embodiments mentioned for $R^1$ and/or $R^2$ and/or $R^3$ above.

In one embodiment, when $R^3$ represents hydrogen, $R^4$ is selected from the group consisting of halogen, cyano, $C_{1-6}$alkyl, $C_{2-6}$alkenyl, $C_{2-6}$alkynyl, halo$C_{1-6}$alkyl, dihalo$C_{1-6}$alkyl, and trihalo$C_{1-6}$alkyl.

Preferably, $R^7$ represents $OR^A$ wherein $R^A$ represents hydrogen or $C_{1-4}$alkyl, for example ethyl or methyl (hereinafter referred to as embodiment $R^7(A)$). More preferably, $R^7$ represents OH (hereinafter referred to as embodiment $R^7(B)$). In embodiments $R^7(A)$ and $R^7(B)$, each of $R^5$, $R^6$, $R^8$ and $R^9$ is preferably independently selected from the group consisting of hydrogen, $OR^A$, $N(R^B)_2$, halogen, cyano, nitro, $C_{1-6}$alkyl, $C_{2-6}$alkenyl, $C_{2-6}$alkynyl, halo$C_{1-6}$alkyl, dihalo$C_{1-6}$alkyl and trihalo$C_{1-6}$alkyl. More preferably, each of $R^5$, $R^6$, $R^8$ and $R^9$ is independently selected from the group consisting of hydrogen, $OR^A$, $N(R^B)_2$, halogen, cyano, nitro, $C_{1-6}$alkyl, halo$C_{1-6}$alkyl, dihalo$C_{1-6}$alkyl and trihalo$C_{1-6}$alkyl. Still more preferably each of $R^5$, $R^6$, $R^8$ and $R^9$ is independently selected from the group consisting of hydrogen, OH, $NH_2$, halogen, cyano, nitro, $C_{1-4}$alkyl, for example methyl, halo$C_{1-4}$alkyl, for example chloro- or fluoro-methyl, dihalo$C_{1-4}$alkyl, for example dichloro- or difluoromethyl, and trihalo$C_{1-4}$alkyl, for example trichloro- or trifluoromethyl. Yet more preferably, each of $R^5$, $R^6$, $R^8$ and $R^9$ is independently selected from the group consisting of hydrogen, halogen, $C_{1-4}$alkyl, for example methyl or ethyl, and trihalo$C_{1-4}$alkyl, for example trichloro- or trifluoromethyl. In one embodiment, each of $R^5$, $R^6$, $R^8$ and $R^9$ independently represents methyl, trifluoromethyl or, especially, hydrogen or halogen, especially fluorine. Yet more preferably, each of $R^5$, $R^6$, $R^8$ and $R^9$ is independently selected from the group consisting of hydrogen and halogen. In one preferred embodiment, each of $R^5$, $R^6$, $R^8$ and $R^9$ represents hydrogen. In an alternative preferred embodiment, one of $R^5$ and $R^6$ represents fluorine and the remainder of $R^5$, $R^6$, $R^8$ and $R^9$ represents hydrogen. The above preferred embodiments for $R^6$ and $R^5$, $R^6$, $R^8$ and $R^9$ may be present together with any of the specific embodiments mentioned for $R^1$ and/or $R^2R^3$ and/or $R^4$ above.

In another aspect of the invention, (hereinafter referred to as embodiment $R^{6/7}(A)$) $R^6$ and $R^7$, together with the atoms they are attached to, preferably form a 5-, 6- or 7-membered cyclic group optionally containing one to three heteroatoms selected from O, N and S, said 5-, 6- or 7-membered cyclic group being optionally substituted with one of more groups selected from $OR^A$, cyano, nitro, $C_{1-6}$alkyl, $C_{2-6}$ alkenyl, $C_{2-6}$alkynyl, halo $C_{1-6}$ alkyl, dihalo $C_{1-6}$ alkyl and trihalo $C_{1-6}$alkyl. More preferably, $R^6$ and $R^7$, together with the atoms they are attached to, form a 5-, 6- or 7-membered cyclic group, especially a 5- or 6-membered cyclic group, optionally containing one to three heteroatoms selected from O and N, said 5-, 6- or 7-membered cyclic group being optionally substituted with one of more groups selected from OH, cyano, nitro, $C_{1-4}$ alkyl, halo$C_{1-4}$ alkyl, dihalo$C_{1-4}$alkyl and trihalo$C_{1-4}$alkyl (hereinafter referred to as embodiment $R^{6/7}(B)$). Most preferably, $R^6$ and $R^7$, together with the atoms they are attached to, form a 5-membered cyclic group optionally containing one or two heteroatoms selected from O and N, said 5-membered cyclic group being optionally substituted with one of more groups selected from OH, cyano, methyl and trifluoromethyl (hereinafter referred to as embodiment $R^{6/7}(C)$). In this aspect, preferably each of $R^5$, $R^8$ and $R^9$ is independently selected from the group consisting of hydrogen, $OR^A$, $N(R^B)_2$, halogen, cyano, nitro, $C_{1-6}$alkyl, halo$C_{1-6}$alkyl, dihalo$C_{1-6}$alkyl and trihalo-$C_{1-6}$alkyl. More preferably each of $R^5$, $R^8$ and $R^9$ is independently selected from the group consisting of hydrogen, OH, $NH_2$, halogen, cyano, nitro, $C_{1-4}$alkyl, for example methyl, halo$C_{1-4}$alkyl, for example chloro- or fluoro-methyl, dihalo$C_{1-4}$alkyl, for example dichloro- or difluoromethyl, and trihalo$C_{1-4}$alkyl, for example trichloro- or trifluoromethyl. Most preferably, each of $R^5$, $R^8$ and $R^9$ is independently selected from the group consisting of hydrogen, halogen, methyl, and trifluoromethyl, especially hydrogen and halogen (hereinafter referred to as embodiment $R^{6/7}$ (D)).

The above preferred embodiments for $R^{6/7}$ and $R^5$, $R^8$ and $R^9$ may be present together with any of the specific embodiments mentioned for $R^1$ and/or $R^2$, $R^3$ and/or $R^4$ above.

Each $R^A$ is preferably independently selected from the group consisting of hydrogen, $C_{1-6}$alkyl, $C_{2-6}$alkenyl, $C_{2-6}$alkynyl and $C_{3-6}$cycloalkyl. More preferably, each $R^A$ is independently selected from the group consisting of hydrogen, $C_{1-4}$alkyl, $C_{2-4}$alkenyl, $C_{2-4}$alkynyl and $C_{3-6}$cycloalkyl. Most preferably, each $R^A$ independently represents hydrogen or $C_{1-4}$alkyl, still more preferably hydrogen, methyl or ethyl, especially hydrogen or methyl.

Each $R^B$ is preferably independently selected from the group consisting of hydrogen and $C_{1-6}$alkyl. In one preferred embodiment, each $R^B$ is $C_{1-4}$alkyl. In another embodiment, each $R^B$ is preferably selected from the group consisting of hydrogen or $C_{1-4}$alkyl, more preferably hydrogen and $C_{1-3}$alkyl, especially methyl or ethyl. In one preferred embodiment, each $R^B$ is hydrogen.

Each $R^C$ is preferably independently selected from the group consisting of hydrogen and $C_{1-4}$alkyl, especially methyl.

Each $R^D$ is preferably independently selected from the group consisting of hydrogen and $C_{1-4}$alkyl, especially methyl.

Each $R^E$ is preferably independently selected from the group consisting of hydrogen and $C_{1-4}$alkyl, especially methyl.

Especially preferred sub-groups of compounds are those in which $R^1$ is one of $R^1A$, $R^1B$, $R^1C$ and $R^1D$, together with one of $R^2A$, $R^2B$, $R^2C$ and $R^2D$, especially $R^2D$, and one of $R^6A$ and $R^7B$, especially $R^7B$. Thus, especially preferred sub-groups of compounds are those in which $R^1$ is one of $R^1A$, $R^1B$, $R^1C$ and $R^1D$, together with $R^2D$, and $R^7B$.

Compounds of the formula (I) include, but are not limited to, the compounds specifically mentioned in the Examples herein, including pharmaceutically acceptable esters, amides, carbamates or salts thereof, including salts of such esters, amides or carbamates.

In the compounds in the Examples, the compound names were generated in accordance with IUPAC by the ACD Labs 8.0/name program, version 8.05 and/or with ISIS DRAW Autonom 2000 and/or ChemBioDraw Ultra version 12.02.

Depending upon the substituents present in compounds of the formula (I), the compounds may form esters, amides, carbamates and/or salts. Salts of compounds of formula (I) which are suitable for use in medicine are those wherein a counterion is pharmaceutically acceptable. However, salts having non-pharmaceutically acceptable counterions are within the scope of the present invention, for example, for use as intermediates in the preparation of the compounds of formula (I) and their pharmaceutically acceptable salts, and physiologically functional derivatives. By the term "physiologically functional derivative" is meant a chemical derivative of a compound of formula (I) having the same physiological function as the free compound of formula (I), for example, by being convertible in the body thereto. Esters, amides and carbamates are examples of physiologically functional derivatives.

Suitable salts according to the invention include those formed with organic or inorganic acids or bases. In particular, suitable salts formed with acids according to the invention include those formed with mineral acids, strong organic carboxylic acids, such as alkanecarboxylic acids of 1 to 4 carbon atoms which are unsubstituted or substituted, for example, by halogen, such as saturated or unsaturated dicarboxylic acids, such as hydroxycarboxylic acids, such as amino acids, or with organic sulfonic acids, such as ($C_1$-$C_4$)-alkyl- or aryl-sulfonic acids which are unsubstituted or substituted, for example by halogen. Pharmaceutically acceptable acid addition salts include those formed from hydrochloric, hydrobromic, sulphuric, nitric, citric, tartaric, acetic, phosphoric, lactic, pyruvic, acetic, trifluoroacetic, succinic, perchloric, fumaric, maleic, glycolic, lactic, salicylic, oxaloacetic, methanesulfonic, ethanesulfonic, p-toluenesulfonic, formic, benzoic, malonic, naphthalene-2-sulfonic, benzenesulfonic, isethionic, ascorbic, malic, phthalic, aspartic, and glutamic acids, lysine and arginine. Other acids such as oxalic, while not in themselves pharmaceutically acceptable, may be useful as intermediates in obtaining the compounds of the invention and their pharmaceutical acceptable acid addition salts.

Pharmaceutically acceptable base salts include ammonium salts, alkali metal salts, for example those of potassium and sodium, alkaline earth metal salts, for example those of calcium and magnesium, and salts with organic bases, for example dicyclohexylamine, N-methyl-D-glucomine, morpholine, thiomorpholine, piperidine, pyrrolidine, a mono-, di- or tri-lower alkylamine, for example ethyl-, tert-butyl-, diethyl-, diisopropyl-, triethyl-, tributyl- or dimethyl-propylanmine, or a mono-, di- or trihydroxy lower alkylamine, for example mono-, di- or triethanolamine. Corresponding internal salts may furthermore be formed.

Compounds of formula (I) may have an appropriate group converted to an ester, an amide or a carbamate. Thus typical ester and amide groups formed from an acid group in the compound of the formula I include —COOR$^G$, —CONR$^G_2$, —SO$_2$OR$^G$, or —SO$_2$N(R$^G$)$_2$, while typical ester and amide and carbamate groups formed from an —OH or —NHR$^G$ group in the compound of the formula (I) include —OC(O)R$^G$, —NR$^G$C(O)R$^G$, —NR$^G$CO$_2$R$^G$, —OSO$_2$R$^G$, and —NR$^G$SO$_2$R$^G$, where R$^G$ is selected from the group consisting of $C_{1-8}$alkyl, $C_{2-8}$alkenyl, $C_{2-8}$alkynyl, $C_{3-8}$cycloalkyl and $C_{3-8}$cycloalkyl$C_{1-8}$alkyl, halo$C_{1-8}$alkyl, dihalo$C_{1-8}$ alkyl, trihalo$C_{1-8}$alkyl, phenyl and phenyl$C_{1-4}$alkyl; more preferably R$^G$ is selected from the group consisting of $C_{1-6}$alkyl, $C_{2-6}$alkenyl, $C_{2-6}$alkynyl, $C_{3-5}$cycloalkyl and $C_{3-8}$cycloalkyl$C_{1-6}$alkyl.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates, such as hydrates, exist when the drug substance incorporates solvent, such as water, in the crystal lattice in either stoichiometric or non-stoichiometric amounts. Drug substances are routinely screened for the existence of hydrates since these may be encountered at any stage of the drug manufacturing process or upon storage of the drug substance or dosage form. Solvates are described in S. Byrn et al, Pharmaceutical Research 12(7), 1995, 954-954, and Water-Insoluble Drug Formulation, $2^{nd}$ ed. R. Liu, CRC Press, page 553, which are incorporated herein by reference. Accordingly, it will be understood by the skilled person that the compounds of formula (I), as well as esters, amides, carbamates and/or salts thereof may therefore be present in the form of solvates. Solvates of compounds of formula (I) which are suitable for use in medicine are those wherein the associated solvent is pharmaceutically acceptable. For example, a hydrate is an example of a pharmaceutically acceptable solvate. However, solvates having non-pharmaceutically acceptable associated solvents may find use as intermediates in the preparation of the compounds of formula (I) and their pharmaceutically acceptable esters, amides, carbamates and/or salts thereof.

A compound which, upon administration to the recipient, is capable of being converted into a compound of formula (I) as described above, or an active metabolite or residue thereof, is known as a "prodrug". A prodrug may, for example, be converted within the body, e.g. by hydrolysis in the blood, into its active form that has medical effects. Pharmaceutical acceptable prodrugs are described in T. Higuchi and V. Stella, Prodrugs as Novel Delivery Systems, Vol. 14 of the A. C. S. Symposium Series (1976); "Design of Prodrugs" ed. H. Bundgaard, Elsevier, 1985; and in Edward B. Roche, ed., Bioreversible Carriers in Drug Design, American Pharmaceutical Association and Pergamon Press, 1987, which are incorporated herein by reference.

The following definitions apply to the terms as used throughout this specification, unless otherwise limited in specific instances.

As used herein, the term "alkyl" means both straight and branched chain saturated hydrocarbon groups. Examples of alkyl groups include methyl, ethyl, n-propyl, iso-propyl, n-butyl, t-butyl, i-butyl, sec-butyl, pentyl and hexyl groups. Among unbranched alkyl groups, there are preferred methyl, ethyl, n-propyl, iso-propyl, n-butyl groups. Among branched alkyl groups, there may be mentioned t-butyl, i-butyl, 1-ethylpropyl and 1-ethylbutyl groups.

As used herein, the term "alkoxy" means the group O-alkyl, where "alkyl" is used as described above. Examples of alkoxy groups include methoxy and ethoxy groups. Other examples include propoxy and butoxy.

As used herein, the term "alkenyl" means both straight and branched chain unsaturated hydrocarbon groups with at least one carbon carbon double bond. Examples of alkenyl groups include ethenyl, propenyl, butenyl, pentenyl and hexenyl. Preferred alkenyl groups include ethenyl, 1-propenyl, 2-propenyl and but-2-enyl.

As used herein, the term "alkynyl" means both straight and branched chain unsaturated hydrocarbon groups with at least one carbon carbon triple bond. Examples of alkynyl groups include ethynyl, propynyl, butynyl, pentynyl and hexynyl. Preferred alkynyl groups include ethynyl, 1-propynyl and 2-propynyl.

As used herein, the term "cycloalkyl" means a saturated group in a ring system. A cycloalkyl group can be monocyclic or bicyclic. A bicyclic group may, for example, be fused or bridged. Examples of monocyclic cycloalkyl groups include cyclopropyl, cyclobutyl and cyclopentyl. Other examples of monocyclic cycloalkyl groups are cyclohexyl, cycloheptyl and cyclooctyl. Examples of bicyclic cycloalkyl groups include bicyclo[2.2.1]hept-2-yl. Preferably, the cycloalkyl group is monocyclic.

As used herein, the term "halogen" means fluorine, chlorine, bromine or iodine. Fluorine, chlorine and bromine are particularly preferred.

As used herein, the term "haloalkyl" means an alkyl group having a halogen substituent, the terms "alkyl" and "halogen" being understood to have the meanings outlined above. Similarly, the term "dihaloalkyl" means an alkyl group having two halogen substituents and the term "trihaloalkyl" means an alkyl group having three halogen substituents. Examples of haloalkyl groups include fluoromethyl, chloromethyl, bromomethyl, fluoromethyl, fluoropropyl and fluorobutyl groups; examples of dihaloalkyl groups include difluoromethyl and difluoroethyl groups; examples of triihaloalkyl groups include trifluoromethyl and trifluoroethyl groups.

As used herein, the term "heterocyclyl" means an aromatic or a non-aromatic cyclic group of carbon atoms wherein from one to three of the carbon atoms is/are replaced by one or more heteroatoms independently selected from nitrogen, oxygen or sulfur. A heterocyclyl group may, for example, be monocyclic or bicyclic. In a bicyclic heterocyclyl group there may be one or more heteroatoms in each ring, or only in one of the rings. A heteroatom may be S, O or N and is preferably O or N. Heterocyclyl groups containing a suitable nitrogen atom include the corresponding N-oxides.

Examples of monocyclic non-aromatic heterocyclyl groups (also referred to as monocyclic heterocycloalkyl rings) include aziridinyl, azetidinyl, pyrrolidinyl, imidazolidinyl, pyrazolidinyl, piperidinyl, piperazinyl, tetrahydrofuranyl, tetrahydropyranyl, morpholinyl, thiomorpholinyl and azepanyl.

Examples of bicyclic heterocyclyl groups in which one of the rings is non-aromatic include dihydrobenzofuranyl, indanyl, indolinyl, isoindolinyl, tetrahydroisoquinolinyl, tetrahydroquinolyl and benzoazepanyl.

Examples of monocyclic aromatic heterocyclyl groups (also referred to as monocyclic heteroaryl groups) include furanyl, thienyl, pyrrolyl, oxazolyl, thiazolyl, imidazolyl, oxadiazolyl, thiadiazolyl, pyridyl, triazolyl, triazinyl, pyridazyl, isothiazolyl, isoxazolyl, pyrazinyl, pyrazolyl and pyrimidinyl, with preferred monocyclic aromatic heterocyclyl groups being furanyl, thienyl, pyrrolyl, oxazolyl, imidazolyl, oxadiazolyl, thiadiazolyl, pyridyl, triazolyl, triazinyl, pyridazyl, isothiazolyl, isoxazolyl, pyrazinyl, pyrazolyl and pyrimidinyl.

Examples of bicyclic aromatic heterocyclyl groups (also referred to as bicyclic heteroaryl groups) include quinoxalinyl, quinazolinyl, pyridopyrazinyl, benzoxazolyl, benzothiophenyl, benzimidazolyl, naphthyridinyl, quinolinyl, benzofuranyl, indolyl, benzothiazolyl, oxazolyl[4,5-b]pyridiyl, pyridopyrimidinyl, isoquinolinyl and benzodroxazole.

Examples of preferred heterocyclyl groups include piperidinyl, tetrahydrofuranyl, tetrahydropyranyl, pyridyl, pyrimidinyl and indolyl. Preferred heterocyclyl groups also include thienyl, thiazolyl, furanyl, pyrazolyl, pyrrolyl, isoxazolyl and imidazolyl.

As used herein the term "cycloalkylalkyl" means a group cycloalkyl-alkyl-attached through the alkyl group, "cycloalkyl" and "alkyl" being understood to have the meanings outlined above.

As mentioned above, the compounds of the invention have activity as estrogen receptor ligands. The compounds of the invention have activity as estrogen receptor modulators, and may be agonists, partial agonists, antagonists, or partial antagonists of the estrogen receptor. Particularly preferred compounds of the invention have activity as an agonist or a partial agonist of ERβ. Preferred compounds of this type are selective agonists of the estrogen receptor-beta (ERβ).

The invention also provides a compound according to the invention, or a composition comprising a compound according to the invention together with a pharmaceutically acceptable carrier, for use as a medicament.

A compound of the invention, or a composition comprising a compound of the invention, may thus be used in the treatment of diseases or disorders associated with estrogen receptor activity. In particular, the compounds of the invention that are agonists or partial agonists of the estrogen receptor may be used in the treatment of diseases or disorders for which selective agonists or partial agonists of the estrogen receptor are indicated. The compounds of the invention that are antagonists or partial antagonists of the estrogen receptor may be used in the treatment of diseases or disorders for which selective antagonists or partial antagonists of the estrogen receptor are indicated.

Clinical conditions for which an agonist or partial agonist is indicated include, but are not limited to, bone loss, bone fractures, osteoporosis, cartilage degeneration, endometriosis, uterine fibroid disease, hot flashes, increased levels of LDL cholesterol, cardiovascular disease, impairment of cognitive functioning, cerebral degenerative disorders, restenosis, gynecomastia, vascular smooth muscle cell proliferation, obesity, incontinence, anxiety, depression, autoimmune disease, inflammation, IBD, TBS, sexual dysfunction, hypertension, retinal degeneration, and lung, colon, breast, uterus, and prostate cancer, lymphoma, and/or disorders related to estrogen functioning.

The compounds of the invention find particular application in the treatment or prophylaxis of the following: bone loss, bone fractures, osteoporosis, cartilage degeneration, endometriosis, uterine fibroid disease, hot flushes, increased levels of LDL cholesterol, cardiovascular disease, impairment of cognitive functioning, age-related mild cognitive impairment, cerebral degenerative disorders, restenosis, gynecomastia, vascular smooth muscle cell proliferation, obesity, incontinence, anxiety, depression, perimenopausal depression, post-partum depression, premenstrual syndrome, manic depression, dementia, obsessive compulsive behavior, attention deficit disorder, attention deficit hyperactivity disorder, sleep disorders, irritability, impulsivity, anger management, hearing disorders, multiple sclerosis, Parkinson's disease, Alzheimer's disease, Huntington's disease, amyotrophic lateral sclerosis, spinal cord injury, stroke, autoimmune disease, inflammation, IBD, IBS, sexual dysfunction, hypertension, retinal degeneration, lung cancer, colon cancer, breast cancer, uterus cancer, prostate cancer, and the bile duct cancer form named cholangiocarcinoma. The compounds of the invention also find particular application in the treatment or prophylaxis of the following: benign prostatic hyperplasia, lower urinary tract symptoms, overactive bladder, interstitial cystitis, painful bladder symptoms, vaginal atrophy, wound healing, chronic pain, sepsis, inflammatory and neuropathic pain, ovarian cancer, melanoma, lymphoma (B-cell lymphoma, T-cell lymphoma), atherosclerosis, left ventricular hypertrophy, congestive heart failure, mesothelioma, gallbladder cancer and extra-hepatic cholangiocarcinoma.

Preferably, the compounds of the invention find application in the treatment or prophylaxis of the following: bone loss, bone fractures, osteoporosis, cartilage degeneration, endometriosis, uterine fibroid disease, hot flushes, increased levels of LDL cholesterol, cardiovascular disease, restenosis, gynecomastia, vascular smooth muscle cell proliferation, obesity, incontinence, anxiety, depression, perimenopausal depression, post-partum depression, premenstrual syndrome, manic depression, dementia, obsessive compulsive behavior, attention deficit disorder, attention deficit hyperactivity disorder, sleep disorders, irritability, impulsivity, anger management, hearing disorders, spinal cord injury, stroke, autoimmune disease, inflammation, IBD, IBS, sexual dysfunction, hypertension, retinal degeneration, lung cancer, colon cancer, breast cancer, uterus cancer, prostate cancer, the bile duct cancer form named cholangiocarcinoma, benign prostatic hyperplasia, lower urinary tract symptoms, overactive bladder, interstitial cystitis, painful bladder symptoms, vaginal atrophy, wound healing, chronic pain, sepsis, inflammatory and neuropathic pain, ovarian cancer, melanoma, lymphoma, atherosclerosis, left ventricular hypertrophy, congestive heart failure, mesothelioma, gallbladder cancer and extra-hepatic cholangiocarcinoma.

In combination with drugs that are known to induce vasomotor symptoms, the compounds of the invention find utility as follows: in combination with SERMs such as tamoxifen, in its use for the treatment of breast cancer, and raloxifene, used for the treatment and/or prevention of osteoporosis, to alleviate SERM-induced vasomotor symptoms; in combination with an aromatase inhibitor, used for the treatment of breast cancer or endometriosis, to alleviate aromatase inhibitor-induced vasomotor symptoms; and in male prostate cancer patients that have undergone androgen deprivation therapy.

In one embodiment of the invention, the present compounds finds particular application in the treatment or prophylaxis of depression, perimenopausal depression, post-partum depression, premenstrual syndrome and manic depression.

The treatment or prophylaxis of hot flashes (or hot flushes) in males, is preferable for patients that have had an androgen ablation for treatment of prostate cancer.

The phrase "depression" includes but is not limited to, major depressive disorder, dysthymic disorder, bipolar disorder, cyclothymic disorder, mood disorder due to a general medical condition, substance-induced mood misorder, seasonal affective disorder (SAD), postpartum depression and premenstrual dysphoric disorder.

The invention also provides a method for the treatment or prophylaxis of a condition associated with a disease or disorder associated with estrogen receptor activity in a mammal, which comprises administering to the mammal a therapeutically effective amount of a compound according to the invention, or a composition comprising a compound according to the invention together with a pharmaceutically acceptable carrier. Clinical conditions mediated by an estrogen receptor that may be treated by the method of the invention are preferably those described above.

The invention also provides the use of a compound according to the invention, for the manufacture of a medicament for the treatment or prophylaxis of a condition associated with a disease or disorder associated with estrogen receptor activity. Clinical conditions mediated by an estrogen receptor that may be treated by the method of the invention are preferably those described above.

The amount of active ingredient which is required to achieve a therapeutic effect will, of course, vary with the particular compound, the route of administration, the subject under treatment, including the type, species, age, weight, sex, and medical condition of the subject and the renal and hepatic function of the subject, and the particular disorder or disease being treated, as well as its severity. An ordinarily skilled physician, veterinarian or clinician can readily determine and prescribe the effective amount of the drug required to prevent, counter or arrest the progress of the condition.

Oral dosages of the present invention, when used for the indicated effects, will range between about 0.01 mg per kg of body weight per day (mg/kg/day) to about 100 mg/kg/day, preferably 0.01 mg per kg of body weight per day (mg/kg/day) to 10 mg/kg/day, and most preferably 0.1 to 5.0 mg/kg/day, for adult humans. For oral administration, the compositions are preferably provided in the form of tablets or other forms of presentation provided in discrete units containing 0.01, 0.05, 0.1, 0.5, 1.0, 2.5, 5.0, 10.0, 15.0, 25.0, 50.0, 100, and 500 milligrams of the active ingredient for the symptomatic adjustment of the dosage to the patient to be treated. A medicament typically contains from about 0.01 mg to about 500 mg of the active ingredient, preferably from about 1 mg to about 100 mg of active ingredient. Intravenously, the most preferred doses will range from about 0.1 to about 10 mg/kg/minute during a constant rate infusion. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

While it is possible for the active ingredient to be administered alone, it is preferable for it to be present in a pharmaceutical formulation or composition. Accordingly, the invention provides a pharmaceutical formulation or composition comprising a compound according to the invention, and a pharmaceutically acceptable diluent, excipient or carrier (collectively referred to herein as "carrier" materials). Pharmaceutical compositions of the invention may take the form of a pharmaceutical formulation as described below.

The pharmaceutical formulations according to the invention include those suitable for oral, parenteral (including subcutaneous, intradermal, intramuscular, intravenous [bolus or infusion], and intraarticular), inhalation (including fine particle dusts or mists which may be generated by means of various types of metered does pressurized aerosols), nebulizers or insufflators, rectal, intraperitoneal and topical (including dermal, buccal, sublingual, and intraocular) administration, although the most suitable route may depend upon, for example, the condition and disorder of the recipient.

The formulations may conveniently be presented in unit dosage form and may be prepared by any of the methods well known in the art of pharmacy. All methods include the step of bringing the active ingredient into association with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets, pills or tablets each containing a predetermined amount of the active ingredient; as a powder or granules; as a solution or a suspension in an aqueous liquid or a non-aqueous liquid, for example as elixirs, tinctures, suspensions or syrups; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein. The present compounds can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps. The present compounds can also be administered liposomally.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate, calcium sulfate, sorbitol, glucose and/or lactose and/or other excipients, binders, extenders, disintegrants, diluents and lubricants such as those known in the art. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Disintegrators include without limitation starch, methylcellulose, agar, bentonite, xanthan gum and the like. The compounds of formula (I) can also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use. Lubricants used in these dosage forms include sodium oleate, sodium stearate, magnesium stearate, sodium benzoate, sodium acetate, sodium chloride and the like. For oral administration in liquid form, the oral drug components can be combined with any oral, non-toxic, pharmaceutically acceptable inert carrier such as ethanol, glycerol, water, and the like.

The compounds of the present invention can also be administered in the form of liposome delivery systems, such as small unilamellar vesicles, large unilamellar vesicles and multilamellar vesicles. Liposomes can be formed from a variety of phospholipids, 1,2-dipalmitoylphosphatidylcholine, phosphatidyl ethanolamine (cephaline), or phosphatidylcholine (lecithin).

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example saline or water-for-injection, immediately prior to use. Extemporaneous injection solutions and suspensions may be prepared from sterile powders, granules and tablets of the kind previously described. Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Exemplary compositions for nasal, aerosol or inhalation administration include solutions in saline, which can contain, for example, benzyl alcohol or other suitable preservatives, absorption promoters to enhance bioavailability, and/or other solubilizing or dispersing agents such as those known in the art.

Formulations for rectal administration may be presented as a suppository with the usual carriers such as cocoa butter, synthetic glyceride esters or polyethylene glycol. Such carriers are typically solid at ordinary temperatures, but liquefy and/or dissolve in the rectal cavity to release the drug.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerine or sucrose and acacia. Exemplary compositions for topical administration include a topical carrier such as Plastibase (mineral oil gelled with polyethylene).

Preferred unit dosage formulations are those containing an effective dose, as hereinbefore recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavouring agents.

Whilst a compound of the invention may be used as the sole active ingredient in a medicament, it is also possible for the compound to be used in combination with one or more further therapeutic agents. Thus, the invention also provides a compound according to the invention together with a further therapeutic agent, for simultaneous, sequential or separate administration. Such further therapeutic agents may be further compounds according to the invention, or they may be different therapeutic agents, for example an antidepressant, an anxiolytic, an anti-psychotic, an agent useful in the prevention or treatment of osteoporosis, an agent useful in the prevention or treatment of cancer or other pharmaceutically active material. For example, the compounds of the instant invention may be effectively administered in combination with effective amounts of other agents such as an antidepressant, an anxiolytic, an anti-psychotic, an organic bisphosphonate or a cathepsin K inhibitor. In one preferred embodiment, the compounds of the invention may be effectively administered in combination with an effective amount of an antidepressant. Nonlimiting examples of antidepressants include noradrenaline reuptake inhibitors (NRI), selective serotonin reuptake inhibitors, monoamine oxidase inhibitors, tricyclic antidepressants (TCA), dopamine reuptake inhibitors (DRI), opioids, selective seretonic reuptake enhancers, tetracyclic antidepressants, reversible inhibitors of monoamine oxidase, melatonin agonists, serotonin and noradrenaline reuptake inhibitors (SNRI), corticotropin releasing factor antagonists, α-adrenoreceptor antagonists, 5HT1α receptor agonists and antagonists, lithium and atypical anti-psychotics. Examples of antidepressants of the SSRI class include Fluoxetine and Sertraline; examples of antidepressants of the SNRI class Venlafaxine, Citalopram, Paroxetine, Escitalopram, Fluvoxamine; examples of antidepressants of the SNRI class include Duloxetine; examples of antidepressants of the DRI and NRI classes include Bupropion; examples of antidepressants of the TCA class include Amitriptyline and Dothiepin (Dosulepin). Examples of atypical antipsychotics include: Clozapine, Olanzapine, Risperidone, Quetiapine, Ziprasidone and Dopamine partial agonists. Nonlimiting examples of anxiolytics include benzodiazepines and non-benzodiazapines. Examples of benzodiazepines include lorazepam, alprazolam, and diazepam. Examples of non-benzodiazapines include Buspirone (Buspar®), barbiturates and meprobamate. One or more of those further anti-depressants may be used in combination.

Examples of anti-cancer agents include tamoxifen or an aromatase inhibitor, used in treatment of breast cancer.

In the event that hot flashes are induced by a particular treatment, a compound of the invention may be used in combination therapy with the agent of such treatment. Nonlimiting examples of such combination treatment therapies include: a compound of the invention in combination with tamoxifene treatment of breast cancer, a compound of the invention in combination with aromatase inhibitor treatment of breast cancer or a compound of the invention in combination with raloxifene treatment of osteoporosis.

Nonlimiting examples of above-mentioned organic bisphosphonates include adendronate, clodronate, etidronate, ibandronate, incadronate, minodronate, neridronate, risedronate, piridronate, pamidronate, tiludronate, zoledronate, pharmaceutically acceptable salts or esters thereof, and mixtures thereof.

Preferred organic biphosphonates include alendronate and pharmaceutically acceptable salts and mixtures thereof. Most preferred is alendronate monosodium trihydrate.

The precise dosage of the bisphosphonate will vary with the dosing schedule, the oral potency of the particular bisphosphonate chosen, the age, size, sex and condition of the mammal or human, the nature and severity of the disorder to be treated, and other relevant medical and physical factors. Thus, a precise pharmaceutically effective amount cannot be specified in advance and can be readily determined by the caregiver or clinician. An appropriate amount can be determined by routine experimentation from animal models and human clinical studies. Generally, an appropriate amount of bisphosphonate is chosen to obtain a bone resorption inhibiting effect, i.e. a bone resorption inhibiting amount of the bisphonsphonate is administered. For humans, an effective oral dose of bisphosphonate is typically from about 1.5 to about 6000 µg/kg of body weight and preferably about 10 to about 2000 µg/kg of body weight.

For human oral compositions comprising alendronate, pharmaceutically acceptable salts thereof, or pharmaceutically acceptable derivatives thereof, a unit dosage typically comprises from about 8.75 mg to about 140 mg of the alendronate compound, on an alendronic acid active weight basis, i.e. on the basis of the corresponding acid.

The compounds of the present invention can be used in combination with other agents useful for treating estrogen-mediated conditions. The individual components of such combinations can be administered separately at different times during the course of therapy or concurrently in divided or single combination forms. The present invention is therefore to be understood as embracing all such regimes of simultaneous or alternating treatment and the term "administering" is to be interpreted accordingly. It will be understood that the scope of combinations of the compounds of this invention with other agents useful for treating estrogen-mediated conditions includes in principle any combination with any pharmaceutical composition useful for treating disorders related to estrogen functioning.

The above other therapeutic agents, when employed in combination with the compounds of the present invention, may be used, for example, in those amounts indicated in the Physicians' Desk Reference (PDR) or as otherwise determined by one of ordinary skill in the art.

Where the compounds of the invention are utilized in combination with one or more other therapeutic agent(s), either concurrently or sequentially, the following combination ratios and dosage ranges are preferred:

When combined with an antidepressant, an anxiolytic, an anti-psychotic, an organic bisphosphonate or a cathepsin K inhibitor, the compounds of formula (I) may be employed in a weight ratio to the additional agent within the range from about 10:1 to about 1:10.

The compounds of the invention as described above also find use, optionally in labelled form, as a diagnostic agent for the diagnosis of conditions associated with a disease or disorder associated with estrogen receptor activity. For example, such a compound may be radioactively labelled.

The compounds of the invention as described above, optionally in labelled form, also find use as a reference compound in methods of identifying ligands for the estrogen receptor (i.e. discovering other agonists, partial agonists, antagonists or partial antagonists of the estrogen receptor). Thus, the invention provides a method of identifying an estrogen receptor ligand which comprises use of a compound of the invention or a compound of the invention in labelled form, as a reference compound. For example, such a method may involve a competitive binding experiment in which binding of a compound of the invention to the estrogen receptor is reduced by the presence of a further compound which has estrogen receptor-binding characteristics, for example stronger estrogen receptor-binding characteristics than the compound of the invention in question.

Numerous synthetic routes to the compounds of the present invention can be devised by any person skilled in the art and the possible synthetic routes described below do not limit the invention. Many methods exist in the literature for the synthesis of biphenyls, for example: *Metal-catalyzed Cross-coupling reactions*, A. Meijere, F. Diederich, 2004; N. Miyaura et al. *Chem. Rev.,* 1995, 7, 2457-2483; D. Lesuisse et al, *Bioorg. Med. Chem. Lett.,* 2001, 11, 1709-1712; C. Yang et al, *Bioorg. Med. Chem. Lett.,* 2004, 12, 2553-2570; WO 2009/130434 and WO 2006/105442. A number of possible synthetic routes are shown schematically below. Where appropriate, any initially produced compound according to the invention can be converted into another compound according to the invention by known methods.

General method I

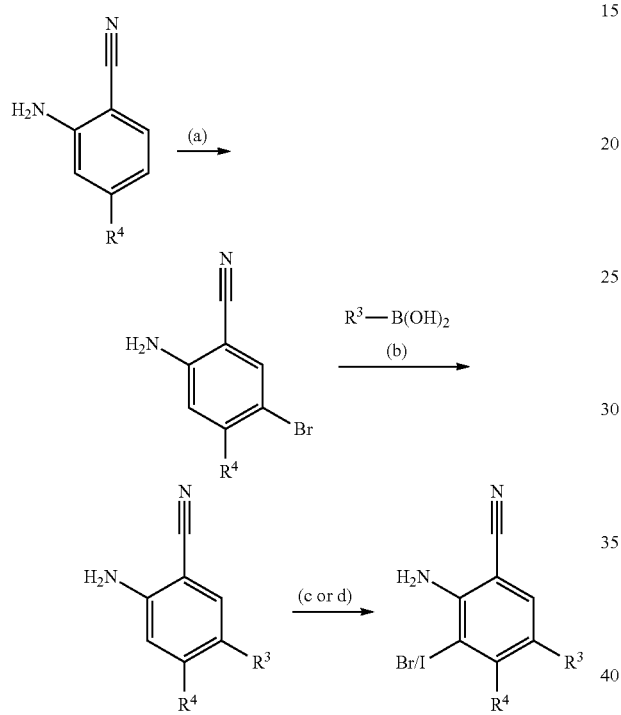

(a) NBS, DCM; (b) PdOAc$_2$, K$_2$CO$_3$, RuPhos, toluene/H$_2$O or PdCl$_2$(PPh$_3$)$_2$, K$_2$CO$_3$, DME/EtOH/H$_2$O; (c) NBS, AcOH; (d) I$_2$, AgSO$_4$, EtOH General Method I as shown in the reaction scheme above was used for the synthesis of intermediates used in general methods II-VI. Full experimental details of the individual steps of the general method applicable for the synthesis of the intermediates are described in Intermediates A and B.

General method II

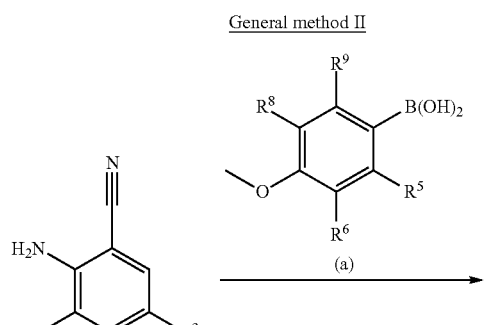

Obtained according to general method I

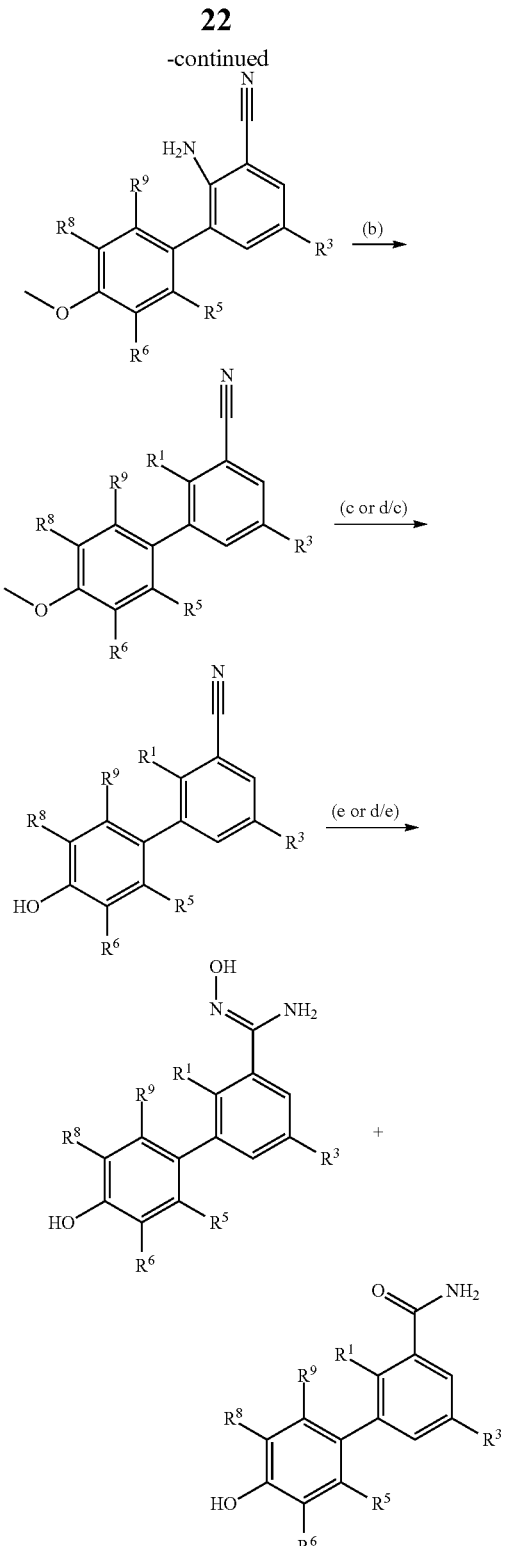

(a) Suzuki coupling I or II; (b) CuBr$_2$ or CH$_2$I$_2$, t-butyl nitrite, MeCN; (c) BBr$_3$, DCM; (d) Suzuki coupling I or II; (e) NH$_2$OH (aq), MeOH or DMSO or MeOH/DMSO;
Suzuki couplings:
 I) PdOAc$_2$, K$_2$CO$_3$, RuPhos, toluene/H$_2$O;
 II) PdCl$_2$(PPh$_3$)$_2$, K$_2$CO$_3$, DME/EtOH/H$_2$O General Method II as shown in the reaction scheme above was used for the synthesis of the following Examples: 1-14, 85 and -103-105, 297, 298, 300-303, 312-318, 320, 321, 328, 343, 344, 346 and 352-360. Full experimental details of the individual steps of the general method applicable for the synthesis of the final compounds of those Examples are described in Examples 1 and 328.

General method III

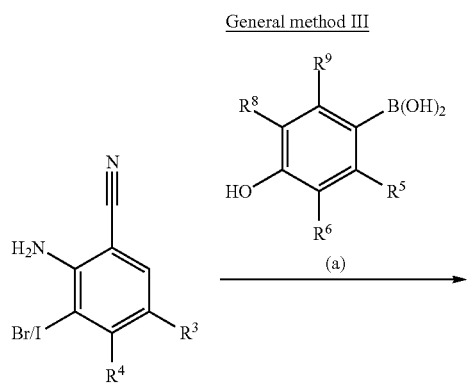

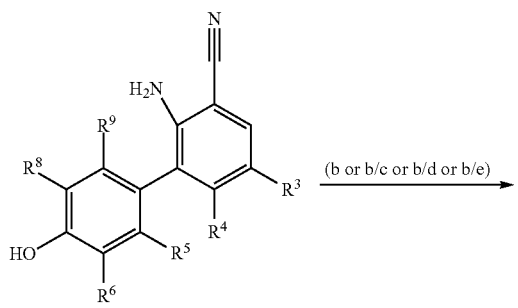

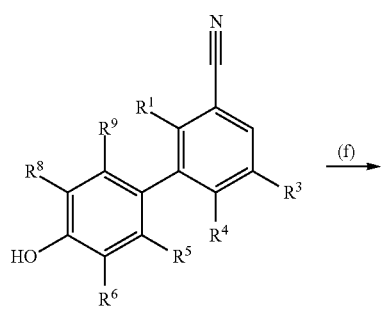

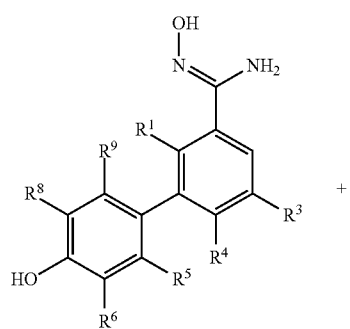

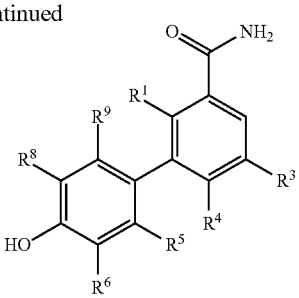

(a) Suzuki coupling I or II; (b) CuBr$_2$ or CH$_2$I$_2$ or R$^1$—Br, t-butyl nitrite, MeCN;
(c) Suzuki coupling I or II; (d) R$_1$-stannane, PdCl$_2$(PPh$_3$)$_2$, Dioxane or THF;
(e) R$^1$—MgCl, ZnCl$_2$, THF; (f) NH$_2$OH (aq), MeOH or DMSO or MeOH/DMSO.
Suzuki couplings:
I) PdOAc$_2$, K$_2$CO$_3$, RuPhos or SPhos, toluene/H$_2$O;
II) PdCl$_2$(PPh$_3$)$_2$, K$_2$CO$_3$, DME/EtOH/H$_2$O General Method III as shown in the reaction scheme above was used for the synthesis of the following Examples: 15-49, 59-66, 72, 75-84, 86-91, 93-102, 106-116, 122-296, 304-309 and 322-327. Full experimental details of the individual steps of the general method applicable for the synthesis of the final compounds of those Examples are described in Examples 15-18, 59, 61, 72, 277, 284, 287-289, 322, 326 and 327.

General method IV

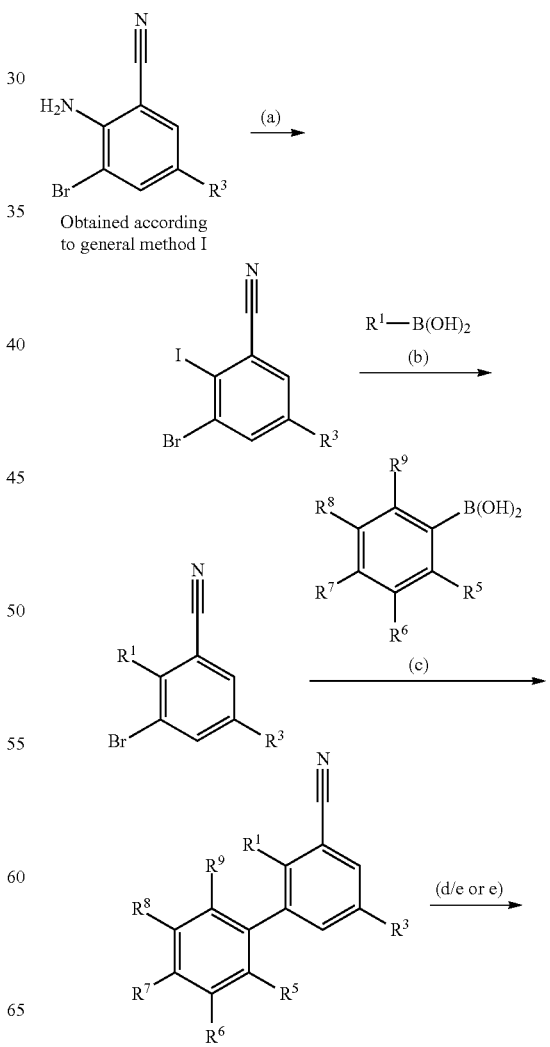

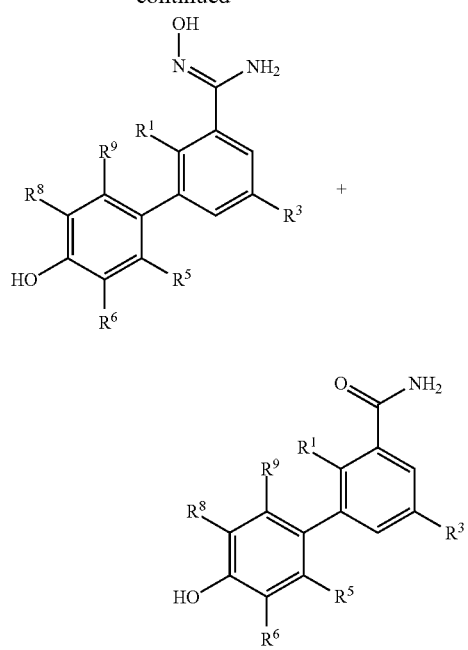

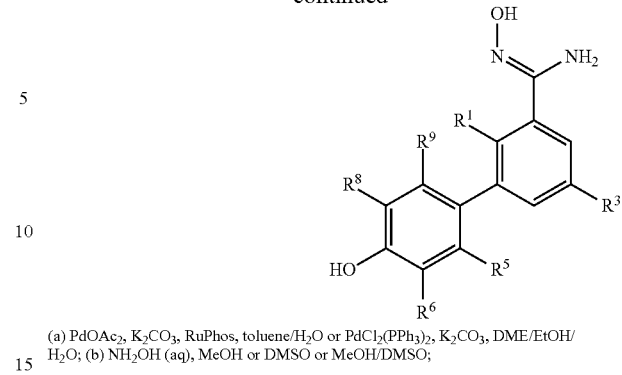

(a) PdOAc₂, K₂CO₃, RuPhos, toluene/H₂O or PdCl₂(PPh₃)₂, K₂CO₃, DME/EtOH/H₂O; (b) NH₂OH (aq), MeOH or DMSO or MeOH/DMSO;

General Method V as shown in the reaction scheme above was used for the synthesis of the following Examples: 67-71 and 119-121. Full experimental details of the individual steps of the general method applicable for the synthesis of the final compounds of those Examples are described in Example 67.

General method VI

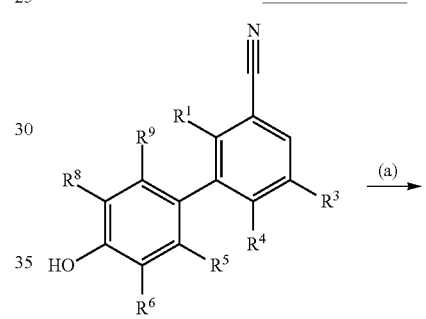

Obtained according to general methods II or III

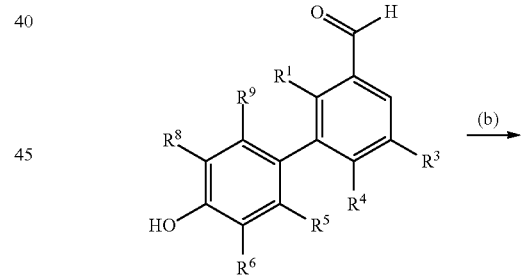

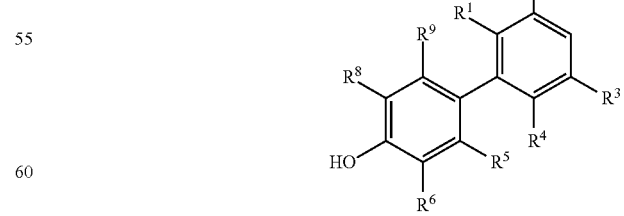

(a) DIBAL-H, DCM; (b) NH₂OH (aq), i-PrOH/DMSO (a) CH₂I₂, t-butyl nitrite, MeCN; (b) PdCl₂(PPh₃)₂, K₂CO₃, DME/EtOH/H₂O; (c) PdCl₂(PPh₃)₂, K₂CO₃, DME/EtOH/H₂O; (d) BBr₃, DMC; (e) NH₂OH (aq), MeOH or DMSO or MeOH/DMSO General Method IV as shown in the reaction scheme above was used for the synthesis of the following Examples: 50-58, 299, 310, 329-342, 345, 347, 348 and 350. Full experimental details of the individual steps of the general method applicable for the synthesis of the final compounds of those Examples are described in Examples 50 and 51.

General method V

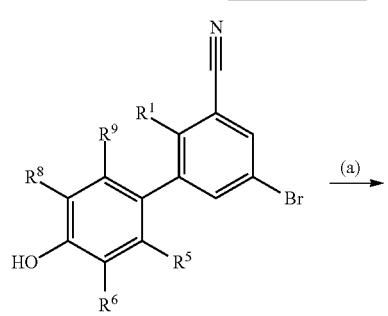

Obtained according to general methods II or III

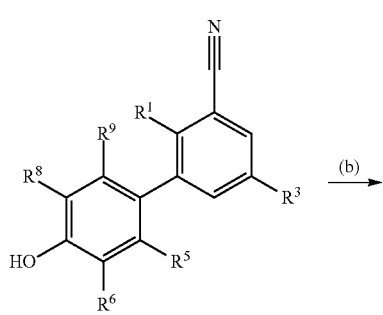

General Method VI as shown in the reaction scheme above was used for the synthesis of the following Examples: 73 and 92. Full experimental details of the individual steps of the general method applicable for the synthesis of the final compounds of those Examples are described in Example 73.

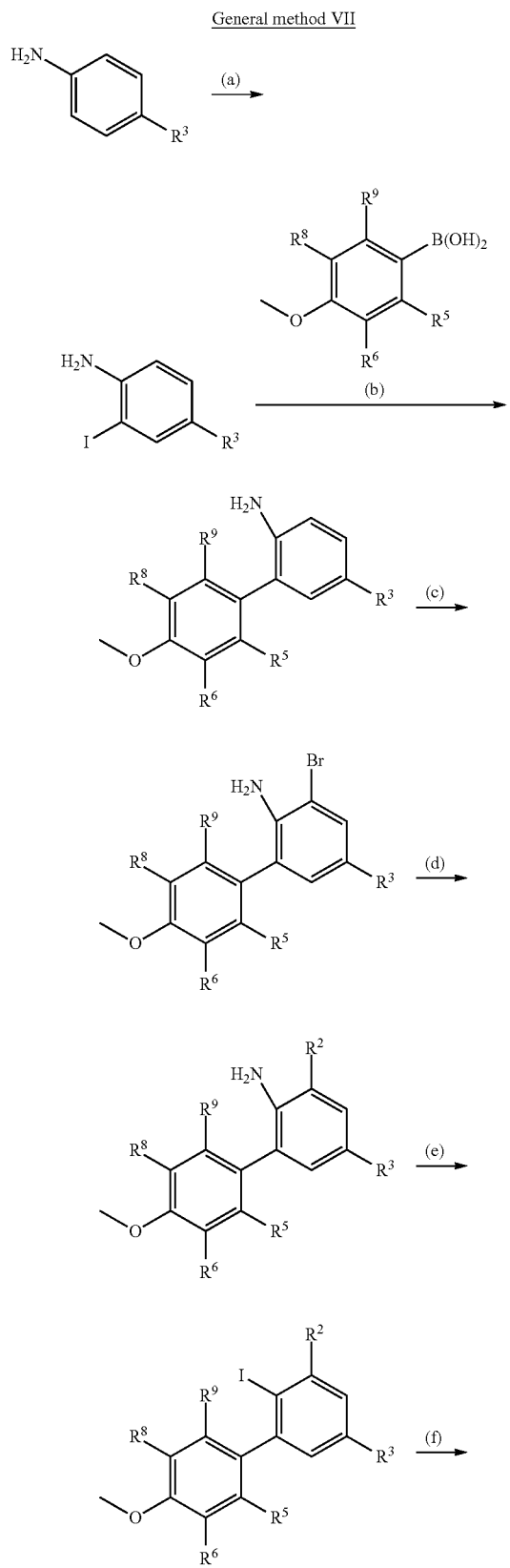

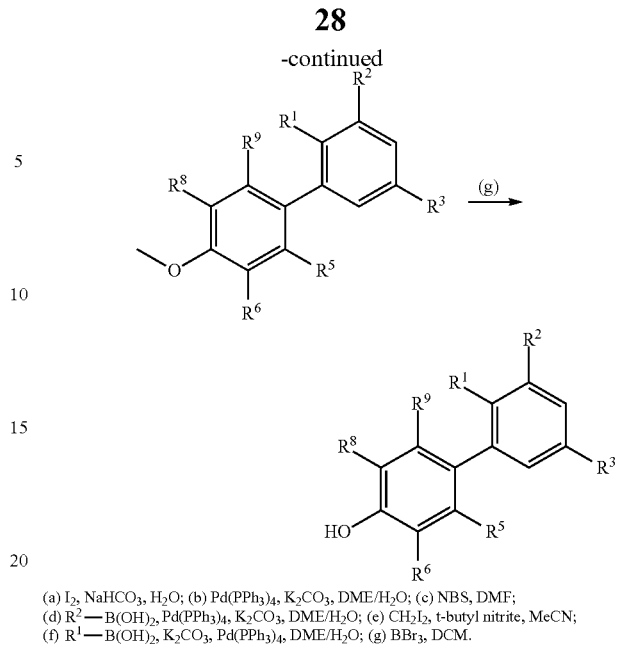

(a) I₂, NaHCO₃, H₂O; (b) Pd(PPh₃)₄, K₂CO₃, DME/H₂O; (c) NBS, DMF; (d) R²—B(OH)₂, Pd(PPh₃)₄, K₂CO₃, DME/H₂O; (e) CH₂I₂, t-butyl nitrite, MeCN; (f) R¹—B(OH)₂, K₂CO₃, Pd(PPh₃)₄, DME/H₂O; (g) BBr₃, DCM.

General Method VII as shown in the reaction scheme above was used for the synthesis of the following Examples: 74, 117 and 118. Full experimental details of the individual steps of the general method applicable for the synthesis of the final compounds of those Examples are described in Example 74.

Synthesis of Intermediate A

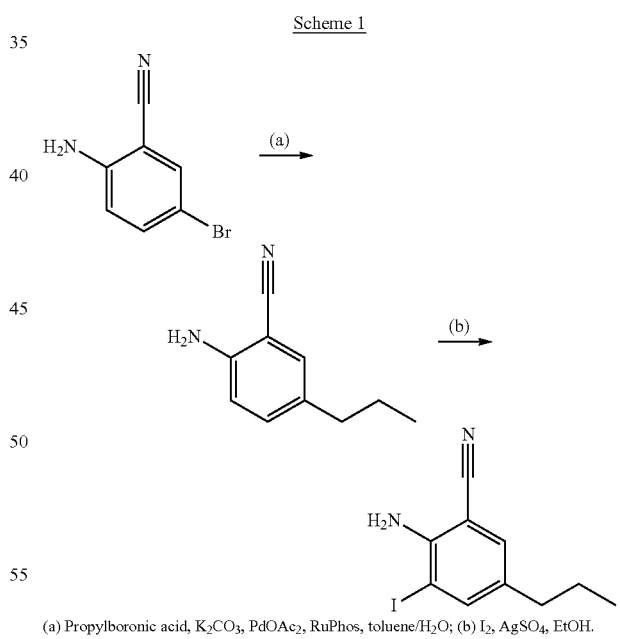

(a) Propylboronic acid, K₂CO₃, PdOAc₂, RuPhos, toluene/H₂O; (b) I₂, AgSO₄, EtOH.

Step (a):

2-amino-5-bromobenzonitrile (25 mg, 0.13 mmol), propylboronic acid (78.08 mg, 0.89 mmol), Pd(OAc)₂ (5.70 mg, 0.03 mmol), RuPhos (23.68 mg, 0.05 mmol) and K₂CO₃ (87.68 mg, 0.63 mmol) were mixed in toluene/water (2 mL, 10:1) under nitrogen. The reaction mixture was heated in microwave at 140° C. for 20 min, cooled to room temperature and filtered through celite. The solvent was evaporated under reduced pressure and the crude product was purified on silica using EtOAc/n-heptane (10-20% EtOAc) as mobile phase. 17.1 mg 2-amino-5-propylbenzonitrile was obtained as yellowish oil.

Step (b):

2-amino-5-propylbenzonitrile (71.4 mg, 0.45 mmol) was dissolved in EtOH (3 mL). Iodine (113.11 mg, 0.45 mmol) and AgSO$_4$ (138.95 mg, 0.45 mmol) were added. The reaction mixture was stirred at room temperature for 1 h and was then filtered through celite. The solvent was evaporated under reduced pressure and the crude product was purified on silica using EtOAc/n-heptane (5:95) as mobile phase. 99.7 mg 2-amino-3-iodo-5-propylbenzonitrile was obtained as a straw coloured solid.

Synthesis of Intermediate B

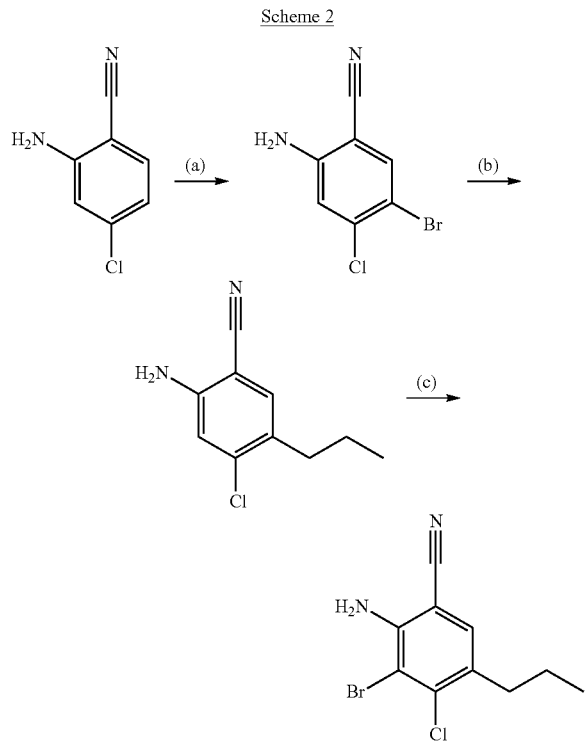

(a) NBS, DCM; (b) Propylboronic acid, K$_2$CO$_3$, PdOAc$_2$, RuPhos, toluene/H$_2$O; NBS, AcOH.

Step (a):

2-amino-4-chlorobenzonitrile (765 mg, 5.01 mmol) was dissolved in DCM (10 mL) and NBS (1160 mg, 6.52 mmol) was added at 0° C. The cooling bath was removed and the reaction mixture was stirred at room temperature for 3 h. The solvent was evaporated under reduced pressure and the crude product was purified on silica using DCM as mobile phase. 750 mg 2-amino-5-bromo-4-chlorobenzonitrile was obtained.

Step (b):

2-amino-5-bromo-4-chlorobenzonitrile (212 mg, 0.92 mmol), propylboronic acid (80.5 mg, 0.92 mmol), Pd(OAc)$_2$ (10.3 mg, 0.05 mmol), RuPhos (42.7 mg, 0.09 mmol) and K$_2$CO$_3$ (633 mg, 4.6 mmol) were mixed in toluene/water (3 mL, 10:1) under nitrogen. The reaction mixture was heated in microwave at 120° C. for 20 min. H$_2$O was added and the aqueous mixture was extracted with DCM and EtOAc. The combined organic phases were filtered through a phase separator and the solvent was evaporated under reduced pressure. The crude product was purified on preparative HPLC. 100 mg 2-amino-4-chloro-5-propylbenzonitrile was obtained.

Step (c):

2-amino-4-chloro-5-propylbenzonitrile (100 mg, 0.51 mmol) was dissolved in HOAc (3.6 mL) and NBS (91.4 mg, 0.51 mmol) was added. The mixture was stirred at room temperature for 1 h. The solvent was evaporated under reduced pressure and the crude product was purified on silica using EtOAc/n-heptane (20% EtOAc) as mobile phase. 117 mg 2-amino-3-bromo-4-chloro-5-propylbenzonitrile was obtained.

Synthesis of Intermediate C

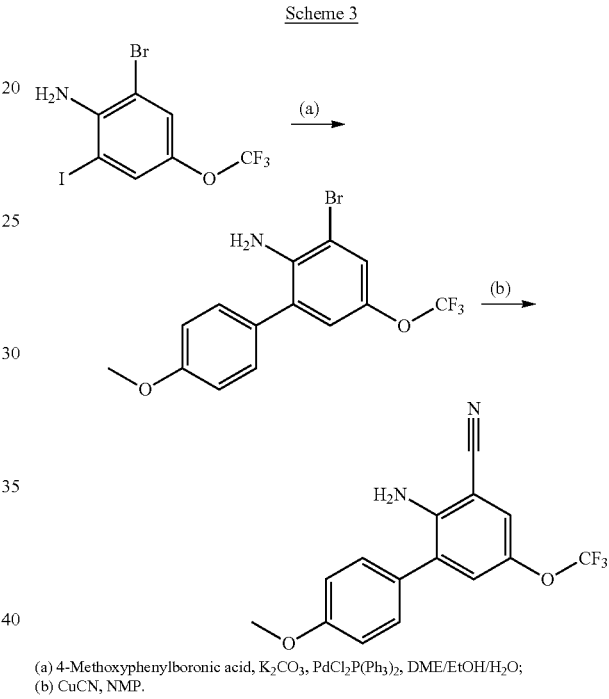

(a) 4-Methoxyphenylboronic acid, K$_2$CO$_3$, PdCl$_2$P(Ph$_3$)$_2$, DME/EtOH/H$_2$O; (b) CuCN, NMP.

Step (a):

2-bromo-6-iodo-4-(trifluoromethoxy)aniline (300 mg, 0.79 mmol), 4-methoxyphenylboronic acid (131 mg, 0.86 mmol), PdCl$_2$(PPh$_3$)$_2$ (27.6 mg, 0.04 mmol) and K$_2$CO$_3$ (434 mg, 3.14 mmol) were mixed in DME/EtOH/H$_2$O (10 mL, 4:1:1) under nitrogen. The reaction mixture was heated in microwave at 130° C. for 20 min. The solvent was concentrated, the residue was dissolved in EtOAc and filtered through a plug of silica. The crude product was purified on silica using EtOAc/n-heptane (2.5-5% EtOAc) as mobile phase. 199 mg 3-bromo-4'-methoxy-5-(trifluoromethoxy)-[1,1'-biphenyl]-2-amine was obtained as a white solid.

Step (b):

3-bromo-4'-methoxy-5-(trifluoromethoxy)-[1,1'-biphenyl]-2-amine (199 mg, 0.55 mmol) and CuCN (54.1 mg, 0.60 mmol were mixed in NMP (1 mL) under nitrogen. The reaction mixture was heated in microwave at 175° C. for 30 min and then at 180° C. for 75 min. EtOAc (10 mL) was added and the mixture was washed with NH$_3$OH (25%, aq) and brine. The combined aqueous layers were extracted with EtOAc (3×) and the combined organic layers were dried with brine and over Na$_2$SO$_4$. The solvent was concentrated and the crude product was purified on silica using EtOAc/ n-heptane (5-20% EtOAc) as mobile phase. 138 mg 2-amino-4'-methoxy-5-(trifluoromethoxy)-[1,1'-biphenyl]-3-carbonitrile was obtained as a yellow oil.

The following Examples illustrate the invention.

Example 1

N',4'-dihydroxy-2-(3-methylthiophen-2-yl)-5-propyl-[1,1'-biphenyl]-3-carboximidamide (E1)

Scheme 4

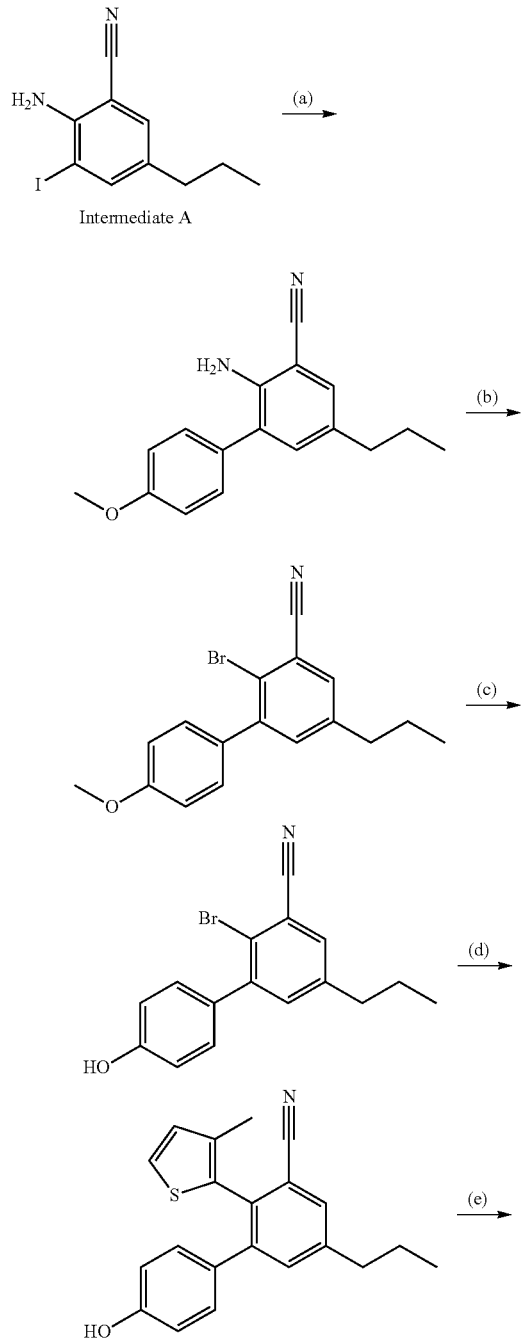

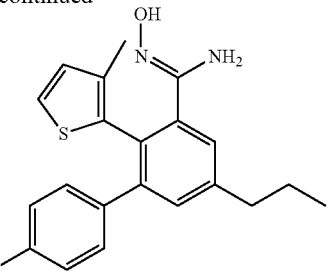

(a) 4-Methoxyphenylboronic acid, PdOAc$_2$, K$_2$CO$_3$, RuPhos, toluene/H$_2$O;
(b) CuBr$_2$, t-butyl nitrite, MeCN; (c) BBr$_3$, DCM; (d) 3-Methylthiophene-2-boronic acid, PdOAc$_2$, K$_2$CO$_3$, RuPhos, toluene/H$_2$O; (e) NH$_2$OH (aq), MeOH Step (a):

2-amino-3-iodo-5-propylbenzonitrile (99.7 mg, 0.35 mmol), 4-methoxyphenylboronic acid (158.8 mg, 1.05 mmol), Pd(OAc)$_2$ (7.82 mg, 0.03 mmol), RuPhos (32.5 mg, 0.0 mmol) and K$_2$CO$_3$ (240.8 mg, 1.74 mmol) were mixed in toluene/water (5 mL, 10:1) under nitrogen. The reaction mixture was heated in microwave at 140° C. for 20 min, cooled to room temperature and filtered through celite. The solvent was evaporated under reduced pressure and the crude product was purified on silica using EtOAc/n-heptane (5-10% EtOAc) as mobile phase. 17.1 mg 2-amino-4'-methoxy-5-propylbiphenyl-3-carbonitrile was obtained as straw coloured oil.

Step (b):

2-amino-4'-methoxy-5-propylbiphenyl-3-carbonitrile (91.0 mg, 0.34 mmol) and CuBr$_2$ (152.6 mg, 0.68 mmol) were mixed in MeCN (3.5 mL). t-Butyl nitrite (35.23 mg, 0.34 mmol) was added. The reaction mixture was stirred at room temperature for 0.5 h. The solvent was evaporated under reduced pressure and the crude product was filtered through silica using DCM as mobile phase. 113 mg 2-bromo-4'-methoxy-5-propylbiphenyl-3-carbonitrile was obtained as yellowish oil.

Step (c):

2-Bromo-4'-methoxy-5-propylbiphenyl-3-carbonitrile (113 mg, 0.34 mmol) was dissolved in DCM (2 mL) under nitrogen and the solution was cooled to −78° C. BBr$_3$ (1.71 mL, 1M) was added. The reaction mixture was stirred at 0° C. for 0.5 h and then at room temperature for 0.5 h. MeOH (415 ̄ 1) was added at 0° C. to quench the reaction. NaHCO$_3$ (25 mL, sat.) and EtOAc (25 mL) were added, the phases were partitioned and the aqueous phase was extracted twice with EtOAc. The combined organic phases were washed with brine, dried over Na$_2$SO$_4$ and concentrated under reduced pressure. The crude product was purified on silica using EtOAc/n-heptane (0-20% EtOAc) as mobile phase. 102.1 mg 2-bromo-4'-hydroxy-5-propylbiphenyl-3-carbonitrile was obtained as a colourless solid.

Step (d):

2-Bromo-4'-hydroxy-5-propylbiphenyl-3-carbonitrile (25 mg, 0.08 mmol), 3-methylthiophene-2-boronic acid (22.45 mg, 0.16 mmol), Pd(OAc)$_2$ (3.55 mg, 0.02 mmol), RuPhos (14.76 mg, 0.03 mmol) and K$_2$CO$_3$ (54.63 mg, 0.40 mmol) were mixed in toluene/water (1 mL, 10:1) under nitrogen. The reaction mixture was heated in microwave at 140° C. for 20 min, cooled to room temperature and filtered through celite. The solvent was evaporated under reduced pressure and the crude product was purified on silica using EtOAc/n-heptane (10-20% EtOAc) as mobile phase. 9.7 mg 4'-hydroxy-2-(3-methylthiophen-2-yl)-5-propylbiphenyl-3-carbonitrile was obtained.

Step (e):

4'-hydroxy-2-(3-methylthiophen-2-yl)-5-propylbiphenyl-3-carbonitrile (9.7 mg, 0.03 mmol) was treated with hydroxylamine (200 eq, 16 M, aq) in MeOH (1 mL). The reaction mixture was heated in microwave at 120° C. for 15 min under nitrogen. The solvent was evaporated under reduced pressure and the crude product was purified on preparative HPLC using MeCN/acidic $H_2O$ (5-50% MeCN) as mobile phase. N',4'-dihydroxy-2-(3-methylthiophen-2-yl)-5-propyl-[1,1'-biphenyl]-3-carboximidamide (E1) ES/MS m/z: 367.4 (M+H), 365.2 (M−H); $^1$H NMR (MeOD$_3$, 500 MHz): δ 7.33 (s, 1H), 7.29 (s, 1H), 7.22 (d, 1H, J=4.8 Hz), 6.92 (m, 2H), 6.68 (d, 1H, J=4.8 Hz), 6.59 (m, 2H), 2.69 (t, 2H, J=7.5 Hz), 1.74 (s, 3H), 1.72 (m, 2H) and 1.00 (t, 3H, J=7.4 Hz). was obtained as a solid. The title compound was identified by $^1$H-NMR which showed that the oxime product was a single isomer, but did not confirm whether the (E) or (Z) oxime isomer had been obtained.

Examples 2-14

Examples 2-14 were prepared using a method analogous to that used to synthesise Example 1 above. Full experimental details of the individual steps of the general methods are described in Example 1 above. For examples 2, 3 and 6-14 identification of the title compounds by $^1$H-NMR showed that the oxime product was a single isomer, but did not confirm whether the (E) or (Z) oxime isomer had been obtained.

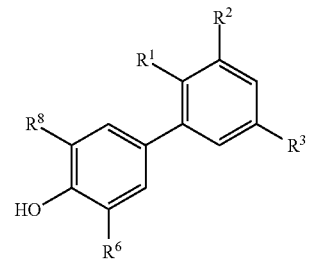

E 2    2-(3,5-dimethylisoxazol-4-yl)-N',4'-dihydroxy-5-methyl-[1,1'-biphenyl]-3-carboximidamide
$R^1$ = 3,5-dimethylisoxazol-4-yl    $R^2$ = N-hydroxy carbaimidoyl    $R^3$ = methyl    $R^6$ = H    $R^8$ = H
ES/MS m/z: 338.18 (pos. M + H), 336.27 (neg. M − H); $^1$H NMR (MeOD, 500 MHz): δ 7.34 (s, 1H), 7.32 (s, 1H), 6.89 (m, 2H), 6.67 (m, 2H), 2.44 (s, 3H), 2.07 (s, 3H) and 1.84 (s, 3H).

E 3    2-(3,5-dimethylisoxazol-4-yl)-N',4'-dihydroxy-5-propyl-[1,1'-biphenyl]-3-carboximidamide
$R^1$ = 3,5-dimethylisoxazol-4-yl    $R^2$ = N-hydroxy carbaimidoyl    $R^3$ = propyl    $R^6$ = H    $R^8$ = H
ES/MS m/z: 366.27 (pos. M + H), 364.22 (neg. M − H); $^1$H NMR (Acetone-d6, 500 MHz): δ 7.32 (d, 1H, J = 1.7 Hz), 7.28 (d, 1H, J = 1.7 Hz), 6.94 (m, 2H), 6.74 (m, 2H), 2.69, (t, 2H, J = 7.7 Hz), 2.01 (s, 3H), 1.82 (s, 3H), 1.72 (m, 2H) and 0.99 (t, 3H, J = 7.2 Hz).

E 4    2-(3,5-dimethylisoxazol-4-yl)-4'-hydroxy-5-propyl-[1,1'-biphenyl]-3-carboxamide
$R^1$ = 3,5-dimethylisoxazol-4-yl    $R^2$ = carbamoyl    $R^3$ = propyl    $R^6$ = H    $R^8$ = H
ES/MS m/z: 351.3 (pos. M + H), 349.2 (neg. M − H); $^1$H NMR (Acetone-d6, 500 MHz): 7.36 (d, 1H, J = 1.7 Hz), 7.30 (d, 1H, J = 1.7 Hz), 6.96 (m, 2H), 6.75 (m, 2H), 2.70, (t, 2H, J = 7.6 Hz), 2.04 (s, 3H), 1.84 (s, 3H), 1.72 (m, 2H) and 0.99 (t, 3H, J = 7.3 Hz).

E 5    2-(3,5-dimethylisoxazol-4-yl)-4'-hydroxy-5-propyl-[1,1'-biphenyl]-3-carbonitrile
$R^1$ = 3,5-dimethylisoxazol-4-yl    $R^2$ = CN    $R^3$ = propyl    $R^6$ = H    $R^8$ = H
ES/MS m/z: 333.25 (pos. M + H), 331.18 (neg. M − H); $^1$H NMR (Acetone-d6, 500 MHz): 7.71 (d, 1H, J = 1.7 Hz), 7.61 (d, 1H, J = 1.7 Hz), 7.04 (m, 2H), 6.80 (m, 2H), 2.77, (t, 2H, J = 7.5 Hz), 2.15 (s, 3H), 1.84 (s, 3H), 1.75 (m, 2H) and 0.99 (t, 3H, J = 7.6 Hz).

E 6    N',4'-dihydroxy-5-methyl-2-(3-methylthiophen-2-yl)-[1,1'-biphenyl]-3-carboximidamide
$R^1$ = 3-methylthiophen-2-yl    $R^2$ = N-hydroxy carbaimidoyl    $R^3$ = methyl    $R^6$ = H    $R^8$ = H
ES/MS m/z: 339.2 (pos. M + H), 337.17 (neg. M − H); $^1$H NMR (MeOD, 500 MHz): δ 7.33 (s, 1H), 7.27 (s, 1H), 7.21 (d, 1H, J = 5.1 Hz), 6.91 (m, 2H), 6.67 (d, 1H, J = 5.1 Hz), 6.58 (m, 2H), 2.43 (s, 3H) and 1.73 (s, 3H).

E 7    3',5'-difluoro-N',4'-dihydroxy-2-(3-methylthiophen-2-yl)-5-propyl-[1,1'-biphenyl]-3-carboximidamide
$R^1$ = 3-methylthiophen-2-yl    $R^2$ = N-hydroxy carbaimidoyl    $R^3$ = propyl    $R^6$ = F    $R^8$ = F
ES/MS m/z: 403.14 (pos. M + H), 401.2 (neg. M − H); $^1$H NMR (MeOD, 500 MHz): δ 7.34 (br s, 1H), 7.33 (s, 1H), 7.27 (d, 1H, J = 5.1 Hz), 6.74 (d, 1H, J = 5.1 Hz), 6.63 (m, 2H), 2.70 (t, 2H, J = 7.6 Hz), 1.80 (s, 3H), 1.72 (m, 2H) and 1.00 (t, 3H, J = 7.3 Hz).

E 8    2-(3,5-dimethylisoxazol-4-yl)-3',5'-difluoro-N',4'-dihydroxy-5-propyl-[1,1'-biphenyl]-3-carboximidamide
$R^1$ = 3,5-dimethylisoxazol-4-yl    $R^2$ = N-hydroxy carbaimidoyl    $R^3$ = propyl    $R^6$ = F    $R^8$ = F
ES/MS m/z: 402.22 (pos. M + H), 400.22 (neg. M − H); $^1$H NMR (MeOD, 500 MHz): δ 7.38 (d, 1H, J = 1.9 Hz), 7.35 (d, 1H, J = 1.9 Hz), 6.63 (m, 2H), 2.71 (t, 2H, J = 7.4 Hz), 2.11 (s, 3H), 1.89 (s, 3H), 1.72 (m, 2H) and 1.01 (t, 3H, J = 7.4 Hz).

E 9    5-bromo-N',4'-dihydroxy-2-(3-methylthiophen-2-yl)-[1,1'-biphenyl]-3-carboximidamide
$R^1$ = 3-methylthiophen-2-yl    $R^2$ = N-hydroxy carbaimidoyl    $R^3$ = Br    $R^6$ = H    $R^8$ = H
ES/MS m/z: 405.03 (pos. M + H), 401.08 (neg. M − H); $^1$H NMR (Acetone-d6, 500 MHz): δ 7.60 (d, 1H, J = 2.2 Hz), 7.58 (d, 1H, J = 2.2 Hz), 7.28 (d, 1H, J = 5.1 Hz), 6.97 (m, 2H), 6.71-6.68 (m, 3H) and 1.77 (s, 3H).

E 10    5-bromo-N',4'-dihydroxy-2-iodo-[1,1'-biphenyl]-3-carboximidamide
$R^1$ = phenyl    $R^2$ = N-hydroxy carbaimidoyl    $R^3$ = Br    $R^6$ = H    $R^8$ = H
ES/MS m/z: 383.13 (pos. M + H), 383.18 (neg. M − H); $^1$H NMR (Acetone-d6, 500 MHz): δ 7.56 (d, 1H, J = 2.2 Hz), 7.55 (d, 1H, J = 2.2 Hz), 7.18-7.15 (m, 3H), 7.12-7.10 (m, 2H), 6.87 (m, 2H) and 6.64 (m, 2H).

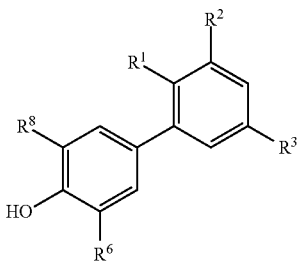

| | |
|---|---|
| E 11 | 5''-fluoro-N',4-dihydroxy-2'',5'-dimethyl-[1,1':2',1''-terphenyl]-3'-carboximidamide |
| | $R^1$ = 5-fluoro-2-methylphenyl    $R^2$ = N-hydroxy carbaimidoyl    $R^3$ = methyl    $R^6$ = H    $R^8$ = H |
| | ES/MS m/z: 349.34 (pos. M + H), 351.27 (neg. M − H); $^1$H NMR (Acetone-d6, 500 MHz): δ 7.28 (d, $^1$H, J = 1.1 Hz), 7.23 (d, 1, J = 1.1 Hz), 6.98-6.89 (m, 4H), 6.82 (m, 1H), 6.63 (m, 2H), 2.42 (s, 3H) and 1.83 (s, 3H). |
| E 12 | 5''-fluoro-4-hydroxy-2'',5'-dimethyl-[1,1':2',1''-terphenyl]-3'-carboxamide |
| | $R^1$ = 5-fluoro-2-methylphenyl    $R^2$ = carbamoyl    $R^3$ = methyl    $R^6$ = H    $R^8$ = H |
| | ES/MS m/z: 336.26 (pos. M + H), 334.3 (neg. M − H); $^1$H NMR (Acetone-d6, 500 MHz): δ 7.34 (d, 1H, J = 1.1 Hz), 7.25 (d, 1, J = 1.1 Hz), 7.00 (dd, 1H, J = 8.4, 6.2 Hz), 6.93-6.89 (m, 3H), 6.84 (m, 1H), 6.64 (m, 2H), 2.43 (s, 3H) and 1.86 (s, 3H). |
| E 13 | 5-chloro-2-(3,5-dimethylisoxazol-4-yl)-N',4'-dihydroxy-[1,1'-biphenyl]-3-carboximidamide |
| | $R^1$ = 3,5-dimethylisoxazol-4-yl    $R^2$ = N-hydroxy carbaimidoyl    $R^3$ = Cl    $R^6$ = H    $R^8$ = H |
| | ES/MS m/z: 358.23 (pos. M + H), 356.24 (neg. M − H); $^1$H NMR (Acetone-d6, 500 MHz): δ 7.47 (d, 1H, J = 2.2 Hz), 7.45 (d, 1H, J = 2.2 Hz), 6.98 (m, 2H), 6.76 (m, 2H), 2.04 (s, 3H) and 1.83 (s, 3H). |
| E 14 | 5-chloro-2-(3,5-dimethylisoxazol-4-yl)-4'-hydroxy-[1,1'-biphenyl]-3-carboxamide |
| | $R^1$ = 3,5-dimethylisoxazol-4-yl    $R^2$ = carbamoyl    $R^3$ = Cl    $R^6$ = H    $R^8$ = H |
| | ES/MS m/z: 343.19 (pos. M + H), 341.26 (neg. M − H); $^1$H NMR (Acetone-d6, 500 MHz): δ 7.52 (d, 1H, J = 2.3 Hz), 7.48 (d, 1H, J = 2.3 Hz), 6.94 (m, 2H), 6.78 (m, 2H), 2.08 (s, 3H) and 1.88 (s, 3H). |

Example 15

2-(3,5-dimethylisoxazol-4-yl)-3'-fluoro-N',4'-dihydroxy-5-propyl-[1,1'-biphenyl]-3-carboximidamide (E15)

Scheme 5

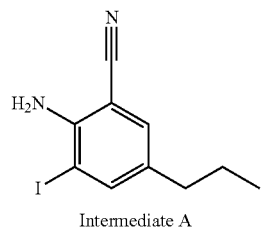

Intermediate A

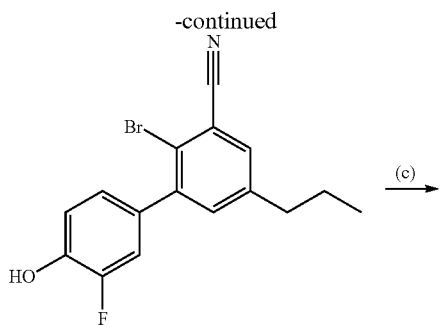

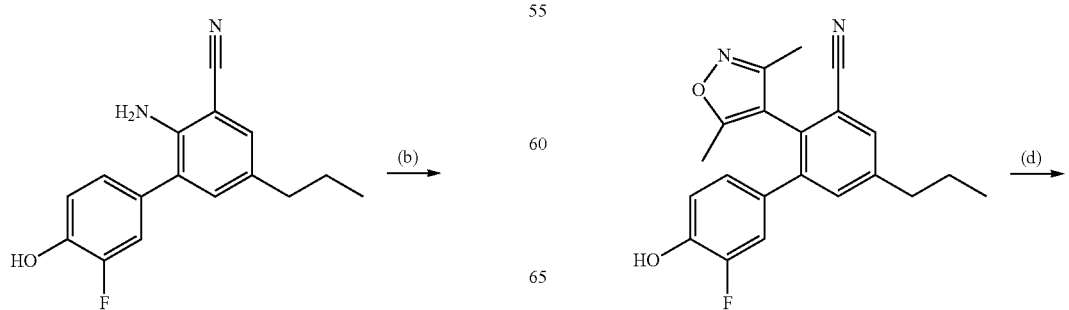

-continued

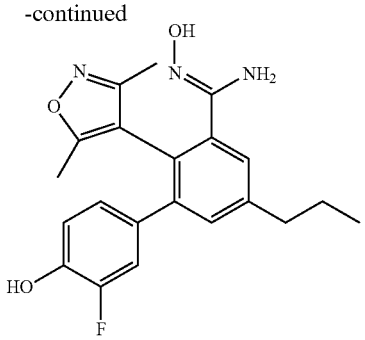

(a) 3-fluoro-4-hydroxyphenylboronic acid, PdCl₂(PPh₃)₂, K₂CO₃, DME/EtOH/H₂O;
(b) CuBr₂, t-butyl nitrite, MeCN; (c) 3,5-Dimethylisoxazole-4-boronic acid, PdOAc₂, K₂CO₃, RuPhos, toluene/H₂O, (d) NH₂OH (aq), DMSO Step (a):
2-amino-3-iodo-5-propylbenzonitrile (150 mg, 0.52 mmol), 3-fluoro-4-hydroxyphenylboronic acid (122.61 mg, 0.79 mmol), PdCl₂(PPh₃)₂ (36.8 mg, 0.05 mmol) and K₂CO₃ (144.9 mg, 1.05 mmol) were mixed in DME/EtOH/H₂O (2 mL, 40:10:1) under nitrogen. The reaction mixture was heated in microwave at 130° C. for 20 min, cooled to room temperature, diluted with DCM and washed with NH₄Cl aq, sat). The mixture was filtered through a phase separator, the solvent was evaporated under reduced pressure and the crude product was purified on silica using EtOAc/n-heptane (20% EtOAc) as mobile phase. 122 mg 2-amino-3'-fluoro-4'-hydroxy-5-propylbiphenyl-3-carbonitrile was obtained.

Step (b):
2-amino-3'-fluoro-4'-hydroxy-5-propylbiphenyl-3-carbonitrile (122.0 mg, 0.45 mmol) and CuBr₂ (201.6 mg, 0.90 mmol) were mixed in dry MeCN (5 mL). t-Butyl nitrite (46.54 mg, 0.45 mmol) was added. The reaction mixture was stirred at room temperature for 0.5 h. The solvent was evaporated under reduced pressure and the crude product was purified on silica using EtOAc/n-heptane (20% EtOAc) as mobile phase. 71.6 mg 2-bromo-3'-fluoro-4'-hydroxy-5-propylbiphenyl-3-carbonitrile was obtained.

Step (c):
2-bromo-3'-fluoro-4'-hydroxy-5-propylbiphenyl-3-carbonitrile (71.0 mg, 0.21 mmol), 3,5-dimethylisoxazole-4-boronic acid (59.9 mg, 0.42 mmol), Pd(OAc)₂ (9.54 mg, 0.04 mmol), RuPhos (39.7 mg, 0.08 mmol) and K₂CO₃ (146 mg, 1.06 mmol) were mixed in toluene/water (2 mL, 10:1) under nitrogen. The reaction mixture was heated in microwave at 140° C. for 20 min, cooled to room temperature and filtered through celite. The solvent was evaporated under reduced pressure and the crude product was purified on silica using EtOAc/n-heptane (20% EtOAc) as mobile phase. 25 mg 2-(3,5-dimethylisoxazol-4-yl)-3'-fluoro-4'-hydroxy-5-propylbiphenyl-3-carbonitrile was obtained.

Step (d):
2-(3,5-dimethylisoxazol-4-yl)-3'-fluoro-4'-hydroxy-5-propylbiphenyl-3-carbonitrile (25 mg, 0.07 mmol) and hydroxylamine (0.5 mL, 16 M, aq) were mixed in DMSO (0.3 mL). The reaction mixture was heated in microwave at 140° C. for 15 min under nitrogen. The crude mixture was purified on preparative HPLC using MeCN/acidic H₂O (5-50% MeCN) as mobile phase. 4.0 mg 2-(3,5-dimethylisoxazol-4-yl)-3'-fluoro-N',4'-dihydroxy-5-propyl-[1,1'-biphenyl]-3-carboximidamide (E15) was obtained. ES/MS m/z: 384.24 (M+H), 382.24 (M−H); ¹H NMR (MeOD, 500 MHz): δ 7.66 (t, 1H, J=1.5 Hz), 7.48-7.43 (m, 3H), 7.25 (m, 1H), 2.68 (t, 2H, J=7.7 Hz), 2.35 (s, 3H), 2.21 (s, 3H), 1.70 (m, 2H) and 0.97 (t, 3H, J=7.2 Hz). The title compound was identified by ¹H-NMR which showed that the oxime product was a single isomer, but did not confirm whether the (E) or (Z) oxime isomer had been obtained.

Examples 16, 17 and 18

2-(2,4-dimethylfuran-3-yl)-4'-hydroxy-5-propyl-[1,1'-biphenyl]-3-carbonitrile (E16)

2-(2,4-dimethylfuran-3-yl)-N',4'-dihydroxy-5-propyl-[1,1'-biphenyl]-3-carboximidamide (E17)

2-(2,4-dimethylfuran-3-yl)-4'-hydroxy-5-propyl-[1,1'-biphenyl]-3-carboxamide (E18)

Scheme 6

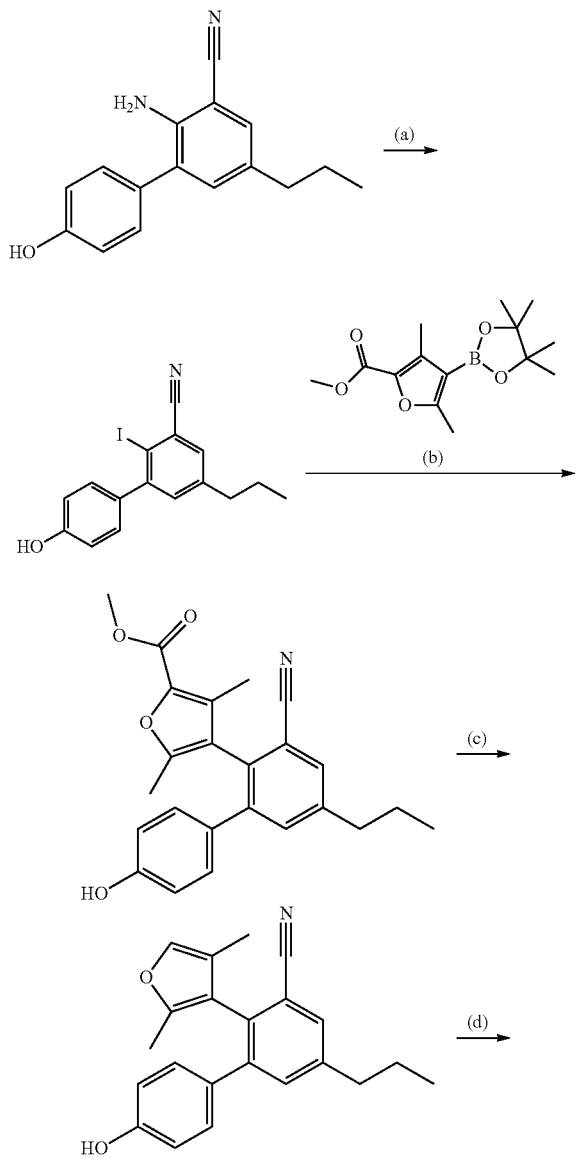

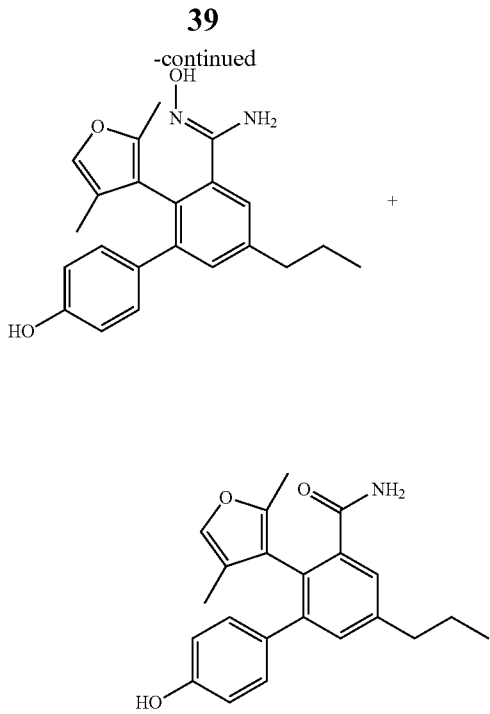

(a) CH$_2$I$_2$, t-butyl nitrite, MeCN; (b) Pd(OAc)$_2$, K$_2$CO$_3$, SPhos, toluene/H$_2$O; (c) 1. NaOH (aq), THF; 2. Cu$_2$O, quinoline; (e) NH$_2$OH (aq), DMSO Step (a):

2-amino-4'-hydroxy-5-propylbiphenyl-3-carbonitrile (144.0 mg, 0.57 mmol), obtained analogous to example 15 step (a), and CH$_2$I$_2$ (3057 mg, 11.4 mmol) were mixed in dry MeCN (1 mL) at 0° C. under nitrogen. t-Butyl nitrite (64.74 mg, 0.63 mmol) was added. The reaction mixture was stirred at 0° C. for 1 h and then at 50° C. for 1 h. After cooling to room temperature DCM was added, the mixture was washed with NaHSO$_3$ (aq) and filtered through a phase separator. The solvent was evaporated under reduced pressure and the crude product was purified on silica using DCM/isohexane (50-100% DCM) as mobile phase. 101 mg 4'-hydroxy-2-iodo-5-propylbiphenyl-3-carbonitrile was obtained.

Step (b):

4'-hydroxy-2-iodo-5-propylbiphenyl-3-carbonitrile (17.0 mg, 0.05 mmol), methyl 3,5-dimethyl-4-(4,4,5,5-tetramethyl-1,3,2-dioxaborolan-2-yl)furan-2-carboxylate (19.7 mg, 0.07 mmol), Pd(OAc)$_2$ (2.10 mg, 0.01 mmol), SPhos (4.37 mg, 0.01 mmol) and K$_2$CO$_3$ (19.4 mg, 0.14 mmol) were mixed in toluene/water (0.7 mL, 5:2) under nitrogen. The reaction mixture was heated in microwave at 140° C. for 20 min, cooled to room temperature and diluted with H$_2$O. The aqueous mixture was extracted with DCM and the organic phase was filtered through a phase separator. The solvent was evaporated under reduced pressure and the crude product was purified on silica using DCM/MeOH (0-2.5% MeOH) as mobile phase. 6.0 mg methyl 4-(3-cyano-4'-hydroxy-5-propylbiphenyl-2-yl)-3,5-dimethylfuran-2-carboxylate was obtained.

Step (c):

4-(3-cyano-4'-hydroxy-5-propylbiphenyl-2-yl)-3,5-dimethylfuran-2-carboxylate (6.0 mg, 0.02 mmol) was dissolved in THF (0.5 mL) and NaOH (0.04 mL, 2M) was added. The reaction mixture was heated in microwave at 130° C. for 15 min, cooled to room temperature and acidified by adding HCl (2M, aq). The aqueous mixture was extracted with DCM, the organic phase was filtered through a phase separator and the solvent was evaporated under reduced pressure. The residue was mixed with Cu$_2$O (2.20 mg, 0.02 mmol) in quinolone (0.5 mL). The mixture was heated in microwave at 195° C. for 30 min. After cooling to room temperature DCM was added, the mixture was washed with HCl (2 M, aq) and filtered through a phase separator. The solvent was evaporated under reduced pressure and the crude product was filtered through a plug of silica using DCM as mobile phase. 2-(2,4-dimethylfuran-3-yl)-4'-hydroxy-5-propyl-[1,1'-biphenyl]-3-carbonitrile (E16) was obtained. ES/MS m/z: 332.23 (M+H), 330.2 (M−H); $^1$H NMR (Acetone-d6, 500 MHz): δ 7.64 (d, 1H, J=1.8 Hz), 7.57 (d, 1H, J=1.8 Hz), 7.18 (q, 1H, J=1.1 Hz), 7.04 (m, 2H), 6.77 (m, 2H), 2.74, (t, 2H, J=7.5 Hz), 1.95 (s, 3H), 1.75 (m, 2H), 1.61 (d, 3H, J=1.1 Hz) and 0.99 (t, 3H, J=7.3 Hz).

Step (d):

2-(2,4-dimethylfuran-3-yl)-4'-hydroxy-5-propyl-[1,1'-biphenyl]-3-carbonitrile and hydroxylamine (0.11 mL, 16 M, aq) were mixed in MeOH (0.5 mL). The reaction mixture was heated in microwave at 120° C. for 30 min under nitrogen. The crude mixture was purified on preparative HPLC using MeCN/acidic H$_2$O (20-60% MeCN) as mobile phase. 1.1 mg 2-(2,4-dimethylfuran-3-yl)-N',4'-dihydroxy-5-propyl-[1,1'-biphenyl]-3-carboximidamide (E17) ES/MS m/z: 365.27 (M+H), 363.36 (M−H); $^1$H NMR (Acetone-d6, 500 MHz): δ 7.30 (d, 1H, J=2.0 Hz), 7.25 (d, 1H, J=2.0 Hz), 7.05 (q, 1H, J=1.2 Hz), 6.97 (m, 2H), 6.71 (m, 2H), 2.67, (t, 2H, J=7.7 Hz), 1.86 (s, 3H), 1.71 (m, 2H), 1.60 (d, 3H, J=1.2 Hz) and 0.99 (t, 3H, J=7.3 Hz) and 2-(2,4-dimethylfuran-3-yl)-4'-hydroxy-5-propyl-[1,1'-biphenyl]-3-carboxamide (E18) ES/MS m/z: 350.25 (M+H), 348.28 (M−H); $^1$H NMR (Acetone-d6, 500 MHz): δ 7.41 (d, 1H, J=1.8 Hz), 7.28 (d, 1H, J=1.8 Hz), 7.07 (q, 1H, J=1.3 Hz), 6.97 (m, 2H), 6.72 (m, 2H), 2.68, (t, 2H, J=7.6 Hz), 1.87 (s, 3H), 1.72 (m, 2H), 1.63 (d, 3H, J=1.3 Hz) and 0.99 (t, 3H, J=7.5 Hz) were obtained. For Example 17 the title compound was identified by $^1$H-NMR which showed that the oxime product was a single isomer, but did not confirm whether the (E) or (Z) oxime isomer had been obtained.

Examples—19-49

Examples 19-49 were prepared using a method analogous to that used to synthesise Examples—15-18 above. Full experimental details of the individual steps of the general methods are described in Examples—15-18 above. For examples 19-49 identification of the title compounds by $^1$H-NMR showed that the oxime product was a single isomer, but did not confirm whether the (E) or (Z) oxime isomer had been obtained.

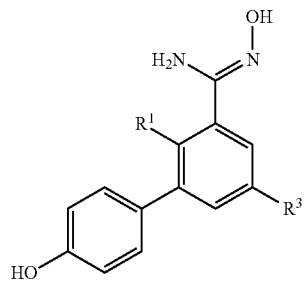

E 19 N',4'-dihydroxy-2-(4-methylthiophen-3-yl)-5-propyl-[1,1'-biphenyl]-3-carboximidamide
$R^1$ = 4-methylthiophen-3-yl $R^3$ = propyl
ES/MS m/z: 367.19 (pos. M + H), 365.21 (neg. M − H); $^1$H NMR (Acetone-d6, 500 MHz): δ 7.29 (d, 1H, J = 1.9 Hz), 7.27 (d, 1H, J = 1.9 Hz), 7.09 (d, 1H, J = 3.2 Hz), 6.94 (m, 2H), 6.86 (m, 1H), 6.66 (m, 2H), 2.68 (t, 2H, J = 7.3 Hz), 1.73 (d, 3H, J = 0.7 Hz), 1.72 (m, 1H) and 0.99 (t, 3H, J = 7.3 Hz).

E 20 N',4-dihydroxy-5'-propyl-2''-(trifluoromethoxy)-[1,1':2',1''-terphenyl]-3'-carboximidamide
$R^1$ = 2-(trifluoromethoxy)phenyl $R^3$ = propyl
ES/MS m/z: 431.28 (pos. M + H), 429.22 (neg. M − H); $^1$H NMR (Acetone-d6, 500 MHz): δ 7.36-7.34 (m, 2H), 7.29 (m, 1H), 7.25 (d, 1H, J = 1.8 Hz), 7.17 (m, 1H), 7.06 (m, 1H), 6.86 (m, 2H), 6.62 (m, 2H), 2.69 (m, 2H, J = 7.5 Hz), 1.72 (m, 2H) and 0.99 (t, 3H, J = 7.3 Hz).

E 21 2-(2,4-dimethylthiophen-3-yl)-N',4'-dihydroxy-5-propyl-[1,1'-biphenyl]-3-carboximidamide
$R^1$ = 2,4-dimethylthiophen-3-yl $R^3$ = propyl
ES/MS m/z: 381.24 (pos. M + H), 379.23 (neg. M − H); $^1$H NMR (Acetone-d6, 500 MHz): δ 7.36 (d, 1H, J = 1.8 Hz), 7.28 (d, 1H, J = 1.8 Hz), 6.90 (m, 2H), 6.68-6.65 (m, 3H), 2.68, (t, 2H, J = 7.8 Hz), 2.01 (s, 3H), 1.80 (d, 3H, J = 1.0 Hz), 1.73 (m, 2H) and 1.00 (t, 3H, J = 7.4 Hz).

E 22 N',4-dihydroxy-5'-propyl-[1,1':2',1''-terphenyl]-3'-carboximidamide
$R^1$ = phenyl $R^3$ = propyl
ES/MS m/z: 347.24 (pos. M + H), 345.36 (neg. M − H); $^1$H NMR (Acetone-d6, 500 MHz): δ 7.26 (d, 1H, J = 1.9 Hz), 7.23 (d, 1H, J = 1.9 Hz), 7.15-7.09 (m, 5H), 6.85 (m, 2H), 6.61 (m, 2H), 2.67 (t, 2H, J = 7.5 Hz), 1.72 (m, 2H) and 1.00 (t, 3H, J = 7.4 Hz).

E 23 2-((E)-2-cyclopropylvinyl)-N',4'-dihydroxy-5-propyl-[1,1'-biphenyl]-3-carboximidamide
$R^1$ = (E)-2-cyclopropylvinyl $R^3$ = propyl
ES/MS m/z: 337.24 (pos. M + H), 335.24 (neg. M − H); $^1$H NMR (Acetone-d6, 500 MHz): δ 7.14 (m, 2H, 7.10 (d, 1H, J = 1.7 Hz), 7.05 (d, 1H, J = 1.7 Hz), 6.87 (m, 2H), 6.34 (d, 1H, J = 16.0 Hz), 5.24 (dd, 1H, J = 16.0, 8.8 Hz), 2.58 (t, 2H, J = 7.4 Hz), 1.64 (m, 2H), 1.33 (m, 1H), 0.99 (t, 3H, J = 7.4 Hz), 0.62 (m, 2H) and 0.21 (m, 2H).

E 24 N',4'-dihydroxy-2-(3-methylbut-2-en-2-yl)-5-propyl-[1,1'-biphenyl]-3-carboximidamide
$R^1$ = 3-methylbut-2-en-2-yl $R^3$ = propyl
ES/MS m/z: 339.27 (pos. M + H), 337.3 (neg. M − H); $^1$H NMR (Acetone-d6, 500 MHz): δ 7.21 (d, 1H, J = 1.9 Hz), 7.11 (d, 1H, J = 1.9 Hz), 7.09 (m, 2H), 6.81 (m, 2H), 2.60 (t, 2H, J = 7.4 Hz), 1.67 (m, 2H), 1.66 (s, 3H), 1.55 (s, 3H), 1.35 (s, 3H) and 0.96 (t, 3H, J = 7.5 Hz).

E 25 N',4-dihydroxy-3''-methyl-5'-propyl-[1,1':2',1''-terphenyl]-3'-carboximidamide
$R^1$ = o-tolyl $R^3$ = propyl
ES/MS m/z: 361.24 (pos. M + H), 358.31 (neg. M − H); $^1$H NMR (Acetone-d6, 500 MHz): δ 7.26 (d, 1H, J = 1.9 Hz), 7.22 (d, 1H, J = 1.9 Hz), 7.02 (m, 1H), 6.96-6.94 (m, 2H), 6.89 (m, 1H), 6.86 (m, 2H), 6.62 (m, 2H), 2.66 (t, 2H, J = 7.3 Hz), 2.17 (s, 3H), 1.72 (m, 2H) and 0.99 (t, 3H, J = 7.3 Hz).

E 26 5''-fluoro-N',4-dihydroxy-2''-methyl-5'-propyl-[1,1':2',1''-terphenyl]-3'-carboximidamide
$R^1$ = 5-fluoro-2-methylphenyl $R^3$ = propyl
ES/MS m/z: 379.22 (pos. M + H), 377.25 (neg. M − H); $^1$H NMR (Acetone-d6, 500 MHz): δ 7.30 (d, 1H, J = 1.8 Hz), 7.25 (d, 1H, J = 1.8 Hz), 6.98-6.89 (m, 4H), 6.82 (m, 1H), 6.63 (m, 2H), 2.69 (m, 2H), J = 7.8 Hz), 1.82 (s, 3H), 1.72 (m, 2H) and 1.00 (t, 3H, J = 7.3 Hz).

E 27 2''-ethyl-N',4-dihydroxy-5'-propyl-[1,1':2',1''-terphenyl]-3'-carboximidamide
$R^1$ = 2-ethylphenyl $R^3$ = propyl
ES/MS m/z: 375.25 (pos. M + H), 373.28 (neg. M − H); $^1$H NMR (Acetone-d6, 500 MHz): δ 7.32 (d, 1H, J = 1.8 Hz), 7.24 (d, 1H, J = 1.8 Hz), 7.16-7.13 (, 2H), 7.09-7.03 (m, 2H), 6.87 (m, 2H), 6.59 (m, 2H), 2.68 (t, 2H, J = 7.4 Hz), 2.31 (m, 1H), 2.12 (m, 1H), 1.72 (m, 2H), 1.00 (t, 3H, J = 7.6 Hz) and 0.90 (t, 3H, J = 7.6 Hz).

E 28 N',4'-dihydroxy-5-propyl-2-(thiophen-2-yl)-[1,1'-biphenyl]-3-carboximidamide
$R^1$ = thiophen-2-yl $R^3$ = propyl
ES/MS m/z: 353.19 (pos. M + H), 351.23 (neg. M − H); $^1$H NMR (Acetone-d6, 500 MHz): δ 7.29 (dd, 1H, J = 5.0, 1.0 Hz), 7.26 (d, 1H, J = 1.7 Hz), 7.23 (d, 1H, J = 1.7 Hz), 6.95 (m, 2H), 6.86 (dd, 1H, J = 5.0, 3.4 Hz), 6.81 (dd, 1H, J = 3.4, 1.0 Hz), 6.68 (m, 2H), 2.66 (t, 2H, J = 7.2 Hz), 1.70 (m, 2H) and 0.98 (t, 3H, 7.2 Hz).

E 29 N',4'-dihydroxy-5-propyl-2-(quinolin-5-yl)-[1,1'-biphenyl]-3-carboximidamide
$R^1$ = quinolin-5-yl $R^3$ = propyl
ES/MS m/z: 398.24 (pos. M + H), 396.27 (neg. M − H); $^1$H NMR (MeOD, 500 MHz): δ 8.67 (dd, 1H, J = 4.3, 1.8 Hz), 7.90-7.86 (m, 2H), 7.66 (m, 1H), 7.51 (dd, 1H, J = 7.2, 1.0 Hz), 7.41 (s, 2H), 7.28 (dd, 1H, J = 8.5, 4.3 Hz), 6.74 (m, 2H), 6.36 (m, 2H), 2.77 (t, 2H, J = 7.6 Hz), 1.78 (m, 2H) and 1.05 (t, 3H, 7.4 Hz).

E 30 3''-chloro-N',4-dihydroxy-5'-propyl-[1,1':2',1''-terphenyl]-3'-carboximidamide
$R^1$ = 3-chlorophenyl $R^3$ = propyl
ES/MS m/z: 381.17 (pos. M + H), 379.21 (neg. M − H); $^1$H NMR (Acetone-d6, 500 MHz): δ 7.28 (d, 1H, J = 1.4 Hz), 7.25 (d, 1H, J = 1.4 Hz), 7.17-7.12 (m, 3H), 7.04 (m, 1H), 6.86 (m, 2H), 6.65 (m, 2H), 2.68 (t, 2H, J = 7.5 Hz), 1.71 (m, 2H) and 0.99 (t, 3H, J = 7.3 Hz).

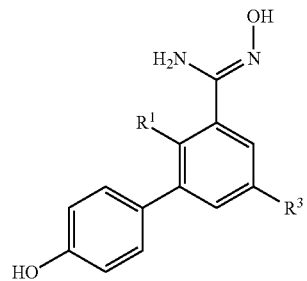

E 31  N',4'-dihydroxy-5-propyl-2-(pyridin-3-yl)-[1,1'-biphenyl]-3-carboximidamide
R¹ = pyridin-3-yl          R³ = propyl
ES/MS m/z: 348.27 (pos. M + H), 346.34 (neg. M − H); ¹H NMR (MeOD, 500 MHz): δ 8.31 (dd, 1H, J = 4.9, 1.5 Hz), 8.22 (d, 1H, J = 1.5 Hz), 7.61 (m, 1H), 7.37 (d, 1H, J = 1.9 Hz), 7.36 (d, 1H, J = 1.9 Hz), 7.28 (dd, 1H, J = 4.9, 7.8 Hz), 6.82 (m, 2H), 6.59 (m, 2H), 2.72 (t, 2H, J = 7.5 Hz), 1.73 (m, 2H) and 1.00 (t, 3H, J = 7.4 Hz).

E 32  2-(benzofuran-5-yl)-N',4'-dihydroxy-5-propyl-[1,1'-biphenyl]-3-carboximidamide
R¹ = benzofuran-5-yl          R³ = propyl
ES/MS m/z: 387.25 (pos. M + H), 385.35 (neg. M − H); ¹H NMR (Acetone-d6, 500 MHz): δ 7.75 (d, 1H, J = 2.2 Hz), 7.38 (d, 1H, J = 1.6 Hz), 7.30 (d, 1H, J = 8.6 Hz), 7.28 (d, 1H, J = 1.8 Hz), 7.24 (d, 1H, J = 1.8 Hz), 7.05 (dd, 1H, J = 8.6, 1.9 Hz), 6.86 (m, 2H), 6.75 (dd, 1H, J = 2.2, 0.8 Hz), 6.58 (m, 2H), 2.68 (t, 2H, J = 7.3 Hz), 1.72 (m, 2H) and 1.01 (t, 3H, 7.3 Hz).

E 33  4''-chloro-N',4-dihydroxy-5'-propyl-[1,1':2',1''-terphenyl]-3'-carboximidamide
R¹ = 4-chlorophenyl          R³ = propyl
ES/MS m/z: 381.23 (pos. M + H), 379.25 (neg. M − H); ¹H NMR (Acetone-d6, 500 MHz): δ 7.26 (d, 1H, J = 1.8 Hz), 7.23 (d, 1H, J = 1.8 Hz), 7.16 (m, 2H), 7.09 (m, 2H), 6.86 (m, 2H), 6.68 (m, 2H), 2.67 (t, 2H, J = 7.7 Hz), 1.71 (m, 2H) and 0.99 (t, 3H, 7.5 Hz).

E 34  N',4-dihydroxy-5-propyl-2-(pyridin-4-yl)-[1,1'-biphenyl]-3-carboximidamide
R¹ = pyridin-4-yl          R³ = propyl
ES/MS m/z: 348.29 (pos. M + H), 346.33 (neg. M − H); ¹H NMR (MeOD, 500 MHz): δ 8.28 (m, 2H, 7.33 (d, 1H, J = 1.8 Hz), 7.31 (d, 1H, J = 1.8 Hz), 7.18 (m, 2H), 6.83 (m, 2H), 6.59 (m, 2H), 2.70 (t, 2H, J = 7.4 Hz), 1.72 (m, 2H) and 1.00 (t, 3H, 7.3 Hz).

E 35  N',4'-dihydroxy-2-(1-phenylvinyl)-5-propyl-[1,1'-biphenyl]-3-carboximidamide
R¹ = 1-phenylvinyl          R³ = propyl
ES/MS m/z: 373.27 (pos. M + H), 371.32 (neg. M − H); ¹H NMR (Acetone-d6, 500 MHz): δ 7.28 (d, 1H, J = 1.6 Hz), 7.13 (d, 1H, J = 1.6 Hz), 7.10-7.05 (m, 5H), 6.97 (m, 2H), 6.59 (m, 2H), 5.67 (d, 1H, J = 1.3 Hz), 5.23 (d, 1H, J = 1.3 Hz), 2.66 (t, 2H, J = 7.5 Hz), 1.70 (m, 2H) and 0.98 (t, 3H, 7.4 Hz).

E 36  2-(5-chlorothiophen-2-yl)-N',4'-dihydroxy-5-propylbiphenyl-3-carboximidamide
R¹ = 5-chlorothiophen-2-yl          R³ = propyl
ES/MS m/z: 387.19 (pos. M + H), 385.28 (neg. M − H); ¹H NMR (Acetone-d6, 500 MHz): δ 7.25 (d, 1H, J = 1.9 Hz), 7.23 (d, 1H, J = 1.9 Hz), 7.00 (m, 2H), 6.77 (d, 1H, J = 3.8 Hz), 6.73 (m, 2H), 6.62 (d, 1H, J = 3.8 Hz), 2.66 (t, 2H, J = 7.3 Hz), 1.69 (m, 2H) and 0.98 (t, 3H, 7.3 Hz).

E 37  5''-fluoro-N',4-dihydroxy-2''-methoxy-5'-propyl-[1,1':2',1''-terphenyl]-3'-carboximidamide
R¹ = 5-fluoro-2-methoxyphenyl          R³ = propyl
ES/MS m/z: 395.24 (pos. M + H), 393.26 (neg. M − H); ¹H NMR (Acetone-d6, 500 MHz): δ 7.27 (d, 1H, J = 1.5 Hz), 7.20 (d, 1H, J = 1.5 Hz), 6.92-6.87 (m, 3H), 6.79-6.73 (m, 2H), 6.63 (m, 2H), 3.52 (s, 3H), 2.67 (t, 2H, J = 7.6 Hz), 1.72 (m, 2H) and 1.00 (t, 3H, 7.6 Hz).

E 38  N',4-dihydroxy-2-(isoquinolin-6-yl)-5-propyl-[1,1'-biphenyl]-3-carboximidamide
R¹ = isoquinolin-6-yl          R³ = propyl
ES/MS m/z: 398.25 (pos. M + H), 396.29 (neg. M − H); ¹H NMR (MeOD, 500 MHz): δ 9.12 (s, 1H), 8.35 (d, 1H, J = 6.1 Hz), 7.86 (d, 1H, J = 8.8 Hz), 7.73 (s, 1H), 7.66 (d, 1H, J = 5.7 Hz), 7.40 (dd, 1H, J = 8.5, 1.5 Hz), 7.37 (d, 1H, J = 1.7 Hz), 7.36 (d, 1H, J = 1.7 Hz), 6.84 (m, 2H), 6.50 (m, 2H), 2.73 (t, 2H, J = 7.8 Hz), 1.75 (m, 2H) and 1.02 (t, 3H, 7.4 Hz).

E 39  2-(benzofuran-3-yl)-N',4'-dihydroxy-5-propyl-[1,1'-biphenyl]-3-carboximidamide
R¹ = benzofuran-3-yl          R³ = propyl
ES/MS m/z: 387.2 (pos. M + H), 385.24 (neg. M − H); ¹H NMR (Acetone-d6, 500 MHz): δ 7.59 (s, 1H), 7.37 (m, 1H), 7.32 (d, 1H, J = 1.8 Hz), 7.31 (d, 1H, J = 1.8 Hz), 7.15 (m, 1H), 7.09 (d, 1H, J = 7.7 Hz), 7.02 (m, 2H), 6.98 (m, 1H), 6.57 (m, 2H), 2.71 (t, 2H, J = 7.3 Hz), 1.74 (m, 2H) and 1.01 (t, 3H, 7.3 Hz).

E 40  5''-fluoro-N',4-dihydroxy-2''-methoxy-5'-(trifluoromethyl)-[1,1':2',1''-terphenyl]-3'-carboximidamide
R¹ = 5-fluoro-2-methoxyphenyl          R³ = CF₃
ES/MS m/z: 421.2 (pos. M + H), 419.24 (neg. M − H); ¹H NMR (Acetone-d6, 500 MHz): δ 7.72 (d, 1H, J = 1.3 Hz), 7.64 (d, 1H, J = 1.3 Hz), 6.98-6.94 (m, 3H), 6.84-6.81 (m, 2H), 6.68 (m, 2H) and 3.53 (s, 3H).

E 41  5''-fluoro-N',4-dihydroxy-2''-methyl-5'-(trifluoromethyl)-[1,1':2',1''-terphenyl]-3'-carboximidamide
R¹ = 5-fluoro-2-methylphenyl          R³ = CF₃
ES/MS m/z: 405.28 (pos. M + H), 403.29 (neg. M − H); ¹H NMR (Acetone-d6, 500 MHz): δ 7.75 (d, 1H, J = 1.4 Hz), 7.70 (d, 1H, J = 1.4 Hz), 7.04-6.96 (m, 4H), 6.89 (m, 1H), 6.68 (m, 2H) and 1.84 (s, 3H).

E 42  N',4-dihydroxy-2''-methyl-5'-(trifluoromethyl)-[1,1':2',1''-terphenyl]-3'-carboximidamide
R¹ = o-tolyl          R³ = CF₃
ES/MS m/z: 387.26 (pos. M + H), 385.3 (neg. M − H); ¹H NMR (Acetone-d6, 500 MHz): δ 7.75 (d, 1H, J = 1.5 Hz), 7.68 (d, 1H, J = 1.5 Hz), 7.19 (dd, 1H, J = 7.3, 1.5 Hz), 7.15-7.07 (m, 2H), 7.02 (d, 1H, J = 7.3 Hz), 6.94 (m, 2H), 6.64 (m, 2H) and 1.88 (s, 3H).

E 43  N',4-dihydroxy-5'-(trifluoromethyl)-[1,1':2',1''-terphenyl]-3'-carboximidamide
R¹ = phenyl          R³ = CF₃
ES/MS m/z: 373.2 (pos. M + H), 371.25 (neg. M − H); ¹H NMR (Acetone-d6, 500 MHz): δ 7.71 (d, 1H, J = 1.5 Hz), 7.68 (d, 1H, J = 1.5 Hz), 7.21-7.14 (m, 5H), 6.91 (m, 2H) and 6.66 (m, 2H).

-continued

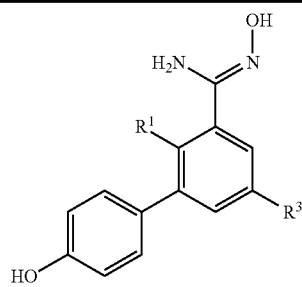

| | |
|---|---|
| E 44 | N',4'-dihydroxy-2-(4-methylthiophen-3-yl)-5-(trifluoromethyl)-[1,1'-biphenyl]-3-carboximidamide |
| | $R^1$ = 4-methylthiophen-3-yl     $R^3$ = $CF_3$ |
| | ES/MS m/z: 393.21 (pos. M + H), 391.25 (neg. M − H); $^1$H NMR (Acetone-d6, 500 MHz): δ 7.73 (d, 1H, J = 1.6 Hz), 7.69 (d, 1H, J = 1.6 Hz), 7.21 (d, 1H, J = 3.2 Hz), 7.00 (m, 2H), 6.92 (m, 1H), 6.70 (m, 2H) and 1.75 (d, 3H, J = 0.9 Hz). |
| E 45 | 2-(2,4-dimethylthiophen-3-yl)-N',4'-dihydroxy-5-(trifluoromethyl)-[1,1'-biphenyl]-3-carboximidamide |
| | $R^1$ = 2,4-dimethylthiophen-3-yl     $R^3$ = $CF_3$ |
| | ES/MS m/z: 407.2 (pos. M + H), 405.28 (neg. M − H); $^1$H NMR (Acetone-d6, 500 MHz): δ 7.80 (d, 1H, J = 1.9 Hz), 7.72 (d, 1H, J = 1.9 Hz), 6.96 (m, 2H), 6.74 (q, 1H, J = 1.1 Hz), 6.71 (m, 2H), and 1.82-1.81 (m, 6H). |
| E 46 | 2'',5''-difluoro-N',4-dihydroxy-5'-propyl-[1,1':2',1''-terphenyl]-3'-carboximidamide |
| | $R^1$ = 2,5-difluorophenyl     $R^3$ = propyl |
| | ES/MS m/z: 383.27 (pos. M + H), 381.32 (neg. M − H); $^1$H NMR (Acetone-d6, 500 MHz): δ 7.44 (s, 1H), 7.31 (s, 1H), 6.88 (m, 2H), 6.68 (m, 2H), 6.55 (d, 1H, J = 2.5 Hz), 5.74 (d, 1H, J = 2.5 Hz), 3.21 (s, 3H), 2.68 (t, 2H, J = 7.6 Hz), 1.72 (m, 2H), 1.57 (s, 3H) and 1.00 (t, 3H, 7.3 Hz). |
| E 47 | 2-(1,3-dimethyl-1H-pyrrol-2-yl)-N',4'-dihydroxy-5-propyl-[1,1'-biphenyl]-3-carboximidamide |
| | $R^1$ = 1,3-dimethyl-1H-pyrrol-2-yl     $R^3$ = propyl |
| | ES/MS m/z: 364.31 (pos. M + H), 362.31 (neg. M − H); $^1$H NMR (Acetone-d6, 500 MHz): δ 7.44 (s, 1H), 7.31 (s, 1H), 6.88 (m, 2H), 6.68 (m, 2H), 6.55 (d, 1H, J = 2.5 Hz), 5.74 (d, 1H, J = 2.5 Hz), 3.21 (s, 3H), 2.68 (t, 2H, J = 7.6 Hz), 1.72 (m, 2H), 1.57 (s, 3H) and 1.00 (t, 3H, 7.3 Hz). |
| E 48 | 3'',5''-difluoro-N',4-dihydroxy-5'-propyl-[1,1':2',1''-terphenyl]-3'-carboximidamide |
| | $R^1$ = 3,5-difluorophenyl     $R^3$ = propyl |
| | ES/MS m/z: 383.27 (pos. M + H), 381.32 (neg. M − H); $^1$H NMR (Acetone-d6, 500 MHz): δ 7.28 (d, 1H, J = 1.8 Hz), 7.25 (d, 1H, J = 1.8 Hz), 6.90 (m, 2H), 6.78 (m, 1H), 6.73-6.67 (m, 4H), 2.68 (t, 2H, J = 7.3 Hz), 1.72 (m, 2H) and 0.99 (t, 3H, J = 7.3 Hz). |
| E 49 | 2-(2,4-dimethylfuran-3-yl)-N',4'-dihydroxy-5-(trifluoromethyl)-[1,1'-biphenyl]-3-carboximidamide |
| | $R^1$ = 2,4-dimethylfuran-3-yl     $R^3$ = $CF_3$ |
| | ES/MS m/z: 383.27 (pos. M + H), 381.32 (neg. M − H); $^1$H NMR (Acetone-d6, 500 MHz): δ 7.28 (d, 1H, J = 1.8 Hz), 7.25 (d, 1H, J = 1.8 Hz), 6.90 (m, 2H), 6.78 (m, 1H), 6.73-6.67 (m, 4H), 2.68 (t, 2H, J = 7.3 Hz), 1.72 (m, 2H) and 0.99 (t, 3H, J = 7.3 Hz). |

Example 50

3'-chloro-5'-fluoro-N',4'-dihydroxy-2-(3-methylthiophen-2-yl)-5-propylbiphenyl-3-carboximidamide (E50)

Scheme 7

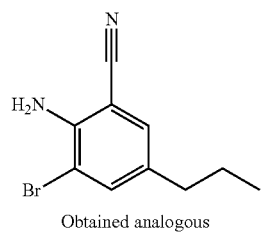

Obtained analogous to intermediate B (a)

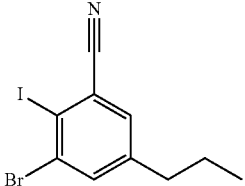

(b)

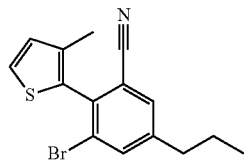

(c)

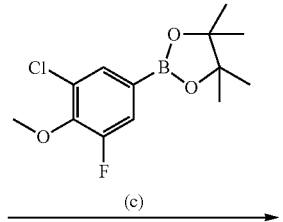

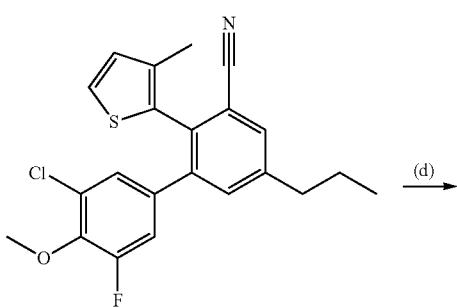

(d)

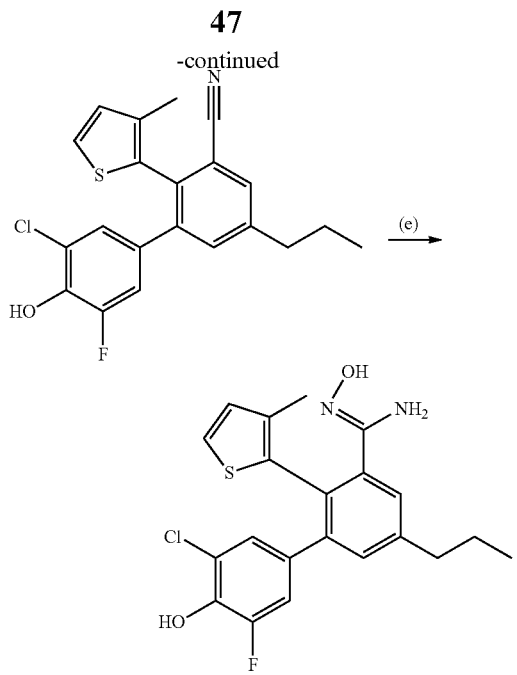

(a) CH₂I₂, t-butyl nitrite, MeCN; (b) 3-methylthiophen-2-ylboronic acid, PdCl₂(PPh₃)₂, K₂CO₃, DME/EtOH/H₂O; (c) PdCl₂(PPh₃)₂, K₂CO₃, DME/EtOH/H₂O; (d) BBr₃, DMC; (e) NH₂OH (aq), DMSO.

Step (a):

2-amino-3-bromo-5-propylbenzonitrile (296.0 mg, 1.24 mmol) and CH₂I₂ (1657 mg, 6.19 mmol) were mixed in dry MeCN (3 mL) at 0° C. under nitrogen. t-Butyl nitrite (255.3 mg, 2.48 mmol) was added. The reaction mixture was stirred at 0° C. for 0.5 h and then at 50° C. for 1 h. After cooling to room temperature DCM was added, the mixture was washed with NaHSO₃ (aq) and filtered through a phase separator. The solvent was evaporated under reduced pressure and the crude product was purified on silica using DCM/isohexane (25% DCM) as mobile phase. 320 mg 3-bromo-2-iodo-5-propylbenzonitrile was obtained.

Step (b):

2-amino-3-iodo-5-propylbenzonitrile (63 mg, 0.18 mmol), 3-methylthiophen-2-ylboronic acid (30.67 mg, 0.22 mmol), PdCl₂(PPh₃)₂ (12.63 mg, 0.02 mmol) and K₂CO₃ (74.63 mg, 0.54 mmol) were mixed in DME/EtOH/H₂O (0.51 mL, 40:10:1) under nitrogen. The reaction mixture was heated in microwave at 125° C. for 20 min, cooled to room temperature, diluted with DCM and washed with H₂O. The mixture was filtered through a phase separator, the solvent was evaporated under reduced pressure and the crude product was purified on silica using DCM/isohexane (10-50% isohexane) as mobile phase. 32 mg 3-bromo-2-(3-methylthiophen-2-yl)-5-propylbenzonitrile was obtained.

Step (c):

3-bromo-2-(3-methylthiophen-2-yl)-5-propylbenzonitrile (20 mg, 0.06 mmol), 2-(3-chloro-5-fluoro-4-methoxyphenyl)-4,4,5,5-tetramethyl-1,3,2-dioxaborolane (35.8 mg, 0.12 mmol), PdCl₂(PPh₃)₂ (4.38 mg, 0.01 mmol) and K₂CO₃ (25.9 mg, 0.19 mmol) were mixed in DME/EtOH/H₂O (1 mL, 40:10:1) under nitrogen. The reaction mixture was heated in microwave at 140° C. for 20 min, cooled to room temperature, diluted with DCM and washed with NH₄Cl (aq). The mixture was filtered through a phase separator, the solvent was evaporated under reduced pressure and the crude product was purified on silica using EtOAc/n-heptane (15% EtOAc) as mobile phase. 21 mg 3'-chloro-5'-fluoro-4'-methoxy-2-(3-methylthiophen-2-yl)-5-propylbiphenyl-3-carbonitrile was obtained.

Step (d):

3'-chloro-5'-fluoro-4'-methoxy-2-(3-methylthiophen-2-yl)-5-propylbiphenyl-3-carbonitrile (17 mg, 0.04 mmol) was dissolved in DCM (5 mL) under nitrogen and the solution was cooled to 0° C. BBr₃ (0.26 mL, 1M) was added. The reaction mixture was stirred at 0° C. for 0.5 h, at room temperature for 2 h and then at 4° C. for 16 h. HCl (1M) and H₂O were added to quench the reaction and the aqueous mixture was extracted with DCM. The organic phase was filtered through a phase separator, the solvent was evaporated under reduced pressure and the crude product was purified on silica using EtOAc/n-heptane (20% EtOAc) as mobile phase. 15.0 mg 3'-chloro-5'-fluoro-4'-hydroxy-2-(3-methylthiophen-2-yl)-5-propylbiphenyl-3-carbonitrile was obtained.

Step (e):

3'-chloro-5'-fluoro-4'-hydroxy-2-(3-methylthiophen-2-yl)-5-propylbiphenyl-3-carbonitrile (15 mg, 0.04 mmol) and hydroxylamine (0.5 mL, 16 M, aq) were mixed in DMSO (0.3 mL). The reaction mixture was heated in microwave at 140° C. for 15 min under nitrogen. The crude mixture was purified on preparative HPLC using MeCN/acidic H₂O (5-60% MeCN) as mobile phase. 4.0 mg 3'-chloro-5'-fluoro-N',4'-dihydroxy-2-(3-methylthiophen-2-yl)-5-propyl-[1,1'-biphenyl]-3-carboximidamide (E50) was obtained. ES/MS m/z: 419.1 (M+H), 417.14 (M−H); ¹H NMR (MeOD, 500 MHz): δ 7.34 (d, 1H, J=1.7 Hz), 7.33 (d, 1H, J=1.7 Hz), 7.26 (d, 1H, J=5.2 Hz), 6.88 (t, 1H, J=1.8 Hz), 6.74-6.72 (m, 2H), 2.70 (t, 2H, J=7.4 Hz), 1.80 (s, 3H), 1.73 (m, 2H) and 1.00 (t, 3H, J=7.3 Hz). The title compound was identified by ¹H-NMR which showed that the oxime product was a single isomer, but did not confirm whether the (E) or (Z) oxime isomer had been obtained.

Example 51

N'-hydroxy-3-(1H-indazol-5-yl)-2-(3-methylthiophen-2-yl)-5-propylbenzimidamide (E51)

Scheme 8

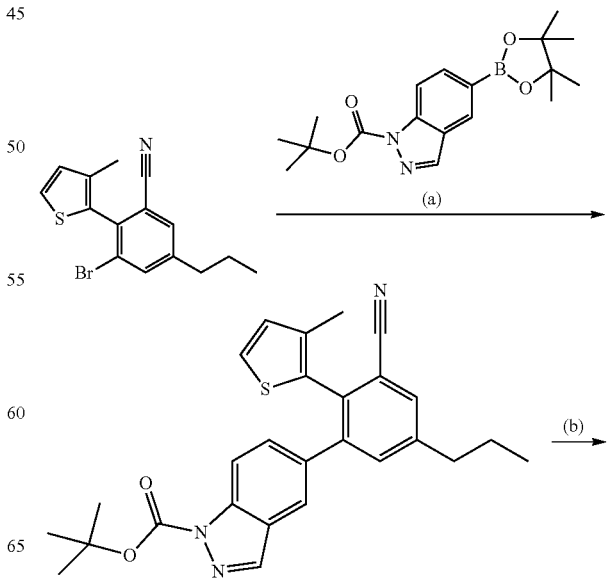

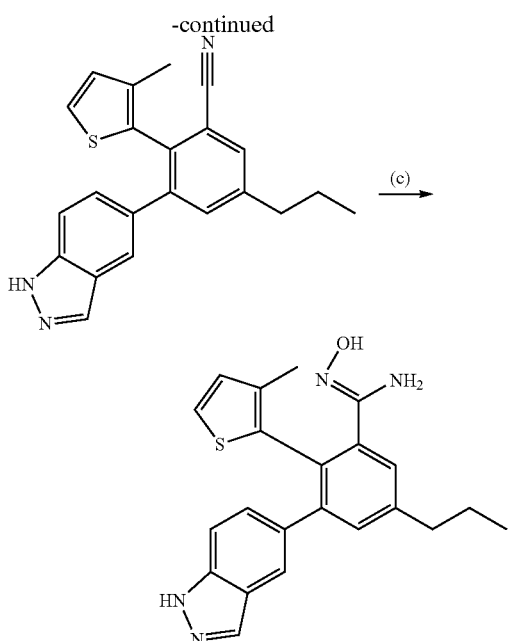

(a) K₂CO₃, PdCl₂(PPh₃)₂, DME/EtOH/H₂O; (b) CF₃COOH, DCM; (d) NH₂OH, DMSO

Step (a):

3-bromo-2-(3-methylthiophen-2-yl)-5-propylbenzonitrile (20 mg, 0.06 mmol), tert-butyl 5-(4,4,5,5-tetramethyl-1,3,2-dioxaborolan-2-yl)-1H-indazole-1-carboxylate (43.0 mg, 0.12 mmol), PdCl₂(PPh₃)₂ (4.38 mg, 0.01 mmol) and K₂CO₃ (25.9 mg, 0.19 mmol) were mixed in DME/EtOH/H₂O (1 mL, 40:10:1) under nitrogen. The reaction mixture was heated in microwave at 140° C. for 20 min, cooled to room temperature, diluted with DCM and washed with NH₄Cl (aq). The mixture was filtered through a phase separator and the solvent was evaporated under reduced pressure. 12 mg crude product tert-butyl 5-(3-cyano-2-(3-methylthiophen-2-yl)-5-propylphenyl)-1H-indazole-1-carboxylate was obtained.

Step (b):

tert-butyl 5-(3-cyano-2-(3-methylthiophen-2-yl)-5-propylphenyl)-1H-indazole-1-carboxylate was dissolved in DCM (2 mL) and TFA (2 mL). The mixture was stirred at room temperature for 1 h. NaHCO₃ (aq, sat) was added and the aqueous mixture was extracted with DCM. The organic phase was evaporated under reduced pressure and 9.0 mg 3-(1H-indazol-5-yl)-2-(3-methylthiophen-2-yl)-5-propylbenzonitrile was obtained as a crude mixture.

Step (c):

3-(1H-indazol-5-yl)-2-(3-methylthiophen-2-yl)-5-propylbenzonitrile and hydroxylamine (0.3 mL, 16 M, aq) were mixed in DMSO (0.3 mL). The reaction mixture was heated in microwave at 140° C. for 15 min under nitrogen. The crude mixture was purified on preparative HPLC using MeCN/acidic H₂O (5-60% MeCN) as mobile phase. 2.5 mg N'-hydroxy-3-(1H-indazol-5-yl)-2-(3-methylthiophen-2-yl)-5-propylbenzimidamide (E51) was obtained. ES/MS m/z: 391.25 (M+H); The title compound was identified by ¹H-NMR which showed that the oxime product was a single isomer, but did not confirm whether the (E) or (Z) oxime isomer had been obtained.

Examples 52-58

Examples 52-58 were prepared using a method analogous to that used to synthesise Example 50 above. Full experimental details of the individual steps of the general methods are described in Example 50 above. For examples 52-58 identification of the title compounds by ¹H-NMR showed that the oxime product was a single isomer, but did not confirm whether the (E) or (Z) oxime isomer had been obtained.

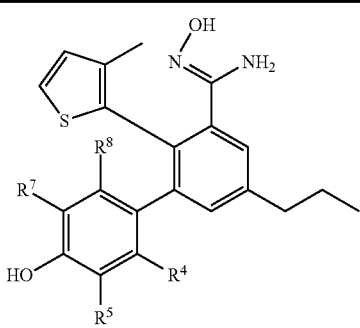

E 52     3'-fluoro-N',4'-dihydroxy-2-(3-methylthiophen-2-yl)-5-propyl-[1,1'-biphenyl]-3-carboximidamide
$R^4$ = H      $R^5$ = F      $R^7$ = H      $R^8$ = H
ES/MS m/z: 385.22 (pos. M + H), 383.2 (neg. M − H); ¹H NMR (MeOD, 500 MHz): δ 7.35 (d, 1H, J = 1.6 Hz), 7.32 (d, 1H, J = 1.6 Hz), 7.25 (d, 1H, J = 5.2 Hz), 6.77-6.71 (m, 4H), 2.70 (t, 2H, J = 7.5 Hz), 1.77 (s, 3H), 1.72 (m, 2H) and 1.00 (t, 3H, J = 7.4 Hz).

E 53     3'-chloro-N',4'-dihydroxy-2-(3-methylthiophen-2-yl)-5-propyl-[1,1'-biphenyl]-3-carboximidamide
$R^4$ = H      $R^5$ = Cl      $R^7$ = H      $R^8$ = H
ES/MS m/z: 401.18 (pos. M + H), 399.19 (neg. M − H); ¹H NMR (MeOD, 500 MHz): δ 7.31 (s, 2H), 7.24 (d, 1H, J = 5.1 Hz), 7.01 (d, 1H, J = 2.2 Hz), 6.86 (dd, 1H, J = 8.4, 2.2 Hz), 6.71 (d, 1H, J = 8.4 Hz), 6.70 (d, 1H, J = 5.1 Hz), 2.69 (t, 2H, J = 7.5 Hz), 1.77 (s, 3H), 1.72 (m, 2H) and 1.00 (t, 3H, J = 7.4 Hz).

E 54     3',5'-dichloro-N',4'-dihydroxy-2-(3-methylthiophen-2-yl)-5-propyl-[1,1'-biphenyl]-3-carboximidamide
$R^4$ = H      $R^5$ = Cl      $R^7$ = Cl      $R^8$ = H
ES/MS m/z: 435.12 (pos. M + H), 433.18 (neg. M − H); ¹H NMR (MeOD, 500 MHz): δ 7.34 (d, 1H, J = 1.4 Hz), 7.32 (d, 1H, J = 1.4 Hz), 7.26 (d, 1H, J = 5.1 Hz), 6.99 (s, 2H), 6.74 (d, 1H, J = 5.1 Hz), 2.70 (t, 2H, J = 7.6 Hz), 1.80 (s, 3H), 1.73 (m, 2H) and 1.00 (t, 3H, J = 7.3 Hz).

-continued

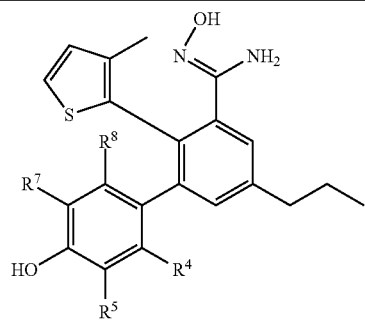

| E 55 | N',4'-dihydroxy-3'-methyl-2-(3-methylthiophen-2-yl)-5-propyl-[1,1'-biphenyl]-3-carboximidamide |
|---|---|
| $R^4$ = H | $R^5$ = Methyl | $R^7$ = H | $R^8$ = H |

ES/MS m/z: 381.24 (pos. M + H), 379.25 (neg. M − H); $^1$H NMR (MeOD, 500 MHz): δ 7.33 (d, 1H, J = 1.9 Hz), 7.28 (d, 1H, J = 1.9 Hz), 7.22 (d, 1H, J = 5.0 Hz), 6.81 (d, 1H, J = 2.1 Hz), 6.73 (dd, 1H, J = 8.2, 2.1 Hz), 6.68 (d, 1H, J = 5.0 Hz), 6.54 (d, 1H, J = 8.2 Hz), 2.69 (t, 2H, J = 7.4 Hz), 2.04 (s, 3H), 1.74 (s, 3H), 1.72 (m, 2H) and 1.00 (t, 3H, J = 7.4 Hz).

| E 56 | 2'-fluoro-N',4'-dihydroxy-2-(3-methylthiophen-2-yl)-5-propyl-[1,1'-biphenyl]-3-carboximidamide |
|---|---|
| $R^4$ = F | $R^5$ = H | $R^7$ = H | $R^8$ = H |

ES/MS m/z: 385.17 (pos. M + H), 383.21 (neg. M − H); $^1$H NMR (MeOD, 500 MHz): δ 7.33 (d, 1H, J = 1.9 Hz), 7.25 (d, 1H, J = 1.9 Hz), 7.16 (d, 1H, J = 5.0 Hz), 6.77 (t, 1H, J = 8.5 Hz), 6.67 (d, 1H, J = 5.0 Hz), 6.40-6.37 (m, 2H), 2.68 (t, 2H, J = 7.5 Hz), 1.85 (s, 3H), 1.71 (m, 2H) and 0.99 (t, 3H, J = 7.7 Hz).

| E 57 | 2',3'-difluoro-N',4'-dihydroxy-2-(3-methylthiophen-2-yl)-5-propyl-[1,1'-biphenyl]-3-carboximidamide |
|---|---|
| $R^4$ = F | $R^5$ = F | $R^7$ = H | $R^8$ = H |

ES/MS m/z: 403.14 (pos. M + H), 401.25 (neg. M − H); $^1$H NMR (MeOD, 500 MHz): δ 7.37 (d, 1H, J = 1.9 Hz), 7.28 (br s, 1H), 7.18 (d, 1H, J = 5.1 Hz), 6.69 (d, 1H, J = 5.1 Hz), 6.58 (m, 1H), 6.50 (m, 1H), 2.69 (t, 2H, J = 7.4 Hz), 1.88 (s, 3H), 1.72 (m, 2H) and 1.00 (t, 3H, J = 7.6 Hz).

| E 58 | 2',5'-difluoro-N',4'-dihydroxy-2-(3-methylthiophen-2-yl)-5-propyl-[1,1'-biphenyl]-3-carboximidamide |
|---|---|
| $R^4$ = F | $R^5$ = H | $R^7$ = F | $R^8$ = H |

ES/MS m/z: 403.21 (pos. M + H), 401.31 (neg. M − H); $^1$H NMR (MeOD, 500 MHz): δ 7.37 (s, 1H), 7.31 (s, 1H), 7.22 (d, 1H, J = 5.1 Hz), 6.71 (d, 1H, J = 5.1 Hz), 6.64 (dd, 1H, J = 11.4, 6.9 Hz), 6.55 (dd, 1H, J = 10.8, 7.5 Hz), 2.70 (t, 2H, J = 7.5 Hz), 1.87 (s, 3H), 1.72 (m, 2H) and 1.00 (t, 3H, J = 7.2 Hz).

Example 59

N',4'-dihydroxy-2-(2-methylallyl)-5-propyl-[1,1'-biphenyl]-3-carboximidamide (E59)

Scheme 9

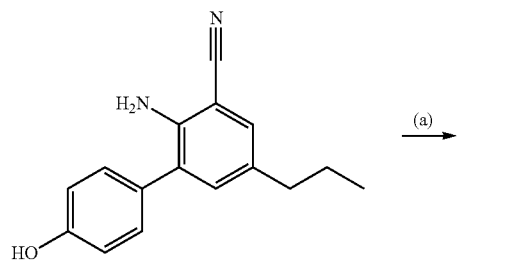

(a) ↓

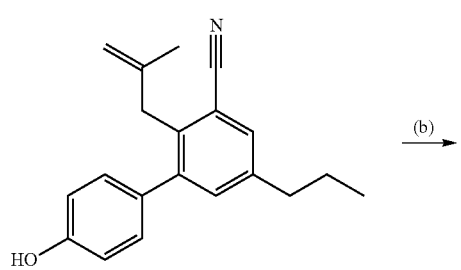

(b) ↓

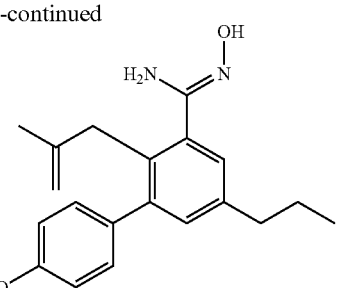

(a) 3-Bromo-2-methylpropene, t-butyl nitrite, MeCN;
(b) NH$_2$OH, DMSO

Step (a):

2-amino-4'-hydroxy-5-propylbiphenyl-3-carbonitrile (30.0 mg, 0.12 mmol), obtained analogous to example 15 step (a), was dissolved in dry MeCN under nitrogen. 3-Bromo-2-methylpropene (80.3 mg, 0.59 mmol) and t-butyl nitrite (14.7 mg, 0.14 mmol) were added. The reaction mixture was stirred at 60° C. for 1 h. After cooling to room temperature DCM was added, the mixture was washed with H$_2$O and filtered through a phase separator. The solvent was evaporated under reduced pressure and the crude product was purified on preparative HPLC using MeCN/acidic H$_2$O (20-100% MeCN) as mobile phase. 4.0 mg 4'-hydroxy-2-(2-methylallyl)-5-propylbiphenyl-3-carbonitrile was obtained.

Step (b):

4'-hydroxy-2-(2-methylallyl)-5-propylbiphenyl-3-carbonitrile (4.0 mg, 0.01 mmol) and hydroxylamine (0.1 mL, 16 M, aq) were mixed in DMSO (0.4 mL). The reaction mixture was heated in microwave at 140° C. for 15 min under nitrogen. The crude mixture was purified on preparative HPLC using MeCN/acidic H₂O (5-60% MeCN) as mobile phase. 1.05 mg N',4'-dihydroxy-2-(2-methylallyl)-5-propyl-[1,1'-biphenyl]-3-carboximidamide (E59) was obtained. ES/MS m/z: 325.28 (M+H), 323.36 (M−H); ¹H NMR (Acetone-d6, 500 MHz): δ 7.19 (d, 2H, J=2.1 Hz), 7.13 (m, 2H), 7.03 (d, 1H, J=2.1 Hz), 6.84 (m, 2H), 4.67 (m, 1H), 4.23 (m, 1H), 3.44 (s, 2H), 2.60 (t, 2H, J=7.5 Hz), 1.66 (m, 2H), 1.56 (s, 3H) and 0.94 (t, 3H, J=7.3 Hz). The title compound was identified by ¹H-NMR which showed that the oxime product was a single isomer, but did not confirm whether the (E) or (Z) oxime isomer had been obtained.

Example 60

2-allyl-N',4'-dihydroxy-5-propyl-[1,1'-biphenyl]-3-carboximidamide (E60)

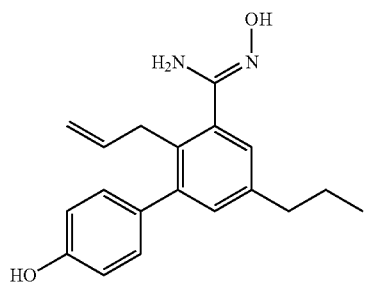 [SMILES: C=CCc1c(/C(N)=N/O)cc(CCC)cc1-c1ccc(O)cc1]

Example 60 was prepared using a method analogous to that used to synthesise Example 60 above. Full experimental details of the individual steps of the general methods are described in Example 60 above. ES/MS m/z: 311.28 (M+H), 309.29 (M−H); ¹H NMR (Acetone-d6, 500 MHz): δ 7.16 (d, 1H, J=1.9 Hz), 7.11 (m, 2H), 7.01 (d, 1H, J=1.9 Hz), 6.87 (m, 2H), 5.83 (m, 1H), 4.76 (m, 1H), 4.64 (m, 1H), 3.51 (m, 2H), 2.58 (t, 2H, J=7.4 Hz), 1.64 (m, 2H) and 0.94 (t, 3H, J=7.2 Hz). The title compound was identified by ¹H-NMR which showed that the oxime product was a single isomer, but did not confirm whether the (E) or (Z) oxime isomer had been obtained.

Example 61

N',4'-dihydroxy-5-propyl-2-vinyl-[1,1'-biphenyl]-3-carboximidamide (E 61)

Scheme 10

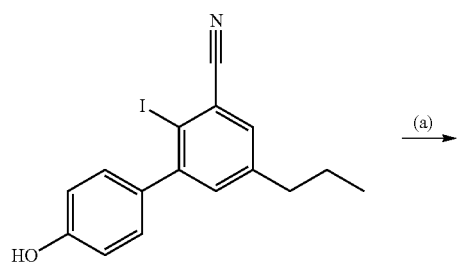

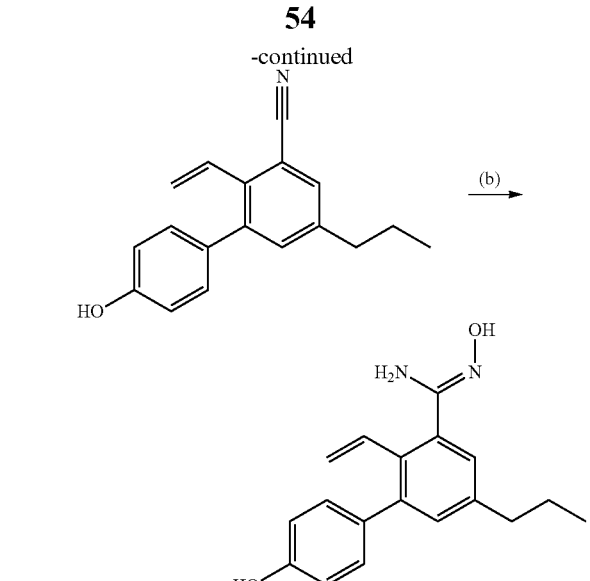

(a) Tributylethenylstannane, PdCl₂(PPh₃)₂, dioxane;
(b) NH₂OH, (aq), DMSO.

Step (a):
4'-hydroxy-2-iodo-5-propylbiphenyl-3-carbonitrile (20 mg, 0.06 mmol), obtained analogous to example 16 step (a), tributylethenylstannane (34.9 mg, 0.11 mmol), PdCl₂(PPh₃)₂ (3.87 mg, 0.01 mmol) were mixed in dioxane (1.5 mL) under nitrogen. The reaction mixture was heated in microwave at 130° C. for 20 min, cooled to room temperature, diluted with DCM and washed with H₂O. The mixture was filtered through a phase separator and the solvent was evaporated under reduced pressure. The crude product was purified on preparative HPLC using MeCN/acidic H₂O (20-100% MeCN) as mobile phase. 9.0 mg 4'-hydroxy-5-propyl-2-vinylbiphenyl-3-carbonitrile was obtained.

Step (b):
4'-hydroxy-5-propyl-2-vinylbiphenyl-3-carbonitrile (7.0 mg, 0.03 mmol) was treated with hydroxylamine (0.1 mL, 16 M, aq) in DMSO (0.4 mL). The reaction mixture was heated in microwave at 140° C. for 15 min under nitrogen. The crude mixture was purified on preparative HPLC using MeCN/acidic H₂O (5-50% MeCN) as mobile phase. 1.05 mg N',4'-dihydroxy-5-propyl-2-vinyl-[1,1'-biphenyl]-3-carboximidamide (E61) ES/MS m/z: 297.23 (M+H), 295.29 (M−H); ¹H NMR (Acetone-d6, 500 MHz): δ 7.16-7.13 (m, 3H), 7.08 (d, 1H, J=1.9 Hz), 6.87 (m, 2H), 6.69 (dd, 1H, J=17.9, 11.6 Hz), 5.31 (dd, 1H, J=17.9, 2.1 Hz), 5.14 (dd, 1H, J=11.6, 2.1 Hz), 2.60 (t, 2H, J=7.6 Hz), 1.66 (m, 2H) and 0.95 (t, 3H, J=7.3 Hz) was obtained. The title compound was identified by ¹H-NMR which showed that the oxime product was a single isomer, but did not confirm whether the (E) or (Z) oxime isomer had been obtained.

Examples 62-66

Examples 62-66 were prepared using a method analogous to that used to synthesise Example 61 above. Full experimental details of the individual steps of the general methods are described in Example 61 above. For examples 62-66 identification of the title compounds by ¹H-NMR showed that the oxime product was a single isomer, but did not confirm whether the (E) or (Z) oxime isomer had been obtained.

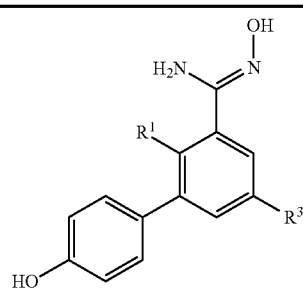

| | | |
|---|---|---|
| E 62 | 5-bromo-N',4'-dihydroxy-2-(1-methyl-1H-imidazol-5-yl)-[1,1'-biphenyl]-3-carboximidamide | |
| $R^1$ = 1-methyl-1H-imidazol-5-yl | | $R^3$ = Br |
| ES/MS m/z: 390.12; 187.12 (pos. M + H), 388.26; 387.16 (neg. M − H); $^1$H NMR (Acetone-d6, 500 MHz): δ 7.63 (d, 1H, J = 2.2 Hz), 7.62 (d, 1H, J = 2.2 Hz), 7.38 (s, 1H), 7.00 (m, 2H), 6.82 (s, 1H), 6.72 (m, 2H) and 2.52 (s, 3H). | | |
| E 63 | N',4'-dihydroxy-5-propyl-2-(pyridin-2-yl)-[1,1'-biphenyl]-3-carboximidamide | |
| $R^1$ = pyridin-2-yl | | $R^3$ = propyl |
| ES/MS m/z: 348.25 (pos. M + H), 346.26 (neg. M − H); $^1$H NMR (Acetone-d6, 500 MHz): δ 8.45 (m, 1H, 7.50 (m, 1H), 7.33 (d, 1H, J = 1.8 Hz), 7.25 (m, 1H, J = 1.8 Hz), 7.13 (m, 1H), 7.00 (m, 1H), 6.86 (m, 2H), 6.61 (m, 2H), 2.69 (t, 2H, J = 7.6 Hz), 1.72 (m, 2H) and 1.00 (t, 3H, J = 7.4 Hz). | | |
| E 64 | N',4'-dihydroxy-2-(2-methoxythiazol-4-yl)-5-propyl-[1,1'-biphenyl]-3-carboximidamide | |
| $R^1$ = 2-methoxythiazol-4-yl | | $R^3$ = propyl |
| ES/MS m/z: 384.2 (pos. M + H), 382.27 (neg. M − H); $^1$H NMR (Acetone-d6, 500 MHz): δ 7.24 (d, 1H, J = 1.7 Hz), 7.19 (d, 1H, J = 1.7 Hz), 6.96 (m, 2H), 6.69 (m, 2H), 6.43 (s, 1H), 3.86 (s, 3H), 2.63 (t, 2H, J = 7.3 Hz), 1.66 (m, 2H) and 0.94 (t, 3H, J = 7.5 Hz). | | |
| E 65 | N',4'-dihydroxy-5-propyl-2-(thiazol-5-yl)-[1,1'-biphenyl]-3-carboximidamide | |
| $R^1$ = thiazol-5-yl | | $R^3$ = propyl |
| ES/MS m/z: 354.24 (pos. M + H), 352.26 (neg. M − H); $^1$H NMR (Acetone-d6, 500 MHz): δ 8.77 (d, 1H, J = 0.6 Hz), 7.55 (d, 1H, J = 0.6 Hz), 7.28 (d, 1H, J = 1.8 Hz), 7.25 (d, 1H, J = 1.8 Hz), 6.94 (m, 2H), 6.71 (m, 2H), 2.68 (t, 2H, J = 7.4 Hz), 1.95 (s, 3H), 1.71 (m, 2H) and 0.99 (t, 3H, 7.5 Hz). | | |
| E 66 | N',4'-dihydroxy-5-propyl-2-(thiazol-2-yl)-[1,1'-biphenyl]-3-carboximidamide | |
| $R^1$ = thiazol-2-yl | | $R^3$ = propyl |
| ES/MS m/z: 354.21 (pos. M + H), 352.23 (neg. M − H); $^1$H NMR (Acetone-d6, 500 MHz): δ 7.69 (d, 1H, J = 3.3 Hz), 7.51 (d, 1H, J = 3.3 Hz), 7.36 (d, 1H, J = 1.9 Hz), 7.29 (d, 1H, J = 1.9 Hz), 6.96 (m, 2H), 6.68 (m, 2H), 2.71 (t, 2H, J = 7.6 Hz), 1.95 (s, 3H), 1.73 (m, 2H) and 0.99 (t, 3H, J = 7.6 Hz). | | |

Example 67

5'-ethyl-N',4-dihydroxy-[1,1':2',1''-terphenyl]-3'-carboximidamide (E67)

Scheme 11

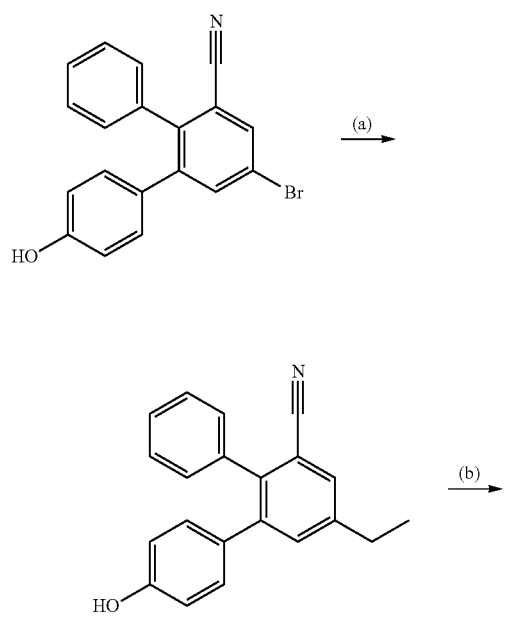

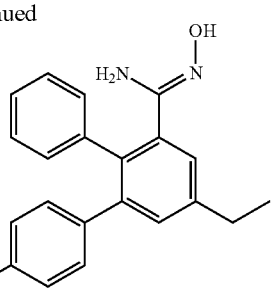

(a) Ethylboronic acid, $K_2CO_3$, PdOAc$_2$, RuPhos, toluene/$H_2O$;
(b) NH$_2$OH (aq), DMSO.

Step (a):

5'-bromo-4-hydroxy-[1,1':2',1''-terphenyl]-3'-carbonitrile (14.0 mg, 0.04 mmol), obtained analogous to example 1 step (a-d), ethylboronic acid (11.8 mg, 0.16 mmol), Pd(OAc)$_2$ (0.90 mg, 0.004 mmol), RuPhos (3.73 mg, 0.008 mmol) and $K_2CO_3$ (27.6 mg, 0.20 mmol) were mixed in toluene/water (0.55 mL, 10:1) under nitrogen. The reaction mixture was heated in microwave at 140° C. for 20 min, cooled to room temperature and diluted with NH$_4$Cl. The aqueous mixture was extracted with DCM and the organic phase was filtered through a phase separator. The solvent was evaporated under reduced pressure and the crude product was purified on preparative HPLC using MeCN/acidic $H_2O$ (20-100% MeCN) as mobile phase. 6.30 mg 5'-ethyl-4-hydroxy-[1,1': 2',1''-terphenyl]-3'-carbonitrile was obtained.

Step (b):

5'-ethyl-4-hydroxy-[1,1':2',1''-terphenyl]-3'-carbonitrile (5.70 mg, 0.02 mmol) and hydroxylamine (0.23 mL, 16 M, aq) were mixed in DMSO (0.7 mL). The reaction mixture was heated in microwave at 130° C. for 30 min under nitrogen. The crude mixture was purified on preparative HPLC using MeCN/acidic $H_2O$ (5-50% MeCN) as mobile phase. 5.30 mg 5'-ethyl-N',4-dihydroxy-[1,1':2',1''-terphenyl]-3'-carboximidamide (E67) was obtained. ES/MS m/z: 333.28 (M+H); $^1$H NMR (Acetone-d6, 500 MHz): δ 7.28 (d, 1H, J=2.0 Hz), 7.24 (d, 1H, J=2.0 Hz), 7.15-7.09 (m, 5H), 6.85 (m, 2H), 6.61 (m, 2H), 2.72 (q, 2H, J=7.6 Hz) and 1.28 (t, 3H, J=7.6 Hz). The title compound was identified by $^1$H-NMR which showed that the oxime product was a single isomer, but did not confirm whether the (E) or (Z) oxime isomer had been obtained.

Examples 68-71

Examples 68-71 were prepared using a method analogous to that used to synthesise Example 67 above. Full experimental details of the individual steps of the general methods are described in Example 67 above. For examples 68-71 identification of the title compounds by $^1$H-NMR showed that the oxime product was a single isomer, but did not confirm whether the (E) or (Z) oxime isomer had been obtained.

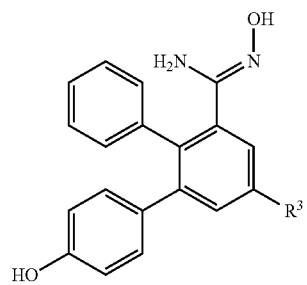

Example 72

2-(2,5-dimethyl-1H-pyrrol-1-yl)-N',4'-dihydroxy-5-(trifluoromethyl)-[1,1'-biphenyl]-3-carboximidamide (E72)

Scheme 12

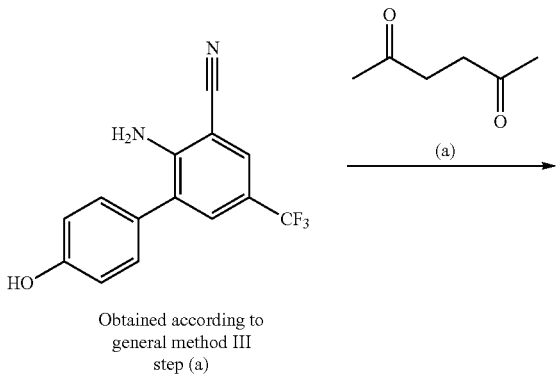

Obtained according to general method III step (a)

E 68  N',4-dihydroxy-5'-isobutyl-[1,1':2',1''-terphenyl]-3'-carboximidamide $R^3$ = isobutyl ES/MS m/z: 361.31 (pos. M + H), 359.33 (neg. M − H); $^1$H NMR (Acetone-d6, 500 MHz): δ 7.24 (d, 1H, J = 1.8 Hz), 7.20 (d, 1H, J = 1.8 Hz), 7.15-7.10 (m, 5H), 6.85 (m, 2H), 6.61 (m, 2H), 2.57 (d, 2H, J = 7.1 Hz), 1.95 (m, 1H) and 0.97 (d, 6H, J = 6.6 Hz).

E 69  N',4-dihydroxy-5'-((E)-prop-1-en-1-yl)-[1,1':2',1''-terphenyl]-3'-carboximidamide $R^3$ = (E)-prop-1-en-1-yl ES/MS m/z: 345.29 (pos. M + H), 343.36 (neg. M − H); $^1$H NMR (CDCl$_3$, 500 MHz): δ 7.54 (d, 1H, J = 1.9 Hz), 7.50 (d, 1H, J = 1.9 Hz), 7.28-7.22 (m, 5H), 6.99 (m, 2H), 6.75 (m, 2H), 6.64 (m, 1H), 6.55 (m, 1H) and 2.03 (dd, 3H, J = 6.4, 1.5 Hz).

E 70  5'-allyl-N',4-dihydroxy-[1,1':2',1''-terphenyl]-3'-carboximidamide $R^3$ = allyl ES/MS m/z: 345.29 (pos. M + H), 343.33 (neg. M − H); $^1$H NMR (Acetone-d6, 500 MHz): δ 7.27 (d, 1H, J = 1.6 Hz), 7.24 (d, 1H, J = 1.6 Hz), 7.15-7.10 (m, 5H), 6.84 (m, 2H), 6.62 (m, 2H), 6.06 (m, 1H), 5.19 (m, 1H), 5.09 (m, 1H), and 3.48 (d, 2H, J = 6.8 Hz).

E 71  5'-butyl-N',4-dihydroxy-[1,1':2',1''-terphenyl]-3'-carboximidamide $R^3$ = butyl ES/MS m/z: 361.31 (pos. M + H), 359.34 (neg. M − H); $^1$H NMR (Acetone-d6, 500 MHz): δ 7.26 (d, 1H, J = 2.1 Hz), 7.23 (d, 1H, J = 2.1 Hz), 7.15-7.09 (m, 5H), 6.85 (m, 2H), 6.61 (m, 2H), 2.70 (t, 2H, J = 7.6 Hz), 1.68 (m, 2H), 1.43 (m, 2H) and 0.96 (t, 3H, J = 7.6 Hz).

-continued

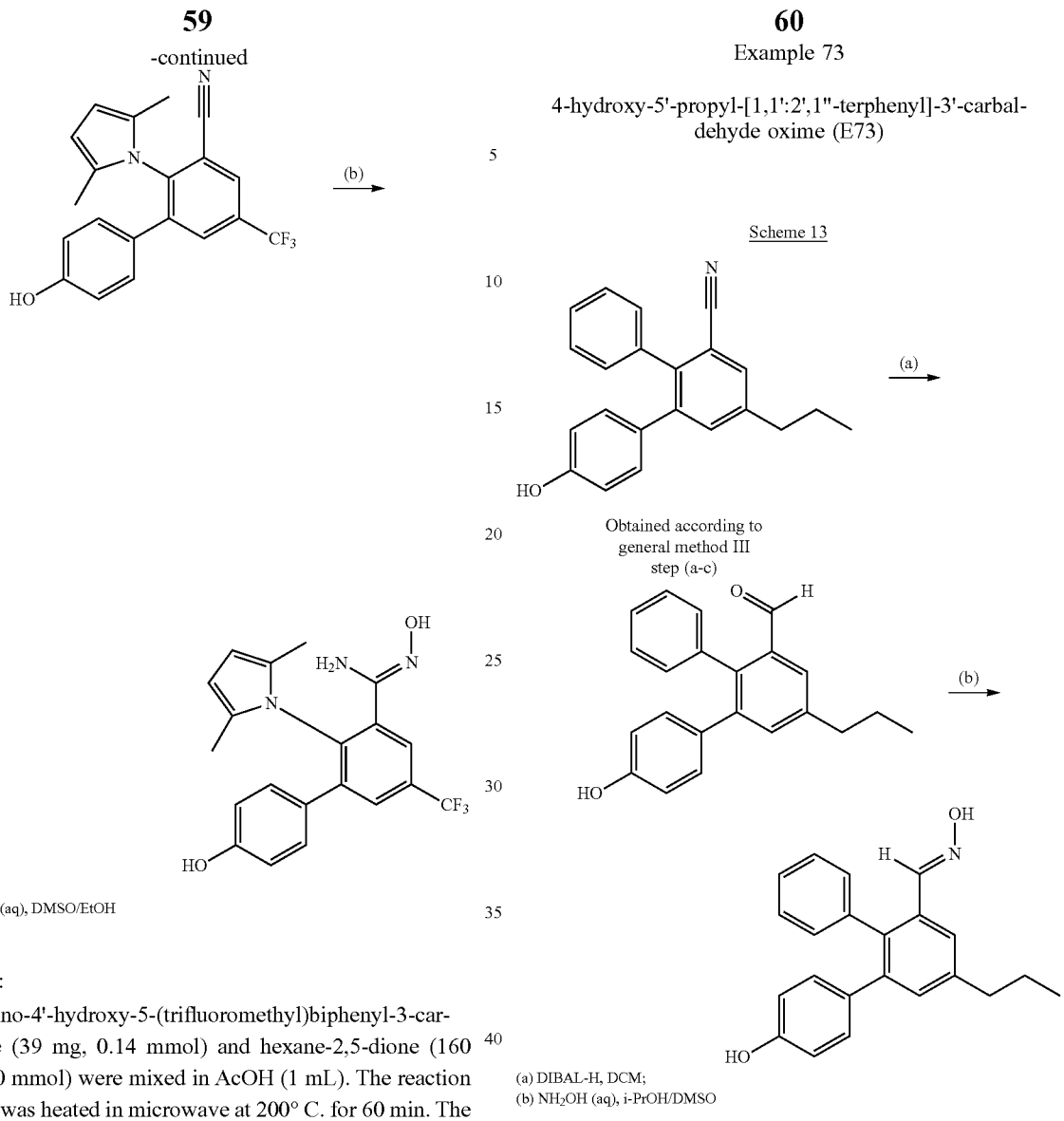

(a) AcOH;
(b) NH₂OH (aq), DMSO/EtOH

Step (a):

2-amino-4'-hydroxy-5-(trifluoromethyl)biphenyl-3-carbonitrile (39 mg, 0.14 mmol) and hexane-2,5-dione (160 mg, 1.40 mmol) were mixed in AcOH (1 mL). The reaction mixture was heated in microwave at 200° C. for 60 min. The solvent was evaporated under reduced pressure and the crude product was purified on silica using DCM/isohexane (25-75% DCM) as mobile phase. 17 mg 2-(2,5-dimethyl-1H-pyrrol-1-yl)-4'-hydroxy-5-(trifluoromethyl)biphenyl-3-carbonitrile was obtained.

Step (b):

2-(2,5-dimethyl-1H-pyrrol-1-yl)-4'-hydroxy-5-(trifluoromethyl)biphenyl-3-carbonitrile (11 mg, 0.03 mmol) and hydroxylamine (0.38 mL, 16 M, aq) were mixed in DMSO/MeOH (0.4 mL 1:1). The reaction mixture was heated in microwave at 120° C. for 45 min under nitrogen. The crude mixture was purified on preparative HPLC using MeCN/acidic H₂O (25-55% MeCN) as mobile phase. 6.30 mg 2-(2,5-dimethyl-1H-pyrrol-1-yl)-N',4'-dihydroxy-5-(trifluoromethyl)-[1,1'-biphenyl]-3-carboximidamide (E72) was obtained. ES/MS m/z: 390.27 (M+H), 388.34 (M−H); ¹H NMR (Acetone-d6, 500 MHz): δ 7.98 (m, 1H), 7.86 (m, 1H), 6.96 (m, 2H), 6.76 (m, 2H), 5.77 (s, 2H) and 1.85 (s, 6H).

Example 73

4-hydroxy-5'-propyl-[1,1':2',1''-terphenyl]-3'-carbaldehyde oxime (E73)

Scheme 13

Obtained according to general method III step (a-c)

(a) DIBAL-H, DCM;
(b) NH₂OH (aq), i-PrOH/DMSO

Step (a):

4-hydroxy-5'-propyl-[1,1':2',1''-terphenyl]-3'-carbonitrile (20 mg, 0.06 mmol) was dissolved in DCM (2 mL). Diisobutylaluminum hydride (90.7 mg, 0.64 mmol) was added dropwise at −78° C. The reaction mixture was stirred at −78° C. for 2 h. HCl (2 M, aq) was added, the mixture was allowed to attain room temperature and was then filtered through a phase separator. The solvent was evaporated under reduced pressure. 18 mg 4-hydroxy-5'-propyl-[1,1':2',1''-terphenyl]-3'-carboxamide was obtained.

Step (b):

4-hydroxy-5'-propyl-[1,1':2',1''-terphenyl]-3'-carboxamide (18 mg, 0.06 mmol) and hydroxylamine (0.35 mL, 16 M, aq) were mixed in DMSO/1-PrOH (0.4 mL 1:1). The reaction mixture was heated in microwave at 130° C. for 20 min under nitrogen. The crude mixture was purified on preparative HPLC using MeCN/acidic H₂O (30-50% MeCN) as mobile phase. 15 mg 4-hydroxy-5'-propyl-[1,1':2',1''-terphenyl]-3'-carbaldehyde oxime (E73) was obtained. ES/MS m/z: 332.27 (M+H), 330.33 (M−H); ¹H NMR (Acetone-d6, 500 MHz): δ 7.75 (d, 1H, J=1.8 Hz), 7.31-7.23 (m, 4H), 7.06 (m, 2H), 6.89 (m, 2H), 6.63 (m, 2H), 2.69 (m, 2H), 1.73 (m, 2H) and 1.00 (t, 3H, J=7.3 Hz).

Example 74
5'-propyl-3'-(1H-pyrazol-4-yl)-[1,1':2',1''-terphenyl]-4-ol (E74)
Scheme 14
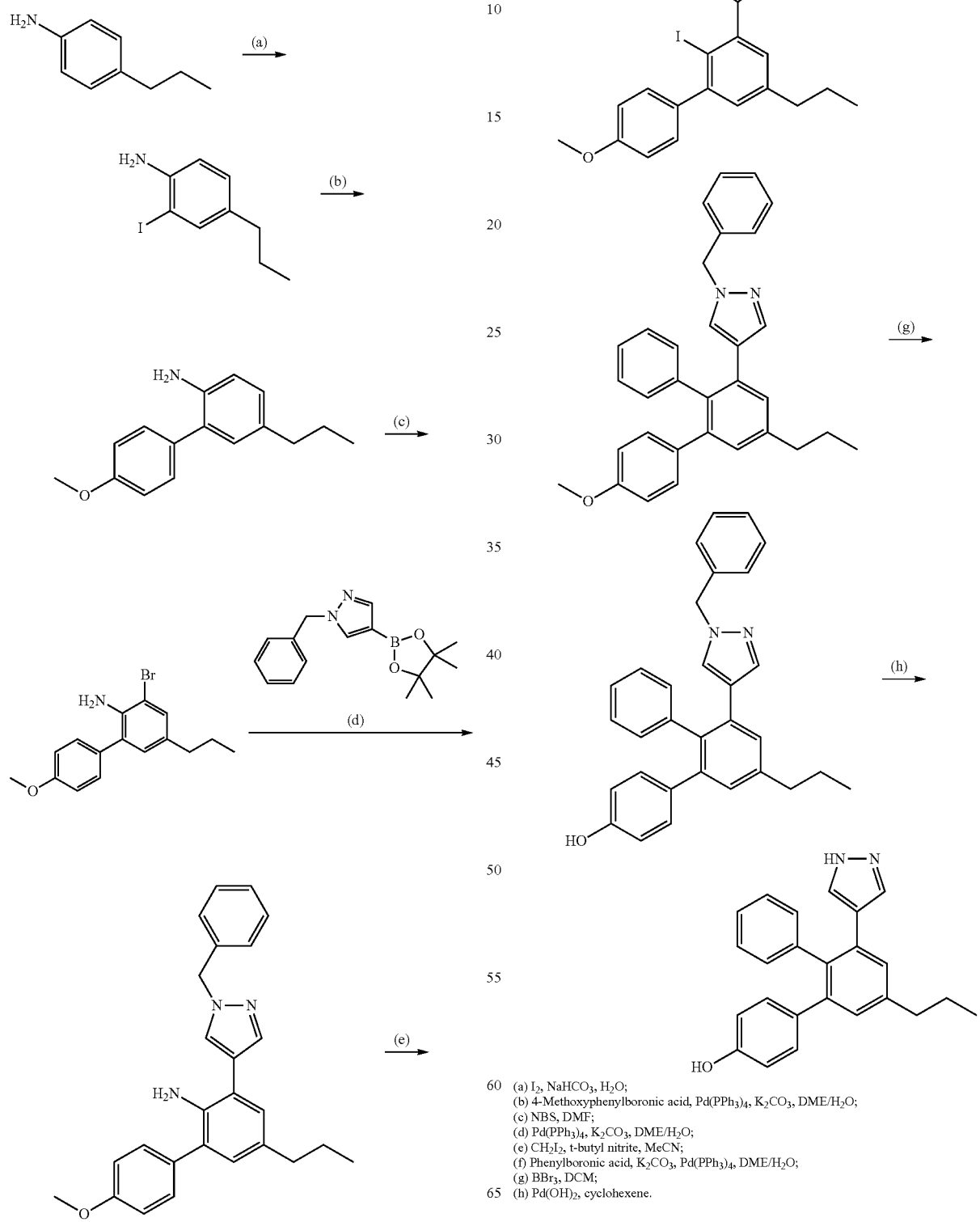
(a) I₂, NaHCO₃, H₂O;
(b) 4-Methoxyphenylboronic acid, Pd(PPh₃)₄, K₂CO₃, DME/H₂O;
(c) NBS, DMF;
(d) Pd(PPh₃)₄, K₂CO₃, DME/H₂O;
(e) CH₂I₂, t-butyl nitrite, MeCN;
(f) Phenylboronic acid, K₂CO₃, Pd(PPh₃)₄, DME/H₂O;
(g) BBr₃, DCM;
(h) Pd(OH)₂, cyclohexene.

Step (a):

A mixture 4-propylaniline (2200 mg, 16.3 mmol) and NaHCO$_3$ (2050 mg, 24.4 mmol) in H$_2$O (30 mL) was cooled in an ice bath. Iodine (4130 mg, 16.3 mmol) was added in portions over 20 min with slight cooling. The reaction mixture was stirred at room temperature for 16 h and was then extracted with EtOAc (3×). The combined organic extracts were dried over Na$_2$SO$_4$ and the solvent was concentrated under reduced pressure. 4100 mg 2-iodo-4-propylaniline was obtained as a brownish solid.

Step (b):

2-Iodo-4-propylaniline (2000 mg, 7.66 mmol), 4-methoxyphenylboronic acid (1164 mg, 7.66 mmol), Pd(PPh$_3$)$_4$ (443 mg, 0.38 mmol) and K$_2$CO$_3$ (4234 mg, 30.64 mmol) were mixed in DME/H$_2$O (30 mL, 1:1). The reaction mixture was degassed with N$_2$ for 5 min and then heated in microwave at 110° C. for 40 min. H$_2$O was added and the aqueous mixture was extracted with EtOAc (3×). The combined organic extracts were washed with water and dried over Na$_2$SO$_4$. The solvent was evaporated under reduced pressure and the crude product was purified on silica using EtOAc/n-heptane (0-10% EtOAc) as mobile phase. 1.17 mg 4'-methoxy-5-propylbiphenyl-2-amine was obtained as yellow oil.

Step (c):

4'-Methoxy-5-propylbiphenyl-2-amine (1170 mg, 4.85 mmol) was dissolved in DMF (12 mL) and NBS (863 mg, 4.85 mmol) was added in portions. The reaction mixture was stirred at room temperature for 3 h and was then partitioned between H$_2$O and DCM. The aqueous layer was extracted with DCM and the combined organic extracts were concentrated under reduced pressure. The crude product was purified on silica using EtOAc/n-heptane (0-5% EtOAc) as mobile phase. 840 mg 3-bromo-4'-methoxy-5-propylbiphenyl-2-amine was obtained as orange oil.

Step (d):

3-bromo-4'-methoxy-5-propylbiphenyl-2-amine (261 mg, 0.82 mmol), 1-benzyl-4-(4,4,5,5-tetramethyl-1,3,2-dioxaborolan-2-yl)-1H-pyrazole (301 mg, 1.06 mmol), Pd(PPh$_3$)-4-(94.2 mg, 0.08 mmol) and K$_2$CO$_3$ (451 mg, 3.26 mmol) were mixed in DME/H$_2$O (12 mL, 1:1). The reaction mixture was flushed with N$_2$ for 10 min and then heated in microwave at 110° C. for 2 h. H$_2$O was added and the aqueous mixture was extracted with DCM (3×). The combined organic extracts were concentrated under reduced pressure and the crude product was purified on silica using EtOAc/n-heptane (0-40% EtOAc) as mobile phase. 294 mg 3-(1-benzyl-1H-pyrazol-4-yl)-4'-methoxy-5-propylbiphenyl-2-amine was obtained as tan oil.

Step (e):

3-(1-Benzyl-1H-pyrazol-4-yl)-4'-methoxy-5-propylbiphenyl-2-amine (290 mg, 0.73 mmol) was dissolved in MeCN (4 mL). CH$_2$I$_2$ (821 mg, 3.06 mmol) was added followed by t-butyl nitrite (188 mg, 1.82 mmol). The reaction mixture was stirred at 50° C. for 48 h. The solvent was evaporated under reduced pressure and the crude product was purified on silica using EtOAc/n-heptane (0-10% EtOAc) as mobile phase. 178 mg 1-benzyl-4-(2-iodo-4'-methoxy-5-propylbiphenyl-3-yl)-1H-pyrazole was obtained as a yellowish semi solid.

Step (f):

1-benzyl-4-(2-iodo-4'-methoxy-5-propylbiphenyl-3-yl)-1H-pyrazole (25 mg, 0.05 mmol), phenylboronic acid (7.79 mg, 0.06 mmol), Pd(PPh$_3$)$_4$ (5.68 mg, 0.005 mmol) and K$_2$CO$_3$ (27.2 mg, 0.20 mmol) were mixed in DME/H$_2$O (2.5 mL, 1:1). The reaction mixture was flushed with N$_2$ for 10 min and then heated in microwave at 130° C. for 30 min. H$_2$O was added and the aqueous mixture was extracted with DCM (3×). The combined organic extracts were concentrated under reduced pressure. 1-benzyl-4-(4-methoxy-5'-propyl-[1,1':2',1''-terphenyl]-3'-yl)-1H-pyrazole was obtained as a crude mixture.

Step (g):

1-benzyl-4-(4-methoxy-5'-propyl-[1,1':2',1''-terphenyl]-3'-yl)-1H-pyrazole (22.6 mg, 0.05 mmol) was dissolved in DCM (4 mL) under nitrogen and the solution was cooled to 0° C. BBr$_3$ (0.25 mL, 1M) was added. The reaction mixture was stirred at 0° C. for 16 h. Ice was added to quench the reaction followed by DCM. The layers were separated and the organic layer was evaporated under reduced pressure. The crude product was purified on preparative HPLC using MeCN/acidic H$_2$O (20-100% MeCN) as mobile phase. 13 mg 3'-(1-benzyl-H-pyrazol-4-yl)-5'-propyl-[1,1':2',1''-terphenyl]-4-ol was obtained as an off white solid.

Step (h):

3'-(1-benzyl-1H-pyrazol-4-yl)-5'-propyl-[1,1':2',1''-terphenyl]-4-ol (7.0 mg, 0.02 mmol) was dissolved in EtOH (2 mL). Cyclohexene (1 mL) was added followed by Pd(OH)$_2$ (20% wt on carbon, 15 mg). The reaction mixture was heated at 80° C. for 27 h and then it was stirred at room temperature for 48 h. The catalyst was removed using PTFE filter and the solvent was evaporated under reduced pressure. The crude product was purified on silica using EtOAc/n-heptane (0-60% EtOAc) as mobile phase. 3.2 mg 5'-propyl-3'-(1H-pyrazol-4-yl)-[1,1':2',1''-terphenyl]-4-ol (E74) was obtained as a white solid. ES/MS m/z: 355.28 (M+H), 353.32 (M−H); $^1$H NMR (Acetone-d6, 500 MHz): δ 7.40 (d, 1H, J=1.9 Hz), 7.17-7.14 (m, 3H), 7.10-7.08 (m, 3H), 6.99-6.96 (m, 2H), 6.90 (m, 2H), 6.61 (m, 2H), 2.68 (t, 2H, J=7.6 Hz), 1.75 (m, 2H) and 1.01 (t, 3H, J=7.4 Hz).

Example 75

Example 75 was prepared using a method analogous to that used to synthesise Example 15 above. Full experimental details of the individual steps of the general methods are described in Example 15 above. Identification of the title compound by $^1$H-NMR showed that the oxime product was a single isomer, but did not confirm whether the (E) or (Z) oxime isomer had been obtained.

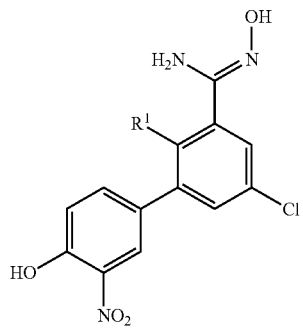

E 75   5-chloro-2-(3,5-dimethylisoxazol-4-yl)-N',4'-dihydroxy-3'-nitro-[1,1'-biphenyl]-3-carboximidamide
R$^1$ = 3,5-dimethylisoxazol-4-yl
ES/MS m/z: 403.14 (pos. M + H), 401.22 (neg. M − H); $^1$H NMR (Acetone-d6, 500 MHz): δ 7.93 (d, 1H, J = 2.3 Hz), 7.61 (d, 1H, J = 2.2 Hz), 7.58 (d, 1H, J = 2.2 Hz), 7.46 (dd, 1H, J = 8.8, 2.3 Hz), 7.13 (d, 1H, J = 8.8 Hz), 2.09 (s, 3H) and 1.88 (s, 3H).

Examples 76-116

Examples 76-116 were prepared using methods analogous to that used to synthesise Examples 1 and 15-18 above. Full experimental details of the individual steps of the general methods are described in Examples 1 and -15-18 above. For examples 76-90, 92, 93, 96, 97, 100 and 102-116 identification of the title compounds by $^1$H-NMR showed that the oxime product was a single isomer, but did not confirm whether the (E) or (Z) oxime isomer had been obtained.

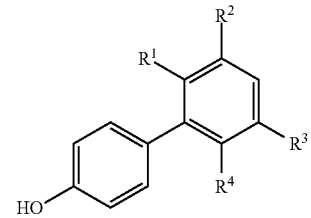

E 76 5'-chloro-5''-fluoro-N',4-dihydroxy-2''-methyl-[1,1':2',1''-terphenyl]-3'-carboximidamide
$R^1$ = 5-fluoro-2-methylphenyl   $R^2$ = N-hydroxy carbaimidoyl   $R^3$ = Cl   $R^4$ = H
ES/MS m/z: 371.18 (pos. M + H), 369.23 (neg. M − H); $^1$H NMR (Acetone-d6, 500 MHz): δ 7.46 (d, 1H, J = 2.2 Hz), 7.42 (d, 1, J = 2.2 Hz), 7.02-6.92 (m, 4H), 6.86 (m, 1H), 6.65 (m, 2H) and 1.83 (s, 3H).

E 77 5'-chloro-5''-fluoro-N',4-dihydroxy-2''-methoxy-[1,1':2',1''-terphenyl]-3'-carboximidamide
$R^1$ = 5-fluoro-2-methoxyphenyl   $R^2$ = N-hydroxy carbaimidoyl   $R^3$ = Cl   $R^4$ = H
ES/MS m/z: 387.19 (pos. M + H), 385.24 (neg. M − H); $^1$H NMR (Acetone-d6, 500 MHz): δ 7.43 (d, 1H, J = 2.2 Hz), 7.37 (d, 1, J = 2.2 Hz), 6.95-6.90 (m, 3H), 6.81-6.77 (m, 2H), 6.65 (m, 2H) and 3.52 (s, 3H).

E 78 5-chloro-N',4-dihydroxy-2-(4-methylthiophen-3-yl)-[1,1'-biphenyl]-3-carboximidamide
$R^1$ = 4-methylthiophen-3-yl   $R^2$ = N-hydroxy carbaimidoyl   $R^3$ = Cl   $R^4$ = H
ES/MS m/z: 359.2 (pos. M + H), 357.22 (neg. M − H); $^1$H NMR (Acetone-d6, 500 MHz): δ 7.44 (d, 1H, J = 1.8 Hz), 7.42 (d, 1, J = 1.8 Hz), 7.15 (t, 1H, J = 2.5 Hz), 6.96 (m, 2H), 6.88 (d, 1H, J = 2.2 Hz), 6.67 (m, 2H) and 1.73 (s, 3H).

E 79 5'-chloro-N',4-dihydroxy-2''-methyl-[1,1':2',1''-terphenyl]-3'-carboximidamide
$R^1$ = o-tolyl   $R^2$ = N-hydroxy carbaimidoyl   $R^3$ = Cl   $R^4$ = H
ES/MS m/z: 353.19 (pos. M + H), 351.28 (neg. M − H); $^1$H NMR (Acetone-d6, 500 MHz): δ 7.46 (d, 1H, J = 2.2 Hz), 7.41 (d, 1, J = 2.2 Hz), 7.16 (dd, 1H, J = 7.3, 1.4 Hz), 7.10 (m, 1H), 7.06 (m, 1H), 6.99 (d, 1H, J = 7.6 Hz), 6.90 (m, 2H), 6.61 (m, 2H) and 1.87 (s, 3H).

E 80 2-(2,4-dimethylthiophen-3-yl)-N',4'-dihydroxy-[1,1'-biphenyl]-3-carboximidamide
$R^1$ = 2,4-dimethylthiophen-3-yl   $R^2$ = N-hydroxy carbaimidoyl   $R^3$ = H   $R^4$ = H
ES/MS m/z: 339.25 (pos. M + H), 337.23 (neg. M − H); $^1$H NMR (Acetone-d6, 500 MHz): δ 7.51 (dd, 1H, J = 6.0, 3.1 Hz), 7.47-7.43 (m, 2H), 6.90 (m, 2H), 6.69-6.66 (m, 3H), 2.02 (s, 3H) and 1.81 (d, 3H, J = 1.1 Hz).

E 81 5-chloro-2-(2,4-dimethylthiophen-3-yl)-N',4'-dihydroxy-[1,1'-biphenyl]-3-carboximidamide
$R^1$ = 2,4-dimethylthiophen-3-yl   $R^2$ = N-hydroxy carbaimidoyl   $R^3$ = Cl   $R^4$ = H
ES/MS m/z: 373.2 (pos. M + H), 371.23 (neg. M − H); $^1$H NMR (Acetone-d6, 500 MHz): δ 7.51 (d, 1H, J = 2.5 Hz), 7.45 (d, 1H, J = 2.5 Hz), 6.92 (m, 2H), 6.71-6.68 (m, 3H), 2.02 (s, 3H) and 1.81 (d, 3H, J = 1.0 Hz).

E 82 2''-chloro-5'-fluoro-N',4-dihydroxy-5'-propyl-[1,1':2',1''-terphenyl]-3'-carboximidamide
$R^1$ = 2-chloro-5-fluorophenyl   $R^2$ = N-hydroxy carbaimidoyl   $R^3$ = propyl   $R^4$ = H
ES/MS m/z: 399.22 (pos. M + H), 397.31 (neg. M − H); $^1$H NMR (Acetone-d6, 500 MHz): δ 7.35 (d, 1H, J = 1.8 Hz), 7.24 (d, 1H, J = 1.8 Hz), 7.21 (dd, 1H, J = 8.9, 5.2 Hz), 7.01 (dd, 1H, J = 9.3, 5.2 Hz), 6.98-6.93 (m, 3H), 6.65 (m, 2H), 2.70 (t, 2H, J = 7.6 Hz), 1.73 (m, 2H) and 1.00 (t, 3H, J = 7.3 Hz).

E 83 6'-chloro-N',4-dihydroxy-5'-propyl-[1,1':2',1''-terphenyl]-3'-carboximidamide
$R^1$ = phenyl   $R^2$ = N-hydroxy carbaimidoyl   $R^3$ = propyl   $R^4$ = Cl
ES/MS m/z: 381.24 (pos. M + H), 379.33 (neg. M − H); $^1$H NMR (acetone-d6, 500 MHz): δ 7.41 (s, 1H), 7.10-7.03 (m, 5H), 6.80 (m, 2H), 6.63 (m, 2H), 2.82 (t, 2H, J = 7.7 Hz), 1.73 (m, 2H) and 1.04 (t, 3H, J = 7.3 Hz).

E 84 N',4-dihydroxy-5'-6'-dipropyl-[1,1':2',1''-terphenyl]-3'-carboximidamide
$R^1$ = phenyl   $R^2$ = N-hydroxy carbaimidoyl   $R^3$ = propyl   $R^4$ = propyl
ES/MS m/z: 389.35 (pos. M + H); $^1$H NMR (Acetone-d6, 500 MHz): δ 7.30 (s, 1H), 7.05-6.99 (m, 5H), 6.79 (m, 2H), 6.62 (m, 2H), 2.70 (m, 2H), 2.43 (m, 2H), 1.71 (m, 2H), 1.35 (m, 2H), 1.06 (t, 3H, J = 7.2 Hz) and 0.73 (t, 3H, J = 7.1 Hz).

E 85 N',4'-dihydroxy-2-(3-methylthiophen-2-yl)-[1,1'-biphenyl]-3-carboximidamide
$R^1$ = 3-methylthiophen-2-yl   $R^2$ = N-hydroxy carbaimidoyl   $R^3$ = H   $R^4$ = H
ES/MS m/z: 325.25 (pos. M + H), 323.3 (neg. M − H); $^1$H NMR (Acetone-d6, 500 MHz): δ 7.47-7.42 (m, 3H), 7.25 (d, 1H, J = 5.0 Hz), 6.96 (m, 2H) and 6.70-6.66 (m, 2H) and 1.77 (s, 3H).

E 86 5'-bromo-6'-chloro-N',4-dihydroxy-[1,1':2',1''-terphenyl]-3'-carboximidamide
$R^1$ = phenyl   $R^2$ = N-hydroxy carbaimidoyl   $R^3$ = Br   $R^4$ = Cl
ES/MS m/z: 419.14 (pos. M + H), 417.28 (neg. M − H); $^1$H NMR (Acetone-d6, 500 MHz): δ 7.78 (s, 1H), 7.12-7.05 (m, 5H), 6.83 (m, 2H) and 6.66 (m, 2H).

E 87 6'-chloro-N',4-dihydroxy-5'-phenyl-[1,1':2',1''-terphenyl]-3'-carboximidamide
$R^1$ = phenyl   $R^2$ = N-hydroxy carbaimidoyl   $R^3$ = phenyl   $R^4$ = Cl
ES/MS m/z: 415.25 (pos. M + H), 413.35 (neg. M − H); $^1$H NMR (Acetone-d6, 500 MHz): δ 7.55-7.41 (m, 6H), 7.12-7.09 (m, 5H), 6.87 (m, 2H) and 6.65 (m, 2H).

E 88 6'-chloro-N',4-dihydroxy-[1,1':2',1''-terphenyl]-3'-carboximidamide
$R^1$ = phenyl   $R^2$ = N-hydroxy carbaimidoyl   $R^3$ = H   $R^4$ = Cl
ES/MS m/z: 339.27 (pos. M + H), 337.29 (neg. M − H); $^1$H NMR (Acetone-d6, 500 MHz): δ 7.71 (d, 1H, J = 2.3 Hz), 7.68 (d, 1H, J = 2.3 Hz), 7.50-7.46 (m, 4H), 7.41 (m, 1H), 7.40 (m, 2H) and 6.94 (m, 2H).

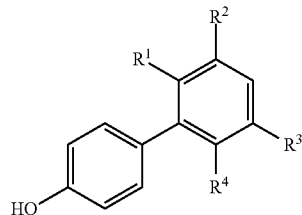

E 89 N',4-dihydroxy-6'-methyl-5'-propyl-[1,1':2',1"-terphenyl]-3'-carboximidamide
$R^1$ = phenyl  $R^2$ = N-hydroxy carbaimidoyl  $R^3$ = propyl  $R^4$ = methyl
ES/MS m/z: 361.35 (pos. M + H), 359.37 (neg. M − H); $^1$H NMR (Acetone-d6, 500 MHz): δ 7.27 (s, 1H), 7.07-7.00 (m, 5H), 6.74 (m, 2H), 6.62 (m, 2H), 2.69 (m, 2H), 2.04 (s, 3H), 1.67 (m, 2H) and 1.04 (t, 3H, J = 7.3 Hz).

E 90 5",6'-difluoro-N',4-dihydroxy-2"-methyl-5'-propyl-[1,1':2',1"-terphenyl]-3'-carboximidamide
$R^1$ = 5-fluoro-2-methylphenyl  $R^2$ = N-hydroxy carbaimidoyl  $R^3$ = propyl  $R^4$ = F
ES/MS m/z: 397.34 (pos. M + H), 395.45 (neg. M − H); $^1$H NMR (Acetone-d6, 500 MHz): δ 7.37 (d, 1H, J = 7.6 Hz), 6.96 (dd, 1H, J = 8.6, 6.2 Hz), 6.92-6.88 (m, 3H), 6.79 (m, 1H), 6.66 (m, 2H), 2.71 (m, 2H), 1.89 (s, 3H), 1.71 (m, 2H) and 1.01 (t, 3H, J = 7.4 Hz).

E 91 5",6'-difluoro-4-dihydroxy-2"-methyl-5'-propyl-[1,1':2',1"-terphenyl]-3'-carboxamide
$R^1$ = 5-fluoro-2-methylphenyl  $R^2$ = carbamoyl  $R^3$ = propyl  $R^4$ = F
ES/MS m/z: 382.29 (pos. M + H), 380.38 (neg. M − H); $^1$H NMR (Acetone-d6, 500 MHz): δ 7.50 (d, 1H, J = 7.4 Hz), 7.00 (dd, 1H, J = 8.4, 5.9 Hz), 6.92 (m, 2H), 6.87 (dd, 1H, J = 9.6, 2.7 Hz), 6.82 (m, 1H), 6.67 (m, 2H), 2.72 (m, 2H), 1.92 (s, 3H), 1.72 (m, 2H) and 1.01 (t, 3H, J = 7.2 Hz).

E 92 4-hydroxy-6'-methyl-5'-propyl-[1,1':2',1"-terphenyl]-3'-carbaldehyde oxime
$R^1$ = phenyl  $R^2$ = hydroxyimino methyl  $R^3$ = propyl  $R^4$ = methyl
ES/MS m/z: 346.33 (pos. M + H), 344.37 (neg. M − H); $^1$H NMR (Acetone-d6, 500 MHz): δ 7.64 (s, 1H), 7.19-7.10 (m, 3H), 6.97 (m, 2H), 6.78 (m, 2H), 6.64 (m, 2H), 2.70 (m, 2H), 2.05 (s, 3H), 1.68 (m, 2H) and 1.05 (t, 3H, J = 7.4 Hz).

E 93 5",6'-difluoro-N',4-dihydroxy-2"-methoxy-5'-propyl-[1,1':2',1"-terphenyl]-3'-carboximidamide
$R^1$ = 5-fluoro-2-methoxyphenyl  $R^2$ = N-hydroxy carbaimidoyl  $R^3$ = propyl  $R^4$ = F
ES/MS m/z: 413.29 (pos. M + H), 411.34 (neg. M − H); $^1$H NMR (Acetone-d6, 500 MHz): δ 7.33 (d, 1H, J = 7.5 Hz), 6.91-6.85 (m, 3H), 6.76-6.73 (m, 2H), 6.65 (m, 2H), 3.55 (s, 3H), 2.69 (m, 2H), 1.70 (m, 2H) and 1.01 (t, 3H, J = 7.2 Hz).

E 94 5",6'-difluoro-4-dihydroxy-2"-methoxy-5'-propyl-[1,1':2',1"-terphenyl]-3'-carboxamide
$R^1$ = 5-fluoro-2-methoxyphenyl  $R^2$ = carbamoyl  $R^3$ = propyl  $R^4$ = F
ES/MS m/z: 398.32 (pos. M + H), 396.4 (neg. M − H); $^1$H NMR (Acetone-d6, 500 MHz): δ 7.47 (d, 1H, J = 7.6 Hz), 6.91-6.87 (m, 3H), 6.80-6.74 (m, 2H), 6.66 (m, 2H), 3.58 (s, 3H), 2.70 (m, 2H), 1.71 (m, 2H) and 1.02 (t, 3H, J = 7.6 Hz).

E 95 6'-fluoro-4-hydroxy-5'-propyl-[1,1':2',1"-terphenyl]-3'-carboxamide
$R^1$ = phenyl  $R^2$ = carbamoyl  $R^3$ = propyl  $R^4$ = F
ES/MS m/z: 350.36 (pos. M + H), 348.41 (neg. M − H); $^1$H NMR (Acetone-d6, 500 MHz): δ 7.44 (d, 1H, J = 7.4 Hz), 7.17-7.13 (m, 3H), 7.07 (m, 2H), 6.85 (m, 2H), 6.65 (m, 2H), 2.71 (m, 2H), 1.71 (m, 2H) and 1.01 (t, 3H, J = 7.4 Hz).

E 96 6'-fluoro-N',4-dihydroxy-2"-methyl-5'-propyl-[1,1':2',1"-terphenyl]-3'-carboximidamide
$R^1$ = o-tolyl  $R^2$ = N-hydroxy carbaimidoyl  $R^3$ = propyl  $R^4$ = F
ES/MS m/z: 379.29 (pos. M + H), 377.33 (neg. M − H); $^1$H NMR (Acetone-d6, 500 MHz): δ 7.38 (d, 1H, J = 7.7 Hz), 7.10-6.95 (m, 4H), 6.88 (m, 2H), 6.62 (m, 2H), 2.71 (m, 2H), 1.93 (s, 3H), 1.71 (m, 2H) and 1.01 (t, 3H, J = 7.2 Hz).

E 97 6-fluoro-N',4'-dihydroxy-2-(4-methylthiophen-3-yl)-5-propyl-[1,1'-biphenyl]-3-carboximidamide
$R^1$ = 4-methylthiophen-3-yl  $R^2$ = N-hydroxy carbaimidoyl  $R^3$ = propyl  $R^4$ = F
ES/MS m/z: 385.25 (pos. M + H), 383.29 (neg. M − H); $^1$H NMR (Acetone-d6, 500 MHz): δ 7.36 (d, 1H, J = 7.7 Hz), 7.06 (d, 1H, J = 3.2 Hz), 6.92 (m, 2H), 6.83 (m, 1H), 6.67 (m, 2H), 2.69 (m, 2H), 1.80 (s, 3H), 1.70 (m, 2H) and 1.00 (t, 3H, J = 7.3 Hz).

E 98 6'-fluoro-4-hydroxy-2"-methyl-5'-propyl-[1,1':2',1"-terphenyl]-3'-carboxamide
$R^1$ = o-tolyl  $R^2$ = carbamoyl  $R^3$ = propyl  $R^4$ = F
ES/MS m/z: 364.31 (pos. M + H), 362.35 (neg. M − H); $^1$H NMR (Acetone-d6, 500 MHz): δ 7.55 (d, 1H, J = 7.7 Hz), 7.10-6.99 (m, 4H), 6.89 (m, 2H), 6.63 (m, 2H), 2.72 (m, 2H), 1.95 (s, 3H), 1.72 (m, 2H) and 1.01 (t, 3H, J = 7.5 Hz).

E 99 6-fluoro-4'-dihydroxy-2-(4-methylthiophen-3-yl)-5-propyl-[1,1'-biphenyl]-3-carboxamide
$R^1$ = 4-methylthiophen-3-yl  $R^2$ = carbamoyl  $R^3$ = propyl  $R^4$ = F
ES/MS m/z: 415.11 (pos. M + H), 413.26 (neg. M − H); $^1$H NMR (Acetone-d6, 500 MHz): δ 7.54 (d, 1H, J = 7.5 Hz), 7.08 (d, 1H, J = 3.3 Hz), 6.93 (m, 2H), 6.89 (m, 1H), 6.69 (m, 2H), 2.71 (m, 2H), 1.83 (s, 3H), 1.71 (m, 2H) and 1.01 (t, 3H, J = 7.5 Hz).

E 100 2-(2,4-dimethylthiophen-3-yl)-6-fluoro-N',4'-dihydroxy-5-propyl-[1,1'-biphenyl]-3-carboxamide
$R^1$ = 2,4-dimethylthiophen-3-yl  $R^2$ = N-hydroxy carbaimidoyl  $R^3$ = propyl  $R^4$ = F
ES/MS m/z: 399.25 (pos. M + H), 397.25 (neg. M − H); $^1$H NMR (Acetone-d6, 500 MHz): δ 7.42 (d, 1H, J = 7.6 Hz), 6.89 (m, 2H), 6.68 (m, 2H), 6.64 (s, 1H), 2.70 (m, 2H), 1.83 (s, 3H), 1.71 (m, 2H) and 1.00 (t, 3H, J = 7.4 Hz).

E 101 5'-chloro-5"-fluoro-4-hydroxy-2"-methoxy-[1,1':2',1"-terphenyl]-3'-carboxamide
$R^1$ = 5-fluoro-2-methoxyphenyl  $R^2$ = carbamoyl  $R^3$ = Cl  $R^4$ = H
ES/MS m/z: 372.18 (pos. M + H), 370.24 (neg. M − H); $^1$H NMR (Acetone-d6, 500 MHz): δ 7.49 (d, 1H, J = 2.4 Hz), 7.40 (d, 1H, J = 2.4 Hz), 6.96-6.92 (m, 3H), 6.83 (dd, 1H, J = 8.9, 4.4 Hz), 6.79 (dd, 1H, J = 8.8, 3.2 Hz), 6.66 (m, 2H) and 3.54 (s, 3H).

-continued

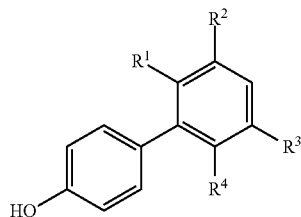

E 102 6'-fluoro-N',4-dihydroxy-5'-propyl-[1,1':2',1''-terphenyl]-3'-carboximidamide
$R^1$ = phenyl          $R^2$ = N-hydroxy carbaimidoyl     $R^3$ = propyl     $R^4$ = F
ES/MS m/z: 365.36 (pos. M + H), 363.43 (neg. M − H); $^1$H NMR (Acetone-d6, 500 MHz): δ 7.33 (d, 1H, J = 7.5 Hz), 7.13-7.06 (m, 5H), 6.84 (m, 2H), 6.64 (m, 2H), 2.69 (m, 2H), 1.70 (m, 2H) and 1.01 (t, 3H, J = 7.4 Hz).

E 103 5''-fluoro-N',4-dihydroxy-2''-methoxy-[1,1':2',1''-terphenyl]-3'-carboximidamide
$R^1$ = 5-fluoro-2-methoxyphenyl   $R^2$ = N-hydroxy carbaimidoyl     $R^3$ = H     $R^4$ = H
ES/MS m/z: 353.26 (pos. M + H), 351.34 (neg. M − H); $^1$H NMR (Acetone-d6, 500 MHz): δ 7.44-7.36 (m, 3H), 6.92-6.88 (m, 3H), 6.80-6.75 (m, 2H), 6.63 (m, 2H) and 3.52 (s, 3H).

E 104 N',4-dihydroxy-[1,1':2',1''-terphenyl]-3'-carboximidamide
$R^1$ = phenyl          $R^2$ = N-hydroxy carbaimidoyl     $R^3$ = H     $R^4$ = H
ES/MS m/z: 305.26 (pos. M + H), 303.3 (neg. M − H); $^1$H NMR (Acetone-d6, 500 MHz): δ 7.44-7.39 (m, 3H), 7.16-7.11 (m, 5H), 6.85 (m, 2H9 and 6.62 (m, 2H).

E 105 5''-fluoro-N',4-dihydroxy-2''-methoxy-[1,1':2',1''-terphenyl]-3'-carboximidamide
$R^1$ = 5-fluoro-2-methylphenyl    $R^2$ = N-hydroxy carbaimidoyl     $R^3$ = H     $R^4$ = H
ES/MS m/z: 337.25 (pos. M + H), 335.33 (neg. M − H); $^1$H NMR (Acetone-d6, 500 MHz): δ 7.47-7.40 (m, 3H), 6.99-6.94 (m, 2H), 6.91 (m, 2H), 6.83 (m, 1H), 6.64 (m, 2H) and 1.83 (s, 3H).

E 106 N',4-dihydroxy-5'-(trifluoromethyl)-2''-vinyl-[1,1':2',1''-terphenyl]-3'-carboximidamide
$R^1$ = 2-vinylphenyl    $R^2$ = N-hydroxy carbaimidoyl     $R^3$ = $CF_3$     $R^4$ = H
ES/MS m/z: 399.24 (pos. M + H), 397.32 (neg. M − H); $^1$H NMR (Acetone-d6, 500 MHz): δ 7.77 (d, 1H, J = 1.6 Hz), 7.67 (d, 1H, J = 1.6 Hz), 7.46 (d, 1H, J = 7.8 Hz), 7.23 (m, 1H), 7.18-7.16 (m, 2H), 6.89 (m, 2H), 6.61 (m, 2H), 6.40 (dd, 1H, J = 17.4, 11.1 Hz), 5.48 (dd, 1H, J = 17.4, 1.3 Hz) and 4.99 (dd, 1H, J = 11.1, 1.3 Hz).

E 107 2''-ethyl-N',4-dihydroxy-5'-(trifluoromethyl)-[1,1':2',1''-terphenyl]-3'-carboximidamide
$R^1$ = 2-ethylphenyl    $R^2$ = N-hydroxy carbaimidoyl     $R^3$ = $CF_3$     $R^4$ = H
ES/MS m/z: 401.25 (pos. M + H), 399.33 (neg. M − H); $^1$H NMR (Acetone-d6, 500 MHz): δ 7.76 (d, 1H, J = 1.6 Hz), 7.68 (d, 1H, J = 1.6 Hz), 7.22-7.19 (m, 2H), 7.13-7.08 (m, 2H), 6.92 (m, 2H), 6.64 (m, 2H), 2.29 (m, 1H), 2.09 (m, 1H) and 0.92 (t, 3H, J = 7.6 Hz).

E 108 3''-fluoro-N',4-dihydroxy-2''-methyl-5'-(trifluoromethyl)-[1,1':2',1''-terphenyl]-3'-carboximidamide
$R^1$ = 3-fluoro-2-methylphenyl    $R^2$ = N-hydroxy carbaimidoyl     $R^3$ = $CF_3$     $R^4$ = H
ES/MS m/z: 405.24 (pos. M + H), 403.28 (neg. M − H); $^1$H NMR (Acetone-d6, 500 MHz): δ 7.76 (d, 1H, J = 1.5 Hz), 7.70 (d, 1H, J = 1.5 Hz), 7.11 (m, 1H), 7.04 (dd, 1H, J = 7.6, 1.1 Hz), 6.96-6.92 (m, 3H), 6.68 (m, 2H) and 1.76 (d, 3H, J = 2.2 Hz).

E 109 3''-fluoro-N',4-dihydroxy-2''-methoxy-5'-(trifluoromethyl)-[1,1':2',1''-terphenyl]-3'-carboximidamide
$R^1$ = 3-fluoro-2-methylphenyl    $R^2$ = N-hydroxy carbaimidoyl     $R^3$ = $CF_3$     $R^4$ = H
ES/MS m/z: 421.2 (pos. M + H), 419.31 (neg. M − H); $^1$H NMR (Acetone-d6, 500 MHz): δ 7.75 (d, 1H, J = 1.5 Hz), 7.67 (d, 1H, J = 1.5 Hz), 7.04 (m, 1H), 6.98 (m, 2H), 6.93-6.89 (m, 2H), 6.68 (m, 2H) and 3.59, 3.58 (two s, 3H).

E 110 5',6'-dichloro-5''-fluoro-N',4-dihydroxy-2''-methyl-[1,1':2',1''-terphenyl]-3'-carboximidamide
$R^1$ = 5-fluoro-2-methylphenyl         $R^2$ = N-hydroxy carbaimidoyl     $R^3$ = Cl     $R^4$ = Cl
ES/MS m/z: 405.17 (pos. M + H), 403.27 (neg. M − H); $^1$H NMR (Acetone-d6, 500 MHz): δ 7.48 (s, 1H), 7.39 (m, 2H), 7.27 (dd, 1H, J = 8.6, 6.1 Hz), 7.05 (m, 1H), 6.99-6.96 (m, 3H) and 2.07 (s, 3H).

E 111 3'',5''-difluoro-N',4-dihydroxy-5'-(trifluoromethyl)-[1,1':2',1''-terphenyl]-3'-carboximidamide
$R^1$ = 3,5-difluorophenyl    $R^2$ = N-hydroxy carbaimidoyl     $R^3$ = $CF_3$     $R^4$ = H
ES/MS m/z: 409.23 (pos. M + H), 407.28 (neg. M − H); $^1$H NMR (Acetone-d6, 500 MHz): δ 7.73 (d, 1H, J = 1.3 Hz), 7.71 (d, 1H, J = 1.3 Hz), 6.97 (m, 2H), 6.87 (m, 1H), 6.81-6.77 (m, 2H) and 6.73 (m, 2H).

E 112 5''-chloro-N',4-dihydroxy-2''-methoxy-5'-(trifluoromethyl)-[1,1':2',1''-terphenyl]-3'-carboximidamide
$R^1$ = 5-chloro-2-methoxyphenyl    $R^2$ = N-hydroxy carbaimidoyl     $R^3$ = $CF_3$     $R^4$ = H
ES/MS m/z: 437.22 (pos. M + H), 435.28 (neg. M − H); $^1$H NMR (Acetone-d6, 500 MHz): δ 7.73 (d, 1H, J = 1.6 Hz), 7.64 (d, 1H, J = 1.6 Hz), 7.20 (dd, 1H, J = 8.8, 2.8 Hz), 7.04 (d, 1H, J = 2.8 Hz), 6.95 (m, 2H), 6.85 (d, 1H, J = 8.8 Hz), 6.68 (m, 2H) and 3.56 (s, 3H).

E 113 2''-ethynyl-N',4-dihydroxy-5'-(trifluoromethyl)-[1,1':2',1''-terphenyl]-3'-carboximidamide
$R^1$ = 2-ethynylphenyl    $R^2$ = N-hydroxy carbaimidoyl     $R^3$ = $CF_3$     $R^4$ = H
ES/MS m/z: 397.23 (pos. M + H), 395.3 (neg. M − H); $^1$H NMR (Acetone-d6, 500 MHz): δ 7.77 (d, 1H, J = 1.4 Hz), 7.66 (d, 1H, J = 1.4 Hz), 7.35 (dd, 1H, J = 7.9, 1.2 Hz), 7.29-7.20 (m, 3H), 6.98 (m, 2H), 6.64 (m, 2H) and 3.47 (s, 1H).

E 114 3''-chloro-5''-fluoro-N',4-dihydroxy-5'-(trifluoromethyl)-[1,1':2',1''-terphenyl]-3'-carboximidamide
$R^1$ = 3-chloro-5-fluorophenyl         $R^2$ = N-hydroxy carbaimidoyl     $R^3$ = $CF_3$     $R^4$ = H
ES/MS m/z: 425.18 (pos. M + H), 423.25 (neg. M − H); $^1$H NMR (Acetone-d6, 500 MHz): δ 7.73 (d, 1H, J = 1.4 Hz), 7.71 (d, 1H, J = 1.4 Hz), 7.10 (m, 1H), 7.01 (m, 1H), 6.97 (m, 2H), 6.92 (m, 1H) and 6.74 (m, 2H).

E 115 5''-fluoro-N',4-dihydroxy-2'',5'-bis(trifluoromethyl)-[1,1':2',1''-terphenyl]-3'-carboximidamide
$R^1$ = 5-fluoro-2-(trifluoromethyl)phenyl    $R^2$ = N-hydroxy carbaimidoyl     $R^3$ = $CF_3$     $R^4$ = H
ES/MS m/z: 459.19 (pos. M + H), 457.29 (neg. M − H); $^1$H NMR (Acetone-d6, 500 MHz): δ 7.84 (d, 1H, J = 1.4 Hz), 7.67 (d, 1H, J = 1.4 Hz), 7.59 (dd, 1H, J = 8.7, 5.5 Hz), 7.23-7.18 (m, 2H), 6.97 (m, 2H) and 6.69 (m, 2H).

-continued

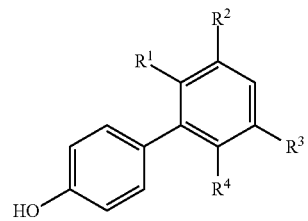

E 116    3",5"-difluoro-N',4-dihydroxy-2"-methoxy-5'-(trifluoromethyl)-[1,1':2',1"-terphenyl]-3'-carboximidamide
$R^1$ = 3,5-difluoro-2-methoxyphenyl      $R^2$ = N-hydroxy carbaimidoyl      $R^3$ = $CF_3$      $R^4$ = H
ES/MS m/z: 439.19 (pos. M + H), 437.31 (neg. M − H); $^1$H NMR (Acetone-d6, 500 MHz): δ 7.86 (d, 1H, J = 1.3 Hz), 7.71 (d, 1H, J = 1.3 Hz), 7.01-6.96 (m, 3H), 6.77-6.70 (m, 3H) and 3.77 (s, 3H).

Examples 117 and 118

Examples 117 and 118 were prepared using a method analogous to that used to synthesise Example 74 above. Full experimental details of the individual steps of the general methods are described in Example 74 above.

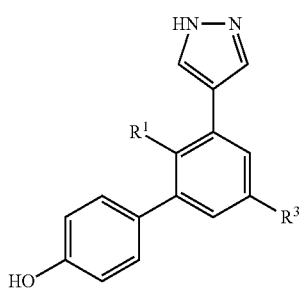

E 117    5'-methyl-3'-(1H-pyrazol-4-yl)-[1,1':2',1"-terphenyl]-4-ol
$R^1$ = phenyl      $R^3$ = methyl
ES/MS m/z: 327.33 (pos. M + H), 325.38 (neg. M − H); $^1$H NMR (Acetone-d6, 500 MHz): δ 7.39 (m, 1H), 7.18-7.14 (m, 3H), 7.09-7.04 (m, 3H), 6.98-6.95 (m, 2H), 6.90 (m, 2H), 6.61 (m, 2H) and 2.42 (s, 3H).

E 118    3",5"-difluoro-5'-propyl-3'-(1H-pyrazol-4-yl)-[1,1':2',1"-terphenyl]-4-ol
$R^1$ = 3,5-difluorophenyl      $R^3$ = propyl
ES/MS m/z: 391.28 (pos. M + H), 389.31 (neg. M − H); $^1$H NMR (Acetone-d6, 500 MHz): δ 7.39 (d, 1H, J = 1.6 Hz), 7.24 (s, 2H), 7.13 (d, 1H, J = 1.6 Hz), 6.94 (m, 2H), 6.80 (m, 1H), 6.69 (m, 2H), 6.64-6.60 (m, 2H), 2.69 (m, 2H), 1.74 (m, 2H) and 1.01 (t, 3H, J = 7.3 Hz).

Examples 119-121

Examples 119-121 were prepared using a method analogous to that used to synthesise Example 67 above. Full experimental details of the individual steps of the general methods are described in Example 67 above. For examples 119-121 identification of the title compounds by $^1$H-NMR showed that the oxime product was a single isomer, but did not confirm whether the (E) or (Z) oxime isomer had been obtained.

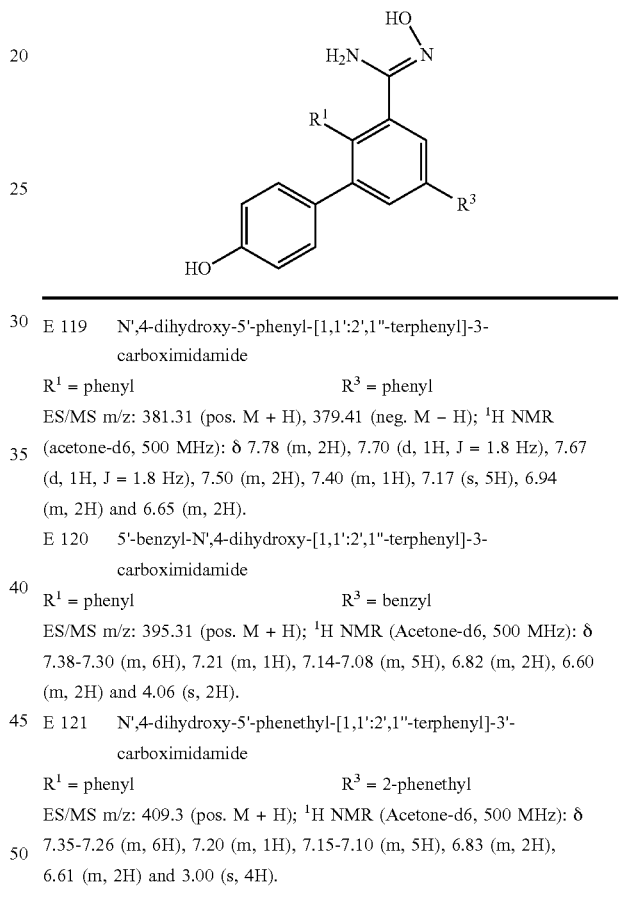

E 119    N',4-dihydroxy-5'-phenyl-[1,1':2',1"-terphenyl]-3'-carboximidamide
$R^1$ = phenyl      $R^3$ = phenyl
ES/MS m/z: 381.31 (pos. M + H), 379.41 (neg. M − H); $^1$H NMR (acetone-d6, 500 MHz): δ 7.78 (m, 2H), 7.70 (d, 1H, J = 1.8 Hz), 7.67 (d, 1H, J = 1.8 Hz), 7.50 (m, 2H), 7.40 (m, 1H), 7.17 (s, 5H), 6.94 (m, 2H) and 6.65 (m, 2H).

E 120    5'-benzyl-N',4-dihydroxy-[1,1':2',1"-terphenyl]-3'-carboximidamide
$R^1$ = phenyl      $R^3$ = benzyl
ES/MS m/z: 395.31 (pos. M + H); $^1$H NMR (Acetone-d6, 500 MHz): δ 7.38-7.30 (m, 6H), 7.21 (m, 1H), 7.14-7.08 (m, 5H), 6.82 (m, 2H), 6.60 (m, 2H) and 4.06 (s, 2H).

E 121    N',4-dihydroxy-5'-phenethyl-[1,1':2',1"-terphenyl]-3'-carboximidamide
$R^1$ = phenyl      $R^3$ = 2-phenethyl
ES/MS m/z: 409.3 (pos. M + H); $^1$H NMR (Acetone-d6, 500 MHz): δ 7.35-7.26 (m, 6H), 7.20 (m, 1H), 7.15-7.10 (m, 5H), 6.83 (m, 2H), 6.61 (m, 2H) and 3.00 (s, 4H).

Examples 122-276

Examples 122-276 were prepared using methods analogous to that used to synthesise Examples 1 and 15 above. Full experimental details of the individual steps of the general methods are described in Examples 1 and 15 above. For examples 122-129, 132, 134-138, 140-159, 162-172, 174-178, 182-184, 186, 188, 190-198, 200-224, 226, 228-257, 259, 261, 263-267, 269-273 and 275 identification of the title compounds by $^1$H-NMR showed that the oxime product was a single isomer, but did not confirm whether the (E) or (Z) oxime isomer had been obtained.

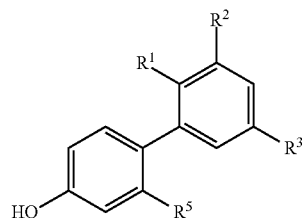

| E 122 | 2,5''-difluoro-N',4-dihydroxy-2''-methyl-5'-(trifluoromethyl)-[1,1':2',1''-terphenyl]-3'-carboximidamide |
|---|---|

R¹ = 5-fluoro-2-methylphenyl)     R² = N-hydroxy carbaimidoyl     R³ = CF$_3$     R⁵ = F
ES/MS m/z: 423.2 (pos. M + H), 421.4 (neg. M − H); $^1$H NMR (MeOD, 500 MHz): δ 7.79 (d, 1H, J = 1.1 Hz), 7.67 (d, 1H, J = 1.1 Hz), 6.99 (dd, 1H, J = 8.5, 5.9 Hz), 6.94 (dd, 1H, J = 9.6, 2.4 Hz), 6.85-6.81 (m, 2H), 6.42-6.37 (m, 2H) and 1.89 (s, 3H).

E 123    2,5''-difluoro-N',4-dihydroxy-2''-methyl-5'-(trifluoromethyl)-[1,1':2',1''-terphenyl]-3'-carboximidamide
R¹ = 5-fluoro-2-methoxyphenyl     R² = N-hydroxy carbaimidoyl     R³ = CF$_3$     R⁵ = F
ES/MS m/z: 439.4 (pos. M + H), 437.3 (neg. M − H); $^1$H NMR (MeOD, 500 MHz): δ 7.75 (d, 1H, J = 1.5 Hz), 7.63 (d, 1H, J = 1.5 Hz), 6.91 (m, 1H), 6.86 (dd, 1H, J = 8.9, 3.2 Hz), 6.80 (m, 1H), 6.74 (dd, 1H, J = 9.0, 4.3 Hz), 6.41-6.37 (m, 2H) and 3.54 (s, 3H).

E 124    2-fluoro-N',4-dihydroxy-2''-methyl-5'-(trifluoromethyl)-[1,1':2',1''-terphenyl]-3'-carboximidamide
R¹ = o-tolyl     R² = N-hydroxy carbaimidoyl     R³ = CF$_3$     R⁵ = F
ES/MS m/z: 405.2 (pos. M + H), 403.7 (neg. M − H); $^1$H NMR (MeOD, 500 MHz): δ 7.79 (s, 1H), 7.67 (s, 1H), 7.15-7.09 (m, 2H), 7.05-7.01 (m, 2H), 6.78 (m, 1H), 6.38-6.34 (m, 2H) and 1.94 (s, 3H).

E 125    2-fluoro-N',4-dihydroxy-5'-(trifluoromethyl)-[1,1':2',1''-terphenyl]-3'-carboximidamide
R¹ = phenyl     R² = N-hydroxy carbaimidoyl     R³ = CF$_3$     R⁵ = F
ES/MS m/z: 391.4 (pos. M + H), 389.5 (neg. M − H); $^1$H NMR (MeOD, 500 MHz): δ 7.77 (d, 1H, J = 1.5 Hz), 7.68 (d, 1H, J = 1.5 Hz), 7.19-7.13 (m, 5H), 6.82 (t, 1H, J = 8.6 Hz), 6.43 (dd, 1H, J = 8.5, 2.3 Hz) and 6.34 (dd, 1H, J = 11.6, 2.3 Hz).

E 126    5''-chloro-2-fluoro-N',4-dihydroxy-2''-methoxy-5'-(trifluoromethyl)-[1,1':2',1''-terphenyl]-3'-carboximidamide
R¹ = 5-chloro-2-methoxyphenyl     R² = N-hydroxy carbaimidoyl     R³ = CF$_3$     R⁵ = F
ES/MS m/z: 455.21 (pos. M + H), 453.24 (neg. M − H); $^1$H NMR (Acetone-d6, 500 MHz): δ 7.79 (d, 1H, J = 1.4 Hz), 7.68 (d, 1H, J = 1.4 Hz), 7.18 (dd, 1H, J = 8.7, 2.7 Hz), 7.08 (d, 1H, J = 2.7 Hz), 6.89 (t, 1H, J = 8.6 Hz), 6.80 (d, 1H, J = 8.7 Hz), 6.52-6.46 (m, 2H) and 3.56 (s, 3H).

E 127    2,3'-difluoro-N',4-dihydroxy-2''-methoxy-5'-(trifluoromethyl)-[1,1':2',1''-terphenyl]-3'-carboximidamide
R¹ = 3-fluoro-2-methoxyphenyl     R² = N-hydroxy carbaimidoyl     R³ = CF$_3$     R⁵ = F
ES/MS m/z: 439.25 (pos. M + H), 437.32 (neg. M − H); $^1$H NMR (Acetone-d6, 500 MHz): δ 7.82 (d, 1H, J = 1.3 Hz), 7.67 (s, 1H), 7.01 (m, 1H), 6.92-6.86 (m, 3H), 6.50-6.47 (m, 2H) and 3.68, 3.67 (two s, 3H).

E 128    2,3'',5''-trifluoro-N',4-dihydroxy-5'-(trifluoromethyl)-[1,1':2',1''-terphenyl]-3'-carboximidamide
R¹ = 3,5-difluorophenyl     R² = N-hydroxy carbaimidoyl     R³ = CF$_3$     R⁵ = F
ES/MS m/z: 427.22 (pos. M + H), 425.27 (neg. M − H); $^1$H NMR (Acetone-d6, 500 MHz): δ 7.80 (d, 1H, J = 1.6 Hz), 7.72 (d, 1H, J = 1.6 Hz), 7.01 (t, 1H, J = 8.6 Hz), 6.86 (m, 1H), 6.81-6.76 (m, 2H), 6.61 (m, 1H) and 6.50 (dd, 1H, J = 11.6, 2.5 Hz).

E 129    2-fluoro-N',4-dihydroxy-5'-(trifluoromethyl)-2''-vinyl-[1,1':2',1''-terphenyl]-3'-carboximidamide
R¹ = 2-vinylphenyl     R² = N-hydroxy carbaimidoyl     R³ = CF$_3$     R⁵ = F
ES/MS m/z: 417.28 (pos. M + H), 415.34 (neg. M − H); $^1$H NMR (Acetone-d6, 500 MHz): δ 7.84 (s, 1H), 7.68 (s, 1H), 7.45 (d, 1H, J = 7.7 Hz), 7.21-7.12 (m, 3H), 6.78 (t, 1H, J = 8.7 Hz), 6.44-6.37 (m, 3H), 5.50 (d, 1H, J = 17.6 Hz) and 5.02 (d, 1H, J = 10.6 Hz).

E 130    5''-chloro-2-fluoro-4-hydroxy-2''-methoxy-5'-(trifluoromethyl)-[1,1':2',1''-terphenyl]-3'-carboxamide
R¹ = 5-chloro-2-methoxyphenyl     R² = carbamoyl     R³ = CF$_3$     R⁵ = F
ES/MS m/z: 440.23 (pos. M + H), 438.27 (neg. M − H); $^1$H NMR (Acetone-d6, 500 MHz): δ 7.86 (d, 1H, J = 1.6 Hz), 7.69 (d, 1H, J = 1.6 Hz), 7.20 (dd, 1H, J = 8.9, 2.5 Hz), 7.09 (d, 1H, J = 2.5 Hz), 6.91 (t, 1H, J = 8.6 Hz), 6.83 (d, 1H, J = 8.9 Hz), 6.53 (dd, 1H, J = 8.4, 2.4 Hz), 6.49 (dd, 1H, J = 11.6, 2.4 Hz) and 3.57 (s, 3H).

E 131    2-fluoro-4-hydroxy-5'-(trifluoromethyl)-2''-vinyl-[1,1':2',1''-terphenyl]-3'-carboxamide
R¹ = 2-vinylphenyl     R² = carbamoyl     R³ = CF$_3$     R⁵ = F
ES/MS m/z: 402.27 (pos. M + H), 400.35 (neg. M − H); $^1$H NMR (Acetone-d6, 500 MHz): δ 7.91 (s, 1H), 7.71 (s, 1H), 7.47 (d, 1H, J = 7.9 Hz), 7.23-7.14 (m, 3H), 6.81 (m, 1H), 6.45-6.38 (m, 3H), 5.52 (dd, 1H, J = 1.3, 17.5 Hz) and 5.04 (dd, 1H, J = 1.3, 11.0 Hz).

E 132    3''-chloro-2,5''-difluoro-N',4-dihydroxy-5'-(trifluoromethyl)-[1,1':2',1''-terphenyl]-3'-carboximidamide
R¹ = 3-chloro-5-fluorophenyl     R² = N-hydroxy carbaimidoyl     R³ = CF$_3$     R⁵ = F
ES/MS m/z: 443.17 (pos. M + H), 441.28 (neg. M − H); $^1$H NMR (Acetone-d6, 500 MHz): δ 7.80 (d, 1H, J = 1.7 Hz), 7.72 (d, 1H, J = 1.7 Hz), 7.09 (m, 1H), 7.03-7.00 (m, 2H), 6.91 (m, 1H), 6.62 (dd, 1H, J = 8.4, 2.4 Hz) and 6.49 (dd, 1H, J = 11.6, 2.4 Hz).

E 133    3''-chloro-2,5''-difluoro-4-hydroxy-5'-(trifluoromethyl)-[1,1':2',1''-terphenyl]-3'-carboxamide
R¹ = 3-chloro-5-fluorophenyl     R² = carbamoyl     R³ = CF$_3$     R⁵ = F
ES/MS m/z: 428.18 (pos. M + H), 426.2 (neg. M − H); $^1$H NMR (Acetone-d6, 500 MHz): δ 7.86 (d, 1H, J = 1.7 Hz), 7.75 (d, 1H, J = 1.7 Hz), 7.13 (m, 1H), 7.07-7.03 (m, 2H), 6.91 (m, 1H), 6.64 (dd, 1H, J = 8.4, 2.4 Hz) and 6.50 (dd, 1H, J = 11.6, 2.4 Hz).

E 134    2''-ethynyl-2-fluoro-N',4-dihydroxy-5'-(trifluoromethyl)-[1,1':2',1''-terphenyl]-3'-carboximidamide
R¹ = 2-ethynylphenyl     R² = N-hydroxy carbaimidoyl     R³ = CF$_3$     R⁵ = F
ES/MS m/z: 415.23 (pos. M + H), 413.29 (neg. M − H); $^1$H NMR (Acetone-d6, 500 MHz): δ 7.83 (d, 1H, J = 1.3 Hz), 7.68 (d, 1H, J = 1.3 Hz), 7.32 (d, 1H, J = 8.0 Hz), 7.29-7.20 (m, 3H), 6.94 (m, 1H), 6.48-6.43 (m, 2H) and 3.48 (s, 1H).

E 135    5'-chloro-3'',5''-difluoro-N',4-dihydroxy-[1,1':2',1''-terphenyl]-3'-carboximidamide
R¹ = 3,5-difluorophenyl     R² = N-hydroxy carbaimidoyl     R³ = Cl     R⁵ = H
ES/MS m/z: 375.19 (pos. M + H), 373.27 (neg. M − H); $^1$H NMR (Acetone-d6, 500 MHz): δ 7.44 (d, 1H, J = 2.2 Hz), 7.43 (d, 1H, J = 2.2 Hz), 6.93 (m, 2H), 6.83 (m, 1H) and 6.76-6.70 (m, 4H).

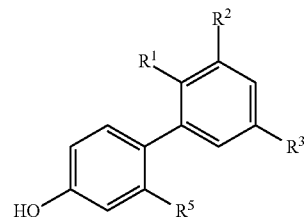

E 136   5'-chloro-3"-fluoro-N',4-dihydroxy-2"-methoxy-[1,1':2',1"-terphenyl]-3'-carboximidamide
$R^1$ = 3-fluoro-2-methoxyphenyl     $R^2$ = N-hydroxy carbaimidoyl     $R^3$ = Cl     $R^5$ = H
ES/MS m/z: 387.19 (pos. M + H), 385.22 (neg. M − H); $^1$H NMR (Acetone-d6, 500 MHz): δ 7.46 (d, 1H, J = 2.1 Hz), 7.39 (d, 1H, J = 2.1 Hz), 7.01 (m, 1H), 6.94 (m, 2H), 6.90-6.88 (m, 2H), 6.66 (m, 2H) and 3.57 (d, 3H, J = 2.8 Hz).

E 137   5',5"-dichloro-N',4-dihydroxy-2"-methoxy-[1,1':2',1"-terphenyl]-3'-carboximidamide
$R^1$ = 5-chloro-2-methoxyphenyl     $R^2$ = N-hydroxy carbaimidoyl     $R^3$ = Cl     $R^5$ = H
ES/MS m/z: 403.14 (pos. M + H), 401.2 (neg. M − H); $^1$H NMR (Acetone-d6, 500 MHz): δ 7.43 (d, 1H, J = 2.3 Hz), 7.37 (d, 1H, J = 2.3 Hz), 7.16 (dd, 1H, J = 8.9, 2.6 Hz), 6.99 (d, 1H, J = 2.6 Hz), 6.92 (m, 2H), 6.82 (d, 1H, J = 8.9 Hz), 6.66 (m, 2H) and 3.55 (s, 3H).

E 138   3"-chloro-2-fluoro-N',4-dihydroxy-2"-methyl-5'-(trifluoromethyl)-[1,1':2',1"-terphenyl]-3'-carboximidamide
$R^1$ = 3-chloro-2-methylphenyl     $R^2$ = N-hydroxy carbaimidoyl     $R^3$ = CF$_3$     $R^5$ = F
ES/MS m/z: 439.18 (pos. M + H), 437.28 (neg. M − H); $^1$H NMR (Acetone-d6, 500 MHz): δ 7.83 (s, 1H), 7.70 (s, 1H), 7.23 (dd, 1H, J = 7.8, 1.3 Hz), 7.11 (m, 1H), 7.05 (m, 1H), 6.88 (t, 1H, J = 8.5 Hz), 6.51 (dd, 1H, J = 8.3, 2.4 Hz), 6.47 (dd, 1H, J = 11.5, 2.4 Hz) and 1.96 (s, 3H).

E 139   3"-chloro-2-fluoro-4-hydroxy-2"-methyl-5'-(trifluoromethyl)-[1,1':2',1"-terphenyl]-3'-carboxamide
$R^1$ = 3-chloro-2-methylphenyl     $R^2$ = carbamoyl     $R^3$ = CF$_3$     $R^5$ = F
ES/MS m/z: 424.2 (pos. M + H), 422.25 (neg. M − H); $^1$H NMR (Acetone-d6, 500 MHz): δ 7.89 (s, 1H), 7.73 (s, 1H), 7.25 (dd, 1H, J = 7.8, 1.6 Hz), 7.11 (m, 1H), 7.08 (m, 1H), 6.92 (t, 1H, J = 8.8 Hz), 6.53 (dd, 1H, J = 8.5, 2.4 Hz), 6.48 (dd, 1H, J = 11.7, 2.4 Hz) and 2.00 (s, 3H).

E 140   N',4-dihydroxy-5'-methyl-2"-vinyl-[1,1':2',1"-terphenyl]-3'-carboximidamide
$R^1$ = 2-vinylphenyl     $R^2$ = N-hydroxy carbaimidoyl     $R^3$ = Me     $R^5$ = H
ES/MS m/z: 345.29 (pos. M + H), 343.34 (neg. M − H); $^1$H NMR (Acetone-d6, 500 MHz): δ 7.42 (d, 1H, J = 7.8 Hz), 7.29 (s, 1H), 7.21 (s, 1H), 7.16 (m, 1H), 7.12-7.09 (m, 2H), 6.83 (m, 2H), 6.56 (m, 2H), 5.45 (dd, 1H, J = 17.5, 10.6 Hz), 5.45 (dd, 1H, J = 17.5, 1.1 Hz), 4.95 (dd, 1H, J = 10.6, 1.1 Hz) and 2.42 (s, 3H).

E 141   3",5"-difluoro-N',4-dihydroxy-2"-methoxy-5'-methyl-[1,1':2',1"-terphenyl]-3'-carboximidamide
$R^1$ = 3,5-difluoro-2-methoxyphenyl     $R^2$ = N-hydroxy carbaimidoyl     $R^3$ = Me     $R^5$ = H
ES/MS m/z: 385.23 (pos. M + H), 383.22 (neg. M − H); $^1$H NMR (Acetone-d6, 500 MHz): δ 7.36 (d, 1H, J = 1.5 Hz), 7.23 (d, 1H, J = 1.5 Hz), 6.95-6.88 (m, 3H), 6.70-6.64 (m, 3H), 3.74 (s, 3H) and 2.43 (s, 3H).

E 142   3"-fluoro-N',4-dihydroxy-2"-methoxy-5'-methyl-[1,1':2',1"-terphenyl]-3'-carboximidamide
$R^1$ = 3-fluoro-2-methoxyphenyl     $R^2$ = N-hydroxy carbaimidoyl     $R^3$ = Me     $R^5$ = H
ES/MS m/z: 367.25 (pos. M + H), 356.29 (neg. M − H); $^1$H NMR (Acetone-d6, 500 MHz): δ 7.28 (s, 1H), 7.21 (s, 1H), 6.97 (m, 1H), 6.92 (m, 2H), 6.88-6.84 (m, 2H), 6.63 (m, 2H), 3.55-3.54 (two s, 3H) and 2.41 (s, 3H).

E 143   5"-fluoro-N',4-dihydroxy-2"-methoxy-5'-methyl-[1,1':2',1"-terphenyl]-3'-carboximidamide
$R^1$ = 5-fluoro-2-methoxyphenyl     $R^2$ = N-hydroxy carbaimidoyl     $R^3$ = Me     $R^5$ = H
ES/MS m/z: 367.25 (pos. M + H), 365.34 (neg. M − H); $^1$H NMR (Acetone-d6, 500 MHz): δ 7.25 (s, 1H), 7.18 (s, 1H), 6.91-6.87 (m, 3H), 6.79-6.73 (m, 2H), 6.62 (m, 2H), 3.52 (s, 3H) and 2.40 (s, 3H).

E 144   3"-chloro-5"-fluoro-N',4-dihydroxy-5'-methyl-[1,1':2',1"-terphenyl]-3'-carboximidamide
$R^1$ = 3-chloro-5-fluorophenyl     $R^2$ = N-hydroxy carbaimidoyl     $R^3$ = Me     $R^5$ = H
ES/MS m/z: 371.24 (pos. M + H), 369.29 (neg. M − H); $^1$H NMR (Acetone-d6, 500 MHz): δ 7.27 (s, 1H), 7.24 (s, 1H), 7.01 (m, 1H), 6.94 (t, 1H, J = 1.5 Hz), 6.89 (m, 2H), 6.83 (m, 1H), 6.69 (m, 2H) and 2.42 (s, 3H).

E 145   5"-chloro-N',4-dihydroxy-2",5'-dimethyl-[1,1':2',1"-terphenyl]-3'-carboximidamide
$R^1$ = 5-chloro-2-methylphenyl     $R^2$ = N-hydroxy carbaimidoyl     $R^3$ = Me     $R^5$ = H
ES/MS m/z: 367.25 (pos. M + H), 365.34 (neg. M − H); $^1$H NMR (Acetone-d6, 500 MHz): δ 7.28 (d, 1H, J = 1.3 Hz), 7.23 (d, 1H, J = 1.3 Hz), 7.18 (d, 1H, J = 2.4 Hz), 7.07 (dd, 1H, J = 8.2, 2.4 Hz), 6.96 (d, 1H, J = 8.2 Hz), 6.89 (m, 2H), 6.63 (m, 2H), 2.42 (s, 3H) and 1.84 (s, 3H).

E 146   5"-chloro-N',4-dihydroxy-2"-methyl-5'-(trifluoromethyl)-[1,1':2',1"-terphenyl]-3'-carboximidamide
$R^1$ = 5-chloro-2-methylphenyl     $R^2$ = N-hydroxy carbaimidoyl     $R^3$ = CF$_3$     $R^5$ = H
ES/MS m/z: 421.1 (pos. M + H), 418.6 (neg. M − H); $^1$H NMR (Acetone-d6, 500 MHz): δ 7.76 (d, 1H, J = 1.4 Hz), 7.69 (d, 1H, J = 1.4 Hz), 7.24 (d, 1H, J = 2.2 Hz), 7.14 (dd, 1H, J = 8.2, 2.2 Hz), 7.02 (d, 1H, J = 8.2 Hz), 6.96 (m, 2H), 6.68 (m, 2H) and 1.85 (s, 3H).

E 147   3"-chloro-N',4-dihydroxy-2"-methyl-5'-(trifluoromethyl)-[1,1':2',1"-terphenyl]-3'-carboximidamide
$R^1$ = 3-chloro-2-methylphenyl     $R^2$ = N-hydroxy carbaimidoyl     $R^3$ = CF$_3$     $R^5$ = H
ES/MS m/z: 421.1 (pos. M + H), 418.6 (neg. M − H); $^1$H NMR (Acetone-d6, 500 MHz): δ 7.76 (d, 1H, J = 1.4 Hz), 7.69 (d, 1H, J = 1.4 Hz), 7.26 (dd, 1H, J = 8.0, 1.2 Hz), 7.17 (dd, 1H, J = 7.6, 1.4 Hz), 7.10 (t, 1H, J = 7.9 Hz), 6.93 (m, 2H), 6.67 (m, 2H) and 1.88 (s, 3H).

E 148   5"-chloro-N',4-dihydroxy-2"-methoxy-5'-methyl-[1,1':2',1"-terphenyl]-3'-carboximidamide
$R^1$ = 5-chloro-2-methoxyphenyl     $R^2$ = N-hydroxy carbaimidoyl     $R^3$ = Me     $R^5$ = H
ES/MS m/z: 383.27 (pos. M + H), 381.24 (neg. M − H); $^1$H NMR (Acetone-d6, 500 MHz): δ 7.25 (d, 1H, J = 1.3 Hz), 7.17 (d, 1H, J = 1.3 Hz), 7.13 (dd, 1H, J = 8.4, 2.8 Hz), 6.96 (d, 1H, J = 2.8 Hz), 6.89 (m, 2H), 6.80 (d, 1H, J = 8.4 Hz), 6.63 (m, 2H), 3.54 (s, 3H) and 2.40 (s, 3H).

E 149   2"-chloro-5"-fluoro-N',4-dihydroxy-5'-methyl-[1,1':2',1"-terphenyl]-3'-carboximidamide
$R^1$ = 5-fluoro-2-methoxyphenyl     $R^2$ = N-hydroxy carbaimidoyl     $R^3$ = Me     $R^5$ = H
ES/MS m/z: 371.24 (pos. M + H), 369.32 (neg. M − H); $^1$H NMR (Acetone-d6, 500 MHz): δ 7.32 (s, 1H), 7.23-7.20 (m, 2H), 7.01-6.92 (m, 4H), 6.65 (m, 2H) and 2.43 (s, 3H).

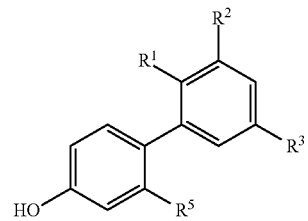

E 150    N',4-dihydroxy-5'-methyl-[1,1':2',1''-terphenyl]-3'-carboximidamide
$R^1$ = phenyl      $R^2$ = N-hydroxy carbaimidoyl      $R^3$ = Me      $R^5$ = H
ES/MS m/z: 317.2 (pos. M + H), 319.1 (neg. M − H); $^1$H NMR (Acetone-d6, 500 MHz): δ 7.24 (s, 1H), 7.22 (s, 1H), 7.14-7.08 (m, 5H), 6.84 (m, 2H), 6.61 (m, 2H) and 2.40 (s, 3H).

E 151    N',4-dihydroxy-3'',5'-dimethyl-[1,1':2',1''-terphenyl]-3'-carboximidamide
$R^1$ = m-tolyl      $R^2$ = N-hydroxy carbaimidoyl      $R^3$ = Me      $R^5$ = H
ES/MS m/z: 333.2 (pos. M + H), 331.3 (neg. M − H); $^1$H NMR (Acetone-d6, 500 MHz): δ 7.24 (s, 1H), 7.21 (s, 1H), 7.02 (m, 1H), 6.95 (d, 1H, J = 7.8 Hz), 6.88 (m, 1H), 6.85 (m, 2H), 6.61 (m, 2H), 2.40 (s, 3H) and 2.17 (s, 3H).

E 152    3''-chloro-N',4-dihydroxy-5'-methyl-[1,1':2',1''-terphenyl]-3'-carboximidamide
$R^1$ = 3-chlorophenyl      $R^2$ = N-hydroxy carbaimidoyl      $R^3$ = Me      $R^5$ = H
ES/MS m/z: 353.3 (pos. M + H), 351.4 (neg. M − H); $^1$H NMR (Acetone-d6, 500 MHz): δ 7.25 (s, 1H), 7.23 (s, 1H), 7.16-7.11 (m, 3H), 7.04 (m, 1H), 6.85 (m, 2H), 6.65 (m, 2H) and 2.41 (s, 3H).

E 153    N',4-dihydroxy-3''-methoxy-5'-methyl-[1,1':2',1''-terphenyl]-3'-carboximidamide
$R^1$ = 3-methoxyphenyl      $R^2$ = N-hydroxy carbaimidoyl      $R^3$ = Me      $R^5$ = H
ES/MS m/z: 349.4 (pos. M + H), 347.2 (neg. M − H); $^1$H NMR (Acetone-d6, 500 MHz): δ 7.24 (s, 1H), 7.23 (s, 1H), 7.04 (t, 1H, J = 7.9 Hz), 6.87 (m, 2H), 6.72-6.64 (m, 3H), 6.63 (m, 2H), 3.62 (s, 3H) and 2.40 (s, 3H).

E 154    4''-fluoro-N',4-dihydroxy-5'-(trifluoromethyl)-[1,1':2',1''-terphenyl]-3'-carboximidamide
$R^1$ = 4-fluorophenyl      $R^2$ = N-hydroxy carbaimidoyl      $R^3$ = $CF_3$      $R^5$ = H
ES/MS m/z: 391.24 (pos. M + H), 389.27 (neg. M − H); $^1$H NMR (Acetone-d6, 500 MHz): δ 7.70 (s, 1H), 7.68 (s, 1H), 7.17 (m, 2H), 6.97 (m, 2H), 6.91 (m, 2H) and 6.69 (m, 2H).

E 155    4''-chloro-N',4-dihydroxy-5'-(trifluoromethyl)-[1,1':2',1''-terphenyl]-3'-carboximidamide
$R^1$ = 4-chlorophenyl      $R^2$ = N-hydroxy carbaimidoyl      $R^3$ = $CF_3$      $R^5$ = H
ES/MS m/z: 407.2 (pos. M + H), 405.25 (neg. M − H); $^1$H NMR (Acetone-d6, 500 MHz): δ 7.70 (s, 1H), 7.68 (s, 1H), 7.23 (m, 2H), 7.15 (m, 2H), 6.92 (m, 2H) and 6.69 (m, 2H).

E 156    N',4-dihydroxy-2''-methoxy-5'-(trifluoromethyl)-[1,1':2',1''-terphenyl]-3'-carboximidamide
$R^1$ = 2-methoxyphenyl      $R^2$ = N-hydroxy carbaimidoyl      $R^3$ = $CF_3$      $R^5$ = H
ES/MS m/z: 403.21 (pos. M + H), 401.27 (neg. M − H); $^1$H NMR (Acetone-d6, 500 MHz): δ 7.72 (d, 1H, J = 1.3 Hz), 7.63 (d, 1H, J = 1.3 Hz), 7.21 (m, 1H), 7.02 (dd, 1H, J = 7.3, 1.6 Hz), 6.92 (m, 2H), 6.85-6.80 (m, 2H), 6.63 (m, 2H) and 3.55 (s, 3H).

E 157    4''-fluoro-N',4-dihydroxy-2''-methoxy-5'-(trifluoromethyl)-[1,1':2',1''-terphenyl]-3'-carboximidamide
$R^1$ = 4-fluoro-2-methoxyphenyl      $R^2$ = N-hydroxy carbaimidoyl      $R^3$ = $CF_3$      $R^5$ = H
ES/MS m/z: 421.2 (pos. M + H), 419.28 (neg. M − H); $^1$H NMR (Acetone-d6, 500 MHz): δ 7.71 (d, 1H, J = 1.4 Hz), 7.63 (d, 1H, J01.4 Hz), 7.04 (dd, 1H, J = 8.4, 6.7 Hz), 6.93 (m, 2H), 6.68-6.64 (m, 3H), 6.59 (m, 1H) and 3.56 (s, 3H).

E 158    N',4-dihydroxy-2''-isopropyl-5'-(trifluoromethyl)-[1,1':2',1''-terphenyl]-3'-carboximidamide
$R^1$ = 2-isopropylphenyl      $R^2$ = N-hydroxy carbaimidoyl      $R^3$ = $CF_3$      $R^5$ = H
ES/MS m/z: 415.25 (pos. M + H), 413.32 (neg. M − H); $^1$H NMR (Acetone-d6, 500 MHz): δ 7.77 (d, 1H, J = 1.6 Hz), 7.68 (d, 1H, J = 1.6 Hz), 7.29-7.23 (m, 2H), 7.17-7.11 (m, 2H), 6.95 (m, 2H), 6.65 (m, 2H), 2.45 (m, 1H), 1.00 (d, 3H, J = 6.8 Hz) and 0.58 (d, 3H, J = 6.8 Hz).

E 159    2-(3,5-dimethylisoxazol-4-yl)-N',4'-dihydroxy-5-(trifluoromethyl)-[1,1'-biphenyl]-3-carboximidamide
$R^1$ = 3,5-dimethylisoxazol-4-yl      $R^2$ = N-hydroxy carbaimidoyl      $R^3$ = $CF_3$      $R^5$ = H
ES/MS m/z: 392.23 (pos. M + H), 390.31 (neg. M − H); $^1$H NMR (MeOD, 500 MHz): δ 7.75 (s, 1H), 7.73 (s, 1H), 6.95 (m, 2H), 6.72 (m, 2H), 2.09 (s, 3H) and 1.86 (s, 3H).

E 160    2-(3,5-dimethylisoxazol-4-yl)-4'-dihydroxy-5-(trifluoromethyl)-[1,1'-biphenyl]-3-carboxamide
$R^1$ = 3,5-dimethylisoxazol-4-yl      $R^2$ = carbamoyl      $R^3$ = $CF_3$      $R^5$ = H
ES/MS m/z: 377.24 (pos. M + H), 375.3 (neg. M − H); $^1$H NMR (MeOD, 500 MHz): δ 7.79 (s, 1H), 7.75 (s, 1H), 6.95 (m, 2H), 6.73 (m, 2H), 2.11 (s, 3H) and 1.86 (s, 3H).

E 161    3''-chloro-4-hydroxy-2''-methyl-5'-(trifluoromethyl)-[1,1':2',1''-terphenyl]-3'-carboxamide
$R^1$ = 3-chloro-2-methylphenyl      $R^2$ = carbamoyl      $R^3$ = $CF_3$      $R^5$ = H
ES/MS m/z: 406.21 (pos. M + H), 404.26 (neg. M − H); $^1$H NMR (Acetone-d6, 500 MHz): δ 7.81 (d, 1H, J01.4 Hz), 7.72 (d, 1H, J = 1.4 Hz), 7.29 (dd, 1H, J = 7.9, 1.4 Hz), 7.18 (dd, 1H, J = 7.7, 1.4 Hz), 7.13 (t, 1H, J = 7.8 Hz), 6.96 (m, 2H), 6.68 (m, 2H) and 1.92 (s, 3H).

E 162    N',4-dihydroxy-2'',5''-dimethyl-5'-(trifluoromethyl)-[1,1':2',1''-terphenyl]-3'-carboximidamide
$R^1$ = 2,5-dimethylphenyl      $R^2$ = N-hydroxy carbaimidoyl      $R^3$ = $CF_3$      $R^5$ = H
ES/MS m/z: 401.25 (pos. M + H), 399.46 (neg. M − H); $^1$H NMR (Acetone-d6, 500 MHz): δ 7.75 (d, 1H, J = 1.3 Hz), 7.67 (d, 1H, J = 1.3 Hz), 7.03 (s, 1H), 6.96-6.93 (m, 3H), 6.90 (d, 1H, J = 7.7 Hz), 6.64 (m, 2H), 2.22 (s, 3H) and 1.82 (s, 3H).

E 163    N',4-dihydroxy-2''-methoxy-5''-methyl-5'-(trifluoromethyl)-[1,1':2',1''-terphenyl]-3'-carboximidamide
$R^1$ = 2-methoxy-5-methylphenyl      $R^2$ = N-hydroxy carbaimidoyl      $R^3$ = $CF_3$      $R^5$ = H
ES/MS m/z: 417.28 (pos. M + H), 415.33 (neg. M − H); $^1$H NMR (Acetone-d6, 500 MHz): δ 7.71 (d, 1H, J = 1.7 Hz), 7.62 (d, 1H, J = 1.7 Hz), 7.01 (dd, 1H, J = 8.4, 1.9 Hz), 6.93 (m, 2H), 6.83 (d, 1H, J = 1.9 Hz), 6.73 (d, 1H, J = 8.4 Hz), 6.64 (m, 2H), 3.53 (s, 3H) and 2.14 (s, 3H), 2.22 (s, 3H) and 1.82 (s, 3H).

-continued

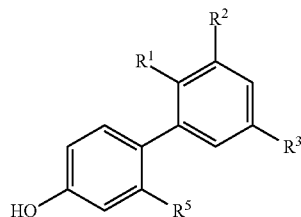

E 164 2''-chloro-N',4-dihydroxy-5''-methyl-5'-(trifluoromethyl)-[1,1':2',1''-terphenyl]-3'-carboximidamide
$R^1$ = 2-chloro-5-methylphenyl    $R^2$ = N-hydroxy carbaimidoyl    $R^3$ = $CF_3$    $R^5$ = H
ES/MS m/z: 421.25 (pos. M + H), 419.31 (neg. M − H); $^1$H NMR (Acetone-d6, 500 MHz): δ 7.78 (d, 1H, J = 1.6 Hz), 7.67 (d, 1H, J = 1.6 Hz), 7.12-7.10 (m, 2H), 7.05 (dd, 1H, J = 8.2, 1.8 Hz), 6.98 (m, 2H), 6.66 (m, 2H) and 2.23 (s, 3H).

E 165 5'-fluoro-N',4-dihydroxy-[1,1':2',1''-terphenyl]-3'-carboximidamide
$R^1$ = phenyl    $R^2$ = N-hydroxy carbaimidoyl    $R^3$ = F    $R^5$ = H
ES/MS m/z: 323.25 (pos. M + H), 321.41 (neg. M − H); $^1$H NMR (Acetone-d6, 500 MHz): δ 7.19-7.15 (m, 5H), 7.12-7.09 (m, 2H), 6.87 (m, 2H) and 6.63 (m, 2H).

E 166 5''-chloro-5'-fluoro-N',4-dihydroxy-2''-methoxy-[1,1':2',1''-terphenyl]-3'-carboximidamide
$R^1$ = 5-chloro-2-methoxyphenyl    $R^2$ = N-hydroxy carbaimidoyl    $R^3$ = F    $R^5$ = H
ES/MS m/z: 387.21 (pos. M + H), 385.24 (neg. M − H); $^1$H NMR (Acetone-d6, 500 MHz): δ 7.20-7.11 (m, 3H), 6.97 (d, 1H, J = 2.7 Hz), 6.92 (m, 2H), 6.82 (d, 1H, J = 8.9 Hz), 6.65 (m, 2H) and 3.55 (s, 3H).

E 167 3'',5'-difluoro-N',4-dihydroxy-2''-methoxy-[1,1':2',1''-terphenyl]-3'-carboximidamide
$R^1$ = 3-fluoro-2-methoxyphenyl    $R^2$ = N-hydroxy carbaimidoyl    $R^3$ = F    $R^5$ = H
ES/MS m/z: 371.28 (pos. M + H), 369.32 (neg. M − H); $^1$H NMR (Acetone-d6, 500 MHz): δ 7.21 (dd, 1H, J = 9.3, 3.0 Hz), 7.15 (dd, 1H, J = 9.5, 3.0 Hz), 7.00 (m, 1H), 6.94 (m, 2H), 6.90-6.85 (m, 2H) and 3.57, 3.56 (two s, 3H).

E 168 3'',5',5''-trifluoro-N',4-dihydroxy-[1,1':2',1''-terphenyl]-3'-carboximidamide
$R^1$ = 3,5-difluorophenyl    $R^2$ = N-hydroxy carbaimidoyl    $R^3$ = F    $R^5$ = H
ES/MS m/z: 359.23 (pos. M + H), 357.3 (neg. M − H); $^1$H NMR (Acetone-d6, 500 MHz): δ 7.20 (m, 2H), 6.93 (m, 2H), 6.82 (m, 1H) and 6.74-6.69 (m, 4H).

E 169 3''-chloro-5',5''-difluoro-N',4-dihydroxy-[1,1':2',1''-terphenyl]-3'-carboximidamide
$R^1$ = 3-chloro-5-fluorophenyl    $R^2$ = N-hydroxy carbaimidoyl    $R^3$ = F    $R^5$ = H
ES/MS m/z: 375.2 (pos. M + H), 373.3 (neg. M − H); $^1$H NMR (Acetone-d6, 500 MHz): δ 7.22-7.18 (m, 2H), 7.05 (m, 1H), 6.95 (m, 1H), 6.93 (m, 2H), 6.85 (m, 1H) and 6.71 (m, 2H).

E 170 5'-fluoro-N',4-dihydroxy-2''-vinyl-[1,1':2',1''-terphenyl]-3'-carboximidamide
$R^1$ = 2-vinylphenyl    $R^2$ = N-hydroxy carbaimidoyl    $R^3$ = F    $R^5$ = H
ES/MS m/z: 349.27 (pos. M + H), 347.45 (neg. M − H); $^1$H NMR (Acetone-d6, 500 MHz): δ 7.44 (d, 1H, J = 7.7 Hz), 7.23 (dd, 1H, J = 9.2, 2.8 Hz), 7.21-7.11 (m, 4H), 6.86 (m, 2H), 6.58 (m, 2H), 6.43 (dd, 1H, J = 17.6, 11.1 Hz), 5.46 (dd, 1H, J = 17.6, 1.4 Hz) and 4.98 (dd, 1H, J = 11.1, 1.4 Hz).

E 171 5'-chloro-N',4-dihydroxy-2'',5''-dimethyl-[1,1':2',1''-terphenyl]-3'-carboximidamide
$R^1$ = 2,5-dimethylphenyl    $R^2$ = N-hydroxy carbaimidoyl    $R^3$ = Cl    $R^5$ = H
ES/MS m/z: 367.25 (pos. M + H), 365.29 (neg. M − H); $^1$H NMR (Acetone-d6, 500 MHz): δ 7.46 (d, 1H, J = 2.6 Hz), 7.39 (d, 1H, J = 2.6 Hz), 6.99 (s, 1H), 6.93-6.87 (m, 4H), 6.62 (m, 2H), 2.20 (s, 3H) and 1.82 (s, 3H).

E 172 N',4-dihydroxy-2'',5''-dimethyl-[1,1':2',1''-terphenyl]-3'-carboximidamide
$R^1$ = 2,5-dimethylphenyl    $R^2$ = N-hydroxy carbaimidoyl    $R^3$ = H    $R^5$ = H
ES/MS m/z: 333.28 (pos. M + H), 331.34 (neg. M − H); $^1$H NMR (Acetone-d6, 500 MHz): δ 7.47-7.38 (m, 3H), 6.99 (s, 1H), 6.91-6.86 (m, 4H), 6.60 (m, 2H), 2.20 (s, 3H) and 1.82 (s, 3H).

E 173 2''-chloro-4-hydroxy-5''-methyl-5'-(trifluoromethyl)-[1,1':2',1''-terphenyl]-3'-carboxamide
$R^1$ = 2-chloro-5-methylphenyl    $R^2$ = carbamoyl    $R^3$ = $CF_3$    $R^5$ = H
ES/MS m/z: 406.19 (pos. M + H), 404.26 (neg. M − H); $^1$H NMR (Acetone-d6, 500 MHz): δ 7.85 (d, 1H, J = 1.6 Hz), 7.72 (d, 1H, J = 1.6 Hz), 7.16 (d, 1H, J = 8.1 Hz), 7.10 (d, 1H, J = 1.9 Hz), 7.06 (dd, 1H, J = 8.1, 1.9 Hz), 7.00 (m, 2H), 6.68 (m, 2H) and 2.23 (s, 3H).

E 174 3''-chloro-N',4-dihydroxy-5''-methyl-5'-(trifluoromethyl)-[1,1':2',1''-terphenyl]-3'-carboximidamide
$R^1$ = 3-chloro-5-methylphenyl    $R^2$ = N-hydroxy carbaimidoyl    $R^3$ = $CF_3$    $R^5$ = H
ES/MS m/z: 421.2 (pos. M + H), 419.26 (neg. M − H); $^1$H NMR (Acetone-d6, 500 MHz): δ 7.71 (s, 1H), 7.68 (s, 1H), 7.05 (s, 1H), 6.97-6.92 (m, 4H), 6.70 (m, 2H) and 2.20 (s, 3H).

E 175 2'',5''-dichloro-N',4-dihydroxy-5'-(trifluoromethyl)-[1,1':2',1''-terphenyl]-3'-carboxamide
$R^1$ = 2,5-dichlorophenyl    $R^2$ = N-hydroxy carbaimidoyl    $R^3$ = $CF_3$    $R^5$ = H
ES/MS m/z: 441.14 (pos. M + H), 439.19 (neg. M − H); $^1$H NMR (Acetone-d6, 500 MHz): δ 7.81 (d, 1H, J = 1.2 Hz), 7.70 (d, 1H, J = 1.2 Hz), 7.32 (m, 1H), 7.27-7.24 (m, 2H), 7.00 (m, 2H) and 6.70 (m, 2H).

E 176 5''-chloro-N',4-dihydroxy-2''-methyl-[1,1':2',1''-terphenyl]-3'-carboximidamide
$R^1$ = 5-chloro-2-methylphenyl    $R^2$ = N-hydroxy carbaimidoyl    $R^3$ = H    $R^5$ = H
ES/MS m/z: 353.26 (pos. M + H), 351.25 (neg. M − H); $^1$H NMR (MeOD, 500 MHz): δ 7.50--7.43 (m, 3H), 7.25 (d, 1H, J = 2.3 Hz), 7.08 (dd, 1H, J = 8.2, 2.3 Hz), 6.95 (d, 1H, J = 8.2 Hz), 6.86 (m, 2H), 6.56 (m, 2H) and 1.81 (s, 3H).

E 177 5''-chloro-N',4-dihydroxy-2''-methoxy-[1,1':2',1''-terphenyl]-3'-carboximidamide
$R^1$ = 5-chloro-2-methoxyphenyl    $R^2$ = N-hydroxy carbaimidoyl    $R^3$ = H    $R^5$ = H
ES/MS m/z: 369.22 (pos. M + H), 367.32 (neg. M − H); $^1$H NMR (MeOD, 500 MHz): δ 7.49-7.43 (m, 3H), 7.17 (dd, 1H, J = 8.9, 2.8 Hz), 6.99 (d, 1H, J = 2.8 Hz), 6.86 (m, 2H), 6.80 (d, 1H, J = 8.9 Hz), 6.57 (m, 2H) and 3.57 (s, 3H).

E 178 3'',5''-difluoro-N',4-dihydroxy-5'-methyl-[1,1':2',1''-terphenyl]-3'-carboximidamid
$R^1$ = 3,5-difluorophenyl    $R^2$ = N-hydroxy carbaimidoyl    $R^3$ = Me    $R^5$ = H
ES/MS m/z: 355.28 (pos. M + H), 353.32 (neg. M − H); $^1$H NMR (Acetone-d6, 500 MHz): δ 7.26 (s, 1H), 7.24 (s, 1H), 6.89 (m, 2H), 6.78 (s, 1H), 6.73-6.67 (m, 4H) and 2.42 (s, 3H).

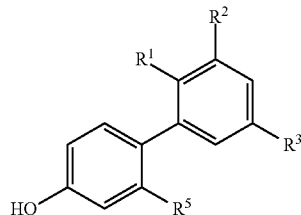

E 179 3",5"-difluoro-4-hydroxy-5'-methyl-[1,1':2',1"-terphenyl]-3'-carboxamide
$R^1$ = 3,5-difluorophenyl   $R^2$ = carbamoyl   $R^3$ = Me   $R^5$ = H
ES/MS m/z: 340.25 (pos. M + H), 338.29 (neg. M − H); $^1$H NMR (Acetone-d6, 500 MHz): δ 7.30 (s, 1H), 7.25 (s, 1H), 6.91 (m, 2H), 6.81 (s, 1H), 6.73-6.68 (m, 4H) and 2.43 (s, 3H).

E 180 3"-chloro-4-hydroxy-5"-methyl-5'-(trifluoromethyl)-[1,1':2',1"-terphenyl]-3'-carboxamide
$R^1$ = 3-chloro-5-methylphenyl   $R^2$ = carbamoyl   $R^3$ = CF$_3$   $R^5$ = H
ES/MS m/z: 406.22 (pos. M + H), 404.26 (neg. M − H); $^1$H NMR (Acetone-d6, 500 MHz): δ 7.76 (s, 1H), 7.70 (s, 1H), 7.09 (s, 1H), 6.98-6.94 (m, 4H), 6.72 (m, 2H) and 2.22 (s, 3H).

E 181 2",5"-dichloro-4-hydroxy-5'-(trifluoromethyl)-[1,1':2',1"-terphenyl]-3'-carboxamide
$R^1$ = 2,5-dichlorophenyl   $R^2$ = carbamoyl   $R^3$ = CF$_3$   $R^5$ = H
ES/MS m/z: 428.12 (pos. M + H), 426.18 (neg. M − H); $^1$H NMR (Acetone-d6, 500 MHz): δ 7.89 (d, 1H, J = 1.4 Hz), 7.75 (d, 1H, J = 1.4 Hz), 7.32-7.27 (m, 3H), 7.02 (m, 2H) and 6.72 (m, 2H).

E 182 3",5"-dichloro-N',4-dihydroxy-5'-(trifluoromethyl)-[1,1':2',1"-terphenyl]-3'-carboximidamide
$R^1$ = 3,5-dichlorophenyl   $R^2$ = N-hydroxy carbaimidoyl   $R^3$ = CF$_3$   $R^5$ = H
ES/MS m/z: 441.14 (pos. M + H), 439.25 (neg. M − H); $^1$H NMR (Acetone-d6, 500 MHz): δ 7.74 (d, 1H, J = 1.6 Hz), 7.71 (d, 1H, J = 1.6 Hz), 7.31 (t, 1H, J = 1.9 Hz), 7.14 (d, 2H, J = 1.9 Hz), 6.97 (m, 2H) and 6.74 (m, 2H).

E 183 3",5"-dichloro-N',4-dihydroxy-5'-methyl-[1,1':2',1"-terphenyl]-3'-carboximidamide
$R^1$ = 3,5-dichlorophenyl   $R^2$ = N-hydroxy carbaimidoyl   $R^3$ = Me   $R^5$ = H
ES/MS m/z: 387.19 (pos. M + H), 385.27 (neg. M − H); $^1$H NMR (Acetone-d6, 500 MHz): δ 7.27 (m, 1H), 7.24 (m, 1H), 7.22 (t, 1H, J02.1 Hz), 7.06 (d, 2H, J = 2.1 Hz), 6.89 (m, 2H), 6.70 (m, 2H) and 2.42 (s, 3H).

E 184 2-(3,5-dimethylisoxazol-4-yl)-2'-fluoro-N',4-dihydroxy-5-(trifluoromethyl)-[1,1'-biphenyl]-3-carboximidamide
$R^1$ = 3,5-dimethylisoxazol-4-yl   $R^2$ = N-hydroxy carbaimidoyl   $R^3$ = CF$_3$   $R^5$ = F
ES/MS m/z: 410.21 (pos. M + H), 408.29 (neg. M − H); $^1$H NMR (Acetone-d6, 500 MHz): δ 7.83 (d, 1H, J = 1.9 Hz), 7.73 (d, 1H, J = 1.9 Hz), 7.08 (t, 1H, J = 8.7 Hz), 6.68 (dd, 1H, J = 8.7, 2.3 Hz), 6.54 (dd, 1H, J = 11.8, 2.3 Hz), 2.03 (s, 3H) and 1.90 (s, 3H).

E 185 2-(3,5-dimethylisoxazol-4-yl)-2'-fluoro-4'-hydroxy-5(trifluoromethyl)-[1,1'-biphenyl]-3-carboxamide
$R^1$ = 3,5-dimethylisoxazol-4-yl   $R^2$ = carbamoyl   $R^3$ = CF$_3$   $R^4$ = F
ES/MS m/z: 395.22 (pos. M + H), 393.28 (neg. M − H); $^1$H NMR (Acetone-d6, 500 MHz): δ 7.88 (d, 1H, J = 1.8 Hz), 7.77 (d, 1H, J = 1.8 Hz), 7.10 (t, 1H, J = 8.6 Hz), 6.69 (dd, 1H, J = 8.6, 2.4 Hz), 6.55 (dd, 1H, J = 11.8, 2.4 Hz), 2.07 (s, 3H) and 1.92 (s, 3H).

E 186 3",5"-difluoro-N',4-dihydroxy-[1,1':2',1"-terphenyl]-3'-carboximidamide
$R^1$ = 3,5-difluorophenyl   $R^2$ = N-hydroxy carbaimidoyl   $R^3$ = H   $R^5$ = H
ES/MS m/z: 341.23 (pos. M + H), 339.33 (neg. M − H); $^1$H NMR (MeOD, 500 MHz): δ 7.49-7.43 (m, 3H), 6.86 (m, 2H), 6.76-6.70 (m, 3H) and 6.62 (m, 2H).

E 187 3",5"-difluoro-4-hydroxy-[1,1':2',1"-terphenyl]-3'-carboxamide
$R^1$ = 3,5-difluorophenyl   $R^2$ = carbamoyl   $R^3$ = H   $R^5$ = H
ES/MS m/z: 326.24 (pos. M + H), 324.29 (neg. M − H); $^1$H NMR (Acetone-d6, 500 MHz): δ 7.51-7.47 (m, 2H), 7.44 (m, 1H), 6.93 (m, 2H), 6.83 (m, 1H) and 6.76-6.69 (m, 4H).

E 188 3"-fluoro-N',4-dihydroxy-2"-methoxy-[1,1':2',1"-terphenyl]-3'-carboximidamide
$R^1$ = 3-fluoro-2-methoxyphenyl   $R^2$ = N-hydroxy carbaimidoyl   $R^3$ = H   $R^5$ = H
ES/MS m/z: 353.26 (pos. M + H), 351.32 (neg. M − H); $^1$H NMR (MeOD, 500 MHz): δ 7.52-7.45 (m, 3H), 7.01 (m, 1H), 6.93-6.86 (m, 4H), 6.60 (m, 2H) and 3.57, 3.56 (two s, 3H).

E 189 3"-fluoro-4-hydroxy-2"-methoxy-[1,1':2',1"-terphenyl]-3'-carboxamide
$R^1$ = 3-fluoro-2-methoxyphenyl   $R^2$ = carbamoyl   $R^3$ = H   $R^5$ = H
ES/MS m/z: 338.27 (pos. M + H), 336.28 (neg. M − H); $^1$H NMR (Acetone-d6, 500 MHz): δ 7.53 (dd, 1H; J = 7.6, 1.5 Hz), 7.46 (t, 1H, J = 7.6 Hz), 7.41 (dd, 1H, J = 7.6, 1.5 Hz), 7.00 (m, 1H), 6.94 (m, 2H), 6.91-6.86 (m, 2H), 6.65 (m, 2H) and 3.60, 3.59 (two s, 3H).

E 190 2"-ethyl-N',4-dihydroxy-[1,1':2',1"-terphenyl]-3'-carboximidamide
$R^1$ = 2-ethylphenyl   $R^2$ = N-hydroxy carbaimidoyl   $R^3$ = H   $R^5$ = H
ES/MS m/z: 333.32 (pos. M + H), 331.44 (neg. M − H); $^1$H NMR (MeOD, 500 MHz): δ 7.53-7.45 (m, 3H), 7.21-7.18 (m, 2H), 7.13-7.08 (m, 2H), 6.86 (m, 2H), 6.52 (m, 2H), 2.28 (m, 1H), 2.09 (m, 1H) and 0.89 (t, 3H, J = 7.6 Hz).

E 191 4"-chloro-2"-fluoro-N',4-dihydroxy-5'-methyl-[1,1':2',1"-terphenyl]-3'-carboximidamide
$R^1$ = 4-chloro-2-fluorophenyl   $R^2$ = N-hydroxy carbaimidoyl   $R^3$ = Me   $R^5$ = H
ES/MS m/z: 371.24 (pos. M + H), 369.28 (neg. M − H); $^1$H NMR (Acetone-d6, 500 MHz): δ 7.31 (s, 1H), 7.22 (s, 1H), 7.18 (t, 1H, J08.1 Hz), 7.05 (dd, 1H, J = 8.4, 2.0 Hz), 6.07 (dd, 1H, J = 9.4, 2.0 Hz), 6.89 (m, 2H), 6.66 (m, 2H) and 2.09 (s, 3H).

E 192 4"-chloro-3"-fluoro-N',4-dihydroxy-5'-methyl-[1,1':2',1"-terphenyl]-3'-carboximidamide
$R^1$ = 4-chloro-3-fluorophenyl   $R^2$ = N-hydroxy carbaimidoyl   $R^3$ = Me   $R^5$ = H
ES/MS m/z: 371.24 (pos. M + H), 369.19 (neg. M − H); $^1$H NMR (Acetone-d6, 500 MHz): δ 7.28-7.23 (m, 3H), 7.01 (dd, 1H, J = 10.6, 1.9 Hz), 6.91-6.86 (m, 3H), 6.67 (m, 2H) and 2.09 (s, 3H).

E 193 N',4-dihydroxy-2"-methoxy-[1,1':2',1"-terphenyl]-3'-carboximidamide
$R^1$ = 3-methoxyphenyl   $R^2$ = N-hydroxy carbaimidoyl   $R^3$ = H   $R^5$ = H
ES/MS m/z: 335.28 (pos. M + H), 333.35 (neg. M − H); $^1$H NMR (Acetone-d6, 500 MHz): δ 7.53-7.45 (m, 3H), 7.21-7.18 (m, 2H), 7.13-7.08 (m, 2H), 6.86 (m, 2H), 6.52 (m, 2H), 2.28 (m, 1H), 2.09 (m, 1H) and 0.89 (t, 3H, J = 7.6 Hz).

-continued

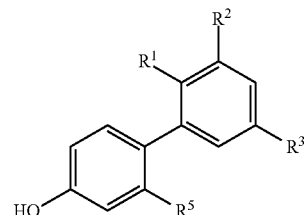

E 194   5'-chloro-N',4-dihydroxy-2"-methoxy-[1,1':2',1"-terphenyl]-3'-carboximidamide
R$^1$ = 3-methoxyphenyl    R$^2$ = N-hydroxy carbaimidoyl    R$^3$ = Cl    R$^5$ = H
ES/MS m/z: 369.21 (pos. M + H), 367.27 (neg. M − H); $^1$H NMR (Acetone-d6, 500 MHz): δ 7.43 (d, 1H, J = 2.2 Hz), 7.35 (d, 1H, J = 2.2 Hz), 7.18 (m, 1H), 6.97 (dd, 1H, J = 7.4, 1.7 Hz), 6.89 (m, 2H), 6.82 (d, 1H, J = 8.2 Hz), 6.78 (m, 1H), 6.61 (m, 2H) and 3.55 (s, 3H).

E 195   4"-fluoro-N',4-dihydroxy-2"-methoxy-[1,1':2',1"-terphenyl]-3'-carboximidamide
R$^1$ = 4-fluoro-2-methoxyphenyl    R$^2$ = N-hydroxy carbaimidoyl    R$^3$ = H    R$^5$ = H
ES/MS m/z: 353.26 (pos. M + H), 351.31 (neg. M − H); $^1$H NMR (Acetone-d6, 500 MHz): δ 7.42 (dd, 1H, J = 7.3, 1.9 Hz), 7.40 (t, 1H, J = 7.3 Hz), 7.34 (dd, 1H, J = 7.3, 1.9 Hz), 6.98 (t, 1H, J = 7.8 Hz), 6.88 (m, 2H), 6.64-6.60 (m, 3H), 6.54 (m, 1H) and 3.55 (s, 3H).

E 196   5''-chloro-4''-fluoro-N',4-dihydroxy-2"-methoxy-[1,1':2',1"-terphenyl]-3'-carboximidamide
R$^1$ = 4-fluoro-2-methoxyphenyl    R$^2$ = N-hydroxy carbaimidoyl    R$^3$ = Cl    R$^5$ = H
ES/MS m/z: 387.19 (pos. M + H), 385.27 (neg. M − H); $^1$H NMR (Acetone-d6, 500 MHz): δ 7.42 (d, 1H, J = 2.2 Hz), 7.35 (d, 1H, J = 2.2 Hz), 6.99 (dd, 1H, J = 8.5, 6.9 Hz), 6.89 (, m, 2H), 6.66-6.61 (m, 3H), 6.56 (m, 1H) and 3.55 (s, 3H).

E 197   3"-chloro-N',4-dihydroxy-5',5"-dimethyl-[1,1':2',1"-terphenyl]-3'-carboximidamide
R$^1$ = 3-chloro-5-methylphenyl    R$^2$ = N-hydroxy carbaimidoyl    R$^3$ = Me    R$^5$ = H
ES/MS m/z: 367.25 (pos. M + H), 365.31 (neg. M − H); $^1$H NMR (Acetone-d6, 500 MHz): δ 7.24 (s, 1H), 7.21 (s, 1H), 6.98 (s, 1H), 6.91 (s, 1H), 6.88-6.85 (m, 3H), 6.65 (m, 2H), 2.40 (s, 3H) and 2.17 (s, 3H).

E 198   2",5"-dichloro-N',4-dihydroxy-5'-methyl-[1,1':2',1"-terphenyl]-3'-carboximidamide
R$^1$ = 2,5-dichlorophenyl    R$^2$ = N-hydroxy carbaimidoyl    R$^3$ = Me    R$^5$ = H
ES/MS m/z: 387.19 (pos. M + H), 385.2 (neg. M − H); $^1$H NMR (Acetone-d6, 500 MHz): δ 7.33 (d, 1H, J = 1.0 Hz), 7.23-7.17 (m, 4H), 6.93 (m, 2H), 6.65 (m, 2H) and 2.43 (s, 3H).

E 199   3",5"-difluoro-4-hydroxy-5'-(trifluoromethyl)-[1,1':2',1"-terphenyl]-3'-carboxamide
R$^1$ = 3,5-difluorophenyl    R$^2$ = carbamoyl    R$^3$ = CF$_3$    R$^5$ = H
ES/MS m/z: 394.19 (pos. M + H), 392.25 (neg. M − H); $^1$H NMR (Acetone-d6, 500 MHz): δ 7.78 (s, 1H), 7.73 (s, 1H), 7.00 (m, 2H), 6.91 (m, 1H), 6.81 (m, 2H) and 6.74 (m, 2H).

E 200   N',4-dihydroxy-4",5'-dimethyl-[1,1':2',1"-terphenyl]-3'-carboximidamide
R$^1$ = p-tolyl    R$^2$ = N-hydroxy carbaimidoyl    R$^3$ = Me    R$^5$ = H
ES/MS m/z: 333.3 (pos. M + H), 331.23 (neg. M − H); $^1$H NMR (Acetone-d6, 500 MHz): δ 7.23 (s, 1H), 7.19 (s, 1H), 6.99-6.94 (m, 4H), 6.85 (m, 2H), 6.62 (m, 2H), 2.39 (s, 3H) and 2.25 (s, 3H).

E 201   N',4-dihydroxy-2",4",5'-trimethyl-[1,1':2',1"-terphenyl]-3'-carboximidamide
R$^1$ = 2,4-dimethylphenyl    R$^2$ = N-hydroxy carbaimidoyl    R$^3$ = Me    R$^5$ = H
ES/MS m/z: 347.31 (pos. M + H), 345.27 (neg. M − H); $^1$H NMR (Acetone-d6, 500 MHz): δ 7.27 (d, 1H, J = 1.¤ Hz), 7.20 (d, 1H, J = 1.4 Hz), 7.01 (d, 1H, J = 7.7 Hz), 6.90-6.84 (m, 3H), 6.60 (m, 2H), 2.40 (s, 3H), 2.22 (s, 3H) and 1.83 (s, 3H).

E 202   4"-fluoro-N',4-dihydroxy-5'-methyl-[1,1':2',1"-terphenyl]-3'-carboximidamide
R$^1$ = 4-fluorophenyl    R$^2$ = N-hydroxy carbaimidoyl    R$^3$ = Me    R$^5$ = H
ES/MS m/z: 337.24 (pos. M + H), 335.37 (neg. M − H); $^1$H NMR (Acetone-d6, 500 MHz): δ 7.23 (s, 1H), 7.22 (s, 1H), 7.10 (m, 2H), 6.90 (m, 2H), 6.84 (m, 2H), 6.64 (m, 2H) and 2.40 (s, 3H).

E 203   2",4"-difluoro-N',4-dihydroxy-5'-methyl-[1,1':2',1"-terphenyl]-3'-carboximidamide
R$^1$ = 2,4-difluorophenyl    R$^2$ = N-hydroxy carbaimidoyl    R$^3$ = Me    R$^5$ = H
ES/MS m/z: 355.28 (pos. M + H), 353.33 (neg. M − H); $^1$H NMR (Acetone-d6, 500 MHz): δ 7.29 (s, 1H), 7.22 (s, 1H), 7.19 (m, 1H), 6.89 (m, 2H), 6.82 (m, 1H), 6.73 (m, 1H), 6.65 (m, 2H) and 2.42 (s, 3H).

E 204   5"-chloro-5'-fluoro-N',4-dihydroxy-2"-methyl-[1,1':2',1"-terphenyl]-3'-carboximidamide
R$^1$ = 5-chloro-2-methylphenyl    R$^2$ = N-hydroxy carbaimidoyl    R$^3$ = F    R$^5$ = H
ES/MS m/z: 371.24 (pos. M + H), 369.16 (neg. M − H); $^1$H NMR (Acetone-d6, 500 MHz): δ 7.22 (dd, 1H, J = 9.0, 2.8 Hz), 7.19-7.17 (m, 2H), 7.10 (dd, 1H, J = 8.2, 2.4 Hz), 6.98 (d, 1H, J08.2 Hz), 6.92 (m, 2H), 6.66 (m, 2H) and 1.84 (s, 3H).

E 205   5',5"-difluoro-N',4-dihydroxy-2"-methyl-[1,1':2',1"-terphenyl]-3'-carboximidamide
R$^1$ = 5-fluoro-2-methoxyphenyl    R$^2$ = N-hydroxy carbaimidoyl    R$^3$ = F    R$^5$ = H
ES/MS m/z: 371.26 (pos. M + H), 369.19 (neg. M − H); $^1$H NMR (Acetone-d6, 500 MHz): δ 7.18 (dd, 1H, J = 9.0, 2.6 Hz), 7.13 (dd, 1H, J = 9.6, 2.9 Hz), 6.94-6.89 (m, 3H), 6.81-6.75 (m, 2H), 6.65 (m, 2H) and 3.53 (s, 3H).

E 206   2"-chloro-5'-fluoro-N',4-dihydroxy-5"-methyl-[1,1':2',1"-terphenyl]-3'-carboximidamide
R$^1$ = 2-chloro-5-methylphenyl    R$^2$ = N-hydroxy carbaimidoyl    R$^3$ = F    R$^5$ = H
ES/MS m/z: 371.24 (pos. M + H), 369.17 (neg. M − H); $^1$H NMR (Acetone-d6, 500 MHz): δ 7.23 (dd, 1H, J = 9.1, 2.8 Hz), 7.16 (dd, 1H, J = 9.4, 2.8 Hz), 7.09-7.07 (m, 2H), 7.01 (dd, 1H, J = 8.2, 2.4 Hz), 6.94 (m, 2H), 6.63 (m, 2H) and 2.21 (s, 3H).

E 207   2",5"-dichloro-5'-fluoro-N',4-dihydroxy-[1,1':2',1"-terphenyl]-3'-carboximidamide
R$^1$ = 2,5-dichlorophenyl    R$^2$ = N-hydroxy carbaimidoyl    R$^3$ = F    R$^5$ = H
ES/MS m/z: 391.18 (pos. M + H), 389.07; 391.10 (neg. M − H); $^1$H NMR (Acetone-d6, 500 MHz): δ 7.29-7.17 (m, 5H), 6.96 (m, 2H) and 6.67 (m, 2H).

E 208   5"-fluoro-N',4-dihydroxy-2"-methoxy-[1,1':2',1"-terphenyl]-3'-carboximidamide
R$^1$ = 2-methoxyphenyl    R$^2$ = N-hydroxy carbaimidoyl    R$^3$ = F    R$^5$ = H
ES/MS m/z: 353.26 (pos. M + H), 351.21 (neg. M − H); $^1$H NMR (Acetone-d6, 500 MHz): δ 7.19-7.16 (m, 2H), 7.11 (dd, 1H, J = 9.5, 2.6 Hz), 6.96 (dd, 1H, J = 7.5, 1.7 Hz), 6.89 (m, 2H), 6.82 (d, 1H, J = 8.3 Hz), 6.77 (t, 1H, J = 7.5 Hz), 6.61 (m, 2H) and 3.55 (s, 3H).

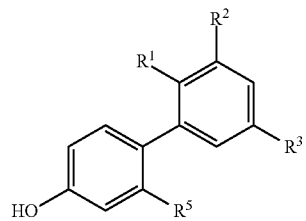

E 209 4",5'-difluoro-N',4-dihydroxy-2"-methoxy-[1,1':2',1"-terphenyl]-3'-carboximidamide
R$^1$ = 4-fluoro-2-methoxyphenyl    R$^2$ = N-hydroxy carbaimidoyl    R$^3$ = F    R$^5$ = H
ES/MS m/z: 371.26 (pos. M + H), 369.17 (neg. M − H); $^1$H NMR (Acetone-d6, 500 MHz): δ 7.17 (dd, 1H, J = 9.3, 3.0 Hz), 7.12 (dd, 1H, J = 9.5, 2.7 Hz), 6.97 (dd, 1H, J = 8.4, 6.9 Hz), 6.89 (m, 2H), 6.65-6.61 (m, 3H), 6.55 (m, 1H) and 3.55 (s, 3H).

E 210 5'-fluoro-N',4-dihydroxy-2",5"-dimethyl-[1,1':2',1"-terphenyl]-3'-carboximidamide
R$^1$ = 2,5-dimethylphenyl    R$^2$ = N-hydroxy carbaimidoyl    R$^3$ = F    R$^5$ = H
ES/MS m/z: 351.3 (pos. M + H), 349.23 (neg. M − H); $^1$H NMR (Acetone-d6, 500 MHz): δ 7.21 (dd, 1H, J = 9.3, 2.9 Hz), 7.16 (dd, 1H, J = 9.8, 2.9 Hz), 6.98 (s, 1H), 6.93-6.87 (m, 4H), 6.62 (m, 2H), 2.20 (s, 3H) and 1.81 (s, 3H).

E 211 5'-fluoro-N',4-dihydroxy-2"-methoxy-5"-methyl-[1,1':2',1"-terphenyl]-3'-carboximidamide
R$^1$ = 2-methoxy-5-methylphenyl    R$^2$ = N-hydroxy carbaimidoyl    R$^3$ = F    R$^5$ = H
ES/MS m/z: 367.32 (pos. M + H), 365.21 (neg. M − H); $^1$H NMR (Acetone-d6, 500 MHz): δ 7.16 (dd, 1H, J = 9.3, 2.7 Hz), 7.10 (dd, 1H, J = 9.6, 2.7 Hz), 6.98 (dd, 1H, J = 8.3, 2.1 Hz), 6.91 (m, 2H), 6.78 (d, 1H, J = 2.1 Hz), 6.71 (d, 1H, J = 8.3 Hz), 6.61 (m, 2H), 3.53 (s, 3H) and 2.13 (s, 3H).

E 212 N',4-dihydroxy-2"-methoxy-5"-methyl-[1,1':2',1"-terphenyl]-3'-carboximidamide
R$^1$ = 2-methoxy-5-methylphenyl    R$^2$ = N-hydroxy carbaimidoyl    R$^3$ = H    R$^5$ = H
ES/MS m/z: 349.4 (pos. M + H), 347.2 (neg. M − H); $^1$H NMR (MeOD, 500 MHz): δ 7.50-7.42 (m, 3H), 7.01 (dd, 1H, J = 8.7, 2.3 Hz), 6.86 (m, 2H), 6.78 (d, 1H, J = 2.3 Hz), 6.74 (d, 1H, J = 8.7 Hz), 6.54 (m, 2H), 3.56 (s, 3H) and 2.14 (s, 3H).

E 213 N',4-dihydroxy-2"-methoxy-5',5"-dimethyl-[1,1':2',1"-terphenyl]-3'-carboximidamide
R$^1$ = 2-methoxy-5-methylphenyl    R$^2$ = N-hydroxy carbaimidoyl    R$^3$ = Me    R$^5$ = H
ES/MS m/z: 363.33 (pos. M + H), 361.36 (neg. M − H); $^1$H NMR (Acetone-d6, 500 MHz): δ 7.23 (s, 1H), 7.15 (s, 1H), 6.94 (dd, 1H, J = 8.1, 2.0 Hz), 6.76 (d, 1H, J = 2.0 Hz), 6.69 (d, 1H, J = 8.1 Hz), 6.59 (m, 2H), 3.52 (s, 3H), 2.39 (s, 3H) and 2.12 (s, 3H).

E 214 4"-fluoro-N',4-dihydroxy-2"-methoxy-5'-methyl-[1,1':2',1"-terphenyl]-3'-carboximidamide
R$^1$ = 4-fluoro-2-methoxyphenyl    R$^2$ = N-hydroxy carbaimidoyl    R$^3$ = Me    R$^5$ = H
ES/MS m/z: 367.3 (pos. M + H), 365.26 (neg. M − H); $^1$H NMR (Acetone-d6, 500 MHz): δ 7.23 (s, 1H), 7.16 (s, 1H), 6.95 (m, 1H), 6.87 (m, 2H), 6.63-6.59 (m, 3H), 6.53 (m, 1H), 3.55 (s, 3H) and 2.39 (s, 3H).

E 215 2"-chloro-N',4-dihydroxy-5',5"-dimethyl-[1,1':2',1"-terphenyl]-3'-carboximidamide
R$^1$ = 2-chloro-5-methylphenyl    R$^2$ = N-hydroxy carbaimidoyl    R$^3$ = Me    R$^5$ = H
ES/MS m/z: 367.25 (pos. M + H), 365.27 (neg. M − H); $^1$H NMR (Acetone-d6, 500 MHz): δ 7.29 (s, 1H), 7.21 (s, 1H), 7.07-7.05 (m, 2H), 6.98 (dd, 1H, J = 8.1, 2.2 Hz), 6.92 (m, 2H), 6.61 (m, 2H), 2.42 (s, 3H) and 2.20 (s, 3H).

E 216 N',4-dihydroxy-5'-methyl-2"-(trifluoromethoxy)-[1,1':2',1"-terphenyl]-3'-carboximidamide
R$^1$ = 2-(trifluoromethoxy)phenyl    R$^2$ = N-hydroxy carbaimidoyl    R$^3$ = Me    R$^5$ = H
ES/MS m/z: 403.21 (pos. M + H), 401.26 (neg. M − H); $^1$H NMR (Acetone-d6, 500 MHz): δ 7.34-7.26 (m, 3H), 7.23 (d, 1H, J = 1.4 Hz), 7.16 (m, 1H), 7.05 (m, 1H), 6.85 (m, 2H), 6.61 (m, 2H) and 2.42 (s, 3H).

E 217 N',4-dihydroxy-2"methoxy-5'-methyl-[1,1':2',1"-terphenyl]-3'-carboximidamide
R$^1$ = 2-methoxyphenyl    R$^2$ = N-hydroxy carbaimidoyl    R$^3$ = Me    R$^5$ = H
ES/MS m/z: 349.27 (pos. M + H), 347.33 (neg. M − H); $^1$H NMR (Acetone-d6, 500 MHz): δ 7.24 (s, 1H), 7.18-7.13 (m, 2H), 6.94 (dd, 1H, J = 7.4, 1.7 Hz), 6.87 (m, 2H), 6.80 (dd, 1H, J = 8.1, 0.5 Hz), 6.76 (m, 1H), 6.59 (m, 2H), 3.54 (s, 3H) and 2.39 (s, 3H).

E 218 3",5"-difluoro-N',4-dihydroxy-5'-methoxy-[1,1':2',1"-terphenyl]-3'-carboximidamide
R$^1$ = 3,5-difluorophenyl    R$^2$ = N-hydroxy carbaimidoyl    R$^3$ = Methoxy    R$^5$ = H
ES/MS m/z: 371.24 (pos. M + H), 369.27 (neg. M − H); $^1$H NMR (Acetone-d6, 500 MHz): δ 7.00 (d, J = 2.7 Hz, 1H), 6.95 (d, J = 2.8 Hz, 1H), 6.91 (m, 2H), 6.76 (m, J = 2.9 Hz, 1H), 6.71-6.64 (m, 4H), 3.90 (s, 3H).

E 219 5"-fluoro-N',4-dihydroxy-2",5'-dimethoxy-[1,1':2',1"-terphenyl]-3'-carboximidamide
R$^1$ = 5-fluoro-2-methoxyphenyl    R$^2$ = N-hydroxy carbaimidoyl    R$^3$ = Methoxy    R$^5$ = H
ES/MS m/z: 383.23 (pos. M + H), 381.27 (neg. M − H); $^1$H NMR (Acetone-d6, 500 MHz): δ 6.99 (d, J = 2.8 Hz, 1H), 6.93-6.86 (m, 4H), 6.76 (dd, J = 4.6, 9.0 Hz, 1H), 6.73 (dd, J = 3.2, 9.1 Hz, 1H), 6.63 (m, 2H), 3.88 (s, 3H), 3.52 (s, 3H).

E 220 2-(5-fluoro-2-methoxypyridin-3-yl)-N',4-dihydroxy-5-methyl-[1,1'-biphenyl]-3-carboximidamide
R$^1$ = 5-fluoro-2-methoxypyridin-3-yl    R$^2$ = N-hydroxy carbaimidoyl    R$^3$ = Me    R$^5$ = H
ES/MS m/z: 368.23 (pos. M + H), 366.27 (neg. M − H); $^1$H NMR (Acetone-d6, 500 MHz): δ 7.83 (d, 1H, J = 3.0 Hz), 7.28 (d, 1H, J = 1.8 Hz), 7.20-7.18 (m, 2H), 6.89 (m, 2H), 6.66 (m, 2H), 3.59 (s, 3H) and 2.42 (s, 3H).

E 221 N',4-dihydroxy-5-methyl-2-(2-methylpyridin-3-yl)-[1,1'-biphenyl]-3-carboximidamide
R$^1$ = 2-methylpyridin-3-yl    R$^2$ = N-hydroxy carbaimidoyl    R$^3$ = Me    R$^5$ = H
ES/MS m/z: 334.23 (pos. M + H), 332.28 (neg. M − H); $^1$H NMR (Acetone-d6, 500 MHz): δ 8.23 (dd, 1H, J = 4.8, 1.7 Hz), 7.49 (dd, 1H, J = 7.6, 1.7 Hz), 7.30 (s, 1H), 7.25 (s, 1H), 7.03 (dd, 1H, J = 7.6, 5.0 Hz), 6.86 (m, 2H), 6.62 (m, 2H), 2.43 (s, 3H) and 2.08 (s, 3H).

E 222 N',4-dihydroxy-2-(2-methoxypyridin-3-yl)-5-methyl-[1,1'-biphenyl]-3-carboximidamide
R$^1$ = 2-methoxypyridin-3-yl    R$^2$ = N-hydroxy carbaimidoyl    R$^3$ = Me    R$^5$ = H
ES/MS m/z: 350.25 (pos. M + H), 348.28 (neg. M − H); $^1$H NMR (Acetone-d6, 500 MHz): δ 7.95 (dd, 1H, J = 5.1, 1.9 Hz), 7.30 (dd, 1H, J = 6.9, 1.9 Hz), 7.26 (s, 1H), 7.18 (s, 1H), 6.86 (m, 2H), 6.76 (dd, 1H, J = 7.3, 5.1 Hz), 6.62 (m, 2H), 3.63 (s, 3H) and 2.41 (s, 3H).

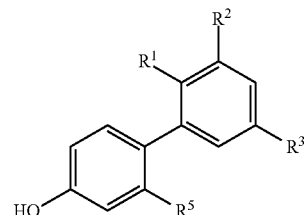

E 223 2-(3,5-dimethylisothiazol-4-yl)-N',4'-dihydroxy-5-methyl-[1,1'-biphenyl]-3-carboximidamide
$R^1$ = 3,5-dimethylisothiazol-4-yl    $R^2$ = N-hydroxy carbaimidoyl    $R^3$ = Me    $R^5$ = H
ES/MS m/z: 354.5 (pos. M + H), 352.6 (neg. M − H); $^1$H NMR (Acetone-d6, 500 MHz): δ 7.14-7.11 (m, 3H), 7.09-7.07 (m, 2H), 6.99 (d, J = 2.8 Hz, 1H), 6.94 (d, J = 2.8 Hz, 1H), 6.86 (m, 2H), 6.61 (m, 2H), 3.88 (s, 3H).

E 224 N',4-dihydroxy-5'-methoxy-[1,1':2',1''-terphenyl]-3-carboximidamide
$R^1$ = phenyl    $R^2$ = N-hydroxy carbaimidoyl    $R^3$ = Methoxy    $R^5$ = H
ES/MS m/z: 335.28 (pos. M + H), 333.29 (neg. M − H); $^1$H NMR (Acetone-d6, 500 MHz): δ 7.14-7.11 (m, 3H), 7.09-7.07 (m, 2H), 6.99 (d, J = 2.8 Hz, 1H), 6.94 (d, J = 2.8 Hz, 1H), 6.86 (m, 2H), 6.61 (m, 2H), 3.88 (s, 3H).

E 225 2-(3,5-dimethylisothiazol-4-yl)-4'-hydroxy-5-methyl-[1,1'-biphenyl]-3-carboxamide
$R^1$ = 3,5-dimethylisothiazol-4-yl    $R^2$ = carbamoyl    $R^3$ = Me    $R^5$ = H
ES/MS m/z: 339.2 (pos. M + H), 337.29 (neg. M − H); $^1$H NMR (Acetone-d6, 500 MHz): δ 7.39 (d, J = 1.0 Hz, 1H), 7.31 (d, J = 0.9 Hz, 1H), 6.88 (m, 2H), 6.69 (m, 2H), 2.45 (s, 3H), 2.16 (s, 3H) and 2.02 (s, 3H).

E 226 5-chloro-2-(5-fluoro-2-methoxypyridin-3-yl)-N',4'-dihydroxy-[1,1'-biphenyl]-3-carboximidamide
$R^1$ = 5-fluoro-2-methoxypyridin-3-yl    $R^2$ = N-hydroxy carbaimidoyl    $R^3$ = Cl    $R^5$ = H
ES/MS m/z: 388.17 (pos. M + H), 386.24 (neg. M − H); $^1$H NMR (Acetone-d6, 500 MHz): δ 7.86 (d, J = 3.0 Hz, 1H), 7.47 (d, J = 2.3 Hz, 1H), 7.39 (d, J = 2.3 Hz, 1H), 7.25 (dd, J = 3.0, 8.5 Hz, 1H), 6.92 (m, 2H), 6.69 (m, 2H) and 3.60 (s, 3H).

E 227 2-(5-fluoro-2-methoxypyridin-3-yl)-4'-hydroxy-5-methyl-[1,1'-biphenyl]-3-carboxamide
$R^1$ = 5-fluoro-2-methoxypyridin-3-yl    $R^2$ = carbamoyl    $R^3$ = Cl    $R^5$ = H
ES/MS m/z: 368.23 (pos. M + H), 366.3 (neg. M − H); $^1$H NMR (Acetone-d6, 500 MHz): δ 7.83 (d, J = 3.0 Hz, 1H), 7.28 (d, J = 1.0 Hz, 1H), 7.20-7.18 (m, 2H), 6.89 (m, 2H), 6.66 (m, 2H), 3.59 (s, 3H) and 2.42 (s, 3H).

E 228 2-(3,5-dimethylisothiazol-4-yl)-N',4'-dihydroxy-5-(trifluoromethyl)-[1,1'-biphenyl]-3-carboximidamide
$R^1$ = 3,5-dimethylisothiazol-4-yl    $R^2$ = N-hydroxy carbaimidoyl    $R^3$ = $CF_3$    $R^5$ = H
ES/MS m/z: 408.18 (pos. M + H), 406.25 (neg. M − H); $^1$H NMR (Acetone-d6, 500 MHz): δ 7.81 (d, J = 1.4 Hz, 1H), 7.75 (d, J = 1.4 Hz, 1H), 6.94 (m, 2H), 6.73 (m, 2H), 2.17 (s, 3H), 2.01 (s, 3H).

E 229 5-chloro-2-(3,5-dimethylisothiazol-4-yl)-N',4'-dihydroxy-[1,1'-biphenyl]-3-carboximidamide
$R^1$ = 3,5-dimethylisothiazol-4-yl    $R^2$ = N-hydroxy carbaimidoyl    $R^3$ = Cl    $R^5$ = H
ES/MS m/z: 374.18 (pos. M + H), 372.18 (neg. M − H); $^1$H NMR (Acetone-d6, 500 MHz): δ 7.52 (d, J = 2.3 Hz, 1H), 7.47 (d, J = 2.3 Hz, 1H), 6.90 (m, 2H), 6.71 (m, 2H), 2.15 (s, 3H), 2.00 (s, 3H).

E 230 4''-fluoro-N',4-dihydroxy-2''-methyl-5'-(trifluoromethyl)-[1,1':2',1''-terphenyl]-3'-carboximidamide
$R^1$ = 4-fluoro-2-methylphenyl    $R^2$ = N-hydroxy carbaimidoyl    $R^3$ = $CF_3$    $R^5$ = H
ES/MS m/z: 405.24 (pos. M + H), 403.2 (neg. M − H); $^1$H NMR (Acetone-d6, 500 MHz): δ 7.74 (d, J = 1.4 Hz, 1H), 7.69 (d, J = 1.4 Hz, 1H), 7.22 (dd, J = 6.0, 8.4 Hz, 1H), 6.95 (m, 2H), 6.86 (m, 1H), 6.80 (dd, J = 2.7, 10.1 Hz, 1H), 6.67 (m, 2H), 1.88 (s, 3H).

E 231 2'',4''-difluoro-N',4-dihydroxy-5'-(trifluoromethyl)-[1,1':2',1''-terphenyl]-3'-carboximidamide
$R^1$ = 2,4-difluorophenyl    $R^2$ = N-hydroxy carbaimidoyl    $R^3$ = $CF_3$    $R^5$ = H
ES/MS m/z: 409.17 (pos. M + H), 407.18 (neg. M − H); $^1$H NMR (Acetone-d6, 500 MHz): δ 7.78 (d, J = 1.5 Hz, 1H), 7.69 (d, J = 1.4 Hz, 1H), 7.28 (m, J = 4.7 Hz, 1H), 6.96 (m, 2H), 6.89 (m, 1H), 6.80 (m, 1H), 6.70 (m, 2H).

E 232 N',4-dihydroxy-2-(4-methylpyridin-3-yl)-5-(trifluoromethyl)-[1,1'-biphenyl]-3-carboximidamide
$R^1$ = 4-methylpyridin-3-yl    $R^2$ = N-hydroxy carbaimidoyl    $R^3$ = $CF_3$    $R^5$ = H
ES/MS m/z: 388.17 (pos. M + H), 386.23 (neg. M − H); $^1$H NMR (Acetone-d6, 500 MHz): δ 8.33 (s, 1H), 8.25 (d, J = 5.0 Hz, 1H), 7.78 (s, 1H), 7.72 (s, 1H), 6.99 (d, J = 5.1 Hz, 1H), 6.94 (m, 2H), 6.67 (m, 2H), and 1.89 (s, 3H).

E 233 2-(2,5-dimethylpyridin-3-yl)-N',4-dihydroxy-5-(trifluoromethyl)-[1,1'-biphenyl]-3-carboximidamide
$R^1$ = 2,5-dimethylpyridin-3-yl    $R^2$ = N-hydroxy carbaimidoyl    $R^3$ = $CF_3$    $R^5$ = H
ES/MS m/z: 402.16 (pos. M + H), 400.25 (neg. M − H); $^1$H NMR (Acetone-d6, 500 MHz): δ 8.14 (d, J = 1.9 Hz, 1H), 7.76 (d, J = 1.4 Hz, 1H), 7.70 (d, J = 1.4 Hz, 1H), 7.40 (d, J = 1.9 Hz, 1H), 6.94 (m, 2H), 6.67 (m, 2H), 2.22 (s, 3H) and 1.99 (s, 3H).

E 234 2''-chloro-4''-fluoro-N',4-dihydroxy-5'-(trifluoromethyl)-[1,1':2',1''-terphenyl]-3'-carboximidamide
$R^1$ = 2-chloro-4-fluorophenyl    $R^2$ = N-hydroxy carbaimidoyl    $R^3$ = $CF_3$    $R^5$ = H
ES/MS m/z: 425.11 (pos. M + H), 423.16 (neg. M − H); $^1$H NMR (MeOD, 500 MHz): δ 7.75 (s, 1H), 7.69 (s, 1H), 7.27 (dd, J = 6.1, 8.6 Hz, 1H), 7.08 (dd, J = 2.5, 8.8 Hz, 1H), 6.97 (m, 1H), 6.92 (m, 2H), 6.61 (m, 2H).

E 235 4'',5''-difluoro-N',4-dihydroxy-2''-methyl-5'-(trifluoromethyl)-[1,1':2',1''-terphenyl]-3'-carboximidamide
$R^1$ = 4,5-difluoro-2-methylphenyl    $R^2$ = N-hydroxy carbaimidoyl    $R^3$ = $CF_3$    $R^5$ = H
ES/MS m/z: 423.15 (pos. M + H), 421.23 (neg. M − H); $^1$H NMR (Acetone-d6, 500 MHz): δ 8.25 (d, J = 1.1 Hz, 1H), 8.03 (d, J = 1.2 Hz, 1H), 7.36 (dd, J = 8.2, 11.0 Hz, 1H), 7.22 (dd, J = 8.1, 11.6 Hz, 1H), 7.08 (m, 2H), 6.77 (m, 2H), 1.94 (s, 3H).

E 236 2'',5''-difluoro-N',4-dihydroxy-5'-(trifluoromethyl)-[1,1':2',1''-terphenyl]-3'-carboximidamide
$R^1$ = 2,5-difluorophenyl    $R^2$ = N-hydroxy carbaimidoyl    $R^3$ = $CF_3$    $R^5$ = H
ES/MS m/z: 409.16 (pos. M + H), 407.2 (neg. M − H); $^1$H NMR (Acetone-d6, 500 MHz): δ 7.79 (d, J = 1.3 Hz, 1H), 7.70 (d, J = 1.3 Hz, 1H), 7.06-6.98 (m, 4H), 6.94 (m, 1H), 6.71 (m, 2H).

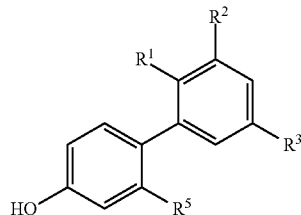

E 237  N',4'-dihydroxy-2-(pyridin-3-yl)-5-(trifluoromethyl)-[1,1'-biphenyl]-3-carboximidamide
$R^1$ = pyridin-3-yl  $R^2$ = N-hydroxy carbaimidoyl  $R^3$ = $CF_3$  $R^5$ = H
ES/MS m/z: 374.18 (pos. M + H), 372.23 (neg. M − H); $^1$H NMR (Acetone-d6, 500 MHz): δ 8.37 (dd, J = 1.6, 4.8 Hz, 1H), 8.31 (d, J = 1.9 Hz, 1H), 7.75 (d, J = 1.3 Hz, 1H), 7.72 (d, J = 1.5 Hz, 1H), 7.53 (m, 1H), 7.19 (m, 1H), 6.92 (m, 2H), 6.69 (m, 2H).

E 238  2-(2,3-dihydrobenzofuran-7-yl)-N',4'-dihydroxy-5-(trifluoromethyl)-[1,1'-biphenyl]-3-carboximidamide
$R^1$ = 2,3-dihydrobenzofuran-7-yl  $R^2$ = N-hydroxy carbaimidoyl  $R^3$ = $CF_3$  $R^5$ = H
ES/MS m/z: 415.18 (pos. M + H), 413.24 (neg. M − H); $^1$H NMR (Acetone-d6, 500 MHz): δ 7.72 (d, J = 1.0 Hz, 1H), 7.64 (d, J = 1.2 Hz, 1H), 7.07 (dd, J = 0.8, 7.3 Hz, 1H), 6.96 (m, 2H), 6.85 (d, J = 7.5 Hz, 1H), 6.69 (t, J = 7.5 Hz, 2H), 6.65 (m, 2H), 4.41 (m, 1H), 4.11 (q, J = 8.9 Hz, 1H), 3.11 (m, 1H), 3.02 (m, 1H).

E 239  2-(benzofuran-7-yl)-N',4'-dihydroxy-5-(trifluoromethyl)-[1,1'-biphenyl]-3-carboximidamide
$R^1$ = benzofuran-7-yl  $R^2$ = N-hydroxy carbaimidoyl  $R^3$ = $CF_3$  $R^5$ = H
ES/MS m/z: 413.15 (pos. M + H), 411.24 (neg. M − H); $^1$H NMR (Acetone-d6, 500 MHz): δ 7.81 (d, J = 1.2 Hz, 1H), 7.72 (d, J = 1.2 Hz, 1H), 7.57 (d, J = 2.2 Hz, 1H), 7.50 (dd, J = 1.2, 7.6 Hz, 1H), 7.17 (dd, J = 1.0, 7.4 Hz, 1H), 7.12 (t, J = 7.5 Hz, 1H), 6.88 (m, 2H), 6.74 (d, J = 2.2 Hz, 1H), 6.52 (m, 2H).

E 240  N',4'-dihydroxy-2-(1-methyl-1H-indol-7-yl)-5-(trifluoromethyl)-[1,1'-biphenyl]-3-carboximidamide
$R^1$ = 1-methyl-1H-indol-7-yl  $R^2$ = N-hydroxy carbaimidoyl  $R^3$ = $CF_3$  $R^5$ = H
ES/MS m/z: 426.16 (pos. M + H), 424.25 (neg. M − H); $^1$H NMR (Acetone-d6, 500 MHz): δ 7.80 (d, J = 1.4 Hz, 1H), 7.71 (d, J = 1.4 Hz, 1H), 7.43 (dd, J = 1.3, 7.7 Hz, 1H), 6.98 (d, J = 3.1 Hz, 1H), 6.94 (dd, J = 1.3, 7.2 Hz, 1H), 6.92-6.88 (m, 3H), 6.51 (m, 2H), 6.31 (d, J = 3.1 Hz, 1H), 3.34 (s, 3H).

E 241  2''-chloro-5''-fluoro-N',4-dihydroxy-5'-(trifluoromethyl)-[1,1':2',1''-terphenyl]-3'-carboximidamide
$R^1$ = 2-chloro-5-fluorophenyl  $R^2$ = N-hydroxy carbaimidoyl  $R^3$ = $CF_3$  $R^5$ = H
ES/MS m/z: 425.11 (pos. M + H), 423.18 (neg. M − H); $^1$H NMR (Acetone-d6, 500 MHz): δ 7.81 (d, J = 1.4 Hz, 1H), 7.70 (d, J = 1.3 Hz, 1H), 7.27 (dd, J = 5.1, 8.8 Hz, 1H), 7.10 (dd, J = 3.1, 9.1 Hz, 1H), 7.04 (dd, J = 3.1, 8.5 Hz, 2H), 7.01 (m, 2H), 6.70 (m, 2H).

E 242  5''-chloro-2''-fluoro-N',4-dihydroxy-5'-(trifluoromethyl)-[1,1':2',1''-terphenyl]-3'-carboximidamide
$R^1$ = 5-chloro-2-fluorophenyl  $R^2$ = N-hydroxy carbaimidoyl  $R^3$ = $CF_3$  $R^5$ = H
ES/MS m/z: 425.11 (pos. M + H), 423.15 (neg. M − H); $^1$H NMR (Acetone-d6, 500 MHz): δ 7.80 (d, J = 1.4 Hz, 1H), 7.70 (d, J = 1.3 Hz, 1H), 7.29-7.26 (m, 2H), 7.00-6.96 (m, 3H), 6.72 (m, 2H).

E 243  2-(4-fluorobenzofuran-7-yl)-N',4'-dihydroxy-5-(trifluoromethyl)-[1,1'-biphenyl]-3-carboximidamide
$R^1$ = 4-fluorobenzofuran-7-yl  $R^2$ = N-hydroxy carbaimidoyl  $R^3$ = $CF_3$  $R^5$ = H
ES/MS m/z: 431.13 (pos. M + H), 429.22 (neg. M − H); $^1$H NMR (Acetone-d6, 500 MHz): δ 7.80 (d, J = 1.4 Hz, 1H), 7.72 (d, J = 1.5 Hz, 1H), 7.61 (d, J = 2.2 Hz, 1H), 7.19 (dd, J = 5.2, 8.2 Hz, 1H), 6.93-6.88 (m, 4H), 6.83 (m, 2H).

E 244  3'',4''-difluoro-N',4-dihydroxy-5'-(trifluoromethyl)-[1,1':2',1''-terphenyl]-3'-carboximidamide
$R^1$ = 3,4-difluorophenyl  $R^2$ = N-hydroxy carbaimidoyl  $R^3$ = $CF_3$  $R^5$ = H
ES/MS m/z: 409.4 (pos. M + H), 407.2 (neg. M − H); $^1$H NMR (Acetone-d6, 500 MHz): δ 7.70 (s, 1H), 7.69 (s, 1H), 7.10-7.03 (m, 2H), 6.93-6.87 (m, 3H), 6.65 (m, 2H).

E 245  5'-chloro-2'',4''-difluoro-N',4-dihydroxy-[1,1':2',1''-terphenyl]-3'-carboximidamide
$R^1$ = 2,4-difluorophenyl  $R^2$ = N-hydroxy carbaimidoyl  $R^3$ = Cl  $R^5$ = H
ES/MS m/z: 375.2 (pos. M + H), 373.3 (neg. M − H); $^1$H NMR ($CD_3CN$, 500 MHz): δ 7.48 (d, J = 2.3 Hz, 1H), 7.45 (d, J = 2.3 Hz, 1H), 7.15 (m, 1H), 6.90 (m, 2H), 6.84 (m, 1H), 6.75 (m, 1H), 6.62 (m, 2H).

E 246  5'-chloro-2'',4''-difluoro-N',4-dihydroxy-[1,1':2',1''-terphenyl]-3'-carboximidamide
$R^1$ = 2,5-difluorophenyl  $R^2$ = N-hydroxy carbaimidoyl  $R^3$ = Cl  $R^5$ = H
ES/MS m/z: 375.2 (pos. M + H), 373.3 (neg. M − H); $^1$H NMR ($CD_3CN$, 500 MHz): δ 7.49 (d, J = 2.3 Hz, 1H), 7.46 (d, J = 2.3 Hz, 1H), 6.99 (m, 1H), 6.95-6.87 (m, 4H), 6.62 (m, 2H).

E 247  2-(benzo[d][1,3]dioxol-4-yl)-N',4'-dihydroxy-5-(trifluoromethyl)-[1,1'-biphenyl]-3-carboximidamide
$R^1$ = benzo[d][1,3]dioxol-4-yl  $R^2$ = N-hydroxy carbaimidoyl  $R^3$ = $CF_3$  $R^5$ = H
ES/MS m/z: 417.14 (pos. M + H), 415.21 (neg. M − H); $^1$H NMR (Acetone-d6, 500 MHz): δ 7.74 (d, J = 1.5 Hz, 1H), 7.67 (t, J = 0.9 Hz, 1H), 6.98 (m, 2H), 6.72-6.68 (m, 5H), 5.80 (d, J = 1.1 Hz, 1H), 5.38 (d, J = 1.0 Hz, 1H).

E 248  3'',4'',5''-trifluoro-N',4-dihydroxy-5'-(trifluoromethyl)-[1,1':2',1''-terphenyl]-3'-carboximidamide
$R^1$ = 3,4,5-trifluorophenyl  $R^2$ = N-hydroxy carbaimidoyl  $R^3$ = $CF_3$  $R^5$ = H
ES/MS m/z: 427.1 (pos. M + H), 425 (neg. M − H); $^1$H NMR (MeOD, 500 MHz): δ 7.71 (s, 1H), 7.70 (s, 1H), 6.92-6.85 (m, 4H), 6.69 (m, 2H).

E 249  5'-chloro-3'',4''-difluoro-N',4-dihydroxy-[1,1':2',1''-terphenyl]-3'-carboximidamide
$R^1$ = 3,4-difluorophenyl  $R^2$ = N-hydroxy carbaimidoyl  $R^3$ = Cl  $R^5$ = H
ES/MS m/z: 375.2 (pos. M + H), 373 (neg. M − H); $^1$H NMR (MeOD, 500 MHz): δ 7.45 (d, J = 2.3 Hz, 1H), 7.44 (d, J = 2.3 Hz, 1H), 7.05 (m, 1H), 6.99 (m, 1H), 6.89-6.84 (m, 3H), 6.62 (m, 2H).

E 250  5'-chloro-3'',4'',5''-trifluoro-N',4-dihydroxy-[1,1':2',1''-terphenyl]-3'-carboximidamide
$R^1$ = 3,4,5-trifluorophenyl  $R^2$ = N-hydroxy carbaimidoyl  $R^3$ = Cl  $R^5$ = H
ES/MS m/z: 393.2 (pos. M + H), 391.3 (neg. M − H); $^1$H NMR (MeOD, 500 MHz): δ 7.47 (d, J = 2.3 Hz, 1H), 7.46 (d, J = 2.2 Hz, 1H), 6.89-6.80 (m, 4H), 6.66 (m, 2H).

E 251  5-chloro-N',4'-dihydroxy-2-(4-methylpyridin-3-yl)-[1,1'-biphenyl]-3-carboximidamide
$R^1$ = 4-methylpyridin-3-yl  $R^2$ = N-hydroxy carbaimidoyl  $R^3$ = Cl  $R^5$ = H
ES/MS m/z: 354.2 (pos. M + H), 391.3; $^1$H NMR (MeOD, 500 MHz): δ 8.28 (s, 1H), 8.19 (d, J = 5.0 Hz, 1H), 7.49 (m, 2H), 7.09 (d, J = 5.1 Hz, 1H), 6.85 (m, 2H), 6.57 (m, 2H), 1.92 (s, 3H).

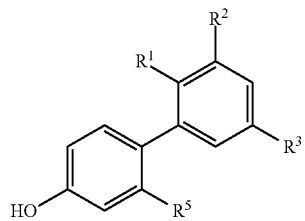

E 252 5',5''-dichloro-2''-fluoro-N',4-dihydroxy-[1,1':2',1''-terphenyl]-3'-carboximidamide
$R^1$ = 5-chloro-2-fluorophenyl        $R^2$ = N-hydroxy carbaimidoyl        $R^3$ = Cl        $R^5$ = H
ES/MS m/z: 391.07 (pos. M + H), 389.07 (neg. M − H); $^1$H NMR (MeOD, 500 MHz): δ 7.48 (d, J = 2.3 Hz, 1H), 7.45 (d, J = 2.3 Hz, 1H), 7.21-7.19 (m, 2H), 6.89-6.87 (m, 3H), 6.60 (m, 2H).

E 253 2'',5'-dichloro-5''-fluoro-N',4-dihydroxy-[1,1':2',1''-terphenyl]-3'-carboximidamide
$R^1$ = 2-chloro-5-fluorophenyl        $R^2$ = N-hydroxy carbaimidoyl        $R^3$ = Cl        $R^5$ = H
ES/MS m/z: 391.07 (pos. M + H), 389.07 (neg. M − H); $^1$H NMR (MeOD, 500 MHz): δ 7.49 (d, J = 2.2 Hz, 1H), 7.45 (d, J = 2.2 Hz, 1H), 7.23 (dd, J = 5.1, 8.8 Hz, 1H), 7.01 (dd, J = 3.0, 9.0 Hz, 1H), 6.96 (m, 1H), 6.91 (m, 2H), 6.59 (m, 2H).

E 254 5'-chloro-2''-fluoro-N',4-dihydroxy-5''-methyl-[1,1':2',1''-terphenyl]-3'-carboximidamide
$R^1$ = 2-fluoro-5-methylphenyl        $R^2$ = N-hydroxy carbaimidoyl        $R^3$ = Cl        $R^5$ = H
ES/MS m/z: 371.11 (pos. M + H), 369.13 (neg. M − H); $^1$H NMR (MeOD, 500 MHz): δ 7.47 (d, J = 2.3 Hz, 1H), 7.46 (d, J = 2.3 Hz, 1H), 7.02 (m, 1H), 6.96 (dd, J = 1.9, 7.0 Hz, 1H), 6.87 (m, 2H), 6.78 (t, J = 8.9 Hz, 1H), 6.57 (m, 2H), 2.20 (s, 3H).

E 255 5'-chloro-2''-fluoro-N',4-dihydroxy-4''-methyl-[1,1':2',1''-terphenyl]-3'-carboximidamide
$R^1$ = 2-fluoro-4-methylphenyl        $R^2$ = N-hydroxy carbaimidoyl        $R^3$ = Cl        $R^5$ = H
ES/MS m/z: 371.13 (pos. M + H), 369.14 (neg. M − H); $^1$H NMR (MeOD, 500 MHz): δ 7.47 (d, J = 2.2 Hz, 1H), 7.46 (d, J = 2.2 Hz, 1H), 7.01 (t, J = 7.8 Hz, 1H), 6.88-6.83 (m, 3H), 6.75 (d, J = 10.5 Hz, 1H), 6.57 (m, 2H), 2.27 (s, 3H).

E 256 2-(5-fluoro-2-methoxypyridin-3-yl)-N',4'-dihydroxy-5-(trifluoromethyl)-[1,1'-biphenyl]-3-carboximidamide
$R^1$ = 5-fluoro-2-methoxypyridin-3-yl        $R^2$ = N-hydroxy carbaimidoyl        $R^3$ = CF$_3$        $R^5$ = H
ES/MS m/z: 422.14 (pos. M + H), 420.13 (neg. M − H); $^1$H NMR (CDCl$_3$, 500 MHz): δ 7.89 (d, J = 3.0 Hz, 1H), 7.79 (d, J = 2.1 Hz, 1H), 7.68 (d, J = 2.1 Hz, 1H), 7.11 (dd, J = 3.0, 7.9 Hz, 1H), 6.89 (m, 2H), 6.66 (m, 2H), 4.62 (s, broad, 2H) and 3.68 (s, 3H).

E 257 5'-chloro-N',4-dihydroxy-2'',4''-dimethoxy-[1,1':2',1''-terphenyl]-3'-carboximidamide
$R^1$ = 2,4-dimethoxyphenyl        $R^2$ = N-hydroxy carbaimidoyl        $R^3$ = Cl        $R^5$ = H
ES/MS m/z: 399.13 (pos. M + H), 397.12 (neg. M − H); $^1$H NMR (MeOD, 500 MHz): δ 7.42 (s, 2H), 6.87-6.85 (m, 3H), 6.56 (m, 2H), 6.39-6.37 (m, 2H), 3.74 (s, 3H), 3.54 (s, 3H).

E 258 5'-chloro-4-hydroxy-2'',4''-dimethoxy-[1,1':2',1''-terphenyl]-3'-carbonitrile
$R^1$ = 2,4-dimethoxyphenyl        $R^2$ = CN        $R^3$ = Cl        $R^5$ = H
ES/MS m/z: 366.13 (pos. M + H), 364.16 (neg. M − H); $^1$H NMR (MeOD, 500 MHz): δ 7.73 (d, J = 2.3 Hz, 1H), 7.62 (d, J = 2.3 Hz, 1H), 6.89 (m, 2H), 6.84 (d, J = 8.4 Hz, 1H), 6.60 (m, 2H), 6.50 (d, J = 2.3 Hz, 1H), 6.46 (dd, J = 2.3, 8.4 Hz, 1H), 3.78 (s, 3H), 3.61 (s, 3H).

E 259 5-chloro-2-(5-chloro-2-methoxypyridin-3-yl)-N',4'-dihydroxy-[1,1'-biphenyl]-3-carboximidamide
$R^1$ = 5-chloro-2-methoxypyridin-3-yl        $R^2$ = N-hydroxy carbaimidoyl        $R^3$ = Cl        $R^5$ = H
ES/MS m/z: 404.07 (pos. M + H), 402.12 (neg. M − H); $^1$H NMR (MeOD, 500 MHz): δ 7.94 (d, J = 2.6 Hz, 1H), 7.47 (d, J = 2.2 Hz, 1H), 7.42 (d, J = 2.3 Hz, 1H), 7.39 (d, J = 2.6 Hz, 1H), 6.86 (m, 2H), 6.61 (m, 2H), 3.65 (s, 3H).

E 260 5-chloro-2-(5-chloro-2-methoxypyridin-3-yl)-4'-dihydroxy-[1,1'-biphenyl]-3-carboxamide
$R^1$ = 5-chloro-2-methoxypyridin-3-yl        $R^2$ = carbamoyl        $R^3$ = Cl        $R^5$ = H
ES/MS m/z: 389.05 (pos. M + H), 387.1 (neg. M − H); $^1$H NMR (MeOD, 500 MHz): δ 7.95 (d, J = 2.6 Hz, 1H), 7.53 (d, J = 2.2 Hz, 1H), 7.46 (d, J = 2.3 Hz, 1H), 7.31 (d, J = 2.6 Hz, 1H), 6.86 (m, 2H), 6.63 (m, 2H), 3.69 (s, 3H).

E 261 5-chloro-2-(2,5-dimethylpyridin-3-yl)-N',4'-dihydroxy-[1,1'-biphenyl]-3-carboximidamide
$R^1$ = 2,5-dimethylpyridin-3-yl        $R^2$ = N-hydroxy carbaimidoyl        $R^3$ = Cl        $R^5$ = H
ES/MS m/z: 368.13 (pos. M + H), 366.22 (neg. M − H); $^1$H NMR (MeOD, 500 MHz): δ 8.10 (d, J = 1.7 Hz, 1H), 7.53 (d, J = 1.9 Hz, 1H), 7.49 (q, J = 2.3 Hz, 2H), 6.84 (m, 2H), 6.58 (m, 2H), 2.27 (s, 3H), 2.00 (s, 3H).

E 262 5-chloro-2-(2,5-dimethylpyridin-3-yl)-4'-hydroxy-[1,1'-biphenyl]-3-carboxamide
$R^1$ = 2,5-dimethylpyridin-3-yl        $R^2$ = carbamoyl        $R^3$ = Cl        $R^5$ = H
ES/MS m/z: 353.12 (pos. M + H), 351.14 (neg. M − H); $^1$H NMR (MeOD, 500 MHz): δ 8.10 (d, J = 1.7 Hz, 1H), 7.53 (d, J = 2.2 Hz, 1H), 7.49 (d, J = 2.3 Hz, 1H), 7.46 (d, J = 1.8 Hz, 1H), 6.85 (m, 2H), 6.59 (m, 2H), 2.27 (s, 3H), 2.02 (s, 3H).

E 263 2-(benzo[d][1,3]dioxol-4-yl)-5-chloro-N',4'-dihydroxy-[1,1'-biphenyl]-3-carboximidamide
$R^1$ = benzo[d][1,3]dioxol-4-yl        $R^2$ = N-hydroxy carbaimidoyl        $R^3$ = Cl        $R^5$ = H
ES/MS m/z: 383.07 (pos. M + H), 381.11 (neg. M − H); $^1$H NMR (MeOD, 500 MHz): δ 7.47 (s, 2H), 6.90 (m, 2H), 6.72-6.59 (m, 5H), 5.77 (d, J = 1.2 Hz, 1H), 5.40 (d, J = 1.1 Hz, 1H).

E 264 5-chloro-N',4'-dihydroxy-2-(naphthalen-2-yl)-[1,1'-biphenyl]-3-carboximidamide
$R^1$ = naphthalen-2-yl        $R^2$ = N-hydroxy carbaimidoyl        $R^3$ = Cl        $R^5$ = H
ES/MS m/z: 389.11 (pos. M + H), 387.17 (neg. M − H); $^1$H NMR (MeOD, 500 MHz): δ 7.75 (m, 1H), 7.69-7.67 (m, 2H), 7.62 (d, J = 8.5 Hz, 1H), 7.46 (m, 2H), 7.40 (m, 2H), 7.17 (dd, J = 1.6, 8.4 Hz, 1H), 6.85 (m, 2H), 6.50 (m, 2H).

E 265 5-chloro-N',4'-dihydroxy-2-(isoquinolin-6-yl)-[1,1'-biphenyl]-3-carboximidamide
$R^1$ = isoquinolin-6-yl        $R^2$ = N-hydroxy carbaimidoyl        $R^3$ = Cl        $R^5$ = H
ES/MS m/z: 390.09 (pos. M + H), 388.17 (neg. M − H); $^1$H NMR (MeOD, 500 MHz): δ 9.13 (s, 1H), 8.35 (d, 1H), 8.18 (s, 1H), 7.88 (d, 1H), 7.74 (s, 1H), 7.67 (d, 1H), 7.53 (m, 2H), 7.39 (dd, 1H), 6.85 (dd, 2H), 6.51 (dd, 2H).

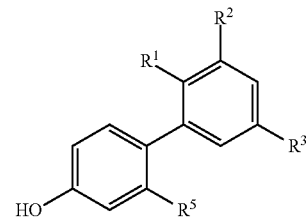

E 266    5-chloro-N',4'-dihydroxy-2-(quinolin-6-yl)-[1,1'-biphenyl]-3-carboximidamide
$R^1$ = quinolin-6-yl      $R^2$ = N-hydroxy carbaimidoyl      $R^3$ = Cl      $R^5$ = H
ES/MS m/z: 390.09 (pos. M + H), 388.17 (neg. M − H); $^1$H NMR (MeOD, 500 MHz): δ 8.77 (dd, J = 1.6, 4.4 Hz, 1H), 8.21 (s, 1H), 7.79 (d, J = 8.7 Hz, 1H), 7.74 (d, J = 1.8 Hz, 1H), 7.52 (m, 2H), 7.48 (m, 2H), 6.86 (m, 2H), 6.52 (m, 2H).

E 267    5-chloro-N',4'-dihydroxy-2-(1-methyl-1H-benzo[d]imidazol-5-yl)-[1,1'-biphenyl]-3-carboximidamide
$R^1$ = 1-methyl-1H-benzo[d]imidazol-5-yl      $R^2$ = N-hydroxy carbaimidoyl      $R^3$ = Cl      $R^5$ = H
ES/MS m/z: 393.16 (pos. M + H), 391.07 (neg. M − H); $^1$H NMR (MeOD, 500 MHz): δ 8.06 (s, 1H), 7.46 (m, 3H), 7.37 (d, J = 8.3 Hz, 1H), 7.10 (dd, J = 1.5, 8.4 Hz, 1H), 6.83 (m, 2H), 6.50 (m, 2H), 3.85 (s, 3H).

E 268    5-chloro-4'-hydroxy-2-(1-methyl-1H-benzo[d]imidazol-5-yl)-[1,1'-biphenyl]-3-carboxamide
$R^1$ = 1-methyl-1H-benzo[d]imidazol-5-yl      $R^2$ = carbamoyl      $R^3$ = Cl      $R^5$ = H
ES/MS m/z: 378.13 (pos. M + H), 376.09 (neg. M − H); $^1$H NMR (MeOD, 500 MHz): δ 8.07 (s, 1H), 7.45 (m, 3H), 7.38 (d, J = 8.4 Hz, 1H), 7.08 (dd, J = 1.5, 8.4 Hz, 1H), 6.83 (m, 2H), 6.50 (m, 2H), 3.85 (s, 3H).

E 269    2-(5-chloro-2-methoxypyridin-3-yl)-N',4'-dihydroxy-5-(trifluoromethyl)-[1,1'-biphenyl]-3-carboximidamide
$R^1$ = 5-chloro-2-methoxypyridin-3-yl      $R^2$ = N-hydroxy carbaimidoyl      $R^3$ = CF$_3$      $R^5$ = H
ES/MS m/z: 438.1 (pos. M + H), 436.07 (neg. M − H); $^1$H NMR (CDCl$_3$, 500 MHz): δ 8.00 (t, J = 1.7 Hz, 1H), 7.80 (d, J = 1.4 Hz, 1H), 7.68 (d, J = 1.4 Hz, 1H), 7.31 (d, J = 2.6 Hz, 1H), 6.90 (m, 2H), 6.68 (m, 2H), 3.69 (s, 3H).

E 270    2''-fluoro-N',4-dihydroxy-5''-methyl-5'-(trifluoromethyl)-[1,1':2',1''-terphenyl]-3'-carboximidamide
$R^1$ = 2-fluoro-5-methylphenyl      $R^2$ = N-hydroxy carbaimidoyl      $R^3$ = CF$_3$      $R^5$ = H
ES/MS m/z: 405.14 (pos. M + H), 403.12 (neg. M − H); $^1$H NMR (CDCl$_3$, 500 MHz): δ 7.79 (d, J = 1.3 Hz, 1H), 7.71 (t, J = 0.9 Hz, 1H), 7.02 (m, 1H), 6.95 (m, 2H), 6.83-6.81 (m, 2H), 6.66 (m, 2H), 2.21 (s, 3H).

E 271    5-chloro-2-(6-chloro-2-methoxypyridin-3-yl)-N',4'-dihydroxy-[1,1'-biphenyl]-3-carboximidamide
$R^1$ = 6-chloro-2-methoxypyridin-3-yl      $R^2$ = N-hydroxy carbaimidoyl      $R^3$ = Cl      $R^5$ = H
ES/MS m/z: 404.06 (pos. M + H), 402.1 (neg. M − H); $^1$H NMR (MeOD, 500 MHz): δ 7.45 (d, J = 2.3 Hz, 1H), 7.41 (d, J = 2.3 Hz, 1H), 7.34 (d, J = 7.7 Hz, 1H), 6.85 (m, 2H), 6.82 (d, J = 7.6 Hz, 1H), 6.61 (m, 2H), 3.65 (s, 3H).

E 272    5-chloro-N',4'-dihydroxy-2-(2-methoxy-5-methylpyridin-3-yl)-[1,1'-biphenyl]-3-carboximidamide
$R^1$ = 2-methoxy-5-methylpyridin-3-yl      $R^2$ = N-hydroxy carbaimidoyl      $R^3$ = Cl      $R^5$ = H
ES/MS m/z: 384.15 (pos. M + H), 382.24 (neg. M − H); $^1$H NMR (MeOD, 500 MHz): δ 7.77 (d, J = 1.6 Hz, 1H), 7.43 (d, J = 2.2 Hz, 1H), 7.40 (d, J = 2.3 Hz, 1H), 7.24 (d, J = 2.2 Hz, 1H), 6.84 (m, 2H), 6.58 (m, 2H), 3.62 (s, 3H), 2.14 (s, 3H).

E 273    5-chloro-2-(cyclopent-1-en-1-yl)-N',4'-dihydroxy-[1,1'-biphenyl]-3-carboximidamide
$R^1$ = cyclopent-1-en-1-yl      $R^2$ = N-hydroxy carbaimidoyl      $R^3$ = Cl      $R^5$ = H
ES/MS m/z: 329.16 (pos. M + H), 327.23 (neg. M − H); $^1$H NMR (MeOD, 500 MHz): δ 7.34 (t, J = 1.6 Hz, 2H), 7.14 (m, 2H), 6.77 (m, 2H), 2.32 (m, 2H), 2.10 (m, 2H), 1.73 (m, 2H).

E 274    5-chloro-2-(cyclopent-1-en-1-yl)-4'-hydroxy-[1,1'-biphenyl]-3-carboxamide
$R^1$ = cyclopent-1-en-1-yl      $R^2$ = carbamoyl      $R^3$ = Cl      $R^5$ = H
ES/MS m/z: 314.12 (pos. M + H), 312.22 (neg. M − H); $^1$H NMR (MeOD, 500 MHz): δ 7.32 (d, J = 2.2 Hz, 1H), 7.29 (d, J = 2.2 Hz, 1H), 7.15 (m, 2H), 6.77 (m, 2H), 5.71 (t, J = 2.0 Hz, 1H), 2.32 (m, 2H), 2.08 (m, 2H), 1.72 (m, 2H).

E 275    2-(cyclopent-1-en-1-yl)-N',4'-dihydroxy-5-(trifluoromethyl)-[1,1'-biphenyl]-3-carboximidamide
$R^1$ = cyclopent-1-en-1-yl      $R^2$ = N-hydroxy carbaimidoyl      $R^3$ = CF$_3$      $R^5$ = H
ES/MS m/z: 363.17 (pos. M + H), 361.25 (neg. M − H); $^1$H NMR (MeOD, 500 MHz): δ 7.60 (d, J = 1.2 Hz, 1H), 7.57 (d, J = 1.3 Hz, 1H), 7.17 (m, 2H), 6.79 (m, 2H), 5.75 (t, J = 2.0 Hz, 1H), 2.34 (m, 2H), 2.15 (m, 2H), 1.75 (m, 2H).

E 276    2-(cyclopent-1-en-1-yl)-4'-hydroxy-5-(trifluoromethyl)-[1,1'-biphenyl]-3-carboxamide
$R^1$ = cyclopent-1-en-1-yl      $R^2$ = N-hydroxy carbaimidoyl      $R^3$ = CF$_3$      $R^5$ = H
ES/MS m/z: 348.18 (pos. M + H), 346.21 (neg. M − H); $^1$H NMR (MeOD, 500 MHz): δ 7.59 (d, J = 1.3 Hz, 1H), 7.54 (d, J = 1.4 Hz, 1H), 7.18 (m, 2H), 6.80 (m, 2H), 5.78 (m, 1H), 2.35 (m, 2H), 2.12 (m, 2H), 1.75 (m, 2H).

Example 277

5'-bromo-5"-fluoro-N',4-dihydroxy-2"-methoxy-[1,1':2',1"-terphenyl]-3'-carboximidamide (E277)

Scheme 15

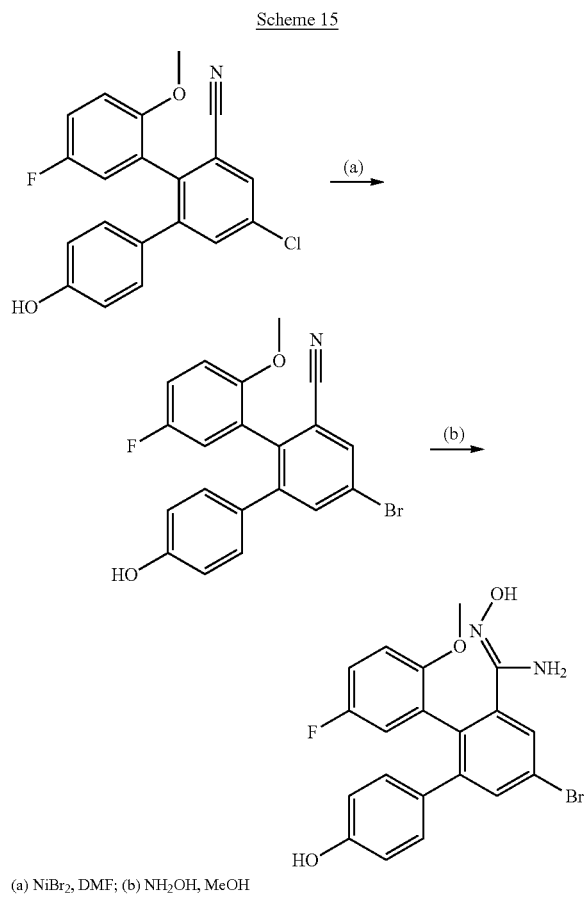

(a) NiBr$_2$, DMF; (b) NH$_2$OH, MeOH

Step (a):

5'-chloro-5"-fluoro-4-hydroxy-2"-methoxy-[1,1':2',1"-terphenyl]-3'-carbonitrile (15.0 mg, 0.04 mmol), obtained analogous to example 15 step (a)-(c), and NiBr$_2$ (18.4 mg, 0.08 mmol) were mixed in dry DMF under nitrogen. The reaction mixture was heated at 170° C. for 25 min in microwave. After cooling to room temperature HCl (1M) was added, the mixture was extracted with EtOAc and DCM and filtered through a phase separator. The solvent was evaporated under reduced pressure and the crude product was purified on preparative HPLC using MeCN/acidic H$_2$O (20-100% MeCN) as mobile phase. 8.0 mg 5'-bromo-5"-fluoro-4-hydroxy-2"-methoxy-[1,1':2',1"-terphenyl]-3'-carbonitrile was obtained.

Step (b):

5'-bromo-5"-fluoro-4-hydroxy-2"-methoxy-[1,1':2',1"-terphenyl]-3'-carbonitrile (8.0 mg, 0.02 mmol) and hydroxylamine (0.25 mL, 16 M, aq) were mixed in MeOH (1 mL). The reaction mixture was heated in microwave at 130° C. for 15 min under nitrogen. The crude mixture was purified on preparative HPLC using MeCN/acidic H$_2$O (5-50% MeCN) as mobile phase. 2.0 mg 5'-bromo-5"-fluoro-N',4-dihydroxy-2"-methoxy-[1,1':2',1"-terphenyl]-3'-carboximidamide (E277) was obtained. ES/MS m/z: 431.16 (M+H), 431.21 (M−H); $^1$H NMR (Acetone-d6, 500 MHz): 7.57 (d, 1H, J=2.3 Hz), 7.51 (d, 1H, J=2.3 Hz), 6.95-6.90 (m, 3H), 6.81-6.77 (m, 2H), 6.65 (m, 2H) and 3.53 (s, 3H). The title compound was identified by $^1$H-NMR which showed that the oxime product was a single isomer, but did not confirm whether the (E) or (Z) oxime isomer had been obtained.

Examples 278-283

Examples 278-283 were prepared using a method analogous to that used to synthesise Example 277 above. Full experimental details of the individual steps of the general methods are described in Examples 15 and 277 above. For examples 278-283 identification of the title compounds by $^1$H-NMR showed that the oxime product was a single isomer, but did not confirm whether the (E) or (Z) oxime isomer had been obtained.

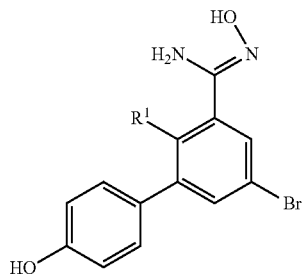

E 278  5'-bromo-5"-fluoro-N',4-dihydroxy-2"-methyl-[1,1':2',1"-terphenyl]-3'-carboximidamide
R$^1$ = 5-fluoro-2-methylphenyl
ES/MS m/z: 417.14 (pos. M + H), 415.17 (neg. M − H); $^1$H NMR (Acetone-d6, 500 MHz): δ 7.60 (d, 1H, J = 2.2 Hz), 7.56 (d, 1H, J = 2.2 Hz), 7.01-6.92 (m, 4H), 6.85 (m, 1H), 6.65 (m, 2H) and 1.83 (s, 3H).
E 279  5'-bromo-3"-fluoro-N',4-dihydroxy-2"-methoxy-[1,1':2',1"-terphenyl]-3'-carboximidamide
R$^1$ = 3-fluoro-2-methoxyphenyl
ES/MS m/z: 431.18; 433.16; 435.21 (pos. M + H); $^1$H NMR (Acetone-d6, 500 MHz): δ 7.60 (d, 1H, J = 2.2 Hz), 7.54 (d, 1H, J = 2.2 Hz), 7.00 (m, 1H), 6.94 (m, 2H), 6.90-6.88 (m, 2H), 6.66 (m, 2H) and 3.58, 3.57 (two s, 3H).

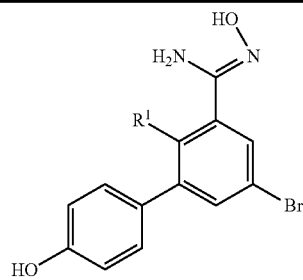

E 280 5'-bromo-N',4-dihydroxy-2",5"-dimethyl-[1,1':2',1"-terphenyl]-3'-carboximidamide
R¹ = 2,5-dimethylphenyl
ES/MS m/z: 411.19; 413.17 (pos. M + H), 409.24; 411.23 (neg. M − H); ¹H NMR (Acetone-d6, 500 MHz): δ 7.60 (d, 1H, J = 2.3 Hz), 7.54 (d, 1H, J = 2.3 Hz), 6.99 (s, 1H), 6.93-6.87 (m, 4H), 6.62 (m, 2H), 2.20 (s, 3H) and 1.82 (s, 3H).
E 281 5'-bromo-N',4-dihydroxy-5"-methoxy-2"-methyl-[1,1':2',1"-terphenyl]-3'-carboximidamide
R¹ = 5-methoxy-2-methylphenyl
ES/MS m/z: 427.16; 429.17 (pos. M + H), 425.23; 427.22 (neg. M − H); ¹H NMR (Acetone-d6, 500 MHz): δ 7.56 (d, 1H, J = 2.2 Hz), 7.48 (d, 1H, J = 2.2 Hz), 6.98 (dd, 1H, J = 8.5, 2.1 Hz), 6.90 (m, 2H), 6.79 (d, 1H, J = 2.1 Hz), 6.71 (d, 1H, J = 8.5 Hz), 6.62 (m, 2H), 3.52 (s, 3H) and 2.13 (s, 3H).
E 282 5'-bromo-N',4-dihydroxy-2"-methoxy-[1,1':2',1"-terphenyl]-3'-carboximidamide
R¹ = 3-methoxyphenyl
ES/MS m/z: 413.15; 415.18 (pos. M + H), 411.21; 413.24 (neg. M − H); ¹H NMR (Acetone-d6, 500 MHz): δ 7.58 (d, 1H, J = 2.2 Hz), 7.50 (d, 1H, J = 2.2 Hz), 7.18 (m, 1H), 6.98 (dd, 1H, J = 7.6, 1.5 Hz), 6.89 (m, 2H), 6.81 (d, 1H, J = 7.6 Hz), 6.78 (m, 1H), 6.61 (m, 2H) and 3.55 (s, 3H).
E 283 5'-bromo-4"-fluoro-N',4-dihydroxy-2"-methoxy-[1,1':2',1"-terphenyl]-3'-carboximidamide
R¹ = 4-fluoro-2-methoxyphenyl
ES/MS m/z: 431.14; 433.15 (pos. M + H), 429.25; 431.39 (neg. M − H); ¹H NMR (Acetone-d6, 500 MHz): δ 7.57 (d, 1H, J = 2.2 Hz), 7.50 (d, 1H, J = 2.2 Hz), 6.99 (dd, 1H, J = 8.4, 6.9 Hz), 6.89 (m, 2H), 6.66-6.61 (m, 3H), 6.56 (m, 1H) and 3.55 (s, 3H).

Example 284

5"-fluoro-N',4-dihydroxy-5'-(trifluoromethyl)-2"-vinyl-[1,1':2',1"-terphenyl]-3'-carboximidamide (E284)

Scheme 16

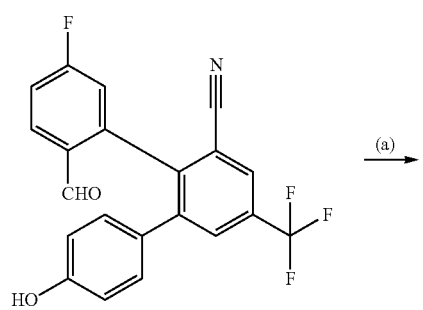

(a) →

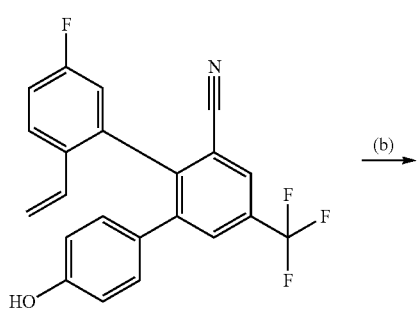

(b) →

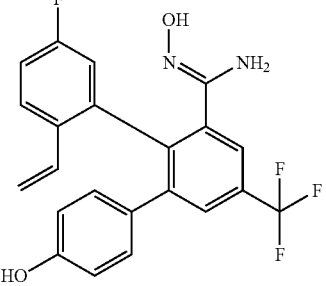

(a) Methyltriphenylphosphonium bromide, lithium 2-methylpropan-2-olate, THF;
(b) NH₂OH, DMSO Step (a):

Methyltriphenylphphosphonium bromide (125 mg, 0.35 mmol) and lithium 2-methylpropan-2-olate (25.6 mg, 0.35 mmol) were mixed in THF (4 mL) under N₂ at 0° C. The mixture was stirred for 30 min. 5"-fluoro-2"-formyl-4-hydroxy-5'-(trifluoromethyl)-[1,1':2',1"-terphenyl]-3'-carbonitrile (15.0 mg, 0.04 mmol), obtained analogous to example 15 step (a)-(c), was added at 0° C. The reaction mixture was then heated at 50° C. for 16 h. After cooling to room temperature H₂O and HCl (2 M) were added. The mixture was extracted with EtOAc and filtered through a phase separator. The solvent was evaporated under reduced pressure and the crude product was purified on silica using MeOH/DCM (1-2% MeOH) as mobile phase. 4.0 mg 5"-fluoro-4-hydroxy-5'-(trifluoromethyl)-2"-vinyl-[1,1':2', 1"-terphenyl]-3'-carbonitrile was obtained.

Step (b):
5"-fluoro-4-hydroxy-5'-(trifluoromethyl)-2"-vinyl-[1,1':2',1"-terphenyl]-3'-carbonitrile (4.0 mg, 0.01 mmol) and hydroxylamine (0.15 mL, 16 M, aq) were mixed in DMSO (0.4 mL). The reaction mixture was heated in microwave at 120° C. for 20 min under nitrogen. The crude mixture was purified on preparative HPLC using MeCN/acidic H$_2$O (15-40% MeCN) as mobile phase. 2.3 mg 5"-fluoro-N',4-dihydroxy-5'-(trifluoromethyl)-2"-vinyl-[1,1':2',1"-terphenyl]-3'-carboximidamide (E284) was obtained. ES/MS m/z: 417.21 (M+H), 415.28 (M−H); $^1$H NMR (Acetone-d6, 500 MHz): 7.56 (d, 1H, J=2.2 Hz), 7.48 (d, 1H, J=2.2 Hz), 6.98 (dd, 1H, J=8.5, 2.1 Hz), 6.90 (m, 2H), 6.79 (d, 1H, J=2.1 Hz), 6.71 (d, 1H, J=8.5 Hz), 6.62 (m, 2H), 3.52 (s, 3H) and 2.13 (s, 3H). The title compound was identified by $^1$H-NMR which showed that the oxime product was a single isomer, but did not confirm whether the (E) or (Z) oxime isomer had been obtained.

Examples 285 and 286

Examples 285 and 286 were prepared using a method analogous to that used to synthesise Example 284 above. Full experimental details of the individual steps of the general methods are described in Examples 15 and 284 above. For examples 285 and 286 identification of the title compounds by $^1$H-NMR showed that the oxime product was a single isomer, but did not confirm whether the (E) or (Z) oxime isomer had been obtained E 285 2,5"-difluoro-N',4-dihydroxy-5'-(trifluoromethyl)-2"-vinyl-[1,1':2',1"-terphenyl]-3'-carboximidamide.
R$^1$ = 5-fluoro-2-vinylphenyl   R$^5$ = F
ES/MS m/z: 435.2 (pos. M + H), 433.3 (neg. M − H); $^1$H NMR (Acetone-d6, 500 MHz): δ 7.84 (d, 1H, J = 1.8 Hz), 7.69 (d, 1H, J = 1.8 Hz), 7.46 (dd, 1H, J = 9.4, 5.8 Hz), 6.99-6.94 (m, 2H), 6.85 (t, 1H, J = 9.2 Hz), 6.48-6.44 (m, 2H), 6.32 (dd, 1H, J = 17.7, 11.2 Hz), 5.44 (dd, 1H, J = 17.7, 1.0 Hz) and 4.99 (dd, 1H, J = 11.1, 1.0 Hz).

E 286 5"-chloro-N',4-dihydroxy-5'-(trifluoromethyl)-2"-vinyl-[1,1':2',1"-terphenyl]-3'-carboximidamide
R$^1$ = 5-chloro-2-vinylphenyl   R$^5$ = H
ES/MS m/z: 433.23 (pos. M + H), 431.28 (neg. M − H); $^1$H NMR (Acetone-d6, 500 MHz): δ 7.77 (d, 1H, J = 1.6 Hz), 7.68 (d, 1H, J = 1.6 Hz), 7.46 (d, 1H, J = 8.2 Hz), 7.24-7.21 (m, 2H), 6.91 (m, 2H), 6.65 (m, 2H), 6.35 (dd, 1H, J = 17.5, 11.0 Hz), 5.50 (dd, 1H, J = 17.5, 0.8 Hz) and 5.03 (dd, 1H, J = 11.0, 0.8 Hz).

Example 287

2"-ethynyl-5"-fluoro-N',4-dihydroxy-5'-(triflorom-ethyl)-[1,1:2',1"-terphenyl]-3'-carboximidamide (E287)

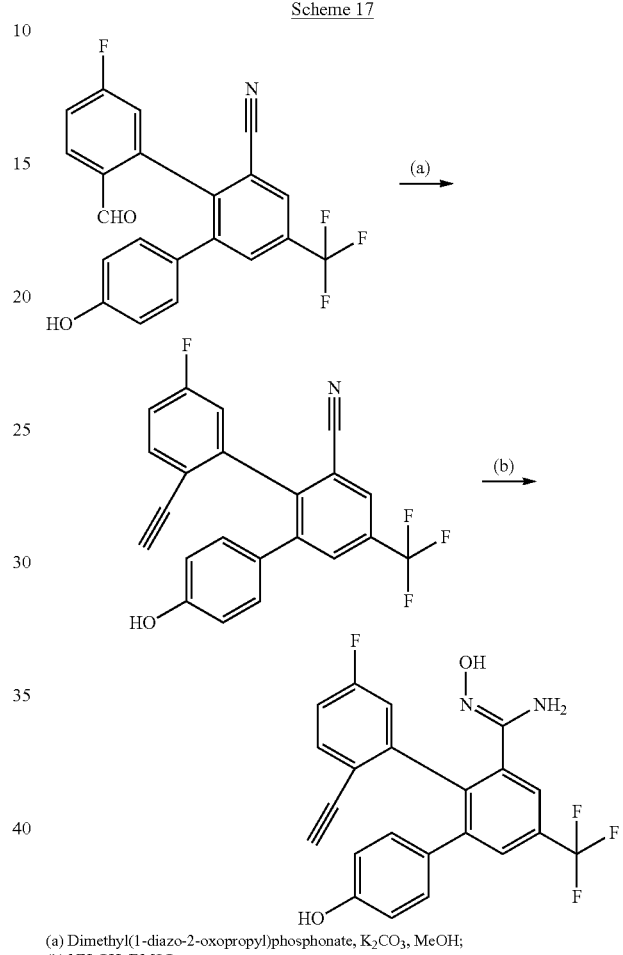

(a) Dimethyl(1-diazo-2-oxopropyl)phosphonate, K$_2$CO$_3$, MeOH;
(b) NH$_2$OH, DMSO Step (a):
5"-fluoro-2"-formyl-4-hydroxy-5'-(trifluoromethyl)-[1,1':2',1"-terphenyl]-3'-carbonitrile (8.0 mg, 0.02 mmol), obtained analogous to example 15 step (a)-(c), and dimethyl (1-diazo-2-oxopropyl)phosphonate (99.7 mg, 0.52 mmol) were mixed in MeOH (1 mL). K$_2$CO$_3$ (66.0 mg, 0.48 mmol) was added and the resulting mixture was stirred for 16 h. NH$_4$Cl (aq) was added, the mixture was extracted with EtOAc and filtered through a phase separator. The solvent was evaporated under reduced pressure and the crude product was purified on preparative HPLC using MeCN/acidic H$_2$O (20-80% MeCN) as mobile phase. 5.0 mg 2"-ethynyl-5"-fluoro-4-hydroxy-5'-(trifluoromethyl)-[1,1':2',1"-terphenyl]-3'-carbonitrile was obtained.

Step (b):
2"-ethynyl-5"-fluoro-4-hydroxy-5'-(trifluoromethyl)-[1,1':2',1"-terphenyl]-3'-carbonitrile (5.0 mg, 0.01 mmol) and hydroxylamine (0.15 mL, 16 M, aq) were mixed in DMSO (0.45 mL). The reaction mixture was heated at 70° C. for 2 h under nitrogen. The crude mixture was purified on preparative HPLC using MeCN/acidic H₂O (15-50% MeCN) as mobile phase. 5.21 mg 2"-ethynyl-5"-fluoro-N',4-dihydroxy-5'-(trifluoromethyl)-[1,1':2',1"-terphenyl]-3'-carboximidamide (E287) was obtained. ES/MS m/z: 415.23 (M+H), 413.29 (M−H); ¹H NMR (Acetone-d6, 500 MHz): 7.78 (d, 1H, J=1.6 Hz), 7.68 (d, 1H, J=1.6 Hz), 7.38 (m, 1H), 7.03-6.99 (m, 4H), 6.68 (m, 2H) and 3.44 (s, 1H). The title compound was identified by ¹H-NMR which showed that the oxime product was a single isomer, but did not confirm whether the (E) or (Z) oxime isomer had been obtained.

Example 288

4-hydroxy-2"-methoxy-5"-methyl-5'-(trifluoromethyl)-[1,1':2',1"-terphenyl]-3'-carboxamide (E288)

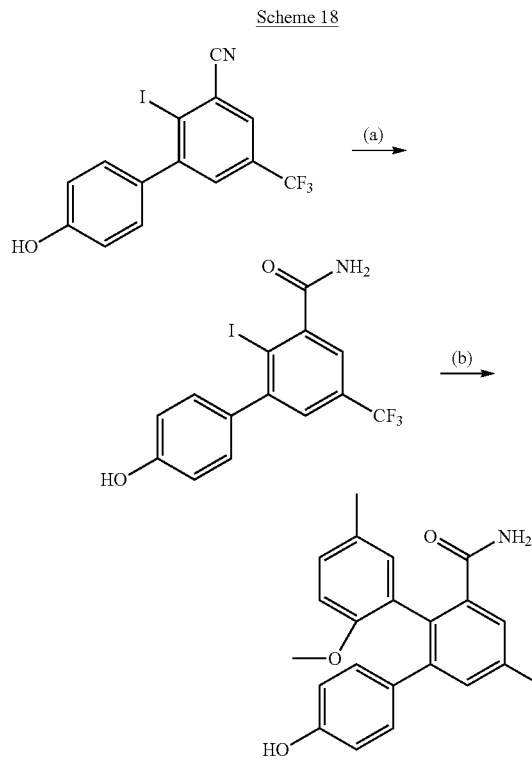

(a) NaOH, H₂O₂, MeOH;
(b) (2-methoxy-5-methylphenyl)boronic acid, PdCl₂(PPh₃)₂, K₂CO₃, DME/EtOH/H₂O Step (a):
4'-hydroxy-2-iodo-5-(trifluoromethyl)-[1,1'-biphenyl]-3-carbonitrile (100 mg, 0.26 mmol), obtained analogous to example 15 step (a) and (b), NaOH (1 M, 5.14 mL) and hydrogen peroxide (12 M, 0.43 mL) were mixed in MeOH (3 mL). The reaction mixture was stirred at room temperature for 1 h. HCl (1 M) was added and the aqueous mixture was extracted with DCM. The combined organic extracts were evaporated under reduced pressure. 407 mg 4'-hydroxy-2-iodo-5-(trifluoromethyl)-[1,1'-biphenyl]-3-carboxamide was obtained.
Step (b):
4'-hydroxy-2-iodo-5-(trifluoromethyl)-[1,1'-biphenyl]-3-carboxamide (20 mg, 0.05 mmol), (2-methoxy-5-methylphenyl)boronic acid (16.3 mg, 0.10 mmol), PdCl₂(PPh₃)₂ (3.45 mg, 0.005 mmol) and K₂CO₃ (20.3 mg, 0.15 mmol) were mixed in DME/EtOH/H₂O (1 mL, 4:1:1) under nitrogen. The reaction mixture was heated in microwave at 130° C. for 30 min, cooled to room temperature, filtered through celite and evaporated under reduced pressure. The crude mixture was purified on preparative HPLC using MeCN/acidic H₂O (0-20% MeCN) as mobile phase. 7.6 mg 4-hydroxy-2"-methoxy-5"-methyl-5'-(trifluoromethyl)-[1,1':2',1"-terphenyl]-3'-carboxamide (E288) was obtained. ES/MS m/z: 402.2 (M+H), 400.4 (M−H); ¹H NMR (MeOD, 500 MHz): 7.73 (d, 1H, J=1.6 Hz), 7.64 (d, 1H, J=1.6 Hz), 7.03 (m, 1H), 6.88 (m, 2H), 6.80 (d, 1H, J=2.0 Hz), 6.74 (d, 1H, J=8.4 Hz), 6.57 (m, 2H), 3.54 (s, 3H) and 2.15 (s, 3H).

Example 289

5'-bromo-5"-chloro-N',4-dihydroxy-2"-methyl-[1,1':2',1"-terphenyl]-3'-carboximidamide (E289)

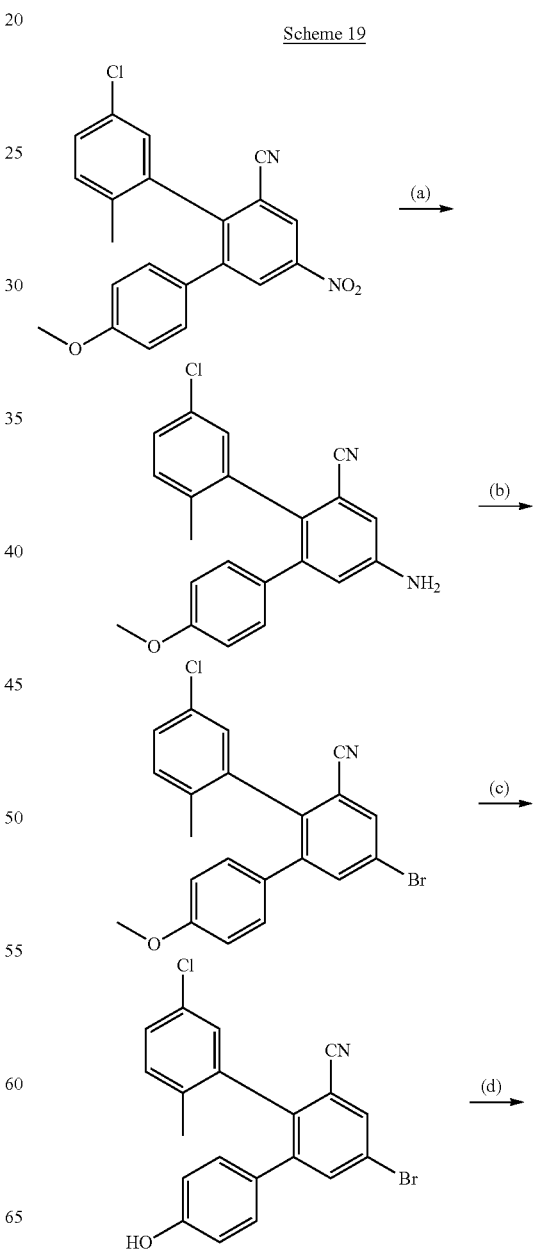

-continued

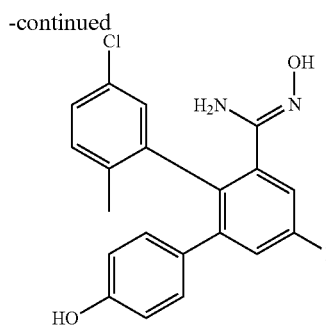

(a) SnCl$_2$*(H$_2$O)$_2$ EtOH;
(b) CuBr$_2$, t-butyl nitrite, MeCN;
(c) BBr$_3$, DCM;
(d) NH$_2$OH (aq), MeOH Step (a):
5"-chloro-4-methoxy-2"-methyl-5'-nitro-[1,1':2',1"-terphenyl]-3'-carbonitrile (50.0 mg, 0.13 mmol), obtained analogous to example 1 step (a), (b), (d) and SnCl$_2$*(H$_2$O)$_2$ (149 mg, 0.66 mmol) were mixed in EtOH (6.6 mL). The reaction mixture was heated at reflux for 5 h. Silica was added and the solvent was concentrated. The crude mixture was purified on silica using EtOAc/n-heptane (1:1) as mobile phase. 40 mg 5'-amino-5"-chloro-4-methoxy-2"-methyl-[1,1':2',1"-terphenyl]-3'-carbonitrile was obtained.

Step (b):
5'-amino-5"-chloro-4-methoxy-2"-methyl-[1,1':2',1"-terphenyl]-3'-carbonitrile (48.0 mg, 0.14 mmol) and CuBr$_2$ (61.5 mg, 0.28 mmol) were mixed in MeCN (1.7 mL). t-Butyl nitrite (21.3 mg, 0.21 mmol) was added. The reaction mixture was stirred at room temperature for 18 h. The solvent was evaporated under reduced pressure and the crude product was filtered through silica using EtOAc/n-heptane (1:1) as mobile phase 5'-bromo-5"-chloro-4-methoxy-2"-methyl-[1,1':2',1"-terphenyl]-3'-carbonitrile was obtained in quantitative yield.

Step (c):
5'-bromo-5"-chloro-4-methoxy-2"-methyl-[1,1':2',1"-terphenyl]-3'-carbonitrile (56.8 mg, 0.14 mmol) was dissolved in DCM (1.7 mL) under nitrogen. BBr$_3$ (0.69 mL, 1M) was added. The reaction mixture was stirred at room temperature for 18 h. DCM and HCl (1M) were added and the phases were separated using a phase separator. The organic phase was evaporated under reduced pressure. 50 mg 5'-bromo-5"-chloro-4-hydroxy-2"-methyl-[1,1':2',1"-terphenyl]-3'-carbonitrile was obtained.

Step (d):
5'-bromo-5"-chloro-4-hydroxy-2"-methyl-[1,1':2',1"-terphenyl]-3'-carbonitrile (50 mg, 0.12 mmol) and hydroxylamine (0.4 mL, 16 M, aq) were mixed in MeOH (0.8 mL). The reaction mixture was heated in microwave at 130° C. for 15 min under nitrogen. The crude mixture was purified on preparative HPLC using MeCN/acidic H$_2$O (5-40% MeCN) as mobile phase. 15.8 mg 5'-bromo-5"-chloro-N',4-dihydroxy-2"-methyl-[1,1':2',1"-terphenyl]-3'-carboximidamide (E289) was obtained. ES/MS m/z: 433.16; 435.19 (M+H), 431.06 (M−H); $^1$H NMR (Acetone-d6, 500 MHz): 7.61 (d, 1H, J=2.2 Hz), 7.56 (d, 1H, J=2.2 Hz), 7.20 (d, 1H, J=2.2 Hz), 7.10 (dd, 1H, J=8.3, 2.2 Hz), 6.99 (d, 1H, J=8.3 Hz), 6.92 (m, 2H), 6.66 (m, 2H) and 1.85 (s, 3H). The title compound was identified by $^1$H-NMR which showed that the oxime product was a single isomer, but did not confirm whether the (E) or (Z) oxime isomer had been obtained.

Examples 290-296

Examples 290-296 were prepared using a method analogous to that used to synthesise Example 289 above. Full experimental details of the individual steps of the general methods are described in Examples 1 and 289 above. For examples 290-296 identification of the title compounds by $^1$H-NMR showed that the oxime product was a single isomer, but did not confirm whether the (E) or (Z) oxime isomer had been obtained.

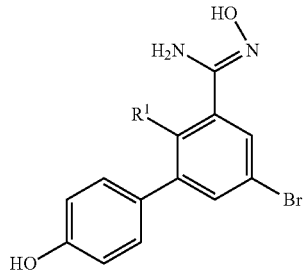

E 290 5'-bromo-3",5"-difluoro-N',4-dihydroxy-[1,1':2',1"-terphenyl]-3'-carboximidamide
R$^1$ = 3,5-difluorophenyl
ES/MS m/z: 419.19 (pos. M + H), 419.06 (neg. M − H); $^1$H NMR (Acetone-d6, 500 MHz): δ 7.59 (d, 1H, J = 2.2 Hz), 7.57 (d, 1H, J = 2.2 Hz), 6.94 (m, 2H), 6.83 (m, 1H) and 6.76-6.70 (m, 4H).

E 291 5'-bromo-3",5"-difluoro-N',4-dihydroxy-[1,1':2',1"-terphenyl]-3'-carboximidamide
R$^1$ = 3-chloro-5-fluorophenyl
ES/MS m/z: 437.15; 439.16 (pos. M + H), 435; 437.10 (neg. M − H); $^1$H NMR (Acetone-d6, 500 MHz): δ 7.59 (d, 1H, J = 2.2 Hz), 7.58 (d, 1H, J = 2.2 Hz), 7.06 (m, 1H), 6.97 (br s, 1H), 6.93 (m, 2H), 6.87 (d, 1H, J = 9.0 Hz) and 6.71 (m, 2H).

E 292 5'-bromo-2"-chloro-5"-fluoro-N',4-dihydroxy-[1,1':2',1"-terphenyl]-3'-carboximidamide
R$^1$ = 2-chloro-5-fluorophenyl
ES/MS m/z: 437.15; 439.15 (pos. M + H), 435.05; 437.00 (neg. M − H); $^1$H NMR (Acetone-d6, 500 MHz): δ 7.66 (d, 1H, J = 2.1 Hz), 7.57 (d, 1H, J = 2.1 Hz), 7.24 (dd, 1H, J = 8.8, 5.2 Hz), 7.05 (dd, 1H, J = 9.2, 2.9 Hz), 7.02-6.95 (m, 3H) and 6.67 (m, 2H).

E 293 5'-bromo-4"-chloro-N',4-dihydroxy-[1,1':2',1"-terphenyl]-3'-carboximidamide
R$^1$ = 4-chlorophenyl
ES/MS m/z: 419.17; 421.14 (pos. M + H), 417.06; 419.17 (neg. M − H); $^1$H NMR (Acetone-d6, 500 MHz): δ 7.29 (m, 2H), 7.15 (m, 2H9, 7.07 (d, 1H, J = 2.5 Hz), 7.01-6.98 (m, 3H) and 6.77 (m, 2H).

-continued

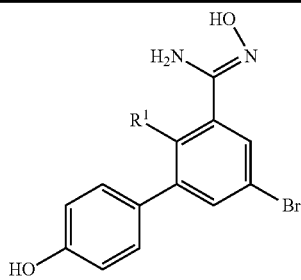

E 294  5'-bromo-2'',5''-dichloro-N',4-dihydroxy-[1,1':2',1''-terphenyl]-3'-carboximidamide
R$^1$ = 2,5-dichlorophenyl
ES/MS m/z: 453.11 (pos. M + H), 451.04 (neg. M − H); $^1$H NMR (Acetone-d6, 500 MHz): δ 7.67 (d, 1H, J = 2.0 Hz), 7.57 (d, 1H, J = 2.0 Hz), 7.27 (m, 1H), 7.24-7.20 (m, 2H), 6.96 (m, 2H) and 6.68 (m, 2H).

E 295  5'-bromo-2''-chloro-N',4-dihydroxy-5''-methyl-[1,1':2',1''-terphenyl]-3'-carboximidamide
R$^1$ = 2-chloro-5-methylphenyl
ES/MS m/z: 433.09 (pos. M + H), 431.17 (neg. M − H); $^1$H NMR (Acetone-d6, 500 MHz): δ 7.63 (d, 1H, J = 2.0 Hz), 7.54 (d, 1H, J = 2.0 Hz), 7.09-7.07 (m, 2H), 7.01 (dd, 1H, J = 8.1, 1.6 Hz), 6.94 (m, 2H), 6.64 (m, 2H) and 2.22 (s, 3H).

E 296  5-bromo-2-(3,5-dimethylisoxazol-4-yl)-N',4'-dihydroxy-[1,1'-biphenyl]-3-carboximidamide
R$^1$ = 3,5-dimethylisoxazol-4-yl
ES/MS m/z: 402.16; 404.19; 406.18 (pos. M + H), 400.19; 402.19; 404.36 (neg. M − H); $^1$H NMR (Acetone-d6, 500 MHz): δ 7.61 (d, J = 2.2 Hz, 1H), 7.59 (d, J = 2.2 Hz, 1H), 6.97 (m, 2H), 6.76 (m, 2H), 2.04 (s, 1H) and 1.83 (s, 1H).

Examples 297-303

Examples 297-303 were prepared using a method analogous to that used to synthesise Examples 1 and 50 above. Full experimental details of the individual steps of the general methods are described in Examples 1 and 50 above. For examples 297 and 299-303 identification of the title compounds by $^1$H-NMR showed that the oxime product was a single isomer, but did not confirm whether the (E) or (Z) oxime isomer had been obtained.

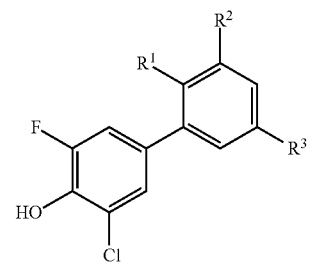

E 297  3-chloro-5-fluoro-N',4-dihydroxy-5'-(trifluoromethyl)-[1,1':2',1''-terphenyl]-3'-carboximidamide
R$^1$ = phenyl         R$^2$ = N-hydroxy carbaimidoyl         R$^3$ = CF$_3$
ES/MS m/z: 425 (pos. M + H), 423.2 (neg. M − H); $^1$H NMR (Acetone-d6, 500 MHz): δ 7.85 (m, 2H), 7.39-7.35 (m, 3H), 7.24 (m, 2H), 7.00 (t, 1H, J = 1.8 Hz) and 6.87 (dd, 1H, J = 11.3, 2.1 Hz).

E 298  3-chloro-5-fluoro-4-hydroxy-5'-(trifluoromethyl)-[1,1':2',1''-terphenyl]-3'-carboxamide
R$^1$ = phenyl         R$^2$ = carbamoyl         R$^3$ = CF$_3$
ES/MS m/z: 410.3 (pos. M + 1), 408.5 (neg. M − H); $^1$H NMR (Acetone-d6$_3$, 500 MHz): δ 7.93 (m, 1H), 7.86 (m, 1H), 7.41-7.39 (m, 3H), 7.26-7.24 (m, 2H), 7.01 (t, J = 1.9 Hz, 1H) and 6.87 (dd, J = 2.1, 11.4 Hz, 1H).

E 299  3,5'-dichloro-3'',5,5''-trifluoro-N',4-dihydroxy-[1,1':2',1''-terphenyl]-3'-carboximidamide
R$^1$ = 3,5-difluorophenyl         R$^2$ = N-hydroxy carbaimidoyl         R$^3$ = Cl
ES/MS m/z: 427.08 (pos. M + H), 425.17 (neg. M − H); $^1$H NMR (Acetone-d6, 500 MHz): δ 7.65 (s, 1H), 7.63 (d, J = 2.0 Hz, 1H), 6.99 (t, J = 1.8 Hz, 1H), 6.96-6.88 (m, 4H).

E 300  3'-chloro-2-(3,5-dimethylisoxazol-4-yl)-5'-fluoro-N',4-dihydroxy-5-(trifluoromethyl)-[1,1'-biphenyl]-3-carboximidamide
R$^1$ = 3,5-dimethylisoxazol-4-yl         R$^2$ = N-hydroxy carbaimidoyl         R$^3$ = CF$_3$
ES/MS m/z: 444.15 (pos. M + H), 442.22 (neg. M − H); $^1$H NMR (Acetone-d6, 500 MHz): δ 7.83 (s, 2H), 7.06 (t, J = 1.8 Hz, 1H), 6.95 (dd, J = 2.1, 11.1 Hz, 1H), 2.11 (s, 3H), 1.91 (s, 3H).

E 301  3-chloro-3'',5,5''-trifluoro-N',4-dihydroxy-5'-(trifluoromethyl)-[1,1':2',1''-terphenyl]-3'-carboximidamide
R$^1$ = 3,5-difluorophenyl         R$^2$ = N-hydroxy carbaimidoyl         R$^3$ = CF$_3$
ES/MS m/z: 461.15 (pos. M + H), 459.16 (neg. M − H); $^1$H NMR (Acetone-d6, 500 MHz): δ 7.81 (s, 1H), 7.80 (d, J = 0.4 Hz, 1H), 7.03 (t, J = 1.9 Hz, 1H), 6.95-6.90 (m, 2H), 6.89-6.84 (m, 2H).

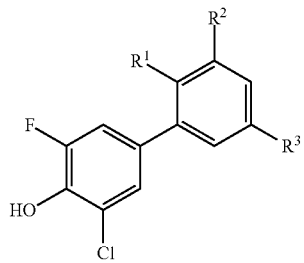

| | |
|---|---|
| E 302 | 3-chloro-5,5''-difluoro-N',4-dihydroxy-2''-methoxy-5'-(trifluoromethyl)-[1,1':2',1''-terphenyl]-3'-carboximidamide |

$R^1$ = 5-fluoro-2-methoxyphenyl    $R^2$ = N-hydroxy carbaimidoyl    $R^3$ = $CF_3$
ES/MS m/z: 473.12 (pos. M + H), 471.23 (neg. M − H); $^1$H NMR (Acetone-d6, 500 MHz): δ 7.79 (s, 1H), 7.74 (s, 1H), 7.03-6.99 (m, 2H), 6.91-6.88 (m, 3H), 3.61 (s, 3H).

| | |
|---|---|
| E 303 | 3-chloro-5-fluoro-N',4-dihydroxy-2''-methoxy-5'-(trifluoromethyl)-[1,1':2',1''-terphenyl]-3'-carboximidamide |

$R^1$ = 2-methoxyphenyl    $R^2$ = N-hydroxy carbaimidoyl    $R^3$ = $CF_3$
ES/MS m/z: 455.16 (pos. M + H), 453.18 (neg. M − H); $^1$H NMR (Acetone-d6, 500 MHz): δ 7.79 (d, J = 1.5 Hz, 1H), 7.72 (d, J = 1.4 Hz, 1H), 7.26 (m, 1H), 7.05 (dd, J = 1.7, 7.4 Hz, 1H), 6.96 (t, J = 1.8 Hz, 1H), 6.91-6.83 (m, 3H), 3.63 (s, 3H).

Examples 304-310

Examples 304-310 were prepared using methods analogous to that used to synthesise Examples 1, 15 and 50 above. Full experimental details of the individual steps of the general methods are described in Examples 1, 15 and 50 above. For examples 304-308 and 310 identification of the title compound by $^1$H-NMR showed that the oxime product was a single isomer, but did not confirm whether the (E) or (Z) oxime isomer had been obtained.

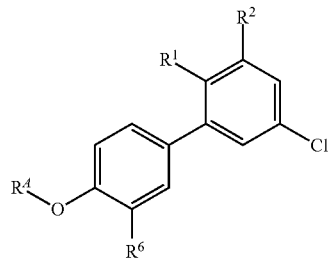

| | |
|---|---|
| E 304 | 5'-chloro-3'',5''-difluoro-N'-hydroxy-4-methoxy-3-methyl-[1,1':2,1''-terphenyl]-3'-carboximidamide |

$R^1$ = 3,5-difluorophenyl    $R^2$ = N-hydroxy carbaimidoyl    $R^A$ = Me    $R^6$ = Me
ES/MS m/z: 403.25 (pos. M + H), 401.3 (neg. M − H); $^1$H NMR (CDCl$_3$, 500 MHz): δ 7.50 (d, 1H, J = 2.3 Hz), 7.46 (d, 1H, J = 2.3 Hz), 6.81 (d, 1H, J = 1.9 Hz), 6.75 (dd, 1H, J = 8.4, 2.4 Hz), 6.70-6.62 (m, 4H), 3.79 (s, 3H) and 2.11 (s, 3H).

| | |
|---|---|
| E 305 | 5'-chloro-3'',5''-difluoro-N',4-dihydroxy-3-methyl-[1,1':2,1''-terphenyl]-3'-carboximidamide |

$R^1$ = 3,5-difluorophenyl    $R^2$ = N-hydroxy carbaimidoyl    $R^A$ = H    $R^6$ = Me
ES/MS m/z: 389.22 (pos. M + H), 387.24 (neg. M − H); $^1$H NMR (Acetone-d6, 500 MHz): δ 7.43 (s, 2H), 6.88 (d, 1H, J = 1.7 Hz), 6.83 (m, 1H), 6.76-6.66 (m, 4H) and 2.10 (s, 3H).

| | |
|---|---|
| E 306 | 5-chloro-2-(3,5-dimethylisoxazol-4-yl)-N',4'-dihydroxy-3'-methyl-[1,1'-biphenyl]-3-carboximidamide |

$R^1$ = 3,5-dimethylisoxazol-4-yl    $R^2$ = N-hydroxy carbaimidoyl    $R^A$ = H    $R^6$ = Me
ES/MS m/z: 372.22 (pos. M + H), 370.27 (neg. M − H); $^1$H NMR (Acetone-d6, 500 MHz): δ 7.46 (d, 1H, J = 2.2 Hz), 7.44 (d, 1H, J = 2.2 Hz), 6.90 (d, 1H, J = 1.7 Hz), 6.77-6.72 (m, 2H), 2.13 (s, 3H), 2.05 (s, 3H) and 1.83 (s, 3H).

| | |
|---|---|
| E 307 | 5'-chloro-N',4-dihydroxy-2'',3-dimethyl-[1,1':2',1''-terphenyl]-3'-carboximidamide |

$R^1$ = o-tolyl    $R^2$ = N-hydroxy carbaimidoyl    $R^A$ = H    $R^6$ = Me
ES/MS m/z: 367.24 (pos. M + H), 365.25 (neg. M − H); $^1$H NMR (Acetone-d6, 500 MHz): δ 7.45 (d, 1H, J = 2.3 Hz), 7.41 (d, 1H, J = 2.3 Hz), 7.16 (dd, 1H, J = 7.1, 1.4 Hz), 7.12-7.05 (m, 2H), 7.00 (m, 1H), 6.83 (d, 1H, J = 1.9 Hz), 6.69 (dd, 1H, J = 8.3, 2.3 Hz), 6.58 (d, 1H, J = 8.3 Hz), 2.03 (s, 3H) and 1.87 (s, 3H).

| | |
|---|---|
| E 308 | 5'-chloro-5''-fluoro-N',4-dihydroxy-2''-methoxy-3-methyl-[1,1':2',1''-terphenyl]-3'-carboximidamide |

$R^1$ = 5-fluoro-2-methoxyphenyl    $R^2$ = N-hydroxy carbaimidoyl    $R^A$ = H    $R^6$ = Me
ES/MS m/z: 401.18 (pos. M + H) 399.25 (neg. M − H); $^1$H NMR (Acetone-d6, 500 MHz): δ 7.42 (d, 1H, J = 2.3 Hz), 7.36 (d, 1H, J = 2.3 Hz), 6.92 (m, 1H), 6.85 (d, 1H, J = 1.8 Hz), 6.81 (dd, 1H, J = 9.0, 4.5 Hz), 6.75 (dd, 1H, J = 9.0, 3.2 Hz), 6.71 (dd, 1H, J = 8.2, 2.2 Hz), 6.61 (d, 1H, J = 8.2 Hz), 3.55 (s, 3H) and 2.07 (s, 3H).

-continued

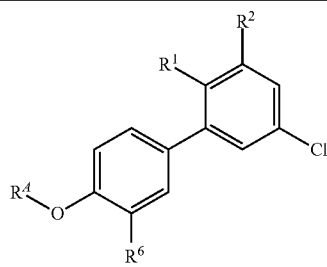

E 309   5'-chloro-5"-fluoro-4-hydroxy-2"-methoxy-3-methyl-[1,1':2',1"-terphenyl]-3'-carboxamide
$R^1$ = 5-fluoro-2-methoxyphenyl   $R^2$ = carbamoyl   $R^A$ = H   $R^6$ = Me
ES/MS m/z: 386.21 (pos. M + H) 384.25 (neg. M − H); $^1$H NMR (Acetone-d6, 500 MHz): δ 7.48 (d, J = 2.3 Hz, 1H), 7.40 (d, J = 2.3 Hz, 1H), 6.94 (m, J = 4.1 Hz, 1H), 6.87 (d, J = 1.9 Hz, 1H), 6.84 (dd, J = 4.5, 9.1 Hz, 1H), 6.77 (dd, J = 3.2, 9.0 Hz, 1H), 6.72 (dd, J = 2.2, 8.3 Hz, 1H), 6.62 (d, J = 8.2 Hz, 1H), 3.56 (s, 3H), 2.07 (s, 3H).

E 310   5'-chloro-3",5"-difluoro-N',4-dihydroxy-3-isopropyl-[1,1':2',1"-terphenyl]-3'-carboximidamide
$R^1$ = 3,5-difluorophenyl   $R^2$ = N-hydroxy carbaimidoyl   $R^A$ = H   $R^6$ = isopropyl
ES/MS m/z: 417.21 (pos. M + H) 415.28 (neg. M − H); $^1$H NMR (Acetone-d6, 500 MHz): δ 7.45 (d, J = 2.3 Hz, 1H), 7.43 (d, J = 2.3 Hz, 1H), 6.89 (dd, J = 2.3, 8.2 Hz, 1H), 6.83 (m, 1H), 6.78-6.71 (m, 4H), 3.19 (m, 1H), 1.00 (d, J =7.0 Hz, 6H).

Example 311

2'-(3,5-dimethylisoxazol-4-yl)-3'-(1H-1,2,3-triazol-4-yl)-5'-(trifluoromethyl)-[1,1'-biphenyl]-4-ol (E311)

Scheme 20

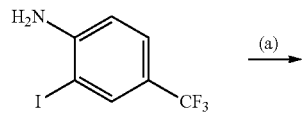

(a)

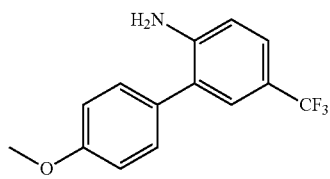

(b)

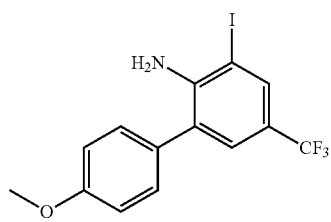

(c)

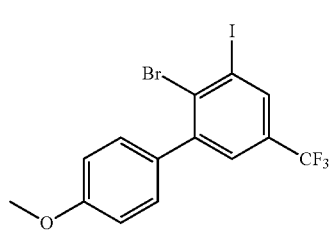

(d)

-continued

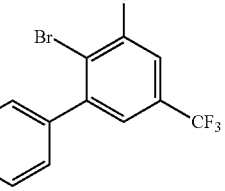

(e)

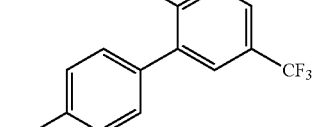

(f)

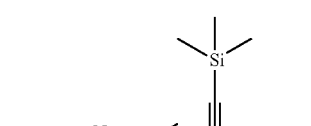

(g)

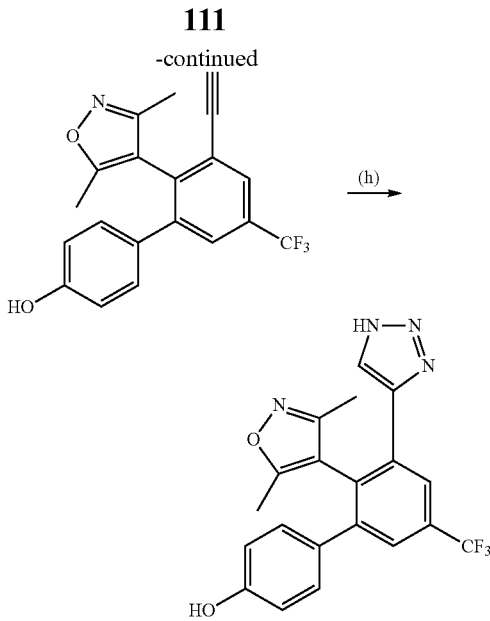

(a) 4-Methoxyphenylboronic acid, K₂CO₃, PdCl₂(PPh₃)₂, DME/EtOH/H₂O;
(b) I₂, AgSO₄, EtOH;
(b) CuBr₂, t-butyl nitrite, MeCN;
(d) BBr₃, DCM;
(e) ethynyltrimethylsilane, CuI, PdCl₂P(Ph₃)₂, Et₃N, THF;
(f) (3,5-dimethylisoxazol-4-yl)boronic acid, PdOAc₂, RuPhos, K₂CO₃, toluene/H₂O;
(g) Bu₃NF, THF;
(h) N₃SiMe₃, CuI, DMF/MeOH.

Step (a):
2-iodo-4-(trifluoromethyl)aniline (2.0 g, 6.97 mmol), 4-methoxyphenylboronic acid (2.12 g, 13.9 mmol), PdCl₂(PPh₃)₂ (244 mg, 0.35 mmol) and K₂CO₃ (3.85 g, 27.8 mmol) were mixed in DME/EtOH/H₂O (24 mL, 4:1:1) under nitrogen. The reaction mixture was heated at 100° C. for 1 h and then stirred at room temperature for 66 h. The mixture was washed with brine (sat, 30 mL) and H₂O (30 mL). The aqueous layers were extracted with DCM (30 ml) and the combined organinc layers were passed through a phase separator. The solvent was evaporated under reduced pressure and the crude product was purified on silica using EtOAc/n-heptane (0-20% EtOAc) as mobile phase. 1.38 g 4'-methoxy-5-(trifluoromethyl)-[1,1'-biphenyl]-2-amine was obtained as red oil.

Step (b):
4'-methoxy-5-(trifluoromethyl)-[1,1'-biphenyl]-2-amine (1.38 g, 5.14 mmol) was dissolved in MeOH (40 mL). Iodine (1.37 g, 5.40 mmol) and AgSO₄ (1.68 g, 5.40 mmol) were added. The reaction mixture was stirred at room temperature for 45 min and was then filtered through celite. The solvent was concentrated under reduced pressure. DCM (50 mL), H₂O (20 mL) and NaHCO₃ (1.4 g) were added to the residue and the resulting mixture was stirred for 16 h. The mixture was filtered through a phase separator. The organic layer was evaporated under reduced pressure and the crude product was purified on silica using EtOAc/n-heptane (2.5-5% EtOAc) as mobile phase. 1.63 g 3-iodo-4'-methoxy-5-(trifluoromethyl)-[1,1'-biphenyl]-2-amine was obtained as yellowish oil.

Step (c):
3-iodo-4'-methoxy-5-(trifluoromethyl)-[1,1'-biphenyl]-2-amine (1.63 g, 4.14 mmol) and CuBr₂ (1.85 g, 8.28 mmol) were mixed in MeCN (50 mL). t-Butyl nitrite (0.64 g, 6.21 mmol) was added. The reaction mixture was stirred at room temperature for 40 min. The solvent was evaporated under reduced pressure and the crude product was purified on silica using EtOAc/n-heptane (0-5% EtOAc) as mobile phase. 1.66 g 2'-bromo-3'-iodo-5'-(trifluoromethyl)-[1,1'-biphenyl]-4-ol was obtained as a white solid.

Step (d):
2'-bromo-3'-iodo-5'-(trifluoromethyl)-[1,1'-biphenyl]-4-ol was obtained (1.66 g, 3.65 mmol) was dissolved in DCM (30 mL) under nitrogen and the solution was cooled to 0° C. BBr₃ (18.2 mL, 1M) was added drop wise at 0° C. After 10 min the cooling bath was removed and the reaction mixture was stirred for 1 h and 45 min. NaHCO₃ (sat) was added and the mixture was stirred for 2 min. The mixture was filtered through a phase separator and the aqueous layer was extracted with DCM. The combined organic layers were evaporated and the crude product was purified on silica using DCMc/n-heptane (0-75% DCM) as mobile phase. 1.48 g 2'-bromo-3'-iodo-5'-(trifluoromethyl)-[1,1'-biphenyl]-4-ol was obtained as white solid.

Step (e):
2'-bromo-3'-iodo-5'-(trifluoromethyl)-[1,1'-biphenyl]-4-ol (200 mg, 0.45 mmol), ethynyltrimethylsilane (66.5 mg, 0.68 mmol), CuI (8.60 mg, 0.045 mmol), PdCl₂(PPh₃)₂ (15.84 mg, 0.02 mmol) and Et₃N (0.188 mL, 1.35 mmol) were mixed in THF (1.5 mL). The reaction mixture was stirred at room temperature for 5 h. The solvent was evaporated and the crude mixture was purified on silica using DCMc/n-heptane (0-50% DCM) as mobile phase. 136 mg 2'-bromo-5'-(trifluoromethyl)-3'-((trimethylsilyl)ethynyl)-[1,1'-biphenyl]-4-ol was obtained as colorless oil.

Step (f):
2'-bromo-5'-(trifluoromethyl)-3'-((trimethylsilyl)ethynyl)-[1,1'-biphenyl]-4-ol (136 mg, 0.33 mmol), 3,5-dimethylisoxazole-4-boronic acid (185 mg, 1.32 mmol), Pd(OAc)₂ (7.39 mg, 0.03 mmol), RuPhos (30.71 mg, 0.07 mmol) and K₂CO₃ (273 mg, 1.97 mmol) were mixed in toluene/water (0.8 mL, 1:1) under nitrogen. The reaction mixture was heated in microwave at 120° C. for 30 min and cooled to room temperature. NH₄Cl (2 mL, sat) was added and the aqueous mixture was extracted with DCM. The combined extracts were evaporated under reduced pressure and the crude product was purified on silica using DCM/n-heptane (50-100% DCM) as mobile phase. 82 mg 2'-(3,5-dimethylisoxazol-4-yl)-5'-(trifluoromethyl)-3'-((trimethylsilyl)ethynyl)-[1,1'-biphenyl]-4-ol was obtained as yellow oil.

Step (g):
2'-(3,5-dimethylisoxazol-4-yl)-5'-(trifluoromethyl)-3'-((trimethylsilyl)ethynyl)-[1,1'-biphenyl]-4-ol (82 mg, 0.19 mmol) was dissolved in THF (1 mL) and Bu₃NF (250 mg, 0.95 mmol) was added. The reaction mixture was stirred at room temperature. After 1 h additional Bu₃NF (250 mg, 0.95 mmol) was added and the stirring continued for 1 h. The solvent was evaporated under reduced pressure and the crude product was purified on silica using DCM/n-heptane (0-100% DCM) as mobile phase. 47 mg 2'-(3,5-dimethylisoxazol-4-yl)-3'-ethynyl-5'-(trifluoromethyl)-[1,1'-biphenyl]-4-ol was obtained as a red semi solid.

Step (h):
2'-(3,5-dimethylisoxazol-4-yl)-3'-ethynyl-5'-(trifluormethyl)-[1,1'-biphenyl]-4-ol (37 mg, 0.10 mmol), CuI (19.7 mg, 0.10 mmol) and N₃SiMe₃ (59.6 mg, 0.52 mmol) were mixed in DMF/MeOH (0.5 mL, 9:1). The reaction mixture was heated in microwave at 140° C. for 30 min under nitrogen. EtOAc was added and the mixture was filtered through celite. The solvent was evaporated under reduced pressure and the crude mixture, dissolved in DMSO, was purified on preparative HPLC using MeCN/acidic H₂O (20-100% MeCN) as mobile phase. 2.9 mg 2'-(3,5-dimethylisoxazol-4-yl)-3'-(1H-1,2,3-triazol-4-yl)-5'-(trifluoromethyl)-[1,1'-biphenyl]-4-ol (E311) was obtained. ES/MS m/z: 401.25 (M+H), 399.3 (M−H); $^1$H NMR (Acetone-d6, 500 MHz): 7.73 (s, 1H), 7.28 (s, 1H), 7.06 (m, 2H), 6.82 (m, 2H), 1.91 (s, 3H), 1.72 (s, 3H).

Examples 312-321

Examples 312-321 were prepared using methods analogous to that used to synthesise Example 1 above. Full experimental details of the individual steps of the general methods are described in Example 1. Intermediate C was used to synthesise examples 312-316. The intermediate used to synthesise examples 318-321 was obtained by an analogous method. For examples 312-314, and 317-319, identification of the title compounds by $^1$H-NMR showed that the oxime product was a single isomer, but did not confirm whether the (E) or (Z) oxime isomer had been obtained.

[Structure: biphenyl with HO- group, R$^1$, R$^2$, R$^3$ substituents]

E 312   N',4-dihydroxy-5'-(trifluoromethoxy)-[1,1":2',1"-terphenyl]-3'-carboximidamide
R$^1$ = phenyl          R$^2$ = N-hydroxy carbaimidoyl          R$^3$ = trifluromethoxy
ES/MS m/z: 389.6 (pos. M + H), 387.4 (neg. M − H); $^1$H NMR (MeOD, 500 MHz): δ 7.36 (s, 1H), 7.20-7.17 (m, 3H), 7.13-7.11 (m, 2H), 6.84 (m, 2H), 6.56 (m, 2H).

E 313   3",5"-difluoro-N',4-dihydroxy-5'-(trifluoromethoxy)-[1,1':2',1"-terphenyl]-3'-carboximidamide
R$^1$ = 3,5-difluorophenyl        R$^2$ = N-hydroxy carbaimidoyl          R$^3$ = trifluoromethoxy
ES/MS m/z: 425.3 (pos. M + H), 423.5 (neg. M − H); $^1$H NMR (MeOD, 500 MHz): δ 7.35 (d, J = 1.7 Hz, 2H), 6.88 (m, 2H), 6.80-6.70 (m, 3H), 6.64 (m, 2H).

E 314   5"-chloro-N',4-dihydroxy-2"-methoxy-5'-(trifluoromethoxy)-[1,1';2',1"-terphenyl]-3'-carboximidamide
R$^1$ = 5-chloro-2-methoxyphenyl    R$^2$ = N-hydroxy carbaimidoyl          R$^3$ = trifluoromethoxy
ES/MS m/z: 453.5 (pos. M + H), 451.4 (neg. M − H); $^1$H NMR (MeOD, 500 MHz): δ 7.36 (s, 1H), 7.33 (s, 1H), 7.19 (dd, J = 2.6, 8.8 Hz, 1H), 7.01 (d, J = 2.6 Hz, 1H), 6.87 (d, J = 8.5 Hz, 2H), 6.81 (d, J = 8.9 Hz, 1H), 6.59 (d, J = 8.5 Hz, 2H), 3.56 (s, 3H).

E 315   4-hydroxy-5'-(trifluoromethoxy)-[1,1':2',1"-terphenyl]-3'-carboxamide
R$^1$ = phenyl          R$^2$ = carbamoyl          R$^3$ = trifluoromethoxy
ES/MS m/z: 374.3 (pos. M + H), 372.1 (neg. M − H); $^1$H NMR (MeOD, 500 MHz): δ 7.34 (m, 1H), 7.31 (m, 1H), 7.21-7.19 (m, 3H), 7.12-7.10 (m, 2H), 6.84 (m, 2H), 6.57 (m, 2H).

E 316   3",5"-difluoro-4-hydroxy-5'-(trifluoromethoxy)-[1,1':2',1"-terphenyl]-3'-carboxamide
R$^1$ = 3,5-difluorophenyl        R$^2$ = carbamoyl          R$^3$ = trifluoromethoxy
ES/MS m/z: 410.6 (pos. M + H), 408.5 (neg. M − H); $^1$H NMR (MeOD, 500 MHz): δ 7.37 (t, J = 1.2 Hz, 1H), 7.34 (d, J = 1.5 Hz, 1H), 6.89 (m, 2H), 6.80 (m, 1H), 6.71 (m, 2H), 6.66 (m, 2H).

E 317   N',4-dihydroxy-5'-isopropyl-[1,1':2',1"-terphenyl]-3'-carboximidamide
R$^1$ = phenyl          R$^2$ = N-hydroxy carbaimidoyl          R$^3$ = isopropyl
ES/MS m/z: 347.3 (pos. M + H), 345.1 (neg. M − H); $^1$H NMR (MeOD, 500 MHz): δ 7.33-7.31 (m, 2H), 7.17-7.15 (m, 3H), 7.11-7.09 (m, 2H), 6.82 (m, 2H), 6.54 (m, 2H), 3.01 (m, 1H), 1.32 (d, J =7.0 Hz, 6H).

E 318   3",5"-difluoro-N',4-dihydroxy-5'-isopropyl-[1,1':2',1"-terphenyl]-3'-carboximidamide
R$^1$ = 3,5-difluorophenyl        R$^2$ = N-hydroxy carbaimidoyl          R$^3$ = isopropyl
ES/MS m/z: 383.3 (pos. M + H), 381.4 (neg. M − H); $^1$H NMR (MeOD, 500 MHz): δ 7.32 (d, J = 1.8 Hz, 1H), 7.30 (d, J = 1.8 Hz, 1H), 6.85 (m, 2H), 6.73-6.69 (m, 3H), 6.62 (m, 2H), 3.00 (m, 1H), 1.31 (d, J = 7.0 Hz, 6H).

E 319   5"-chloro-N',4-dihydroxy-5'-isopropyl-2"-methoxy-[1,1':2',1"-terphenyl]-3'-carboximidamide
R$^1$ = 5-chloro-2-methoxyphenyl    R$^2$ = N-hydroxy carbaimidoyl          R$^3$ = isopropyl
ES/MS m/z: 411.5 (pos. M + H), 409.7 (neg. M − H); $^1$H NMR (MeOD, 500 MHz): δ 7.32 (s, 2H), 7.16 (dd, J = 2.6, 8.8 Hz, 1H), 6.97 (d, J = 2.7 Hz, 1H), 6.85 (m, 2H), 6.80 (d, J = 8.9 Hz, 1H), 6.57 (m, 2H), 3.57 (s, 3H), 3.01 (m, J = 6.9 Hz, 1H), 1.32 (d, J = 6.9 Hz, 6H).

E 320   4-amino-5'-isopropyl-[1,1':2',1"-terphenyl]-3'-carboxamide
R$^1$ = phenyl          R$^2$ = carbamoyl          R$^3$ = isopropyl
ES/MS m/z: 332.3 (pos. M + H), 330.4 (neg. M − H).

E 321   3",5"-difluoro-N',4-dihydroxy-5'-isopropyl-[1,1':2',1"-terphenyl]-3'-carboximidamide
R$^1$= 3,5-difluorophenyl         R$^2$ = carbamoyl          R$^3$ = isopropyl
ES/MS m/z: 368.3 (pos. M + H), 366.1 (neg. M − H); $^1$H NMR (MeOD, 500 MHz): δ 7.35 (d, J = 1.9 Hz, 1H), 7.30 (d, J = 1.9 Hz, 1H), 6.86 (m, 2H), 6.74 (m, 1H), 6.70-6.66 (m, 2H), 6.63 (m, 2H), 3.01 (m, 1H), 1.32 (d, J = 7.0 Hz, 6H).

Example 322

2-(3-cyanofuran-2-yl)-N',4'-dihydroxy-5-(trifluoromethyl)-[1,1'-biphenyl]-3-carboximidamide (E322)

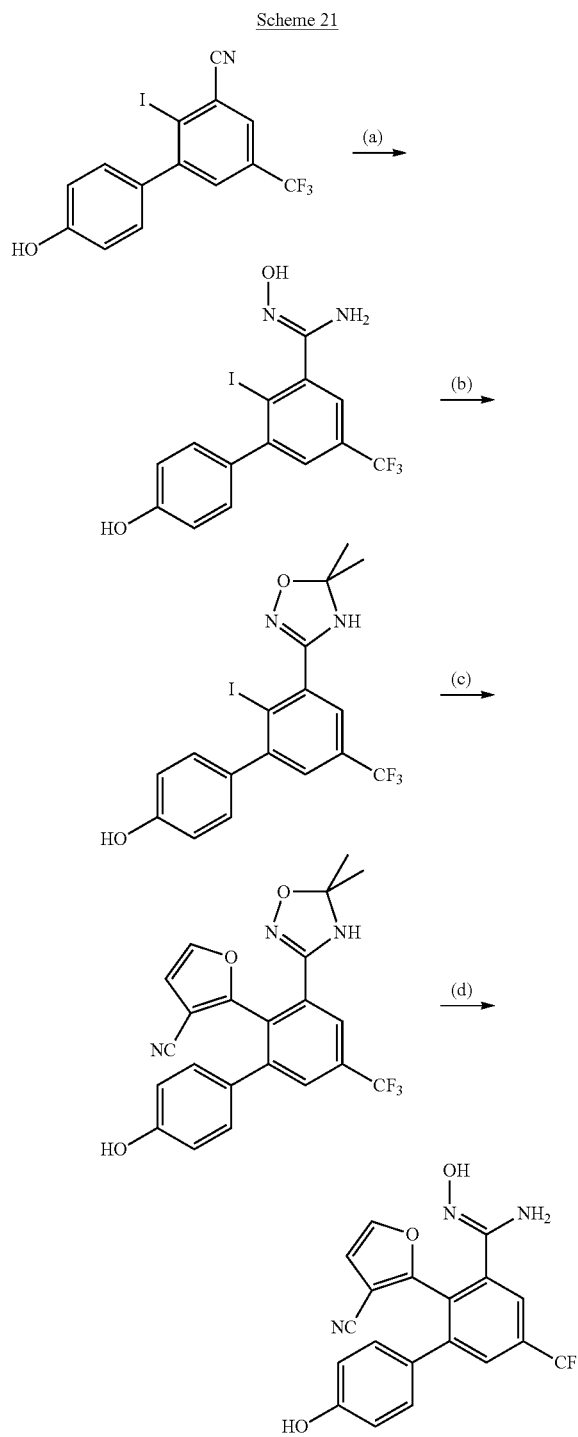

Scheme 21

(a) NH₂OH (aq), MeOH;
(b) Acetone, AcOH;
(c) 2-(tributylstannyl)furan-3-carbonitrile, Pd(OAc)₂, tri(furan-2-yl)phosphine, CuI, THF;
(d) HCl, EtOH.

Step (a):
4'-hydroxy-2-iodo-5-(trifluoromethyl)-[1,1'-biphenyl]-3-carbonitrile (250 mg, 0.64 mmol), obtained analogous to example 15 and hydroxylamine (1.0 mL, 16 M, aq) were mixed in MeOH (3.0 mL). The reaction mixture was heated in microwave at 120° C. for 20 min under nitrogen. HCl (1M) and DCM were added. The phases were separated and the organic phase was evaporated under reduced pressure. 140 mg N',4'-dihydroxy-2-iodo-5-(trifluoromethyl)-[1,1'-biphenyl]-3-carboximidamide was obtained.

Step (b):
N',4'-dihydroxy-2-iodo-5-(trifluoromethyl)-[1,1'-biphenyl]-3-carboximidamide (140 mg, 0.33 mmol) was dissolved in AcOH (5 mL) and acetone (1.18 mL, 16.06 mmol) was added. The reaction mixture was heated at 70° C. for 20 h and then concentrated to dryness. DCM and NaOH (0.5M) were added. The phases were separated and the organic phase was evaporated under reduced pressure. The crude product was purified on silica using EtOAc/n-heptane (10-50% EtOAc) as mobile phase. 117 mg 3'-(5,5-dimethyl-4,5-dihydro-1,2,4-oxadiazol-3-yl)-2'-iodo-5'-(trifluoromethyl)-[1,1'-biphenyl]-4-ol was obtained as a white solid.

Step (c):
3'-(5,5-dimethyl-4,5-dihydro-1,2,4-oxadiazol-3-yl)-2'-iodo-5'-(trifluoromethyl)-[1,1'-biphenyl]-4-ol (10.0 mg, 0.02 mmol), 2-(tributylstannyl)furan-3-carbonitrile (16.5 mg, 0.04 mmol), Pd(OAc)₂ (0.49 mg, 0.002 mmol), tri(furan-2-yl)phosphine (0.93 mg, 0.004 mmol) and CuI (0.41 mg, 0.004 mmol) were mixed in THF (0.5 mL). The reaction mixture was heated in microwave at 100° C. for 30 min under nitrogen. The crude mixture was purified on preparative HPLC using MeCN/acidic H₂O (35-45% MeCN) as mobile phase. 3.0 mg 2-(3-(5,5-dimethyl-4,5-dihydro-1,2,4-oxadiazol-3-yl)-4'-hydroxy-5-(trifluoromethyl)-[1,1'-biphenyl]-2-yl)furan-3-carbonitrile was obtained as a white solid.

Step (d):
2-(3-(5,5-dimethyl-4,5-dihydro-1,2,4-oxadiazol-3-yl)-4'-hydroxy-5-(trifluoromethyl)-[1,1'-biphenyl]-2-yl)furan-3-carbonitrile (3.0 mg, 0.01 mmol) was dissolved in EtOH (0.5 mL) and HCl (conc, 0.05 mL) was added. The reaction mixture was stirred at room temperature for 4 h. DCM/EtOAc and NH₄Cl (sat) were added. The phases were separated and the organic phase was evaporated under reduced pressure. The crude product was purified on preparative HPLC using MeCN/acidic H₂O (20-100% MeCN) as mobile phase. 2.0 mg 2-(3-cyanofuran-2-yl)-N',4'-dihydroxy-5-(trifluoromethyl)-[1,1'-biphenyl]-3-carboximidamide (E322) was obtained as a colorless oil. ES/MS m/z: 388.4 (M+H), 386.2 (M−H); ¹H NMR (Acetone-d6, 500 MHz): 7.92 (d, J=1.3 Hz, 1H), 7.82 (d, J=1.1 Hz, 1H), 7.69 (d, J=2.0 Hz, 1H), 7.02 (m, 2H), 6.80 (m, 2H), 6.68 (d, J=2.1 Hz, 1H). The title compound was identified by ¹H-NMR which showed that the oxime product was a single isomer, but did not confirm whether the (E) or (Z) oxime isomer had been obtained.

Examples 323-325

Examples 323-325 were prepared using a method analogous to that used to synthesise Examples 15 and 322 above. Full experimental details of the individual steps of the general methods are described in Examples 15 and 289 above. For examples 323-325 identification of the title compounds by ¹H-NMR showed that the oxime product was a single isomer, but did not confirm whether the (E) or (Z) oxime isomer had been obtained.

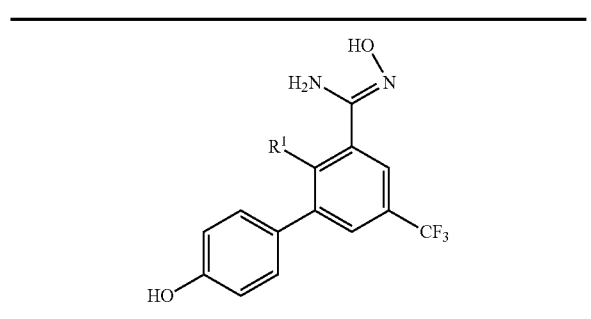

E 323 2-(3-cyanofuran-2-yl)-N',4'-dihydroxy-5-(trifluoromethyl)-[1,1'-biphenyl]-3-carboximidamide
$R^1$ = 3-cyanofuran-2-yl
ES/MS m/z: 402.5 (pos. M + H), 400.3 (neg. M − H); $^1$H NMR (Acetone-d6, 500 MHz): δ 8.00 (d, J = 1.2 Hz, 1H), 7.82 (m, 1H), 7.71 (s, 1H), 7.02 (m, 2H), 6.79 (m, 2H), 3.47 (s, 3H).

E 324 2''-cyano-N',4-dihydroxy-5'-(trifluoromethyl)-[1,1':2',1''-terphenyl]-3'-carboximidamide
$R^1$ = 2-cyanophenyl
ES/MS m/z: 398.3 (pos. M + H), 396.4 (neg. M − H); $^1$H NMR (Acetone-d6, 500 MHz): δ 7.84 (d, J = 1.3 Hz, 1H), 7.73 (t, J = 0.9 Hz, 1H), 7.58 (m, 1H), 7.54 (dd, J = 0.8, 7.8 Hz, 1H), 7.49 (dd, J = 0.6, 7.9 Hz, 1H), 7.40 (m, 1H), 6.95 (m, 2H), 6.67 (m, 2H).

E 325 2-(3-cyano-1-methyl-1H-pyrrol-2-yl)-N',4'-dihydroxy-5-(trifluoromethyl)-[1,1'-biphenyl]-3-carboximidamide
$R^1$ = 3-cyano-1-methyl-1H-pyrrol-2-yl
ES/MS m/z: 401.3 (pos. M + H), 399.1 (neg. M − H); $^1$H NMR (Acetone-d6, 500 MHz): δ 7.35 (d, J = 1.9 Hz, 1H), 7.30 (d, J = 1.9 Hz, 1H), 6.86 (m, 2H), 6.74 (m, 1H), 6.70-6.66 (m, 2H), 6.63 (m, 2H), 3.01 (m, 1H), 1.32 (d, J = 7.0 Hz, 6H).

Example 326

2'-(3,5-dimethylisoxazol-4-yl)-3'-(hydroxymethyl)-5'-(trifluoromethyl)-[1,1'-biphenyl]-4-ol (E326)

Scheme 22

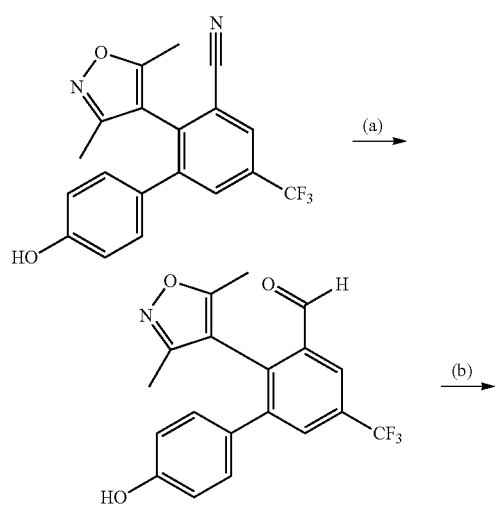

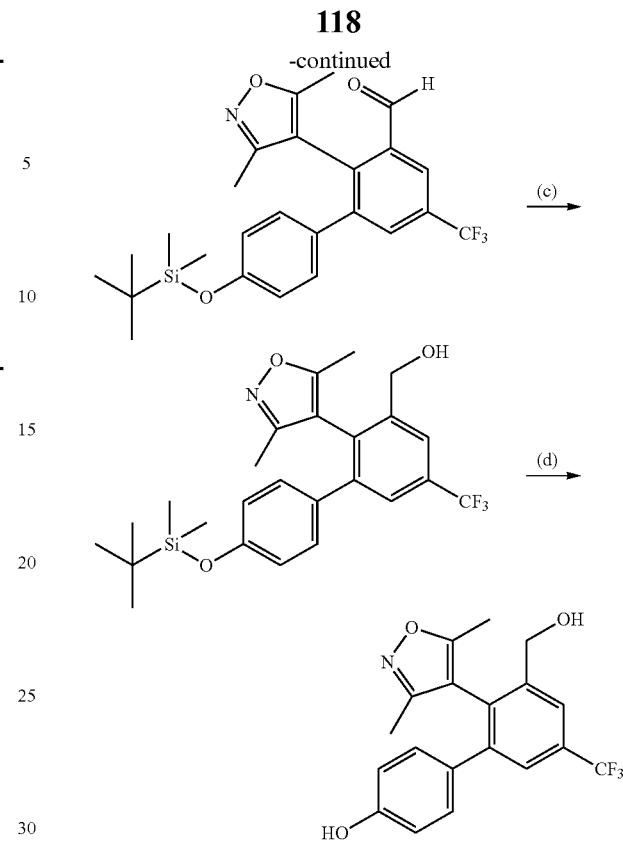

(a) DIBAL-H, DCM;
(b) TBDMSCl, Et$_3$N, DCM;
(c) (trimethylsilyl)methyl magnesium chloride, isopropylmagnesium chloride lithium chloride, ZnCl$_2$, THF;
(d) HCl, THF.

Step (a):
2-(3,5-dimethylisoxazol-4-yl)-4'-hydroxy-5-(trifluoromethyl)-[1,1'-biphenyl]-3-carbonitrile (250 mg, 0.64 mmol) obtained analogous to example 15, was dissolved in DCM (6 mL) and the solution was cooled to −78° C. DIBAL-H (4.19 mL, 1 M) was added drop wise. The reaction mixture was stirred at −78° C. for 1.5 h. HCl (5 mL, 2 M) was added at −78° C. and the mixture was allowed to attain room temperature. Water was added and the aqueous mixture was extracted with DCM. The combined organic extracts were dried with brine and over Na$_2$SO$_4$. The solvent was evaporated and the crude product was filtered through silica using EtOAc as mobile phase. 147 mg 2-(3,5-dimethylisoxazol-4-yl)-4'-hydroxy-5-(trifluoromethyl)-[1,1'-biphenyl]-3-carbaldehyde was obtained as yellow glassy solid.

Step (b):
2-(3,5-dimethylisoxazol-4-yl)-4'-hydroxy-5-(trifluoromethyl)-[1,1'-biphenyl]-3-carbaldehyde (147 mg, 0.41 mmol) and TBDMSCl (91.7 mg, 0.61 mmol) were mixed in DCM (2.5 mL). Et$_3$N (0.17 mL, 1.22 mmol) was added and the reaction mixture was stirred at room temperature for 16 h. The solvent was concentrated and the crude product was purified on silica using EtOAc/n-heptane (5-20% EtOAc) as mobile phase. 162 mg 4'-((tert-butyldimethylsilyl)oxy)-2-(3,5-dimethylisoxazol-4-yl)-5-(trifluoromethyl)-[1,1'-biphenyl]-3-carbaldehyde was obtained as yellow glassy solid.

Step (c):
Anhydrous ZnCl$_2$ (18.5 mg, 0.14 mmol), was dried at 100° C. for 16 h and was then cooled to room temperature. Dry THF (3.5 mL) followed by (trimethylsilyl)methyl magnesium chloride (40 mg, 0.27 mmol) were added. The resulting mixture was stirred for 15 min at room temperature. Isopropylmagnesium chloride lithium chloride (123 mg, 0.85 mmol) was added. The mixture was stirred for 45 min at room temperature and then cooled to 0° C. 4'-((tert-butyldimethylsilyl)oxy)-2-(3,5-dimethylisoxazol-4-yl)-5-(trifluoromethyl)-[1,1'-biphenyl]-3-carbaldehyde (162 mg, 0.34 mmol) dissolved in THF (2.5 mL) was added drop wise at 0° C. and the reaction mixture was stirred at 0° C. for 1.5 h. NH$_4$Cl (sat) was added and the aqueous mixture was extracted with EtOAc. The combined extracts were dried with brine and over Na$_2$SO$_4$. The solvent was evaporated and the crude product was purified on silica using EtOAc/n-heptane (10-30% EtOAc) as mobile phase. 33 mg (4'-((tert-butyldimethylsilyl)oxy)-2-(3,5-dimethylisoxazol-4-yl)-5-(trifluoromethyl)-[1,1'-biphenyl]-3-yl)methanol was obtained.

Step (d):

(4'-((tert-butyldimethylsilyl)oxy)-2-(3,5-dimethylisoxazol-4-yl)-5-(trifluoromethyl)-[1,1'-biphenyl]-3-yl)methanol (33 mg, 0.07 mmol) was dissolved in THF (2 mL) and HCl (1 mL, 2 M) was added. The reaction mixture was stirred at room temperature for 20 h. NaHCO$_3$ (1 M) was added and the solvent was evaporated. The remaining aqeuos mixture was extracted with EtOAc and the combined extracts were dried with brine and over Na$_2$SO$_4$. The solvent was concentrated under reduced pressure and the crude product was purified on silica using EtOAc/n-heptane (30-50% EtOAc) as mobile phase. 8.7 mg 2'-(3,5-dimethylisoxazol-4-yl)-3'-(hydroxymethyl)-5'-(trifluoromethyl)-[1,1'-biphenyl]-4-ol (E326) was obtained as a white solid. ES/MS m/z: 364.4 (M+H), 362.5 (M−H); $^1$H NMR (CDCl$_3$, 500 MHz): δ 7.89 (s, 1H), 7.62 (s, 1H), 6.90 (m, 2H), 6.73 (m, 2H), 4.51 (s, 2H), 2.04 (s, 3H), 1.92 (s, 3H). The title compound was identified by $^1$H-NMR which showed that the oxime product was a single isomer, but did not confirm whether the (E) or (Z) oxime isomer had been obtained.

Example 327

5'-cyano-3",5"-difluoro-N',4-dihydroxy-[1,1':2',1"-terphenyl]-3'-carboximidamide (E327)

Scheme 23

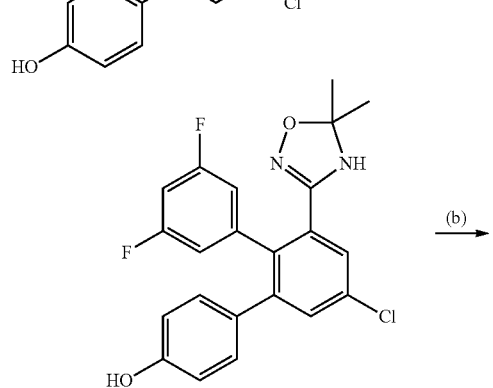

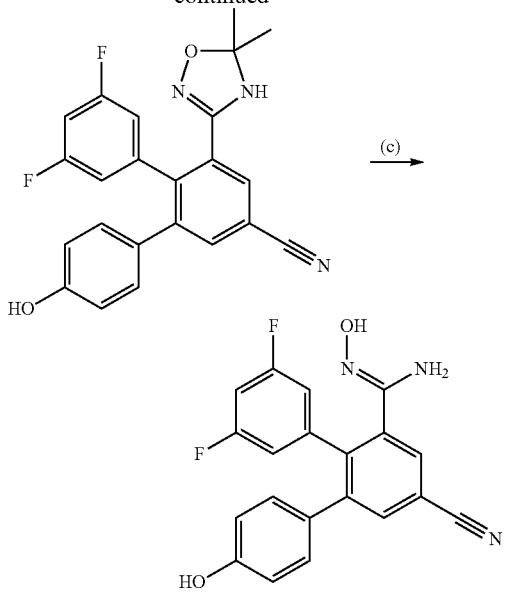

(a) Acetone, TFA;
(b) Zn(CN)$_2$, SPhos, Pd$_2$(dba)$_3$, DMF/H$_2$O;
(c) HCl, EtOH Step (a):

5'-chloro-3",5"-difluoro-N',4-dihydroxy-[1,1':2',1"-terphenyl]-3'-carboximidamide (57 mg, 0.15 mmol) obtained analogous to example 15, was dissolved in acetone (15 mL) and TFA (0.3 mL) was added. The reaction mixture was heated at 80° C. for 110 min and then evaporated to dryness. The crude product was purified on silica using EtOAc/n-heptane (10-50% EtOAc) as mobile phase. 63 mg 5'-chloro-3'-(5,5-dimethyl-4,5-dihydro-1,2,4-oxadiazol-3-yl)-3",5"-difluoro-[1,1':2',1"-terphenyl]-4-ol was obtained as glassy solid.

Step (b):

5'-chloro-3'-(5,5-dimethyl-4,5-dihydro-1,2,4-oxadiazol-3-yl)-3",5"-difluoro-[1,1':2',1"-terphenyl]-4-ol (15.0 mg, 0.04 mmol), SPhos (1.47 mg, 0.004 mmol), Pd$_2$(dba)$_3$ (1.65 mg, 0.002 mmol) and Zn(CN)$_2$ (3.87 mg, 0.041 mmol) were mixed in DMF/H$_2$O (1.5 mL, 99:1) under nitrogen. The reaction mixture was heated in microvawe at 150° C. for 60 min. EtOAc was added and the mixture was filtered through celite. The solvent was evaporated and the crude product was purified on silica using EtOAc/n-heptane (20-40% EtOAc) as mobile phase. 12.6 mg 6'-(5,5-dimethyl-4,5-dihydro-1,2,4-oxadiazol-3-yl)-3,5-difluoro-4"-hydroxy-[1,1':2',1"-terphenyl]-4'-carbonitrile was obtained as glassy solid.

Step (c):

6'-(5,5-dimethyl-4,5-dihydro-1,2,4-oxadiazol-3-yl)-3,5-difluoro-4"-hydroxy-[1,1':2',1"-terphenyl]-4'-carbonitrile (12.6 mg, 0.03 mmol) was dissolved in EtOH (1 mL) and HCl (0.1 mL, conc) was added. The reaction mixture was stirred at room temperature for 4 h. NaHCO$_3$ (sat) was added and the mixture was filtered. The solvent was evaporated under reduced pressure and the crude product was purified on preparative HPLC using MeCN/H$_2$O (10-50% MeCN) as mobile phase. 8.9 mg 5'-cyano-3",5"-difluoro-N',4-dihydroxy-[1,1':2',1"-terphenyl]-3'-carboximidamide (E327) was obtained as a white solid. ES/MS m/z: 366.2 (M+H), 364.3 (M−H); $^1$H NMR (MeOD, 500 MHz): δ 7.79 (d, J=1.7 Hz, 1H), 7.77 (d, J=1.7 Hz, 1H), 6.89 (m, 2H), 6.79 (m, 1H), 6.72 (m, 2H), 6.65 (m, 2H). The title compound was identified by ¹H-NMR which showed that the oxime product was a single isomer, but did not confirm whether the (E) or (Z) oxime isomer had been obtained.

Example 328

N',4'-dihydroxy-2-(pyrrolidin-1-yl)-5-(trifluoromethyl)-[1,1'-biphenyl]-3-carboximidamide (E328)

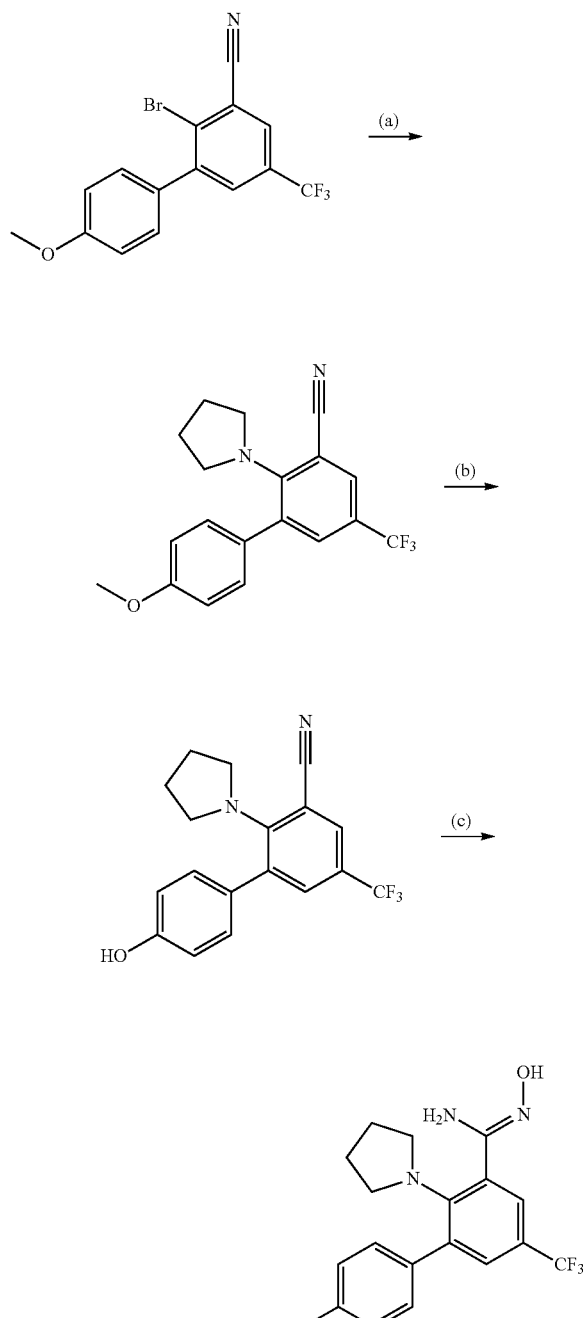

(a) Pyrrolidine, Pd(OAc)₂, BINAP, KOtBu, toluene;
(b) BBr₃, DCM;
(c) NH₂OH (aq), DMF.

Step (a):

2-bromo-4'-methoxy-5-(trifluoromethyl)-[1,1'-biphenyl]-3-carbonitrile (40.0 mg, 0.11 mmol) obtained analogous to example 1, pyrrolidine (15.98 mg, 0.22 mmol), Pd(OAc)₂ (2.52 mg, 0.01 mmol), BINAP (17.48 mg, 0.03 mmol) and KOtBu (12.6 mg, 0.11 mmol) were mixed in toluene (1 mL) under nitrogen. The reaction mixture was heated at 100° C. for 16.5 h. Water (15 mL) and DCM (20 mL) was added. The layers were separated and the aqueous layer was extracted with DCM (5 mL). The combined organic layers were evaporated and the crude product was purified on silica using EtOAc/n-heptane (0-10% EtOAc) as mobile phase. 24 mg 4'-methoxy-2-(pyrrolidin-1-yl)-5-(trifluoromethyl)-[1,1'-biphenyl]-3-carbonitrile was obtained as brown oil.

Step (b):

4'-methoxy-2-(pyrrolidin-1-yl)-5-(trifluoromethyl)-[1,1'-biphenyl]-3-carbonitrile (20.0 mg, 0.06 mmol) was dissolved in DCM (1 mL) under nitrogen. BBr₃ (0.12 mL, 1M) was added. The reaction mixture was stirred at room temperature for 3 h. A few drops MeOH, water and HCl (1M) were added and the phases were partitioned. The aqueous layer was extracted with DCM and the combined organic layers were concentrated under reduced pressure. The crude product was purified on silica using EtOAc/n-heptane (10-20% EtOAc) as mobile phase. 4'-hydroxy-2-(pyrrolidin-1-yl)-5-(trifluoromethyl)-[1,1'-biphenyl]-3-carbonitrile was obtained in quantitative yield.

Step (c):

4'-hydroxy-2-(pyrrolidin-1-yl)-5-(trifluoromethyl)-[1,1'-biphenyl]-3-carbonitrile (6.0 mg, 0.02 mmol) and hydroxylamine (0.06 mL, 16 M, aq) were mixed in DMF (0.5 mL). The reaction mixture was heated in microwave at 100° C. for 30 min under nitrogen. H₂O was added, the mixture was extracted with DCM and the combined organic layers were evaporated. The crude product was purified on preparative HPLC using MeCN/acidic H₂O (10-50% MeCN) as mobile phase. The purification was repeated using MeCN/H₂O (15-50% MeCN) as mobile phase. 0.5 mg N',4'-dihydroxy-2-(pyrrolidin-1-yl)-5-(trifluoromethyl)-[1,1'-biphenyl]-3-carboximidamide (E328) was obtained. ES/MS m/z: 366.23 (M+H), 364.27 (M−H); ¹H NMR (MeOD, 500 MHz): δ 7.39 (d, J=2.1 Hz, 1H), 7.31 (d, J=2.3 Hz, 1H), 7.15 (m, 2H), 6.82 (m, 2H), 3.03 (m, 4H), 1.69 (m, 4H). The title compound was identified by ¹H-NMR which showed that the oxime product was a single isomer, but did not confirm whether the (E) or (Z) oxime isomer had been obtained.

Examples 329-360

Examples 329-360 were prepared using methods analogous to that used to synthesise Examples 1, 50 and example 288 step a above. Full experimental details of the individual steps of the general methods are described in Examples 1, 50 and 288 above. For examples 329-331, 335-343 and 345-360 identification of the title compounds by ¹H-NMR showed that the oxime product was a single isomer, but did not confirm whether the (E) or (Z) oxime isomer had been obtained.

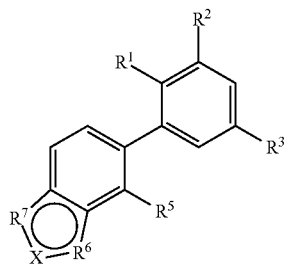

E 329 4-chloro-3',5'-difluoro-N'-hydroxy-6-(1H-indazol-5-yl)-[1,1'-biphenyl]-2-carboximidamide
R1 = 3,5-difluorophenyl  R2 = N-hydroxy carbaimidoyl  R3 = Cl  R5 = H
R6 = C  R7 = N  X = N
ES/MS m/z: 399.18 (pos. M + H), 397.24 (neg. M − H); $^1$H NMR (Acetone-d6, 500 MHz): δ 8.00 (d, 1H, J = 1.0 Hz), 7.61 (m, 1H), 7.53 (d, 1H, J = 2.2 Hz), 7.50 (d, 1H, J = 2.2 Hz), 7.42 (m, 1H), 7.05 (dd, 1H, J = 8.5, 1.5 Hz) and 6.80-6.74 (m, 3H).

E 330 6-(1H-benzo[d]imidazol-5-yl)-4-chloro-3',5'-difluoro-N'-hydroxy-[1,1'-biphenyl]-2-carboximidamide
R1= 3,5-difluorophenyl  R2 = N-hydroxy carbaimidoyl  R3 = Cl  R5 = H
R6 = N  R7 = N  X = C
ES/MS m/z: 399.19 (pos. M + H), 397.24 (neg. M − H); $^1$H NMR (Acetone-d6, 500 MHz): δ 8.13 (s, 1H), 7.52 (m, 1H), 7.49 (d, 1H, J = 2.2 Hz), 7.46 (br s, 1H), 7.39 (br s, 1H), 6.94 (dd, 1H, J = 8.5, 1.6 Hz) and 6.79-6.74 (m, 3H).

E 331 4-chloro-3',5'-difluoro-6-(1H-indol-5-yl)-[1,1'-biphenyl]-2-carboxamide
R1 = 3,5-difluorophenyl  R2 = N-hydroxy carbaimidoyl  R3 = Cl  R5 = H
R6 = C  R7 = N  X = C
ES/MS m/z: 398.18 (pos. M + H), 396.23 (neg. M − H); $^1$H NMR (Acetone-d6, 500 MHz): δ 7.50 (d, 1H, J = 2.4 Hz), 7.46 (d, 1H, J = 2.4 Hz), 7.39 (s, 1H), 7.32 (t, 1H, J = 2.9 Hz), 7.26 (d, 1H, J = 8.2 Hz), 6.80-6.73 (m, 4H) and 6.41 (m, 1H).

E 332 4-chloro-3',5'-difluoro-6-(1H-indol-5-yl)-[1,1'-biphenyl]-2-carboxamide
R1 = 3,5-difluorophenyl  R2 = carbamoyl  R3 = Cl  R5 = H
R6 = C  R7 = N  X = C
ES/MS m/z: 383.21 (pos. M + H), 381.21 (neg. M − H); $^1$H NMR (Acetone-d6, 500 MHz): δ 7.51 (d, 1H, J = 2.1 Hz), 7.50 (d, 1H, J = 2.1 Hz), 7.40 (m, 1H), 7.32 (m, 1H), 7.27 (d, 1H, J = 8.5 Hz), 6.82-6.76 (m, 4H) and 6.42 (m, 1H).

E 333 4-chloro-3',5'-difluoro-6-(1H-indazol-5-yl)-[1,1'-biphenyl]-2-carboxamide
R1 = 3,5-difluorophenyl  R2 = carbamoyl  R3 = Cl  R5 = H
R6 = C  R7 = N  X = N
ES/MS m/z: 384.22 (pos. M + H), 382.22 (neg. M − H); $^1$H NMR (Acetone-d6, 500 MHz): δ 8.00 (d, 1H, J = 0.8 Hz), 7.63 (m, 1H), 7.55 (m, 2H), 7.43 (m, 1H), 7.07 (dd, 1H, J = 8.6, 1.7 Hz) and 6.83-6.76 (m, 3H).

E 334 6-(1H-benzo[d]imidazol-5-yl)-4-chloro-3',5'-difluoro-[1,1'-biphenyl]-2-carboxamide
R1 = 3,5-difluorophenyl  R2 = carbamoyl  R3 = Cl  R5 = H
R6 = N  R7 = C  X = C
ES/MS m/z: 384.2 (pos. M + H), 382.2 (neg. M − H); $^1$H NMR (MeOD, 500 MHz): δ 8.15 (s, 1H), 7.56 (d, 1H, J = 2.2 hz), 7.54 (d, 1H, J = 2.2 Hz), 7.48 (br s, 1H), 7.34 (br s, 1H), 7.01 (dd, 1H, J = 8.2, 1.4 Hz) and 6.76-6.69 (m, 3H).

E 335 3',5'-difluoro-N'-hydroxy-6-(1H-indol-5-yl)-4-methyl-[1,1'-biphenyl]-2-carboximidamide
R1 = 3,5-difluorophenyl  R2 = N-hydroxy carbaimidoyl  R3 = Me  R5 = H
R6 = C  R7 = N  X = C
ES/MS m/z: 378.24 (pos. M + H), 376.23 (neg. M − H); $^1$H NMR (Acetone-d6, 500 MHz): δ 7.35 (s, 1H), 7.31 (s, 1H), 7.29 (t, J = 2.7 Hz, 2H), 7.27 (s, 1H), 7.23 (d, J = 8.4 Hz, 1H), 6.75-6.71 (m, 4H), 6.39 (t, J = 2.0 Hz, 1H), 2.44 (s, 3H).

E 336 3',5'-difluoro-N'-hydroxy-6-(1H-indol-6-yl)-4-methyl-[1,1'-biphenyl]-2-carboximidamide
R1 = 3,5-difluorophenyl  R2 = N-hydroxy carbaimidoyl  R3 = Me  R5 = H
R6 = N  R7 = C  X = C
ES/MS m/z: 378.24 (pos. M + H), 376.24 (neg. M − H); $^1$H NMR (Acetone-d6, 500 MHz): δ 7.39 (d, J = 8.2 Hz, 1H), 7.31 (s, 1H), 7.28 (m, 2H), 7.15 (s, 1H), 6.74-6.69 (m, 4H), 6.39 (m, 1H), 2.43 (s, 3H).

E 337 3',5'-difluoro-N'-hydroxy-6-(1H-indazol-5-yl)-4-methyl-[1,1'-biphenyl]-2-carboximidamide
R1 = 3,5-difluorophenyl  R2 = N-hydroxy carbaimidoyl  R3 = Me  R5 = H
R6 = C  R7 = N  X = N
ES/MS m/z: 379.23 (pos. M + H), 377.26 (neg. M − H); $^1$H NMR (Acetone-d6, 500 MHz): δ 7.97 (s, 1H), 7.56 (t, J = 0.7 Hz, 1H), 7.39 (d, J = 8.6 Hz, 1H), 7.33 (s, 1H), 7.32 (s, 1H), 7.02 (dd, J = 1.6, 8.6 Hz, 1H), 6.75-6.70 (m, 3H), 2.45 (s, 3H).

E 338 3',5'-difluoro-N'-hydroxy-6-(1H-indazol-5-yl)-4-propyl-[1,1'-biphenyl]-2-carboximidamide
R1 = 3,5-difluorophenyl  R2 = N-hydroxy carbaimidoyl  R3 = propyl  R5 = H
R6 = C  R7 = N  X = N
ES/MS m/z: 407.2 (pos. M + H), 405.27 (neg. M − H); $^1$H NMR (Acetone-d6, 500 MHz): δ 7.97 (d, J = 0.9 Hz, 1H), 7.57 (d, J = 0.5 Hz, 1H), 7.39 (d, J = 8.6 Hz, 1H), 7.35 (d, J = 1.9 Hz, 1H), 7.34 (d, J = 1.8 Hz, 1H), 7.02 (dd, J = 1.6, 8.6 Hz, 1H), 6.76-6.70 (m, 3H), 2.71 (t, J = 7.7 Hz, 2H), 1.74 (m, 2H), 1.01 (t, J = 7.3 Hz, 3H).

E 339 3',5'-difluoro-N'-hydroxy-6-(1H-indol-5-yl)-4-propyl-[1,1'-biphenyl]-2-carboximidamide
R1 = 3,5-difluorophenyl  R2 = N-hydroxy carbaimidoyl  R3 = propyl  R5 = H
R6 = C  R7 = N  X = C
ES/MS m/z: 406.22 (pos. M +H), 404.35 (neg. M −H); $^1$H NMR (Acetone-d6, 500 MHz): δ 7.36 (t, J = 0.8 Hz, 1H), 7.32 (d, J = 1.9 Hz, 1H), 7.29 (q, J = 1.8 Hz, 2H), 7.23 (d, J = 8.4 Hz, 1H), 6.78-6.68 (m, 4H), 6.39 (m, 1H), 2.70 (t, J = 7.7 Hz, 2H), 1.74 (m, 2H), 1.01 (t, J = 7.4 Hz, 3H).

E 340 3',5'-difluoro-N'-hydroxy-6-(1H-indazol-5-yl)-4-(trifluoromethyl)-[1,1'-biphenyl-]-2-carboximidamide
R1 = 3,5-difluorophenyl  R2 = N-hydroxy carbaimidoyl  R3 = CF$_3$  R5 = H
R6 = C  R7 = N  X = N
ES/MS m/z: 433.15 (pos. M + H), 431.22 (neg. M − H); $^1$H NMR (Acetone-d6, 500 MHz): δ 8.01 (d, J = 0.9 Hz, 1H), 7.82 (d, J = 1.3 Hz, 1H), 7.79 (d, J = 1.5 Hz, 1H), 7.66 (q, J = 0.8 Hz, 1H), 7.44 (d, J = 8.7 Hz, 1H), 7.08 (dd, J = 1.6, 8.7 Hz, 1H), 6.84-6.79 (m, 3H).

-continued

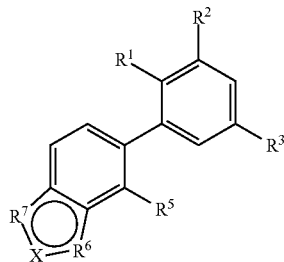

E 341 3',5'-difluoro-N'-hydroxy-6-(1H-indol-6-yl)-4-(trifluoromethyl)-[1,1'-biphenyl]-2-carboximidamide
R1 = 3,5-difluorophenyl    R2 = N-hydroxy carbaimidoyl    R3 = CF$_3$    R5 = H
R6 = N    R7 = C    X = C
ES/MS m/z: 432.17 (pos. M + H), 430.22 (neg. M − H); $^1$H NMR (Acetone-d6, 500 MHz): δ 7.78 (d, J = 1.2 Hz, 1H), 7.75 (d, J = 1.3 Hz, 1H), 7.44 (d, J = 8.2 Hz, 1H), 7.33 (t, J = 2.8 Hz, 1H), 7.25 (d, J = 0.6 Hz, 1H), 6.83-6.77 (m, 4H), 6.43 (m, 1H).

E 342 3',5'-difluoro-N'-hydroxy-6-(1H-indazol-6-yl)-4-(trifluoromethyl)-[1,1'-biphenyl]-2-carboximidamide
R1 = 3,5-difluorophenyl    R2 = N-hydroxy carbaimidoyl    R3 = CF$_3$    R5 = H
R6 = N    R7 = C    X = N
ES/MS m/z: 433.16 (pos. M + H), 431.23 (neg. M − H); $^1$H NMR (Acetone-d6, 500 MHz): δ 8.01 (s, 1H), 7.83 (s, 1H), 7.81 (s, 1H), 7.65 (d, J = 8.3 Hz, 1H), 7.42 (s, 1H), 6.90 (dd, J = 1.4, 8.3 Hz, 1H), 6.85-6.79 (m, 3H).

E 343 3',5'-difluoro-N'-hydroxy-6-(1H-indol-5-yl)-4-(trifluoromethyl)-[1,1'-biphenyl]-2-carboximidamide
R1 = 3,5-difluorophenyl    R2 = N-hydroxy carbaimidoyl    R3 = CF$_3$    R5 = H
R6 = C    R7 = N    X = C
ES/MS m/z: 432.16 (pos. M + H), 430.23 (neg. M − H); $^1$H NMR (Acetone-d6, 500 MHz): δ 7.78 (d, J = 1.3 Hz, 1H), 7.74 (d, J = 1.4 Hz, 1H), 7.43 (t, J = 0.8 Hz, 1H), 7.33 (t, J = 2.8 Hz, 1H), 7.29 (d, J = 8.4 Hz, 1H), 6.83-6.77 (m, 4H), 6.43 (m, 1H).

E 344 3',5'-difluoro-6-(1H-indol-5-yl)-4-(trifluoromethyl)-[1,1'-biphenyl]-2-carboxamide
R1 = 3,5-difluorophenyl    R2 = carbamoyl    R3 = CF$_3$    R5 = H
R6 = C    R7 = N    X = C
ES/MS m/z: 417.14 (pos. M + H), 415.23 (neg. M − H); $^1$H NMR (Acetone-d6, 500 MHz): δ 7.79 (d, J = 0.4 Hz, 2H), 7.45 (t, J = 0.8 Hz, 1H), 7.34 (t, J = 2.8 Hz, 1H), 7.30 (d, J = 8.5 Hz, 1H), 6.86-6.81 (m, 4H), 6.43 (m, 1H).

E 345 3',5'-difluoro-N'-hydroxy-6-(1H-indazol-6-yl)-4-propyl-[1,1'-biphenyl]-2-carboximidamide
R1 = 3,5-difluorophenyl    R2 = N-hydroxy carbaimidoyl    R3 = propyl    R5 = H
R6 = N    R7 = C    X = N
ES/MS m/z: 407.3 (pos. M + H), 405.4 (neg. M − H); $^1$H NMR (Acetone-d6, 500 MHz): δ 7.70 (d, J = 0.9 Hz, 1H), 7.44 (d, J = 8.4 Hz, 1H), 7.41 (d, J =1.9 Hz, 1H), 7.39 (d, J = 1.9 Hz, 1H), 7.21 (dd, J = 7.1, 8.4 Hz, 1H), 6.76 (dd, J = 0.5, 7.2 Hz, 1H), 6.73 (m, 2H), 6.66 (m, 1H), 2.74 (t, J = 7.7 Hz, 2H), 1.75 (m, 2H), 1.01 (t, J = 7.3 Hz, 3H).

E 346 N'-hydroxy-6-(1H-indazol-5-yl)-2'-methoxy-5'-methyl-4-(trifluoromethyl)-[1,1'-biphenyl]-2-carboximidamide
R1 = 2-methoxy-5-methylphenyl    R2 = N-hydroxy carbaimidoyl    R3 = CF$_3$    R5 = H
R6 = C    R7 = N    X = N
ES/MS m/z: 441.5 (pos. M + H), 439.4 (neg. M − H); $^1$H NMR (CD$_3$CN, 500 MHz): δ 7.89 (d, J = 0.9 Hz, 1H), 7.50 (d, J = 0.8 Hz, 1H), 7.50 (d, J = 2.2 Hz, 1H), 7.31 (d, J = 8.7 Hz, 1H), 7.10 (dd, J = 1.6, 8.6 Hz, 1H), 6.97 (m, 1H), 6.77 (d, J = 2.1 Hz, 1H), 6.66 (d, J = 8.4 Hz, 1H), 3.53 (s, 3H), 2.09 (s, 3H).

E 347 5'-chloro-N'-hydroxy-6-(1H-indol-5-yl)-2'-methoxy-4-(trifluoromethyl)-[1,1'-biphenyl]-2-carboximidamide
R1 = 5-chloro-2-methoxyphenyl    R2 = N-hydroxy carbaimidoyl    R3 = CF$_3$    R5 = H
R6 = C    R7 = N    X = C
ES/MS m/z: 460.17 (pos. M + H), 458.22 (neg. M − H); $^1$H NMR (Acetone-d6, 500 MHz): δ 7.74 (s, 1H), 7.71 (s, 1H), 7.39 (d, J = 0.6 Hz, 1H), 7.30 (t, J = 2.7 Hz, 1H), 7.24 (d, J = 8.4 Hz, 1H), 7.12 (dd, J = 2.7, 8.8 Hz, 1H), 7.02 (d, J = 2.6 Hz, 1H), 6.86 (dd, J = 1.6, 8.4 Hz, 1H), 6.80 (d, J = 8.9 Hz, 1H), 6.39 (d, J = 2.2 Hz, 1H), 3.56 (s, 3H).

E 348 5'-chloro-N'-hydroxy-6-(1H-indazol-5-yl)-2'-methoxy-4-(trifluoromethyl)-[1,1'-biphenyl]-2-carboximidamide
R1 = 5-chloro-2-methoxyphenyl    R2 = N-hydroxy carbaimidoyl    R3 = CF$_3$    R5 = H
R6 = C    R7 = N    X = N
ES/MS m/z: 461.15 (pos. M + H), 459.22 (neg. M − H); $^1$H NMR (Acetone-d6, 500 MHz): δ 8.00 (d, J = 0.9 Hz, 1H), 7.84 (d, J = 1.3 Hz, 1H), 7.81 (d, J = 1.3 Hz, 1H), 7.63 (s, 1H), 7.43 (m, 1H), 7.13 (dd, J = 1.6, 8.6 Hz, 1H), 7.08 (m, 1H), 6.97 (m, 1H), 6.87 (m, 1H).

E 349 2',5'-difluoro-N'-hydroxy-6-(1H-indazol-5-yl)-4-(trifluoromethyl)-[1,1'-biphenyl]-2-carboximidamide
R1 = 2,5-difluorophenyl    R2 = N-hydroxy carbaimidoyl    R3 = CF$_3$    R5 = H
R6 = C    R7 = N    X = N
ES/MS m/z: 433.1 (pos. M + H), 431.12 (neg. M − H); $^1$H NMR (Acetone-d6, 500 MHz): δ 8.00 (d, J = 0.9 Hz, 1H), 7.84 (d, J = 1.3 Hz, 1H), 7.81 (d, J = 1.3 Hz, 1H), 7.63 (s, 1H), 7.43 (m, 1H), 7.13 (dd, J = 1.6, 8.6 Hz, 1H), 7.08 (m, 1H), 6.97 (m, 1H), 6.87 (m, 1H).

E 350 3',5'-difluoro-6-(6-fluoro-1H-indol-5-yl)-N'-hydroxy-4-(trifluoromethyl)-[1,1'-biphenyl]-2-carboximidamide
R1 = 3,5-difluorophenyl    R2 = N-hydroxy carbaimidoyl    R3 = CF3    R5 = F
R6 = C    R7 = N    X = C
ES/MS m/z: 450.2 (pos. M + H), 448.1 (neg. M − H); $^1$H NMR (MeOD, 500 MHz): δ 7.80 (s, 1H), 7.76 (s, 1H), 7.27 (d, J = 7.2 Hz, 1H), 7.21 (d, J = 3.3 Hz, 1H), 6.97 (d, J = 10.6 Hz, 1H), 6.77 (d, J = 6.8 Hz, 2H), 6.69 (m, 1H), 6.39 (d, J = 2.8 Hz, 1H).

-continued

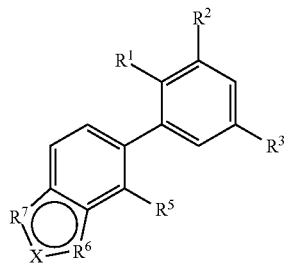

E 351  N'-hydroxy-3-(1H-indazol-5-yl)-2-(naphthalen-1-yl)-5-(trifluoromethyl)benzimidamide
R1 = naphthalen-1-yl          R2 = N-hydroxy carbaimidoyl          R3 = CF$_3$          R5 = H
R6 = C                        R7 = N                                X = N
ES/MS m/z: 447.2 (pos. M + H), 445.4 (neg. M − H); $^1$H NMR (MeOD, 500 MHz): δ 7.88 (s, 1H), 7.87
(d, J = 1.3 Hz, 1H), 7.79 (d, J = 0.4 Hz, 1H), 7.72-7.70 (m, 2H), 7.47 (t, J = 0.7 Hz, 1H), 7.43 (dd, J =
1.0, 8.0 Hz, 1H), 7.38 (dd, J = 1.2, 7.0 Hz, 1H), 7.34-7.26 (m, 3H), 7.06 (d, J = 8.7 Hz, 1H), 6.96 (dd, J = 1.6, 8.7 Hz, 1H).

E 352  2-(benzo[d][1,3]dioxol-4-yl)-N-hydroxy-3-(1H-indazol-5-yl)-5-(trifluoromethyl)benzimidamide
R1 = benzo[d][1,3]dioxol-4-yl  R2 = N-hydroxy carbaimidoyl          R3 = CF$_3$          R5 = H
R6 = C                         R7 = N                                X = N
ES/MS m/z: 441.5 (pos. M + H), 439.7 (neg. M − H).

E 353  4'-fluoro-N'-hydroxy-6-(1H-indazol-5-yl)-2'-methoxy-4-(trifluoromethyl)-[1,1'-biphenyl]-2-carboximidamide
R1 = 4-fluoro-2-methoxyphenyl  R2 = N-hydroxy carbaimidoyl          R3 = CF$_3$          R5 = H
R6 = C                         R7 = N                                X = N
ES/MS m/z: 445.1 (pos. M + H), 443.9 (neg. M − H); $^1$H NMR (CD$_3$CN, 500 MHz): δ 7.91 (s, 1H), 7.75
(s, 2H), 7.49 (s, 1H), 7.33 (d, J = 8.6 Hz, 1H), 7.06 (dd, J = 1.5, 8.6 Hz, 1H), 6.97 (dd, J = 7.0, 8.1 Hz,
1H), 6.55-6.53 (m, 2H), 3.51 (s, 3H).

E 354  N'-hydroxy-6-(1H-indazol-5-yl)-3'-methyl-4-(trifluoromethyl)-[1,1'-biphenyl]-2-carboximidamide
R1 = m-tolyl                   R2 = N-hydroxy carbaimidoyl          R3 = CF$_3$          R5 = H
R6 = C                         R7 = N                                X = N
ES/MS m/z: 411.2 (pos. M + H), 409.4 (neg. M − H); $^1$H NMR (CD$_3$CN, 500 MHz): δ 7.91 (s, 1H), 7.76
(s, 1H), 7.73 (s, 1H), 7.53 (s, 1H), 7.29 (d, J = 8.7 Hz, 1H), 7.01-6.99 (m, 4H), 6.90 (d, J = 7.4 Hz, 1H), 2.14 (s, 3H).

E 355  3',4',5'-trifluoro-N-hydroxy-6-(1H-indazol-5-yl)-4-(trifluoromethyl)-[1,1'-biphenyl]-2-carboximidamide
R1 = 3,4,5-trifluorophenyl     R2 = N-hydroxy carbaimidoyl          R3 = CF$_3$          R5 = H
R6 = C                         R7 = N                                X = N
ES/MS m/z: 451.1 (pos. M + H), 449.3 (neg. M − H); $^1$H NMR (CD$_3$CN, 500 MHz): δ 7.97 (d, J = 0.9 Hz, 1H),
7.82 (t, J = 0.9 Hz, 1H), 7.77 (t, J = 0.9 Hz, 1H), 7.57 (m, 1H), 7.39 (m, 1H), 7.03 (dd, J = 1.7, 8.7 Hz, 1H), 6.88 (m, 2H).

E 356  3',4'-difluoro-N-hydroxy-6-(1H-indazol-5-yl)-4-(trifluoromethyl)-[1,1'-biphenyl]-2-carboximidamide
R1 = 3,4-difluorophenyl        R2 = N-hydroxy carbaimidoyl          R3 = CF$_3$          R5 = H
R6 = C                         R7 = N                                X = N
ES/MS m/z: 432.8 (pos. M + H), 431.6 (neg. M − H); $^1$H NMR (CD$_3$CN, 500 MHz): δ 7.95 (d, J = 1.0
Hz, 1H), 7.81 (t, J = 0.9 Hz, 1H), 7.76 (d, J = 1.3 Hz, 1H), 7.56 (q, J = 0.8 Hz, 1H), 7.35 (m, J = 2.1 Hz,
1H), 7.08-7.00 (m, 3H), 6.88 (m, 1H).

E 357  N'-hydroxy-3-(1H-indazol-5-yl)-2-(2-methoxypyridin-3-yl)-5-(trifluoromethyl)benzimidamide
R1 = 2-methoxypyridin-3-yl     R2 = N-hydroxy carbaimidoyl          R3 = CF$_3$          R5 = H
R6 = C                         R7 = N                                X = N
ES/MS m/z: 427.7 (pos. M + H), 426.2 (neg. M − H); $^1$H NMR (MeOD, 500 MHz): δ 7.95 (d, J = 0.9
Hz, 1H), 7.93 (dd, J = 1.9, 5.1 Hz, 1H), 7.78 (d, J = 1.3 Hz, 1H), 7.76 (d, J = 1.4 Hz, 1H), 7.51 (q, J =
0.8 Hz, 1H), 7.45 (dd, J = 1.9, 7.3 Hz, 1H), 7.34 (d, J = 8.7 Hz, 1H), 7.08 (dd, J = 1.6, 8.6 Hz, 1H), 6.79
(dd, J = 5.1, 7.3 Hz, 1H), 3.63 (s, 3H).

E 358  2-(cyclopent-1-en-1-yl)-N'-hydroxy-3-(1H-indazol-5-yl)-5-(trifluoromethyl)benzimidamide
R1 = cyclopent-1-en-1-yl       R2 = N-hydroxy carbaimidoyl          R3 = CF$_3$          R5 = H
R6 = C                         R7 = N                                X = N
ES/MS m/z: 387.5 (pos. M + H), 385.3 (neg. M − H); $^1$H NMR (MeOD, 500 MHz): δ 8.08 (s, 1H), 7.75
(s, 1H), 7.67 (s, 1H), 7.66 (s, 1H), 7.55 (d, J = 8.7 Hz, 1H), 7.37 (dd, J = 1.3, 8.6 Hz, 1H), 5.75 (s, 1H),
2.29 (m, 2H), 2.12 (m, 2H), 1.67 (m, 2H).

E 359  2-(3,5-dimethylisoxazol-4-yl)-N'-hydroxy-3-(1H-indazol-5-yl)-5-(trifluoromethyl)benzimidamide
R1 = 3,5-dimethylisoxazol-4-yl R2 = N-hydroxy carbaimidoyl          R3 = CF$_3$          R5 = H
R6 = C                         R7 = N                                X = N
ES/MS m/z: 416.6 (pos. M + H), 414.5 (neg. M − H); $^1$H NMR (MeOD, 500 MHz): δ 8.05 (s, 1H), 7.85
(s, 1H), 7.83 (s, 1H), 7.62 (s, 1H), 7.46 (d, J = 8.7 Hz, 1H), 7.10 (dd, J = 1.5, 8.7 Hz, 2.09 (s, 3H), 1.87 (s, 3H).

E 360  2',4'-difluoro-N'-hydroxy-6-(1H-indazol-5-yl)-4-(trifluoromethyl)-[1,1'-biphenyl]-2-carboximidamide
R1 = 2,4-difluorophenyl        R2 = N-hydroxy carbaimidoyl          R3 = CF$_3$          R5 = H
R6 = C                         R7 = N                                X = N
ES/MS m/z: 433.2 (pos. M + H), 431.27 (neg. M − H); $^1$H NMR (MeOD, 500 MHz): δ 7.97 (s, 1H), 7.81
(s, 2H), 7.56 (s, 1H), 7.36 (d, J = 8.6 Hz, 1H), 7.25 (q, J = 7.5 Hz, 1H), 7.08 (d, J = 8.6 Hz, 1H), 6.80 (t,
J = 7.5 Hz, 1H), 6.71 (t, J = 8.6 Hz, 1H).

Binding Assay 1: Estrogen Receptor Binding Assay

The estrogen receptor ligand binding assays are designed as scintillation proximity assays (SPA), employing the use of tritiated estradiol ($^3$H-E2) and recombinant expressed biotinylated estrogen receptor binding domains. The binding domains of human ERα (ERα-LBD, pET-N-AT #1, aa 301-595) and ERβ (ERβ-LBD, pET-N-AT #1, aa 255-530) proteins are produced in E. coli ((BL21, (DE3), pBirA)) at 22 C in 2xLB medium supplemented with 50 uM biotin. After 3 h of IPTG induction (0.55 mM), cells are harvested by centrifugation at 7300×g for 15 min and cell pellets stored frozen in −20 C. Extraction of ERα and ERβ are performed using 5 g of cells suspended in 50 mL of extraction buffer (50 mM Tris, pH 8.0, 100 mM KCl, 4 mM EDTA, 4 mM DDT and 0.1 mM PMSF). The cell suspension is run twice through a Microfluidizer M-1100L (Microfluidics) and centrifuged at 15,000×g for 60 min. The supernatant is aliquoted and stored in −70 C.

Dilute ERα-LBD or ERβ-LBD extracts in assay buffer (18 mM $K_2HPO_4$, 2 mM $KH_2PO_4$, 20 mM $Na_sMoO_4$, 1 mM EDTA, 1 mM TCEP) 1:676 and 1:517 for alpha and beta respectively. The diluted receptor concentrations should be 900 fmol/L. Preincubate the extracts with streptavidin coated polyvinyltoluene SPA beads (RPNQ0007, GE Healthcare) at a concentration of 0.43 mg/mL for 1 hr at room temperature.

Test compounds may be evaluated over a range of concentrations from 157 μM to 37.5 pM. The test compound stock solutions should be made in 100% DMSO at 5× of the final concentration desired for testing in the assay. The amount of DMSO in the test wells of the 384 well plate will be 20%. Add 18 μl aliquots of test compounds to the assay plates followed by 35 μl of the preincubated receptor/SPA bead mix and finally add 35 μl of 3 nM $^3H$-E2. Cover the plates with a plastic sealer, centrifuge for 1 minute at 1000 rpm and equilibrate over night on a shaker at room temperature. The following morning, centrifuge the plates 5 minutes at 2000 rpm and measure on a plate scintillation counter e.g. a PerkinElmer Microbeta 1450 Trilux.

For compounds able to displace 3[H]-E2 from the receptor an $IC_{50}$-value (the concentration required to inhibit 50% of the binding of 3[H]-E2) is determined by a non-linear four parameter logistic model; $b=((bmax-bmin)/(1+(I/IC_{50})S))+$ bmin I is added concentration of binding inhibitor, $IC_{50}$ is the concentration of inhibitor at half maximal binding and S is a slope factor. The Microbeta-instrument generates the mean cpm (counts per minute) value/minute and corrects for individual variations between the detectors thus generating corrected cpm values.

Binding Assay 2: Estrogen Receptor Binding Assay

LanthaScreen® TR-FRET ER alpha competitive binding assay and LanthaScreen® TR-FRET ER beta competitive binding assay were purchased from Invitrogen™.

GST tagged ligand binding domain of human estrogen receptor alpha or human estrogen receptor beta is combined with a terbium chelate labeled anti-GST-anitbody and a fluorescent ligand for estrogen receptors.

The terbium chelate is excited by pulses of light in a fluorescence reader. When the fluorescent ligand is in close proximity, which it will be when bound to the receptor ligand binding domain, part of the energy emitted from the terbium chelate upon relaxation will transfer as light and excite the ligand. Upon successive relaxation of the fluorescent ligand energy is released as light of a second emission wavelength.

The signal ratio of light emitted from the terbium chelate and the fluorescent ligand is calculated and used as a measurement of labeled ligand and receptor interaction. Upon testing of unlabelled ligands this ratio will decrease in a test ligand concentration dependent manner which can be interpreted as a competition binding curve upon analysis. All reagents except test compounds are purchased from Invitrogen™. Reagent concentrations used in this assay are as recommended from Invitrogen™. 200 nl test compounds serially diluted in DMSO are added to empty low volume plates (Corning) with a Mosquito robot (TTP Labtech). The other reagents are prepared as described in the manual provided by Invitrogen™, gently swiveled in a flask and then added to the assay plate with a Multidrop 384 (Titer-tek). The assay plates are covered and quickly mixed on a shaker. After 3 hours equilibration time at ambient room temperature are the plates measured on an EnVision® mulitlabel reader (Perkin Elmer).

Transactivation Assay 1: Transactivation Assay in Human Embryonic Kidney 293 Cells Stably Transfected with pERE-ALP and Human Estrogen Receptor Alpha The expression vector pMThERα contains an insert of wild type human estrogen receptor alpha with deleted leader. The pERE-ALP reporter construct contains the gene for the secreted form of placental alkaline phosphatase (ALP) and the vitellogenin estrogen response element (ERE). The human embryonic kidney 293 cells are transfected in two steps. Firstly, a stable clone mix transfected with the pERE-ALP reporter gene construct and pSV2-Neo for selection is developed. Secondly, the stable clone mix is transfected with pMThERα and a pKSV-Hyg resistance vector for selection. All transfections are performed using Lipofectamine (Invitrogen) according to supplier's recommendations. A selected clone with both pERE-ALP and pMThERα is used for the transactivation assay.

The cells are seeded in 384-well plates at 12 500 cells per well in Ham's F12 Coon's modification (without phenol red) with 10% dextran-coated charcoal treated (DCC) fetal bovine serum (FBS), 2 mM L-glutamine and 50 μg/ml gentamicin. After 24 h incubation (37° C., 5% $CO_2$) the seeding medium is discarded and replaced with 20 μl Ham's F12 Coon's modification (without phenol red) with 1.5% DCC-FCS, 2 mM L-glutamine and supplemented with 100 U/ml penicillin and 100 g/ml streptomycin. The selected compounds are added to the wells in 12 concentrations ranging from 3.3 pM to 33 μM. The compounds are dissolved in 100% dimethylsulphoxide (DMSO) and the final concentration of DMSO in the assay is 0.1%. After 72 h incubation (37° C., 5% $CO_2$) the medium is assayed for ALP activity by a chemiluminescence assay; a 10 μl aliquot of the cell culture medium is mixed with 100 μl assay buffer (0.1 M diethanolamine, 1 mM $MgCl_2$) and 0.5 mM disodium 3-(4-methoxyspiro 1,2-dioxetane-3,2'-(5'-chloro)-tricyclo [3.3.1.13,7]decan-4-yl)phenyl phosphate (CSPD) (Tropix, Applied Biosystems) and incubated for 20 min at 37° C. and 15 min at room temperature before measurement chemiluminescent light signal (one second per well) in a Wallac Microbeta Trilux 1450-028 (PerkinElmer). The half maximal effective concentrations ($EC_{50}$) are calculated from the curves fitted to the concentration-response data with a four parameter logistic model in XLfit software version 2.0 (IDBS) or later.

Transactivation Assay 2: Transactivation Assay in Human Embryonic Kidney 293 Cells Stably Transfected with pERE2-ALP and Human Estrogen Receptor Beta Generation of stable HEK293 cell lines (CRL-1573; American Type Culture Collection) expressing the reporter vector pERE2-ALP and human estrogen receptor beta (hERβ 530) have been described (Mol Pharmacol 1998, 54, 105-112; Endocrinology 2002, 143, 1558-1561).

The cells were seeded in 384-well plates at 12 500 cells per well in Ham's F12 Coon's modification (without phenol red) with 10% dextran-coated charcoal treated (DCC) fetal bovine serum (FBS), 2 mM L-glutamine and 50 μg/ml gentamicin. After 24 h incubation (37° C., 5% CO2) the seeding medium was discarded and replaced with 20 μl Ham's F12 Coon's modification (without phenol red) with 1.5% DCC-FCS, 2 mM L-glutamine and supplemented with 100 U/ml penicillin and 100 μg/ml streptomycin. The selected compounds were added to the wells in 12 concentrations ranging from 3.3 pM to 33 μM. The compounds were dissolved in 100% dimethylsulfoxide (DMSO) and the final concentration of DMSO in the assay was 0.1%. After 72 h incubation (37° C., 5% CO2) the medium was assayed for ALP activity by a chemiluminescence assay; a 10 µl aliquot of the conditioned medium was mixed with 100 µl assay buffer (0.1 M diethanolamine, 1 mM MgCl2) and 0.5 mM disodium 3-(4-methoxyspiro 1,2-dioxetane-3,2'-(5'-chloro)-tricyclo[3.3.1.13,7]decan-4-yl)phenyl phosphate (CSPD) (Tropix, Applied Biosystems) and incubated for 20 min at 37° C. and 15 min at room temperature before measurement of the chemiluminescent signal (one second per well) in a Wallac Microbeta Trilux 1450-028 (PerkinElmer). The ALP activity expressed in LCPS is directly proportional to the level of ALP expressed by the cells. The half maximal effective concentrations of the test compounds (EC50) were calculated from the curves fitted to the concentration-response data with a four parameter logistic model in XLfit software version 2.0 (IDBS) or later.

The Example compounds were tested in transactivation assays 1 and 2.

The compounds of the Examples exhibit one or more of the following:
(i) a potency in the range of $EC_{50}$ 1 to 10,000 nM at the estrogen receptor α-subtype in transactivation assay 1;
(ii) a potency in the range of $EC_{50}$ 0.1 to 10,000 nM at the estrogen receptor β-subtype in transactivation assay 2.

Preferred compounds of the invention are those which display a potency at the estrogen receptor β-subtype at lower concentrations within the $EC_{50}$ range shown above. For example, the compounds of Examples 1-3, 6, 7, 8-11, 13, 17, 19, 21, 22, 24, 25-28, 30, 32, 33, 36, 37, 39-50, 52, 55-58, 67, 70, 71, 73, 78, 79, 81, 82, 85, 106-109, 111-117, 122-140, 142-159, 162-172, 174-178, 182-184, 186-196, 198-224, 226, 228-257, 259-261, 263-266, 269-275, 277-287, 289-299, 301-303, 305-308, 311-318, 322-329, 331, 335, 337, 339-341, 343, 346-358 and 360 exhibit a potency in the range of $EC_{50}$ 0.1 to 100 nM at the estrogen receptor β-subtype in transactivation assay 2.

Preferred compounds of the invention are those which are selective for the estrogen receptor β-subtype over the estrogen receptor α-subtype in the transactivation assays 1 and 2. For example, the compounds of Examples 2, 3, 6, 7, 8-11, 13, 14, 17, 19, 21, 25-27, 30, 31, 33, 37, 39-49, 52, 56, 57, 62, 79, 81, 82, 106-109, 111-115, 122-128, 130-132, 134, 135-137, 139-157, 159, 162-179, 181-186, 188-196, 198, 199, 204-224, 226-239, 241-261, 263, 265, 269-272, 275, 276, 279, 281, 284, 285, 290, 292-296, 298, 300, 302, 303, 306, 308, 311-319, 322-325, 327, 328, 340, 346-349, 351-354, 357, 359 and 360 display selectivity for the estrogen receptor β-subtype of 20 or greater in the transactivation assays; with the compounds of Examples 2, 3, 8, 10, 11, 13, 14, 17, 37, 40-43, 45, 49, 106-109, 111-114, 123, 125, 126, 130, 132, 135-137, 142, 143, 145, 146-149, 151, 152-157, 159, 162-164, 166, 167, 169, 171, 172, 174, 175, 177, 178, 182, 184, 188, 189, 193-196, 198, 203-215, 217-220, 222, 223, 226-239, 241-248, 251-254, 256, 259, 261, 263, 269-272, 279, 281, 284, 290, 292, 294-296, 302, 303, 306, 314, 318, 322, 323, 325, 346-348, 352, 353, 357, 359 and 360 displaying selectivity of 50 or greater.

Some of the Example compounds were also tested in the binding assays 1 and 2. All of those tested showed binding $IC_{50}$ (nM) in the range of 0.1 to 5,000 nM at the estrogen receptor β-subtype. For example, the compounds of Examples 10, 11, 13, 40-43, 72, 76, 77, 79, 82, 90, 96, 97, 100, 102-109, 111-115, 118, 123-132, 134, 135, 137, 156-159, 163, 175, 184, 228, 281, 286 and 296 show binding $IC_{50}$ (nM) of 0.1 to 10. Preferred compounds of the invention are those which are selective for the estrogen receptor β-subtype over the estrogen receptor α-subtype in the binding assays 1 and 2. For example, the compounds of Examples 10, 11, 13, 40-43, 72, 76, 77, 79, 82, 86, 90, 91, 93, 95-98, 100-103, 106-116, 123, 126, 128, 130-132, 134, 137, 150, 159, 163, 175, 177, 184, 281 and 286, displayed selectivity for the estrogen receptor β-subtype of 20 or greater.

The invention claimed is:

1. A compound of formula (I) or a pharmaceutically acceptable ester, amide, carbamate or salt thereof, including a salt of such an ester, amide or carbamate

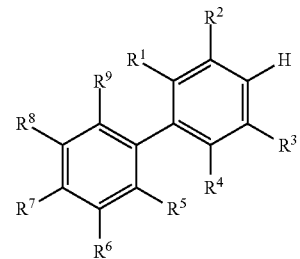

(I)

in which $R^1$ is selected from the group consisting of optionally substituted 5-10 membered heterocyclyl, optionally substituted phenyl, optionally substituted naphthyl, optionally substituted $C_{3-8}$cycloalkyl, optionally substituted $C_{5-6}$cycloalkenyl, optionally substituted phenyl$C_{2-4}$alkenyl, $C_{2-8}$alkenyl, halo$C_{2-8}$alkenyl, dihalo$C_{2-8}$alkenyl, trihalo$C_{2-8}$alkenyl, and $C_{3-8}$cycloalkyl$C_{2-4}$alkenyl, wherein when said heterocyclyl, phenyl or naphthyl group or part of group is substituted, it is substituted with from 1 to 5 substituents, each substituent being independently selected from the group consisting of $OR^A$, $N(R^B)_2$, halogen, cyano, nitro, —C(O)$C_{1-4}$alkyl, $C_{1-6}$alkyl, $C_{2-6}$alkenyl, $C_{2-6}$alkynyl, halo$C_{1-6}$ alkyl, dihalo$C_{1-6}$alkyl and trihalo$C_{1-6}$alkyl, and when said $C_{3-8}$cycloalkyl or $C_{5-6}$cycloalkenyl group is substituted, it is substituted with 1, 2 or 3 substituents selected from $C_{1-5}$alkyl, $C_{1-5}$alkenyl, $C_{1-5}$alkynyl, $C_{1-5}$alkyl substituted with up to 3 halogen atoms, —CO—$C_{1-5}$alkyl, and halogen;

$R^2$ is selected from the group consisting of —C(NH$_2$)=N—OH, —C(O)N(R$^C$)$_2$, cyano, —CHO, —CH=N—OH, —C(O)NH—OH, —C(CO$_2$H)=N—OH, —C(O—$C_{1-4}$alkyl)=NH, —C(NH$_2$)=N—NH$_2$, —C(O)—C(O)—NH$_2$, —C(O)CO$_2$H, —CO$_2$H, —CH$_2$—CO$_2$H, —CH(OH)CO$_2$H, —CH$_2$NH—CONH$_2$, $C_{1-6}$alkyl-NH$_2$, $C_{1-6}$alkyl-OH, —CH$_2$SO$_3$H, —NH—C(NH$_2$)=NH, —NH—C(O)NH$_2$, —N=C(—NH—CH$_2$CH$_2$—NH—), N(R$^B$)$_2$, N(OH)$_2$, NHSO$_2$R$^D$, —S—CN, —S—C(NH$_2$)=NH, —S—C(NH$_2$)=N—OH, SO$_2$N(R$^E$)$_2$, SO$_3$H, cyano$C_{1-6}$alkyl, and optionally substituted 5-10 membered heterocyclyl containing from one to three nitrogen atoms, wherein when said heterocyclyl group is substituted, it is substituted with from 1 to 3 substituents, each substituent being independently selected from the group consisting of $OR^A$, $N(R^B)_2$, halogen, cyano, nitro, —C(O)$C_{1-4}$alkyl, $C_{1-6}$alkyl, $C_{2-6}$alkenyl, $C_{2-6}$alkynyl, halo$C_{1-6}$ alkyl, dihalo$C_{1-6}$alkyl and trihalo$C_{1-6}$alkyl;

$R^3$ is selected from the group consisting of hydrogen, halogen, cyano, $C_{1-6}$alkyl, $C_{2-6}$alkenyl, $C_{2-6}$alkynyl, $C_{3-8}$cycloalkyl, $C_{3-8}$cycloalkyl$C_{1-6}$alkyl, haloC$_{1-6}$alkyl, dihaloC$_{1-6}$alkyl, trihaloC$_{1-6}$alkyl, optionally substituted phenyl, optionally substituted phenylC$_{1-4}$alkyl, optionally substituted 5-10 membered heterocyclyl, and optionally substituted 5-10 membered heterocyclylC$_{1-4}$alkyl, wherein when said phenyl or heterocyclyl group or part of group is substituted, it is substituted with from 1 to 5 substituents, each substituent being independently selected from the group consisting of OR$^A$, N(R$^B$)$_2$, halogen cyano, nitro, C$_{1-6}$alkyl, C$_{2-6}$alkenyl, C$_{2-6}$alkynyl, haloC$_{1-6}$alkyl, dihaloC$_{1-6}$alkyl and trihaloC$_{1-6}$alkyl;

R$^4$ is selected from the group consisting of hydrogen, halogen, cyano, C$_{1-6}$alkyl, C$_{2-6}$alkenyl, C$_{2-6}$alkynyl, and haloC$_{1-6}$alkyl, dihaloC$_{1-6}$alkyl, and trihaloC$_{1-6}$alkyl;

each of R$^5$, R$^6$, R$^8$ and R$^9$ is independently selected from the group consisting of hydrogen, OR$^A$, N(R$^B$)$_2$, halogen, cyano, nitro, —C(O)C$_{1-4}$alkyl, C$_{1-6}$alkyl, C$_{2-6}$alkenyl, C$_{2-6}$alkynyl, haloC$_{1-6}$ alkyl, dihaloC$_{1-6}$alkyl and trihaloC$_{1-6}$alkyl;

R$^7$ is OR$^A$;

or R$^6$ and R$^7$ may, together with the atoms they are attached to, form a 5-, 6- or 7-membered cyclic group optionally containing one to three heteroatoms selected from O, N and S, said 5-, 6- or 7-membered cyclic group being optionally substituted with one of more groups selected from OR$^A$, cyano, nitro, C$_{1-6}$ alkyl, C$_{2-6}$ alkenyl, C$_{2-6}$ alkynyl, halo C$_{1-6}$ alkyl, dihalo C$_{1-6}$ alkyl and trihalo C$_{1-6}$ alkyl; and each R$^A$, each R$^B$, each R$^C$, each R$^D$ and each R$^E$ is independently selected from the group consisting of hydrogen, C$_{1-6}$alkyl, C$_{2-6}$alkenyl, C$_{2-6}$alkynyl, C$_{3-8}$cycloalkyl and C$_{3-8}$cycloalkylC$_{1-6}$alkyl;

each optionally substituted by from 1 to 3 halogen atoms.

2. A compound as claimed in claim 1, in which R$^1$ is selected from the group consisting of optionally substituted 5-10 membered heterocyclyl, optionally substituted phenyl, optionally substituted naphthyl, optionally substituted C$_{5-6}$cycloalkenyl, optionally substituted phenylC$_{2-4}$alkenyl, C$_{2-8}$alkenyl, haloC$_{2-8}$alkenyl, dihaloC$_{2-8}$alkenyl, trihaloC$_{2-8}$alkenyl, and C$_{3-8}$cycloalkylC$_{2-4}$alkenyl, wherein when said heterocyclyl or phenyl or naphthyl group or part of group is substituted, it is substituted with from 1 to 5 substituents, each substituent being independently selected from the group consisting of OR$^A$, N(R$^B$)$_2$, halogen, cyano, nitro, C$_{1-6}$alkyl, haloC$_{1-6}$ alkyl, dihaloC$_{1-6}$alkyl and trihaloC$_{1-6}$alkyl, and wherein when said C$_{5-6}$cycloalkenyl group is substituted, it is substituted with 1 or 2 substitutents selected from halogen atoms and methyl groups.

3. A compound as claimed in claim 2, in which R$^1$ is selected from the group consisting of optionally substituted 5-10 membered heterocyclyl, optionally substituted phenyl, optionally substituted naphthyl, optionally substituted C$_{5-6}$cycloalkenyl, optionally substituted phenylC$_{2-4}$alkenyl, C$_{2-8}$alkenyl, C$_{3-8}$cycloalkyl, and C$_{3-8}$cycloalkylC$_{2-4}$alkenyl, wherein when said heterocyclyl or phenyl or naphthyl group or part of group is substituted, it is substituted with from 1 to 5 substituents, each substituent being independently selected from the group consisting of OR$^A$, halogen, C$_{1-6}$alkyl, haloC$_{1-6}$ alkyl, dihaloC$_{1-6}$alkyl and trihaloC$_{1-6}$alkyl, and wherein where said optionally substituted C$_{5-6}$cycloalkenyl group is substituted, it is substituted with 1 or two substituents selected from halogen atoms and methyl groups.

4. A compound as claimed in claim 1, in which R1 represents an optionally substituted isoxazolyl, isothiazolyl, pyrrolyl, pyrazolyl, pyridyl or pyrrolidinyl group.

5. A compound as claimed in claim 1, in which R$^2$ is selected from the group consisting of —C(NH$_2$)=N—OH, —C(O)N(R$^C$)$_2$, cyano, —CHO, —CH=N—OH, —C(O)NH—OH, —C(CO$_2$H)=N—OH, —C(O—C$_{1-4}$alkyl)=NH, —C(NH$_2$)=N—NH$_2$, —C(O)—C(O)—NH$_2$, —CH$_2$NH—CONH$_2$, C$_{1-6}$alkyl-NH$_2$, —NH—C(NH$_2$)=NH, —NH—C(O)NH$_2$, —N=C(—NH—CH$_2$CH$_2$—NH—), N(OH)—$_2$, —S—CN, —S—C(NH$_2$)=NH, —S—C(NH$_2$)=N—OH, cyanoC$_{1-6}$alkyl, and an optionally substituted 5-6 membered heterocyclyl containing from one to three nitrogen atoms; wherein when said heterocyclyl group is substituted, it is substituted with from 1 to 3 substituents, each substituent being independently selected from the group consisting of OH, halogen, cyano, nitro, C$_{1-4}$alkyl, haloC$_{1-4}$ alkyl, dihaloC$_{1-4}$alkyl and trihaloC$_{1-4}$alkyl.

6. A compound as claimed in claim 5, in which R$^2$ represents —C(NH$_2$)=N—OH, —C(O)NH$_2$, —CH=N—OH, cyano, or pyrazolyl.

7. A compound as claimed in claim 1, in which R$^3$ is selected from the group consisting of hydrogen, halogen, cyano, C$_{1-6}$alkyl, C$_{2-6}$alkenyl, C$_{2-6}$alkynyl, C$_{3-8}$cycloalkyl, C$_{3-8}$cycloalkylC$_{1-6}$alkyl, haloC$_{1-6}$alkyl, dihaloC$_{1-6}$alkyl, trihaloC$_{1-6}$alkyl, phenyl, and phenylC$_{1-4}$alkyl.

8. A compound as claimed in claim 7, in which R$^3$ represents halogen, cyano, C$_{1-6}$alkyl, C$_{2-6}$alkenyl, trihaloC$_{1-6}$alkyl, phenyl, or phenylC$_{1-2}$alkyl.

9. A compound as claimed in claim 1, in which each of R$^5$, R$^6$, R$^8$ and R$^9$ is independently selected from the group consisting of hydrogen, OR$^A$, N(R$^B$)$_2$, halogen, cyano, nitro, C$_{1-6}$alkyl, haloC$_{1-6}$ alkyl, dihaloC$_{1-6}$alkyl and trihaloC$_{1-6}$alkyl.

10. A compound as claimed in claim 9, in which each of R$^5$, R$^6$, R$^8$ and R$^9$ is independently selected from the group consisting of hydrogen, halogen, methyl and trifluoromethyl.

11. A compound as claimed in (claim 1), in which R$^7$ represents OR$^A$.

12. A compound as claimed in claim 11, in which R$^7$ represents OH.

13. A compound as claimed in claim 1, in which each of R$^5$, R$^8$ and R$^9$ is independently selected from the group consisting of hydrogen, OR$^A$, N(R$^B$)$_2$, halogen, cyano, nitro, C$_{1-6}$alkyl, haloC$_{1-6}$alkyl, dihaloC$_{1-6}$alkyl and trihaloC$_{1-6}$alkyl; and R$^6$ and R$^7$, together with the atoms they are attached to, form a 5-, 6- or 7-membered cyclic group optionally containing one to three heteroatoms selected from O, N and S, said 5-, 6- or 7-membered cyclic group being optionally substituted with one of more groups selected from OR$^A$, cyano, nitro, C$_{1-6}$ alkyl, C$_{2-6}$ alkenyl, C$_{2-6}$ alkynyl, halo C$_{1-6}$ alkyl, dihalo C$_{1-6}$ alkyl and trihalo C$_{1-6}$ alkyl.

14. A compound as claimed in claim 13, in which each of R$^5$, R$^8$ and R$^9$ is independently selected from the group consisting of hydrogen and halogen.

15. A compound as claimed in claim 13, in which R$^6$ and R$^7$, together with the atoms they are attached to, form a 5-, 6- or 7-membered cyclic group optionally containing one to three heteroatoms selected from O and N.

16. A compound as claimed in claim 1, which is any one of the following compounds:

N',4'-dihydroxy-2-(3-methylthiophen-2-yl)-5-propyl-[1,1'-biphenyl]-3-carboximidamide 2-(3,5-dimethylisoxazol-4-yl)-N',4'-dihydroxy-5-methyl-[1,1'-biphenyl]-3-carboximidamide 2-(3,5-dimethylisoxazol-4-yl)-N',4'-dihydroxy-5-propyl-[1,1'-biphenyl]-3-carboximidamide 2-(3,5-dimethylisoxazol-4-yl)-4'-hydroxy-5-propyl-[1,1'-biphenyl]-3-carboxamide
2-(3,5-dimethylisoxazol-4-yl)-4'-hydroxy-5-propyl-[1,1'-biphenyl]-3-carbonitrile
N',4'-dihydroxy-5-methyl-2-(3-methylthiophen-2-yl)-[1,1'-biphenyl]-3-carboximidamide
3',5'-difluoro-N',4'-dihydroxy-2-(3-methylthiophen-2-yl)-5-propyl-[1,1'-biphenyl]-3-carboximidamide
2-bromo-3',5'-difluoro-N',4'-dihydroxy-5-propyl-[1,1'-biphenyl]-3-carboximidamide
2-(3,5-dimethylisoxazol-4-yl)-3',5'-difluoro-N',4'-dihydroxy-5-propyl-[1,1'-biphenyl]-3-carboximidamide
5-bromo-N',4'-dihydroxy-2-(3-methylthiophen-2-yl)-[1,1'-biphenyl]-3-carboximidamide
5-bromo-N',4'-dihydroxy-2-iodo-[1,1'-biphenyl]-3-carboximidamide
5'-bromo-N',4-dihydroxy-[1,1':2',1''-terphenyl]-3'-carboximidamide
5''-fluoro-N',4-dihydroxy-2'',5'-dimethyl-[1,1':2',1''-terphenyl]-3'-carboximidamide
5''-fluoro-4-hydroxy-2'',5'-dimethyl-[1,1':2',1''-terphenyl]-3'-carboxamide
5-chloro-2-(3,5-dimethylisoxazol-4-yl)-N',4'-dihydroxy-[1,1'-biphenyl]-3-carboximidamide
5-chloro-2-(3,5-dimethylisoxazol-4-yl)-4'-hydroxy-[1,1'-biphenyl]-3-carboxamide
2-(3,5-dimethylisoxazol-4-yl)-3'-fluoro-N',4'-dihydroxy-5-propyl-[1,1'-biphenyl]-3-carboximidamide
2-(2,4-dimethylfuran-3-yl)-4'-hydroxy-5-propyl-[1,1'-biphenyl]-3-carbonitrile
2-(2,4-dimethylfuran-3-yl)-N',4'-dihydroxy-5-propyl-[1,1'-biphenyl]-3-carboximidamide
2-(2,4-dimethylfuran-3-yl)-4'-hydroxy-5-propyl-[1,1'-biphenyl]-3-carboxamide
N',4'-dihydroxy-2-iodo-5-propyl-[1,1'-biphenyl]-3-carboximidamide
N',4'-dihydroxy-2-(4-methylthiophen-3-yl)-5-propyl-[1,1'-biphenyl]-3-carboximidamide
N',4-dihydroxy-5'-propyl-2''-(trifluoromethoxy)-[1,1':2',1''-terphenyl]-3'-carboximidamide
2-(2,4-dimethylthiophen-3-yl)-N',4'-dihydroxy-5-propyl-[1,1'-biphenyl]-3-carboximidamide
N',4-dihydroxy-5'-propyl-[1,1':2',1''-terphenyl]-3'-carboximidamide
2-((E)-2-cyclopropylvinyl)-N',4'-dihydroxy-5-propyl-[1,1'-biphenyl]-3-carboximidamide
N',4'-dihydroxy-2-(3-methylbut-2-en-2-yl)-5-propyl-[1,1'-biphenyl]-3-carboximidamide
N',4-dihydroxy-3''-methyl-5'-propyl-[1,1':2',1''-terphenyl]-3'-carboximidamide
5''-fluoro-N',4-dihydroxy-2''-methyl-5'-propyl-[1,1':2',1''-terphenyl]-3'-carboximidamide
2''-ethyl-N',4-dihydroxy-5'-propyl-[1,1':2',1''-terphenyl]-3'-carboximidamide
N',4'-dihydroxy-5-propyl-2-(thiophen-2-yl)-[1,1'-biphenyl]-3-carboximidamide
N',4'-dihydroxy-5-propyl-2-(quinolin-5-yl)-[1,1'-biphenyl]-3-carboximidamide
3''-chloro-N',4-dihydroxy-5'-propyl-[1,1':2',1''-terphenyl]-3'-carboximidamide
N',4'-dihydroxy-5-propyl-2-(pyridin-3-yl)-[1,1'-biphenyl]-3-carboximidamide
2-(benzofuran-5-yl)-N',4'-dihydroxy-5-propyl-[1,1'-biphenyl]-3-carboximidamide
4''-chloro-N',4-dihydroxy-5'-propyl-[1,1':2',1''-terphenyl]-3'-carboximidamide
N',4'-dihydroxy-5-propyl-2-(pyridin-4-yl)-[1,1'-biphenyl]-3-carboximidamide
N',4'-dihydroxy-2-(1-phenylvinyl)-5-propyl-[1,1'-biphenyl]-3-carboximidamide
2-(5-chlorothiophen-2-yl)-N',4'-dihydroxy-5-propyl-[1,1'-biphenyl]-3-carboximidamide
5''-fluoro-N',4-dihydroxy-2''-methoxy-5'-propyl-[1,1':2',1''-terphenyl]-3'-carboximidamide
N',4'-dihydroxy-2-(isoquinolin-6-yl)-5-propyl-[1,1'-biphenyl]-3-carboximidamide
2-(benzofuran-3-yl)-N',4'-dihydroxy-5-propyl-[1,1'-biphenyl]-3-carboximidamide
5''-fluoro-N',4-dihydroxy-2''-methoxy-5'-(trifluoromethyl)-[1,1':2',1''-terphenyl]-3'-carboximidamide
5''-fluoro-N',4-dihydroxy-2''-methyl-5'-(trifluoromethyl)-[1,1':2',1''-terphenyl]-3'-carboximidamide
N',4-dihydroxy-2''-methyl-5'-(trifluoromethyl)-[1,1':2',1''-terphenyl]-3'-carboximidamide
N',4-dihydroxy-5'-(trifluoromethyl)-[1,1':2',1''-terphenyl]-3'-carboximidamide
N',4'-dihydroxy-2-(4-methylthiophen-3-yl)-5-(trifluoromethyl)-[1,1'-biphenyl]-3-carboximidamide
2-(2,4-dimethylthiophen-3-yl)-N',4'-dihydroxy-5-(trifluoromethyl)-[1,1'-biphenyl]-3-carboximidamide
N',4'-dihydroxy-2-iodo-5-(trifluoromethyl)-[1,1'-biphenyl]-3-carboximidamide
2'',5''-difluoro-N',4-dihydroxy-5'-propyl-[1,1':2',1''-terphenyl]-3'-carboximidamide
2-(1,3-dimethyl-1H-pyrrol-2-yl)-N',4'-dihydroxy-5-propyl-[1,1'-biphenyl]-3-carboximidamide
3'',5''-difluoro-N',4-dihydroxy-5'-propyl-[1,1':2',1''-terphenyl]-3'-carboximidamide
2-(2,4-dimethylfuran-3-yl)-N',4'-dihydroxy-5-(trifluoromethyl)-[1,1'-biphenyl]-3-carboximidamide
3'-chloro-5'-fluoro-N',4'-dihydroxy-2-(3-methylthiophen-2-yl)-5-propyl-[1,1'-biphenyl]-3-carboximidamide
N'-hydroxy-3-(1H-indazol-5-yl)-2-(3-methylthiophen-2-yl)-5-propylbenzimidamide
3'-fluoro-N',4'-dihydroxy-2-(3-methylthiophen-2-yl)-5-propyl-[1,1'-biphenyl]-3-carboximidamide
3'-chloro-N',4'-dihydroxy-2-(3-methylthiophen-2-yl)-5-propyl-[1,1'-biphenyl]-3-carboximidamide
3',5'-dichloro-N',4'-dihydroxy-2-(3-methylthiophen-2-yl)-5-propyl-[1,1'-biphenyl]-3-carboximidamide
N',4'-dihydroxy-3'-methyl-2-(3-methylthiophen-2-yl)-5-propyl-[1,1'-biphenyl]-3-carboximidamide
2'-fluoro-N',4'-dihydroxy-2-(3-methylthiophen-2-yl)-5-propyl-[1,1'-biphenyl]-3-carboximidamide
2',3'-difluoro-N',4'-dihydroxy-2-(3-methylthiophen-2-yl)-5-propyl-[1,1'-biphenyl]-3-carboximidamide
2',5'-difluoro-N',4'-dihydroxy-2-(3-methylthiophen-2-yl)-5-propyl-[1,1'-biphenyl]-3-carboximidamide
N',4'-dihydroxy-2-(2-methylallyl)-5-propyl-[1,1'-biphenyl]-3-carboximidamide
2-allyl-N',4'-dihydroxy-5-propyl-[1,1'-biphenyl]-3-carboximidamide
N',4'-dihydroxy-5-propyl-2-vinyl-[1,1'-biphenyl]-3-carboximidamide
5-bromo-N',4'-dihydroxy-2-(1-methyl-1H-imidazol-5-yl)-[1,1'-biphenyl]-3-carboximidamide
N',4'-dihydroxy-5-propyl-2-(pyridin-2-yl)-[1,1'-biphenyl]-3-carboximidamide
N',4'-dihydroxy-2-(2-methoxythiazol-4-yl)-5-propyl-[1,1'-biphenyl]-3-carboximidamide
N',4'-dihydroxy-5-propyl-2-(thiazol-5-yl)-[1,1'-biphenyl]-3-carboximidamide N',4'-dihydroxy-5-propyl-2-(thiazol-2-yl)-[1,1'-biphenyl]-3-carboximidamide
5'-ethyl-N',4-dihydroxy-[1,1':2',1"-terphenyl]-3'-carboximidamide
N',4-dihydroxy-5'-isobutyl-[1,1':2',1"-terphenyl]-3'-carboximidamide
N',4-dihydroxy-5'-((E)-prop-1-en-1-yl)-[1,1':2',1"-terphenyl]-3'-carboximidamide
5'-allyl-N',4-dihydroxy-[1,1':2',1"-terphenyl]-3'-carboximidamide
5'-butyl-N',4-dihydroxy-[1,1':2',1"-terphenyl]-3'-carboximidamide
2-(2,5-dimethyl-1H-pyrrol-1-yl)-N',4'-dihydroxy-5-(trifluoromethyl)-[1,1'-biphenyl]-3-carboximidamide
4-hydroxy-5'-propyl-[1,1':2',1"-terphenyl]-3'-carbaldehyde oxime
5'-propyl-3'-(1H-pyrazol-4-yl)-[1,1':2',1"-terphenyl]-4-ol
5-chloro-2-(3,5-dimethylisoxazol-4-yl)-N',4'-dihydroxy-3'-nitro-[1,1'-biphenyl]-3-carboximidamide
5'-chloro-5"-fluoro-N',4-dihydroxy-2"-methyl-[1,1':2',1"-terphenyl]-3'-carboximidamide
5'-chloro-5"-fluoro-N',4-dihydroxy-2"-methoxy-[1,1':2',1"-terphenyl]-3'-carboximidamide
5-chloro-N',4'-dihydroxy-2-(4-methylthiophen-3-yl)-[1,1'-biphenyl]-3-carboximidamide
5'-chloro-N',4-dihydroxy-2"-methyl-[1,1':2',1"-terphenyl]-3'-carboximidamide
2-(2,4-dimethylthiophen-3-yl)-N',4'-dihydroxy-[1,1'-biphenyl]-3-carboximidamide
5-chloro-2-(2,4-dimethylthiophen-3-yl)-N',4'-dihydroxy-[1,1'-biphenyl]-3-carboximidamide
2"-chloro-5"-fluoro-N',4-dihydroxy-5'-propyl-[1,1':2',1"-terphenyl]-3'-carboximidamide
6'-chloro-N',4-dihydroxy-5'-propyl-[1,1':2',1"-terphenyl]-3'-carboximidamide
N',4-dihydroxy-5',6'-dipropyl-[1,1':2',1"-terphenyl]-3'-carboximidamide
N',4'-dihydroxy-2-(3-methylthiophen-2-yl)-[1,1'-biphenyl]-3-carboximidamide
5'-bromo-6'-chloro-N',4-dihydroxy-[1,1':2',1"-terphenyl]-3'-carboximidamide
6'-chloro-N',4-dihydroxy-5'-phenyl-[1,1':2',1"-terphenyl]-3'-carboximidamide
6'-chloro-N',4-dihydroxy-[1,1':2',1"-terphenyl]-3'-carboximidamide
N',4-dihydroxy-6'-methyl-5'-propyl-[1,1':2',1"-terphenyl]-3'-carboximidamide
5",6'-difluoro-N',4-dihydroxy-2"-methyl-5'-propyl-[1,1':2',1"-terphenyl]-3'-carboximidamide
5",6'-difluoro-4-hydroxy-2"-methyl-5'-propyl-[1,1':2',1"-terphenyl]-3'-carboxamide
4-hydroxy-6'-methyl-5'-propyl-[1,1':2',1"-terphenyl]-3'-carbaldehyde oxime
5",6'-difluoro-N',4-dihydroxy-2"-methoxy-5'-propyl-[1,1':2',1"-terphenyl]-3'-carboximidamide
5",6'-difluoro-4-hydroxy-2"-methoxy-5'-propyl-[1,1':2',1"-terphenyl]-3'-carboxamide
6'-fluoro-4-hydroxy-5'-propyl-[1,1':2',1"-terphenyl]-3'-carboxamide
6'-fluoro-N',4-dihydroxy-2"-methyl-5'-propyl-[1,1':2',1"-terphenyl]-3'-carboximidamide
6-fluoro-N',4'-dihydroxy-2-(4-methylthiophen-3-yl)-5-propyl-[1,1'-biphenyl]-3-carboximidamide
6'-fluoro-4-hydroxy-2"-methyl-5'-propyl-[1,1':2',1"-terphenyl]-3'-carboxamide
6-fluoro-4'-hydroxy-2-(4-methylthiophen-3-yl)-5-propyl-[1,1'-biphenyl]-3-carboxamide
2-(2,4-dimethylthiophen-3-yl)-6-fluoro-N',4'-dihydroxy-5-propyl-[1,1'-biphenyl]-3-carboximidamide
5'-chloro-5"-fluoro-4-hydroxy-2"-methoxy-[1,1':2',1"-terphenyl]-3'-carboxamide
6'-fluoro-N',4-dihydroxy-5'-propyl-[1,1':2',1"-terphenyl]-3'-carboximidamide
5"-fluoro-N',4-dihydroxy-2"-methoxy-[1,1':2',1"-terphenyl]-3'-carboximidamide
N',4-dihydroxy-[1,1':2',1"-terphenyl]-3'-carboximidamide
5"-fluoro-N',4-dihydroxy-2"-methyl-[1,1':2',1"-terphenyl]-3'-carboximidamide
N',4-dihydroxy-5'-(trifluoromethyl)-2"-vinyl-[1,1':2',1"-terphenyl]-3'-carboximidamide
2"-ethyl-N',4-dihydroxy-5'-(trifluoromethyl)-[1,1':2',1"-terphenyl]-3'-carboximidamide
3"-fluoro-N',4-dihydroxy-2"-methyl-5'-(trifluoromethyl)-[1,1':2',1"-terphenyl]-3'-carboximidamide
3"-fluoro-N',4-dihydroxy-2"-methoxy-5'-(trifluoromethyl)-[1,1':2',1"-terphenyl]-3'-carboximidamide
5',6'-dichloro-5"-fluoro-N',4-dihydroxy-2"-methyl-[1,1':2',1"-terphenyl]-3'-carboximidamide
3",5"-difluoro-N',4-dihydroxy-5'-(trifluoromethyl)-[1,1':2',1"-terphenyl]-3'-carboximidamide
5"-chloro-N',4-dihydroxy-2"-methoxy-5'-(trifluoromethyl)-[1,1':2',1"-terphenyl]-3'-carboximidamide
2"-ethynyl-N',4-dihydroxy-5'-(trifluoromethyl)-[1,1':2',1"-terphenyl]-3'-carboximidamide
3"-chloro-5"-fluoro-N',4-dihydroxy-5'-(trifluoromethyl)-[1,1':2',1"-terphenyl]-3'-carboximidamide
5"-fluoro-N',4-dihydroxy-2",5'-bis(trifluoromethyl)-[1,1':2',1"-terphenyl]-3'-carboximidamide
3",5"-difluoro-N',4-dihydroxy-2"-methoxy-5'-(trifluoromethyl)-[1,1':2',1"-terphenyl]-3'-carboximidamide
5'-methyl-3'-(1H-pyrazol-4-yl)-[1,1':2',1"-terphenyl]-4-ol
3",5"-difluoro-5'-propyl-3'-(1H-pyrazol-4-yl)-[1,1':2',1"-terphenyl]-4-ol
N',4-dihydroxy-5'-phenyl-[1,1':2',1"-terphenyl]-3'-carboximidamide
5'-benzyl-N',4-dihydroxy-[1,1':2',1"-terphenyl]-3'-carboximidamide
N',4-dihydroxy-5'-phenethyl-[1,1':2',1"-terphenyl]-3'-carboximidamide
2,5"-difluoro-N',4-dihydroxy-2"-methyl-5'-(trifluoromethyl)-[1,1':2',1"-terphenyl]-3'-carboximidamide
2,5"-difluoro-N',4-dihydroxy-2"-methoxy-5'-(trifluoromethyl)-[1,1':2',1"-terphenyl]-3'-carboximidamide
2-fluoro-N',4-dihydroxy-2"-methyl-5'-(trifluoromethyl)-[1,1':2',1"-terphenyl]-3'-carboximidamide
2-fluoro-N',4-dihydroxy-5'-(trifluoromethyl)-[1,1':2',1"-terphenyl]-3'-carboximidamide
5"-chloro-2-fluoro-N',4-dihydroxy-2"-methoxy-5'-(trifluoromethyl)-[1,1':2',1"-terphenyl]-3'-carboximidamide
2,3"-difluoro-N',4-dihydroxy-2"-methoxy-5'-(trifluoromethyl)-[1,1':2',1"-terphenyl]-3'-carboximidamide
2,3",5"-trifluoro-N',4-dihydroxy-5'-(trifluoromethyl)-[1,1':2',1"-terphenyl]-3'-carboximidamide
2-fluoro-N',4-dihydroxy-5'-(trifluoromethyl)-2"-vinyl-[1,1':2',1"-terphenyl]-3'-carboximidamide
5"-chloro-2-fluoro-4-hydroxy-2"-methoxy-5'-(trifluoromethyl)-[1,1':2',1"-terphenyl]-3'-carboxamide
2-fluoro-4-hydroxy-5'-(trifluoromethyl)-2"-vinyl-[1,1':2',1"-terphenyl]-3'-carboxamide
3"-chloro-2,5"-difluoro-N',4-dihydroxy-5'-(trifluoromethyl)-[1,1':2',1"-terphenyl]-3'-carboximidamide 3″-chloro-2,5″-difluoro-4-hydroxy-5′-(trifluoromethyl)-[1,1′:2′,1″-terphenyl]-3′-carboxamide
2″-ethynyl-2-fluoro-N′,4-dihydroxy-5′-(trifluoromethyl)-[1,1′:2′,1″-terphenyl]-3′-carboximidamide
5′-chloro-3″,5″-difluoro-N′,4-dihydroxy-[1,1′:2′,1″-terphenyl]-3′-carboximidamide
5′-chloro-3″-fluoro-N′,4-dihydroxy-2″-methoxy-[1,1′:2′,1″-terphenyl]-3′-carboximidamide
5′,5″-dichloro-N′,4-dihydroxy-2″-methoxy-[1,1′:2′,1″-terphenyl]-3′-carboximidamide
3″-chloro-2-fluoro-N′,4-dihydroxy-2″-methyl-5′-(trifluoromethyl)-[1,1′:2′,1″-terphenyl]-3′-carboximidamide
3″-chloro-2-fluoro-4-hydroxy-2″-methyl-5′-(trifluoromethyl)-[1,1′:2′,1″-terphenyl]-3′-carboxamide
N′,4-dihydroxy-5′-methyl-2″-vinyl-[1,1′:2′,1″-terphenyl]-3′-carboximidamide
3″,5″-difluoro-N′,4-dihydroxy-2″-methoxy-5′-methyl-[1,1′:2′,1″-terphenyl]-3′-carboximidamide
3″-fluoro-N′,4-dihydroxy-2″-methoxy-5′-methyl-[1,1′:2′,1″-terphenyl]-3′-carboximidamide
5″-fluoro-N′,4-dihydroxy-2″-methoxy-5′-methyl-[1,1′:2′,1″-terphenyl]-3′-carboximidamide
3″-chloro-5″-fluoro-N′,4-dihydroxy-5′-methyl-[1,1′:2′,1″-terphenyl]-3′-carboximidamide
5″-chloro-N′,4-dihydroxy-2″,5′-dimethyl-[1,1′:2′,1″-terphenyl]-3′-carboximidamide
5″-chloro-N′,4-dihydroxy-2″-methyl-5′-(trifluoromethyl)-[1,1′:2′,1″-terphenyl]-3′-carboximidamide
3″-chloro-N′,4-dihydroxy-2″-methyl-5′-(trifluoromethyl)-[1,1′:2′,1″-terphenyl]-3′-carboximidamide
5″-chloro-N′,4-dihydroxy-2″-methoxy-5′-methyl-[1,1′:2′,1″-terphenyl]-3′-carboximidamide
2″-chloro-5″-fluoro-N′,4-dihydroxy-5′-methyl-[1,1′:2′,1″-terphenyl]-3′-carboximidamide
N′,4-dihydroxy-5′-methyl-[1,1′:2′,1″-terphenyl]-3′-carboximidamide
N′,4-dihydroxy-3″,5′-dimethyl-[1,1′:2′,1″-terphenyl]-3′-carboximidamide
3″-chloro-N′,4-dihydroxy-5′-methyl-[1,1′:2′,1″-terphenyl]-3′-carboximidamide
N′,4-dihydroxy-3″-methoxy-5′-methyl-[1,1′:2′,1″-terphenyl]-3′-carboximidamide
4″-fluoro-N′,4-dihydroxy-5′-(trifluoromethyl)-[1,1′:2′,1″-terphenyl]-3′-carboximidamide
4″-chloro-N′,4-dihydroxy-5′-(trifluoromethyl)-[1,1′:2′,1″-terphenyl]-3′-carboximidamide
N′,4-dihydroxy-2″-methoxy-5′-(trifluoromethyl)-[1,1′:2′,1″-terphenyl]-3′-carboximidamide
4″-fluoro-N′,4-dihydroxy-2″-methoxy-5′-(trifluoromethyl)-[1,1′:2′,1″-terphenyl]-3′-carboximidamide
N′,4-dihydroxy-2″-isopropyl-5′-(trifluoromethyl)-[1,1′:2′,1″-terphenyl]-3′-carboximidamide
2-(3,5-dimethylisoxazol-4-yl)-N′,4′-dihydroxy-5-(trifluoromethyl)-[1,1′-biphenyl]-3-carboximidamide
2-(3,5-dimethylisoxazol-4-yl)-4′-hydroxy-5-(trifluoromethyl)-[1,1′-biphenyl]-3-carboxamide
3″-chloro-4-hydroxy-2″-methyl-5′-(trifluoromethyl)-[1,1′:2′,1″-terphenyl]-3′-carboxamide
N′,4-dihydroxy-2″,5″-dimethyl-5′-(trifluoromethyl)-[1,1′:2′,1″-terphenyl]-3′-carboximidamide
N′,4-dihydroxy-2″-methoxy-5″-methyl-5′-(trifluoromethyl)-[1,1′:2′,1″-terphenyl]-3′-carboximidamide
2″-chloro-N′,4-dihydroxy-5″-methyl-5′-(trifluoromethyl)-[1,1′:2′,1″-terphenyl]-3′-carboximidamide
5′-fluoro-N′,4-dihydroxy-[1,1′:2′,1″-terphenyl]-3′-carboximidamide
5″-chloro-5′-fluoro-N′,4-dihydroxy-2″-methoxy-[1,1′:2′,1″-terphenyl]-3′-carboximidamide
3″,5′-difluoro-N′,4-dihydroxy-2″-methoxy-[1,1′:2′,1″-terphenyl]-3′-carboximidamide
3″,5′,5″-trifluoro-N′,4-dihydroxy-[1,1′:2′,1″-terphenyl]-3′-carboximidamide
3″-chloro-5′,5″-difluoro-N′,4-dihydroxy-[1,1′:2′,1″-terphenyl]-3′-carboximidamide
5′-fluoro-N′,4-dihydroxy-2″-vinyl-[1,1′:2′,1″-terphenyl]-3′-carboximidamide
5′-chloro-N′,4-dihydroxy-2″,5″-dimethyl-[1,1′:2′,1″-terphenyl]-3′-carboximidamide
N′,4-dihydroxy-2″,5″-dimethyl-[1,1′:2′,1″-terphenyl]-3′-carboximidamide
2″-chloro-4-hydroxy-5″-methyl-5′-(trifluoromethyl)-[1,1′:2′,1″-terphenyl]-3′-carboxamide
3″-chloro-N′,4-dihydroxy-5″-methyl-5′-(trifluoromethyl)-[1,1′:2′,1″-terphenyl]-3′-carboximidamide
2″,5″-dichloro-N′,4-dihydroxy-5′-(trifluoromethyl)-[1,1′:2′,1″-terphenyl]-3′-carboximidamide
5″-chloro-N′,4-dihydroxy-2″-methyl-[1,1′:2′,1″-terphenyl]-3′-carboximidamide
5″-chloro-N′,4-dihydroxy-2″-methoxy-[1,1′:2′,1″-terphenyl]-3′-carboximidamide
3″,5″-difluoro-N′,4-dihydroxy-5′-methyl-[1,1′:2′,1″-terphenyl]-3′-carboximidamide
3″,5″-difluoro-4-hydroxy-5′-methyl-[1,1′:2′,1″-terphenyl]-3′-carboxamide
3″-chloro-4-hydroxy-5″-methyl-5′-(trifluoromethyl)-[1,1′:2′,1″-terphenyl]-3′-carboxamide
2″,5″-dichloro-4-hydroxy-5′-(trifluoromethyl)-[1,1′:2′,1″-terphenyl]-3′-carboxamide
3″,5″-dichloro-N′,4-dihydroxy-5′-(trifluoromethyl)-[1,1′:2′,1″-terphenyl]-3′-carboximidamide
3″,5″-dichloro-N′,4-dihydroxy-5′-methyl-[1,1′:2′,1″-terphenyl]-3′-carboximidamide
2-(3,5-dimethylisoxazol-4-yl)-2′-fluoro-N′,4′-dihydroxy-5-(trifluoromethyl)-[1,1′-biphenyl]-3-carboximidamide
2-(3,5-dimethylisoxazol-4-yl)-2′-fluoro-4′-hydroxy-5-(trifluoromethyl)-[1,1′-biphenyl]-3-carboxamide
3″,5″-difluoro-N′,4-dihydroxy-[1,1′:2′,1″-terphenyl]-3′-carboximidamide
3″,5″-difluoro-4-hydroxy-[1,1′:2′,1″-terphenyl]-3′-carboxamide
3″-fluoro-N′,4-dihydroxy-2″-methoxy-[1,1′:2′,1″-terphenyl]-3′-carboximidamide
3″-fluoro-4-hydroxy-2″-methoxy-[1,1′:2′,1″-terphenyl]-3′-carboxamide
2″-ethyl-N′,4-dihydroxy-[1,1′:2′,1″-terphenyl]-3′-carboximidamide
4″-chloro-2″-fluoro-N′,4-dihydroxy-5′-methyl-[1,1′:2′,1″-terphenyl]-3′-carboximidamide
4″-chloro-3″-fluoro-N′,4-dihydroxy-5′-methyl-[1,1′:2′,1″-terphenyl]-3′-carboximidamide
N′,4-dihydroxy-2″-methoxy-[1,1′:2′,1″-terphenyl]-3′-carboximidamide
5′-chloro-N′,4-dihydroxy-2″-methoxy-[1,1′:2′,1″-terphenyl]-3′-carboximidamide
4″-fluoro-N′,4-dihydroxy-2″-methoxy-[1,1′:2′,1″-terphenyl]-3′-carboximidamide
5′-chloro-4″-fluoro-N′,4-dihydroxy-2″-methoxy-[1,1′:2′,1″-terphenyl]-3′-carboximidamide
3″-chloro-N′,4-dihydroxy-5′,5″-dimethyl-[1,1′:2′,1″-terphenyl]-3′-carboximidamide
2″,5″-dichloro-N′,4-dihydroxy-5′-methyl-[1,1′:2′,1″-terphenyl]-3′-carboximidamide 3",5"-difluoro-4-hydroxy-5'-(trifluoromethyl)-[1,1':2',1"-terphenyl]-3'-carboxamide
N',4-dihydroxy-4",5'-dimethyl-[1,1':2',1"-terphenyl]-3'-carboximidamide
N',4-dihydroxy-2",4",5'-trimethyl-[1,1':2',1"-terphenyl]-3'-carboximidamide
4"-fluoro-N',4-dihydroxy-5'-methyl-[1,1':2',1"-terphenyl]-3'-carboximidamide
2",4"-difluoro-N',4-dihydroxy-5'-methyl-[1,1':2',1"-terphenyl]-3'-carboximidamide
5"-chloro-5'-fluoro-N',4-dihydroxy-2"-methyl-[1,1':2',1"-terphenyl]-3'-carboximidamide
5',5"-difluoro-N',4-dihydroxy-2"-methoxy-[1,1':2',1"-terphenyl]-3'-carboximidamide
2"-chloro-5'-fluoro-N',4-dihydroxy-5"-methyl-[1,1':2',1"-terphenyl]-3'-carboximidamide
2",5"-dichloro-5'-fluoro-N',4-dihydroxy-[1,1':2',1"-terphenyl]-3'-carboximidamide
5'-fluoro-N',4-dihydroxy-2"-methoxy-[1,1':2',1"-terphenyl]-3'-carboximidamide
4",5'-difluoro-N',4-dihydroxy-2"-methoxy-[1,1':2',1"-terphenyl]-3'-carboximidamide
5'-fluoro-N',4-dihydroxy-2",5"-dimethyl-[1,1':2',1"-terphenyl]-3'-carboximidamide
5'-fluoro-N',4-dihydroxy-2"-methoxy-5"-methyl-[1,1':2',1"-terphenyl]-3'-carboximidamide
N',4-dihydroxy-2"-methoxy-5"-methyl-[1,1':2',1"-terphenyl]-3'-carboximidamide
N',4-dihydroxy-2"-methoxy-5',5"-dimethyl-[1,1':2',1"-terphenyl]-3'-carboximidamide
4"-fluoro-N',4-dihydroxy-2"-methoxy-5'-methyl-[1,1':2',1"-terphenyl]-3'-carboximidamide
2"-chloro-N',4-dihydroxy-5',5"-dimethyl-[1,1':2',1"-terphenyl]-3'-carboximidamide
N',4-dihydroxy-5'-methyl-2"-(trifluoromethoxy)-[1,1':2',1"-terphenyl]-3'-carboximidamide
N',4-dihydroxy-2"-methoxy-5'-methyl-[1,1':2',1"-terphenyl]-3'-carboximidamide
3",5"-difluoro-N',4-dihydroxy-5'-methoxy-[1,1':2',1"-terphenyl]-3'-carboximidamide
5"-fluoro-N',4-dihydroxy-2",5'-dimethoxy-[1,1':2',1"-terphenyl]-3'-carboximidamide
2-(5-fluoro-2-methoxypyridin-3-yl)-N',4'-dihydroxy-5-methyl-[1,1'-biphenyl]-3-carboximidamide
N',4'-dihydroxy-5-methyl-2-(2-methylpyridin-3-yl)-[1,1'-biphenyl]-3-carboximidamide
N',4'-dihydroxy-2-(2-methoxypyridin-3-yl)-5-methyl-[1,1'-biphenyl]-3-carboximidamide
2-(3,5-dimethylisothiazol-4-yl)-N',4'-dihydroxy-5-methyl-[1,1'-biphenyl]-3-carboximidamide
N',4-dihydroxy-5'-methoxy-[1,1':2',1"-terphenyl]-3'-carboximidamide
2-(3,5-dimethylisothiazol-4-yl)-4'-hydroxy-5-methyl-[1,1'-biphenyl]-3-carboxamide
5-chloro-2-(5-fluoro-2-methoxypyridin-3-yl)-N',4'-dihydroxy-[1,1'-biphenyl]-3-carboximidamide
2-(5-fluoro-2-methoxypyridin-3-yl)-4'-hydroxy-5-methyl-[1,1'-biphenyl]-3-carboxamide
2-(3,5-dimethylisothiazol-4-yl)-N',4'-dihydroxy-5-(trifluoromethyl)-[1,1'-biphenyl]-3-carboximidamide
5-chloro-2-(3,5-dimethylisothiazol-4-yl)-N',4'-dihydroxy-[1,1'-biphenyl]-3-carboximidamide
4"-fluoro-N',4-dihydroxy-2"-methyl-5'-(trifluoromethyl)-[1,1':2',1"-terphenyl]-3'-carboximidamide
2",4"-difluoro-N',4-dihydroxy-5'-(trifluoromethyl)-[1,1':2',1"-terphenyl]-3'-carboximidamide
N',4'-dihydroxy-2-(4-methylpyridin-3-yl)-5-(trifluoromethyl)-[1,1'-biphenyl]-3-carboximidamide
2-(2,5-dimethylpyridin-3-yl)-N',4'-dihydroxy-5-(trifluoromethyl)-[1,1'-biphenyl]-3-carboximidamide
2"-chloro-4"-fluoro-N',4-dihydroxy-5'-(trifluoromethyl)-[1,1':2',1"-terphenyl]-3'-carboximidamide
4",5"-difluoro-N',4-dihydroxy-2"-methyl-5'-(trifluoromethyl)-[1,1':2',1"-terphenyl]-3'-carboximidamide
2",5"-difluoro-N',4-dihydroxy-5'-(trifluoromethyl)-[1,1':2',1"-terphenyl]-3'-carboximidamide
N',4'-dihydroxy-2-(pyridin-3-yl)-5-(trifluoromethyl)-[1,1'-biphenyl]-3-carboximidamide
2-(2,3-dihydrobenzofuran-7-yl)-N',4'-dihydroxy-5-(trifluoromethyl)-[1,1'-biphenyl]-3-carboximidamide
2-(benzofuran-7-yl)-N',4'-dihydroxy-5-(trifluoromethyl)-[1,1'-biphenyl]-3-carboximidamide
N',4'-dihydroxy-2-(1-methyl-1H-indol-7-yl)-5-(trifluoromethyl)-[1,1'-biphenyl]-3-carboximidamide
2"-chloro-5"-fluoro-N',4-dihydroxy-5'-(trifluoromethyl)-[1,1':2',1"-terphenyl]-3'-carboximidamide
5"-chloro-2"-fluoro-N',4-dihydroxy-5'-(trifluoromethyl)-[1,1':2',1"-terphenyl]-3'-carboximidamide
2-(4-fluorobenzofuran-7-yl)-N',4'-dihydroxy-5-(trifluoromethyl)-[1,1'-biphenyl]-3-carboximidamide
3",4"-difluoro-N',4-dihydroxy-5'-(trifluoromethyl)-[1,1':2',1"-terphenyl]-3'-carboximidamide
5'-chloro-2",4"-difluoro-N',4-dihydroxy-[1,1':2',1"-terphenyl]-3'-carboximidamide
5'-chloro-2",5"-difluoro-N',4-dihydroxy-[1,1':2',1"-terphenyl]-3'-carboximidamide
2-(benzo[d][1,3]dioxol-4-yl)-N',4'-dihydroxy-5-(trifluoromethyl)-[1,1'-biphenyl]-3-carboximidamide
3",4",5"-trifluoro-N',4-dihydroxy-5'-(trifluoromethyl)-[1,1':2',1"-terphenyl]-3'-carboximidamide
5'-chloro-3",4"-difluoro-N',4-dihydroxy-[1,1':2',1"-terphenyl]-3'-carboximidamide
5'-chloro-3",4",5"-trifluoro-N',4-dihydroxy-[1,1':2',1"-terphenyl]-3'-carboximidamide
5-chloro-N',4'-dihydroxy-2-(4-methylpyridin-3-yl)-[1,1'-biphenyl]-3-carboximidamide
5',5"-dichloro-2"-fluoro-N',4-dihydroxy-[1,1':2',1"-terphenyl]-3'-carboximidamide
2",5'-dichloro-5"-fluoro-N',4-dihydroxy-[1,1':2',1"-terphenyl]-3'-carboximidamide
5'-chloro-2"-fluoro-N',4-dihydroxy-5"-methyl-[1,1':2',1"-terphenyl]-3'-carboximidamide
5'-chloro-2"-fluoro-N',4-dihydroxy-4"-methyl-[1,1':2',1"-terphenyl]-3'-carboximidamide
2-(5-fluoro-2-methoxypyridin-3-yl)-N',4'-dihydroxy-5-(trifluoromethyl)-[1,1'-biphenyl]-3-carboximidamide
5'-chloro-N',4-dihydroxy-2",4"-dimethoxy-[1,1':2',1"-terphenyl]-3'-carboximidamide
5'-chloro-4-hydroxy-2",4"-dimethoxy-[1,1':2',1"-terphenyl]-3'-carbonitrile
5-chloro-2-(5-chloro-2-methoxypyridin-3-yl)-N',4'-dihydroxy-[1,1'-biphenyl]-3-carboximidamide
5-chloro-2-(5-chloro-2-methoxypyridin-3-yl)-4'-hydroxy-[1,1'-biphenyl]-3-carboxamide
5-chloro-2-(2,5-dimethylpyridin-3-yl)-N',4'-dihydroxy-[1,1'-biphenyl]-3-carboximidamide
5-chloro-2-(2,5-dimethylpyridin-3-yl)-4'-hydroxy-[1,1'-biphenyl]-3-carboxamide
2-(benzo[d][1,3]dioxol-4-yl)-5-chloro-N',4'-dihydroxy-[1,1'-biphenyl]-3-carboximidamide
5-chloro-N',4'-dihydroxy-2-(naphthalen-2-yl)-[1,1'-biphenyl]-3-carboximidamide 5-chloro-N',4'-dihydroxy-2-(isoquinolin-6-yl)-[1,1'-biphenyl]-3-carboximidamide
5-chloro-N',4'-dihydroxy-2-(quinolin-6-yl)-[1,1'-biphenyl]-3-carboximidamide
5-chloro-N',4'-dihydroxy-2-(1-methyl-1H-benzo[d]imidazol-5-yl)-[1,1'-biphenyl]-3-carboximidamide
5-chloro-4'-hydroxy-2-(1-methyl-1H-benzo[d]imidazol-5-yl)-[1,1'-biphenyl]-3-carboxamide
2-(5-chloro-2-methoxypyridin-3-yl)-N',4'-dihydroxy-5-(trifluoromethyl)-[1,1'-biphenyl]-3-carboximidamide
2"-fluoro-N',4-dihydroxy-5"-methyl-5'-(trifluoromethyl)-[1,1':2',1"-terphenyl]-3'-carboximidamide
5-chloro-2-(6-chloro-2-methoxypyridin-3-yl)-N',4'-dihydroxy-[1,1'-biphenyl]-3-carboximidamide
5-chloro-N',4'-dihydroxy-2-(2-methoxy-5-methylpyridin-3-yl)-[1,1'-biphenyl]-3-carboximidamide
5-chloro-2-(cyclopent-1-en-1-yl)-N',4'-dihydroxy-[1,1'-biphenyl]-3-carboximidamide
5-chloro-2-(cyclopent-1-en-1-yl)-4'-hydroxy-[1,1'-biphenyl]-3-carboxamide
2-(cyclopent-1-en-1-yl)-N',4'-dihydroxy-5-(trifluoromethyl)-[1,1'-biphenyl]-3-carboximidamide
2-(cyclopent-1-en-1-yl)-4'-hydroxy-5-(trifluoromethyl)-[1,1'-biphenyl]-3-carboxamide
5'-bromo-5"-fluoro-N',4-dihydroxy-2"-methoxy-[1,1':2',1"-terphenyl]-3'-carboximidamide
5'-bromo-5"-fluoro-N',4-dihydroxy-2"-methyl-[1,1':2',1"-terphenyl]-3'-carboximidamide
5'-bromo-3"-fluoro-N',4-dihydroxy-2"-methoxy-[1,1':2',1"-terphenyl]-3'-carboximidamide
5'-bromo-N',4-dihydroxy-2",5"-dimethyl-[1,1':2',1"-terphenyl]-3'-carboximidamide
5'-bromo-N',4-dihydroxy-5"-methoxy-2"-methyl-[1,1':2',1"-terphenyl]-3'-carboximidamide
5'-bromo-N',4-dihydroxy-2"-methoxy-[1,1':2',1"-terphenyl]-3'-carboximidamide
5'-bromo-4"-fluoro-N',4-dihydroxy-2"-methoxy-[1,1':2',1"-terphenyl]-3'-carboximidamide
5"-fluoro-N',4-dihydroxy-5'-(trifluoromethyl)-2"-vinyl-[1,1':2',1"-terphenyl]-3'-carboximidamide
2,5"-difluoro-N',4-dihydroxy-5'-(trifluoromethyl)-2"-vinyl-[1,1':2',1"-terphenyl]-3'-carboximidamide
5"-chloro-N',4-dihydroxy-5'-(trifluoromethyl)-2"-vinyl-[1,1':2',1"-terphenyl]-3'-carboximidamide
2"-ethynyl-5"-fluoro-N',4-dihydroxy-5'-(trifluoromethyl)-[1,1':2',1"-terphenyl]-3'-carboximidamide
4-hydroxy-2"-methoxy-5"-methyl-5'-(trifluoromethyl)-[1,1':2',1"-terphenyl]-3'-carboxamide
5'-bromo-5"-chloro-N',4-dihydroxy-2"-methyl-[1,1':2',1"-terphenyl]-3'-carboximidamide
5'-bromo-3",5"-difluoro-N',4-dihydroxy-[1,1':2',1"-terphenyl]-3'-carboximidamide
5'-bromo-3"-chloro-5"-fluoro-N',4-dihydroxy-[1,1':2',1"-terphenyl]-3'-carboximidamide
5'-bromo-2"-chloro-5"-fluoro-N',4-dihydroxy-[1,1':2',1"-terphenyl]-3'-carboximidamide
5'-bromo-4"-chloro-N',4-dihydroxy-[1,1':2',1"-terphenyl]-3'-carboximidamide
5'-bromo-2",5"-dichloro-N',4-dihydroxy-[1,1':2',1"-terphenyl]-3'-carboximidamide
5'-bromo-2"-chloro-N',4-dihydroxy-5"-methyl-[1,1':2',1"-terphenyl]-3'-carboximidamide
5-bromo-2-(3,5-dimethylisoxazol-4-yl)-N',4'-dihydroxy-[1,1'-biphenyl]-3-carboximidamide
3-chloro-5-fluoro-N',4-dihydroxy-5'-(trifluoromethyl)-[1,1':2',1"-terphenyl]-3'-carboximidamide
3-chloro-5-fluoro-4-hydroxy-5'-(trifluoromethyl)-[1,1':2',1"-terphenyl]-3'-carboxamide
3,5'-dichloro-3",5,5"-trifluoro-N',4-dihydroxy-[1,1':2',1"-terphenyl]-3'-carboximidamide
3'-chloro-2-(3,5-dimethylisoxazol-4-yl)-5'-fluoro-N',4'-dihydroxy-5-(trifluoromethyl)-[1,1'-biphenyl]-3-carboximidamide
3-chloro-3",5,5"-trifluoro-N',4-dihydroxy-5'-(trifluoromethyl)-[1,1':2',1"-terphenyl]-3'-carboximidamide
3-chloro-5,5"-difluoro-N',4-dihydroxy-2"-methoxy-5'-(trifluoromethyl)-[1,1':2',1"-terphenyl]-3'-carboximidamide
3-chloro-5-fluoro-N',4-dihydroxy-2"-methoxy-5'-(trifluoromethyl)-[1,1':2',1"-terphenyl]-3'-carboximidamide
5'-chloro-3",5"-difluoro-N'-hydroxy-4-methoxy-3-methyl-[1,1':2',1"-terphenyl]-3'-carboximidamide
5'-chloro-3",5"-difluoro-N',4-dihydroxy-3-methyl-[1,1':2',1"-terphenyl]-3'-carboximidamide
5-chloro-2-(3,5-dimethylisoxazol-4-yl)-N',4'-dihydroxy-3'-methyl-[1,1'-biphenyl]-3-carboximidamide
5'-chloro-N',4-dihydroxy-2",3-dimethyl-[1,1':2',1"-terphenyl]-3'-carboximidamide
5'-chloro-5"-fluoro-N',4-dihydroxy-2"-methoxy-3-methyl-[1,1':2',1"-terphenyl]-3'-carboximidamide
5'-chloro-5"-fluoro-4-hydroxy-2"-methoxy-3-methyl-[1,1':2',1"-terphenyl]-3'-carboxamide
5'-chloro-3",5"-difluoro-N',4-dihydroxy-3-isopropyl-[1,1':2',1"-terphenyl]-3'-carboximidamide
2'-(3,5-dimethylisoxazol-4-yl)-3'-(1H-1,2,3-triazol-4-yl)-5'-(trifluoromethyl)-[1,1'-biphenyl]-4-ol
N',4-dihydroxy-5'-(trifluoromethoxy)-[1,1':2',1"-terphenyl]-3'-carboximidamide
3",5"-difluoro-N',4-dihydroxy-5'-(trifluoromethoxy)-[1,1':2',1"-terphenyl]-3'-carboximidamide
5"-chloro-N',4-dihydroxy-2"-methoxy-5'-(trifluoromethoxy)-[1,1':2',1"-terphenyl]-3'-carboximidamide
4-hydroxy-5'-(trifluoromethoxy)-[1,1':2',1"-terphenyl]-3'-carboxamide
3",5"-difluoro-4-hydroxy-5'-(trifluoromethoxy)-[1,1':2',1"-terphenyl]-3'-carboxamide
N',4-dihydroxy-5'-isopropyl-[1,1':2',1"-terphenyl]-3'-carboximidamide
3",5"-difluoro-N',4-dihydroxy-5'-isopropyl-[1,1':2',1"-terphenyl]-3'-carboximidamide
5"-chloro-N',4-dihydroxy-5'-isopropyl-2"-methoxy-[1,1':2',1"-terphenyl]-3'-carboximidamide
4-amino-5'-isopropyl-[1,1':2',1"-terphenyl]-3'-carboxamide
3",5"-difluoro-4-hydroxy-5'-isopropyl-[1,1':2',1"-terphenyl]-3'-carboxamide
2-(3-cyanofuran-2-yl)-N',4'-dihydroxy-5-(trifluoromethyl)-[1,1'-biphenyl]-3-carboximidamide
2-(4-cyano-1-methyl-1H-pyrazol-5-yl)-N',4'-dihydroxy-5-(trifluoromethyl)-[1,1'-biphenyl]-3-carboximidamide
2"-cyano-N',4-dihydroxy-5'-(trifluoromethyl)-[1,1':2',1"-terphenyl]-3'-carboximidamide
2-(3-cyano-1-methyl-1H-pyrrol-2-yl)-N',4'-dihydroxy-5-(trifluoromethyl)-[1,1'-biphenyl]-3-carboximidamide
2'-(3-dimethylisoxazol-4-yl)-3'-(hydroxymethyl)-5'-(trifluoromethyl)-[1,1'-biphenyl]-4-ol
5'-cyano-3",5"-difluoro-N',4-dihydroxy-[1,1':2',1"-terphenyl]-3'-carboximidamide
N',4'-dihydroxy-2-(pyrrolidin-1-yl)-5-(trifluoromethyl)-[1,1'-biphenyl]-3-carboximidamide
4-chloro-3',5'-difluoro-N'-hydroxy-6-(1H-indazol-5-yl)-[1,1'-biphenyl]-2-carboximidamide 6-(1H-benzo[d]imidazol-5-yl)-4-chloro-3',5'-difluoro-N'-hydroxy-[1,1'-biphenyl]-2-carboximidamide
4-chloro-3',5'-difluoro-N'-hydroxy-6-(1H-indol-5-yl)-[1,1'-biphenyl]-2-carboximidamide
4-chloro-3',5'-difluoro-6-(1H-indol-5-yl)-[1,1'-biphenyl]-2-carboxamide
4-chloro-3',5'-difluoro-6-(1H-indazol-5-yl)-[1,1'-biphenyl]-2-carboxamide
6-(1H-benzo[d]imidazol-5-yl)-4-chloro-3',5'-difluoro-[1,1'-biphenyl]-2-carboxamide
3',5'-difluoro-N'-hydroxy-6-(1H-indol-5-yl)-4-methyl-[1,1'-biphenyl]-2-carboximidamide
3',5'-difluoro-N'-hydroxy-6-(1H-indol-6-yl)-4-methyl-[1,1'-biphenyl]-2-carboximidamide
3',5'-difluoro-N'-hydroxy-6-(1H-indazol-5-yl)-4-methyl-[1,1'-biphenyl]-2-carboximidamide
3',5'-difluoro-N'-hydroxy-6-(1H-indazol-5-yl)-4-propyl-[1,1'-biphenyl]-2-carboximidamide
3',5'-difluoro-N'-hydroxy-6-(1H-indol-5-yl)-4-propyl-[1,1'-biphenyl]-2-carboximidamide
3',5'-difluoro-N'-hydroxy-6-(1H-indazol-5-yl)-4-(trifluoromethyl)-[1,1'-biphenyl]-2-carboximidamide
3',5'-difluoro-N'-hydroxy-6-(1H-indol-6-yl)-4-(trifluoromethyl)-[1,1'-biphenyl]-2-carboximidamide
3',5'-difluoro-N'-hydroxy-6-(1H-indazol-6-yl)-4-(trifluoromethyl)-[1,1'-biphenyl]-2-carboximidamide
3',5'-difluoro-N'-hydroxy-6-(1H-indol-5-yl)-4-(trifluoromethyl)-[1,1'-biphenyl]-2-carboximidamide
3',5'-difluoro-6-(1H-indol-5-yl)-4-(trifluoromethyl)-[1,1'-biphenyl]-2-carboxamide
3',5'-difluoro-N'-hydroxy-6-(1H-indazol-6-yl)-4-propyl-[1,1'-biphenyl]-2-carboximidamide
N'-hydroxy-6-(1H-indazol-5-yl)-2'-methoxy-5'-methyl-4-(trifluoromethyl)-[1,1'-biphenyl]-2-carboximidamide
5'-chloro-N'-hydroxy-6-(1H-indol-5-yl)-2'-methoxy-4-(trifluoromethyl)-[1,1'-biphenyl]-2-carboximidamide
5'-chloro-N'-hydroxy-6-(1H-indazol-5-yl)-2'-methoxy-4-(trifluoromethyl)-[1,1'-biphenyl]-2-carboximidamide
2',5'-difluoro-N'-hydroxy-6-(1H-indazol-5-yl)-4-(trifluoromethyl)-[1,1'-biphenyl]-2-carboximidamide
3',5'-difluoro-6-(6-fluoro-1H-indol-5-yl)-N'-hydroxy-4-(trifluoromethyl)-[1,1'-biphenyl]-2-carboximidamide
N'-hydroxy-3-(1H-indazol-5-yl)-2-(naphthalen-1-yl)-5-(trifluoromethyl)benzimidamide
2-(benzo[d][1,3]dioxol-4-yl)-N'-hydroxy-3-(1H-indazol-5-yl)-5-(trifluoromethyl)benzimidamide
4'-fluoro-N'-hydroxy-6-(1H-indazol-5-yl)-2'-methoxy-4-(trifluoromethyl)-[1,1'-biphenyl]-2-carboximidamide
N'-hydroxy-6-(1H-indazol-5-yl)-3'-methyl-4-(trifluoromethyl)-[1,1'-biphenyl]-2-carboximidamide
3',4',5'-trifluoro-N'-hydroxy-6-(1H-indazol-5-yl)-4-(trifluoromethyl)-[1,1'-biphenyl]-2-carboximidamide
3',4'-difluoro-N'-hydroxy-6-(1H-indazol-5-yl)-4-(trifluoromethyl)-[1,1'-biphenyl]-2-carboximidamide
N'-hydroxy-3-(1H-indazol-5-yl)-2-(2-methoxypyridin-3-yl)-5-(trifluoromethyl)benzimidamide
2-(cyclopent-1-en-1-yl)-N'-hydroxy-3-(1H-indazol-5-yl)-5-(trifluoromethyl)benzimidamide
2-(3,5-dimethylisoxazol-4-yl)-N'-hydroxy-3-(1H-indazol-5-yl)-5-(trifluoromethyl)benzimidamide
2',4'-difluoro-N'-hydroxy-6-(1H-indazol-5-yl)-4-(trifluoromethyl)-[1,1'-biphenyl]-2-carboximidamide
or a pharmaceutically acceptable ester, amide, carbamate or salt thereof, including a salt of such an ester, amide or carbamate.

17. The compound as claimed in claim 1 together with a further therapeutic agent, for simultaneous, sequential or separate administration.

18. A pharmaceutical composition which comprises a compound as claimed in claim 1, together with a pharmaceutically acceptable carrier.

19. A method for modulating estrogen receptor beta activity in a mammal, comprising administering to the mammal a therapeutically effective amount of a compound as claimed in claim 1.

* * * * *